(12) United States Patent
Kuttruff-Coqui et al.

(10) Patent No.: US 11,759,507 B2
(45) Date of Patent: Sep. 19, 2023

(54) PERSONALIZED IMMUNOTHERAPY AGAINST SEVERAL NEURONAL AND BRAIN TUMORS

(71) Applicant: Immatics Biotechnologies GmbH, Tuebingen (DE)

(72) Inventors: Sabrina Kuttruff-Coqui, Tuebingen (DE); Toni Weinschenk, Tuebingen (DE); Jens Fritsche, Tuebingen (DE); Steffen Walter, Houston, TX (US); Norbert Hilf, Tuebingen (DE); Oliver Schoor, Tuebingen (DE); Colette Song, Tuebingen (DE); Harpreet Singh, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 17/851,417

(22) Filed: Jun. 28, 2022

(65) Prior Publication Data
US 2023/0089882 A1    Mar. 23, 2023

Related U.S. Application Data

(63) Continuation of application No. 17/390,583, filed on Jul. 30, 2021, which is a continuation of application (Continued)

(51) Int. Cl.
*C07K 14/47* (2006.01)
*C07K 14/725* (2006.01)
(Continued)

(52) U.S. Cl.
CPC .......... *A61K 39/0011* (2013.01); *A61K 35/17* (2013.01); *C07K 7/06* (2013.01);
(Continued)

(58) Field of Classification Search
None
See application file for complete search history.

(56) References Cited

U.S. PATENT DOCUMENTS 7,030,235 B1    4/2006 Morton et al.
8,080,634 B2    12/2011 Singh et al.
(Continued)

FOREIGN PATENT DOCUMENTS

EP    2111867 A1    10/2009
EP    2119726 A1    11/2009
(Continued)

OTHER PUBLICATIONS

Aksnes, Henriette, et al. "First Things First: Vital Protein Marks by N-Terminal Acetyltransferases," Trends Biochem. Sci., vol. 41, No. 9, pp. 746-760, Sep. 2016.
(Continued)

*Primary Examiner* — Aurora M Fontainhas
(74) *Attorney, Agent, or Firm* — McBee Moore & Vanik IP, LLC

(57) ABSTRACT

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to peptide sequences and their variants derived from HLA class I and class II molecules of human tumor cells that can be used in vaccine compositions for eliciting anti-tumor immune responses.

20 Claims, 8 Drawing Sheets
Specification includes a Sequence Listing.

Related U.S. Application Data

No. 17/165,638, filed on Feb. 2, 2021, which is a continuation of application No. 14/531,472, filed on Nov. 3, 2014, now Pat. No. 10,946,064.

(60) Provisional application No. 61/899,680, filed on Nov. 4, 2013.

(51) Int. Cl.
| | |
|---|---|
| C07K 14/74 | (2006.01) |
| C07K 16/28 | (2006.01) |
| C07K 16/30 | (2006.01) |
| A61P 35/02 | (2006.01) |
| A61P 35/00 | (2006.01) |
| A61K 35/17 | (2015.01) |
| A61K 39/00 | (2006.01) |
| C12N 5/0783 | (2010.01) |
| C07K 14/705 | (2006.01) |
| C07K 7/06 | (2006.01) |
| C07K 7/08 | (2006.01) |
| C12Q 1/6886 | (2018.01) |

(52) U.S. Cl.
CPC ............ *C07K 7/08* (2013.01); *C07K 14/4748* (2013.01); *C07K 14/705* (2013.01); *C07K 14/70539* (2013.01); *C07K 16/2833* (2013.01); *C12Q 1/6886* (2013.01); *A61K 2039/5158* (2013.01); *A61K 2039/572* (2013.01); *A61K 2039/80* (2018.08); *C07K 2319/33* (2013.01); *C12Q 2600/136* (2013.01); *C12Q 2600/158* (2013.01); *C12Q 2600/16* (2013.01)

(56) References Cited

U.S. PATENT DOCUMENTS

| | | | |
|---|---|---|---|
| 8,119,139 B2 | 2/2012 | Weinschenk et al. |
| 8,318,677 B2 | 11/2012 | Weinschenk et al. |
| 8,647,629 B2 | 2/2014 | Rammensee et al. |
| 8,653,035 B2 | 2/2014 | Weinschenk et al. |
| 8,669,230 B2 | 3/2014 | Singh et al. |
| 8,895,514 B2 | 11/2014 | Weinschenk et al. |
| 8,961,985 B2 | 2/2015 | Weinschenk et al. |
| 9,175,040 B2 | 11/2015 | Weinschenk et al. |
| 9,283,267 B2 | 3/2016 | Lewandrowski et al. |
| 9,289,478 B2 | 3/2016 | Lewandrowski et al. |
| 9,498,512 B2 | 11/2016 | Rammensee et al. |
| 9,511,128 B2 | 12/2016 | Singh et al. |
| 9,791,443 B2 | 10/2017 | Weinschenk et al. |
| 9,791,444 B2 | 10/2017 | Weinschenk et al. |
| 9,950,048 B2 | 4/2018 | Singh et al. |
| 9,993,540 B2 | 6/2018 | Weinschenk et al. |
| 10,046,037 B2 | 8/2018 | Weinschenk et al. |
| 10,047,123 B2 | 8/2018 | Weinschenk et al. |
| 10,047,124 B2 | 8/2018 | Weinschenk et al. |
| 10,100,085 B2 | 10/2018 | Weinschenk et al. |
| 10,206,973 B2 | 2/2019 | Garman |
| 10,227,381 B2 | 3/2019 | Weinschenk et al. |
| 10,420,800 B2 | 9/2019 | Weinschenk et al. |
| 10,434,120 B2 | 10/2019 | Weinschenk et al. |
| 10,434,136 B2 | 10/2019 | Rammensee et al. |
| 10,709,735 B2 | 7/2020 | Weinschenk et al. |
| 10,906,936 B2 | 2/2021 | Weinschenk et al. |
| 10,919,931 B2 | 2/2021 | Weinschenk et al. |
| 10,941,181 B2 | 3/2021 | Weinschenk et al. |
| 11,072,645 B2 | 7/2021 | Bunk et al. |
| 11,136,352 B2 | 10/2021 | Weinschenk et al. |
| 11,208,434 B2 | 12/2021 | Weinschenk et al. |
| 2009/0123489 A1 | 5/2009 | Weinschenk et al. |
| 2009/0136528 A1 | 5/2009 | Singh et al. |
| 2010/0158931 A1 | 6/2010 | Weinschenk et al. |
| 2013/0032327 A1 | 12/2013 | Rammensee et al. |
| 2013/0323272 A1 | 12/2013 | Rammensee et al. |
| 2014/0086943 A1 | 3/2014 | Weinschenk et al. |
| 2014/0127242 A1 | 5/2014 | Rammensee et al. |
| 2016/0175357 A1 | 6/2016 | Weinschenk et al. |
| 2016/0355550 A1 | 12/2016 | Weinschenk et al. |
| 2016/0376314 A1 | 12/2016 | Weinschenk et al. |
| 2016/0376315 A1 | 12/2016 | Weinschenk et al. |
| 2016/0376316 A1 | 12/2016 | Weinschenk et al. |
| 2016/0376317 A1 | 12/2016 | Weinschenk et al. |
| 2019/0010190 A1 | 1/2019 | Weinschenk et al. |
| 2020/0078439 A1 | 3/2020 | Rammensee et al. |
| 2020/0345777 A1 | 11/2020 | Weinschenk et al. |
| 2021/0238227 A1 | 8/2021 | Weinschenk et al. |
| 2021/0261614 A1 | 8/2021 | Weinschenk et al. |
| 2021/0380659 A1 | 12/2021 | Bunk et al. |

FOREIGN PATENT DOCUMENTS

| | | |
|---|---|---|
| WO | 2000066734 A1 | 11/2000 |
| WO | 2002006338 A1 | 1/2002 |
| WO | 2003016475 A2 | 2/2003 |
| WO | 2006034334 A2 | 3/2006 |
| WO | 2006091734 A2 | 8/2006 |
| WO | 2009015842 A2 | 2/2009 |
| WO | 2009015843 A1 | 2/2009 |
| WO | 2010037514 A2 | 4/2010 |
| WO | 2011051278 A1 | 5/2011 |
| WO | 2011128448 A1 | 10/2011 |

OTHER PUBLICATIONS

Berge, Stephen M., et al. "Pharmaceutical Salts", J. Pharm. Sci. Vol. 66, No. 1, pp. 1-19, Jan. 1977.

Bergman, Tomas, et al. "Alcoholytic deblocking of N-terminally acetylated peptides and proteins for sequence analysis," FEBS Lett. Vol. 390, No. 2, pp. 199-202, Jul. 1996.

Bhattachar, Shobha N., et al. "Solubility: it's not just for physical chemists," Drug Discov. Today, vol. 11, No. 21-22, pp. 1012-1018, Nov. 2006.

Fosgerau, Keld, et al. "Peptide therapeutics: current status and future directions," Drug Discov. Today. Vol. 20, No. 1, pp. 122-128, Jan. 2015.

GB Office Action from Corresponding GB1319446.9, dated Jul. 15, 2014.

Gheorghe, M.T., et al. "Optimized Alcoholytic Deacetylation of N-Acetyl-Blocked Polypeptides for Subsequent Edman Degradation," Anal. Biochem. Vol. 254, No. 1, pp. 119-125, Dec. 1997.

International Search Report dated Sep. 9, 2015 in PCT/EP2014/073588.

Jensen, P. E., et al. "Peptide exchange in MHC molecules," Immunol. Rev. Vol. 172, pp. 229-238, Dec. 1999.

Maffei, A., et al. "Peptides Bound to Major Histocompatibility Complex Molecules," Peptides. Vol. 19, No. 1, pp. 179-198, 1998.

Myers, Sharon NPL_MYERSR., et al. "Acylation of human insulin with palmitic acid extends the time action of human Insulin in diabetic dogs," Diabetes, vol. 46, No. 4, pp. 637-642, Apr. 1997.

Paulekuhn, G. Steffen, et al. "Trends in active pharmaceutical ingredient salt selection based on analysis of the Orange Book database," J. Med. Chem. Vol. 50, No. 26, pp. 6665-6672, Dec. 2007.

Ponomarenko, Elena A., et al. "The Size of the Human Proteome: The Width and Depth," Int. J. Anal. Chem. pp. 1-6, May 2016.

Reichert, Christian, et al. "Noncovalent PEGylation, An Innovative Subchapter in the Field of Protein Modification," J. Pharm. Sci. Vol. 105, No. 2, pp. 386-390, Feb. 2016.

Yague, J., et al. "An N-Acetylated Natural Ligand of Human Histocompatibility Leukocyte Antigen (Hla)-B39," J. Exp. Med. Vol. 191, No. 12, pp. 2083-2092, Jun. 2000.

Zorzi, Alessandro, et al. "Acylated heptapeptide binds albumin with high affinity and application as tag furnishes long- acting peptides," Nat. Commun. Vol. 8, pp. 1-9, Jul. 2017.

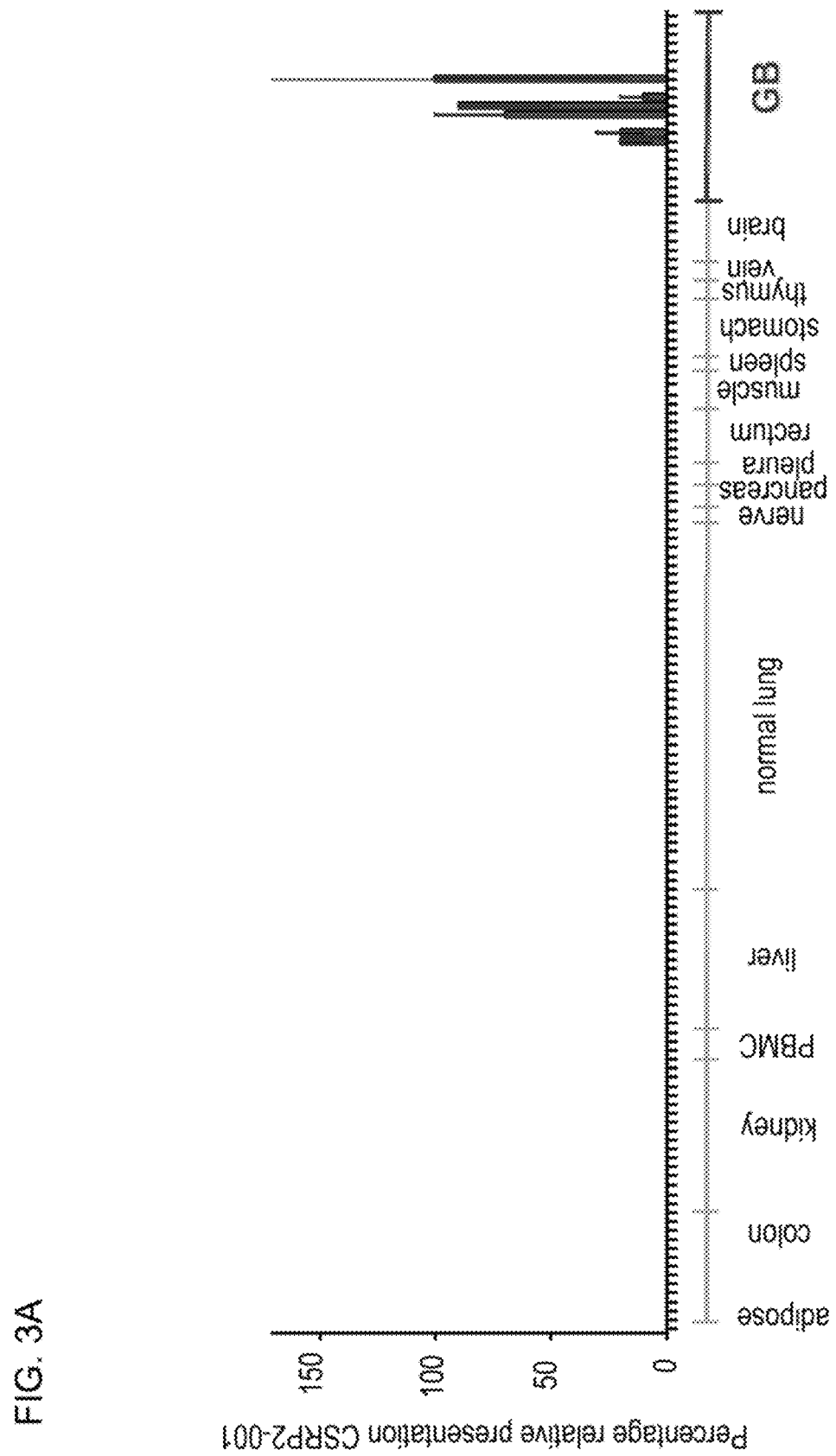

PERSONALIZED IMMUNOTHERAPY AGAINST SEVERAL NEURONAL AND BRAIN TUMORS

CROSS REFERENCE TO RELATED APPLICATIONS

This application is a continuation application of U.S. patent application Ser. No. 17/390,583 filed Jul. 30, 2021, which is a continuation of Ser. No. 17/165,638, filed Feb. 2, 2021, which is a continuation of U.S. patent application Ser. No. 14/531,472, filed Nov. 3, 2014, now U.S. Pat. No. 10,946,064, issued on Mar. 16, 2021, which claims priority to British Patent Application No. 1319446.9 and U.S. Provisional Patent Application No. 61/899,680, both filed Nov. 4, 2013, the contents of which are incorporated herein by reference in their entireties. This application is related to PCT/EP2014/073588, filed Nov. 3, 2014, the contents of which are also incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-037006_Sequence_Listing_ST25.txt" created on 27 Jun. 2022, and 24,384 bytes in size) is submitted concurrently with the instant application, and the entire contents of the Sequence Listing are incorporated herein by reference.

BACKGROUND

Field of the Invention

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to specific peptide sequences and their variants derived from HLA class I and class II molecules of human tumor cells that can be used in vaccine compositions for eliciting anti-tumor immune responses as well as a method for providing optimal vaccines to persons in need.

Description of Related Art

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approx. 40% of all malignant brain tumors and approx. 50% of gliomas. It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable. The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy including gross tumor resection is still less than 10%. Accordingly, there is a strong medical need for an alternative and effective therapeutic method.

Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy.

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the state with no clinical or pathological abnormalities (Pathology and Genetics of the Nervous Systems. 29-39 (IARC Press, Lyon, France, 2000)).

Glioblastoma migrates along myelinated nerves and spreads widely in the central nervous system. In most cases surgical treatment shows only limited sustainable therapeutic effect. Malignant glioma cells evade detection by the host's immune system by producing immunosuppressive agents that impair T cell proliferation and production of the immune-stimulating cytokine IL-2.

Intracranial neoplasms can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

The search for effective treatment of glioblastomas in patients is still ongoing today. Immunotherapy or treatment via recruitment of the immune system, to fight these neoplastic cells has been investigated.

There is an ongoing clinical trial with IMA950, a multi-peptide vaccine conducted in the UK by immatics biotechnologies (Tubingen, Germany). The peptides in the vaccine are exclusively HLA-A*02 peptides.

There remains a need for new efficacious and safe treatment option for glioblastoma and medulloblastoma and other tumors which show an overexpression of the proteins of the present invention, enhancing the well-being of the patients with other HLA alleles or combinations of alleles without using chemotherapeutic agents or other agents which may lead to severe side effects.

SUMMARY

In a first aspect of the present invention, the present invention relates to a peptide comprising an amino acid sequence selected from the group of SEQ ID No. 1 to SEQ ID No. 49, SEQ ID No. 71, and SEQ ID No. 74 to 129, and variant sequences thereof which are at least 90% homologous to SEQ ID No. 1 to SEQ ID No. 49, SEQ ID No. 71, and SEQ ID No. 74 to 129, and wherein said variant induces T cells cross-reacting with said peptide; or a pharmaceutical acceptable salt thereof, wherein said peptide is not a full-length polypeptide.

The present invention further relates to a peptide of the present invention, comprising a sequence that is selected from the group of SEQ ID No. 1 to SEQ ID No. 49, SEQ ID No. 71, and SEQ ID No. 74 to 129, and variant sequences thereof which are at least 90% homolog to SEQ ID No. 1 to SEQ ID No. 49, SEQ ID No. 71, and SEQ ID No. 74 to 129, wherein said peptide or variant has an overall length of between 8 and 100, preferably between 8 and 30, and most preferred between 8 and 14 amino acids.

BRIEF DESCRIPTION OF THE DRAWINGS

FIG. 1A) Exemplary mass spectrum from IGF2BP3-001 demonstrating its presentation on primary tumor sample glioblastoma. NanoESI-LCMS was performed on a peptide pool eluted from the glioblastoma sample 6010. The mass chromatogram for m/z 536.3229±0.001 Da, z=2 shows a peptide peak at the retention time 48.76 min. FIG. 1B) The detected peak in the mass chromatogram at 48.76 min revealed a signal of m/z 536.3229 in the MS spectrum. FIG. 1C) A collisionally induced decay mass spectrum from the selected precursor m/z 536.3229 recorded in the nanoESI-LCMS experiment at the given retention time confirmed the presence of IGF2BP3-001 in the glioblastoma 6010 tumor sample. FIG. 1D) The fragmentation pattern of the synthetic IGF2BP3-001 reference peptide was recorded and compared to the generated natural TUMAP fragmentation pattern shown in C for sequence verification.

FIG. 2A) CSRP2 (Probeset ID: 211126_s_at); FIG. 2B) PTPRZ1 (Probeset ID: 204469_at).

FIGS. 3A-3D: Presentation profiles for selected HLA class I peptides. A presentation profile was calculated for each peptide showing the mean sample presentation as well as replicate variations. The profile juxtaposes samples of the tumor entity of interest to a baseline of normal tissue samples. FIG. 3A) CSRP2-001 (HLA-A*02); FIG. 3B) PTP-012 (HLA-A*02); FIG. 3C) TMEM255A-001 (HLA-A*24); FIG. 3D) PJA2-001 (HLA-A*24).

DETAILED DESCRIPTION OF A PREFERRED EMBODIMENT

Figure 1A:
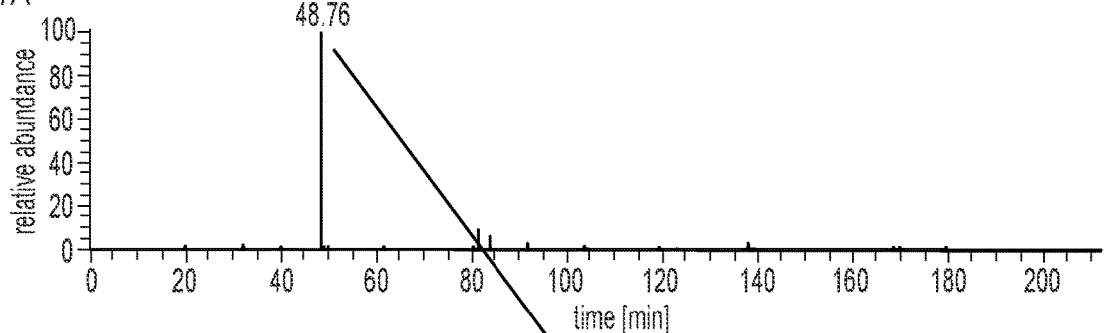
FIGS. 1A-1D.
Figure 1B:
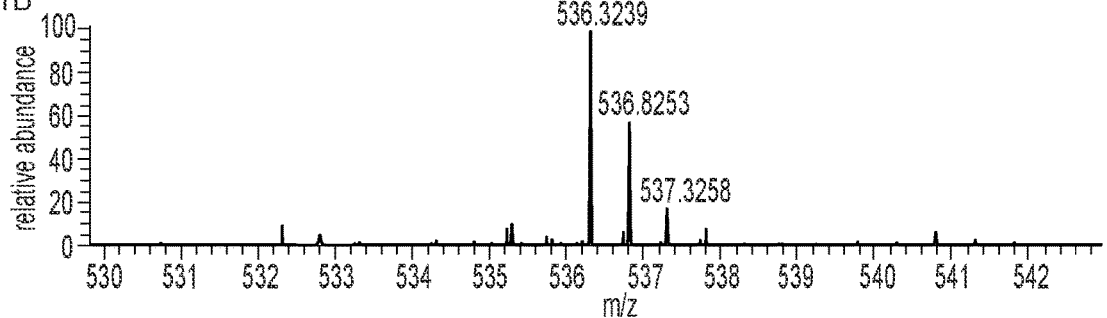
Figure 1C:
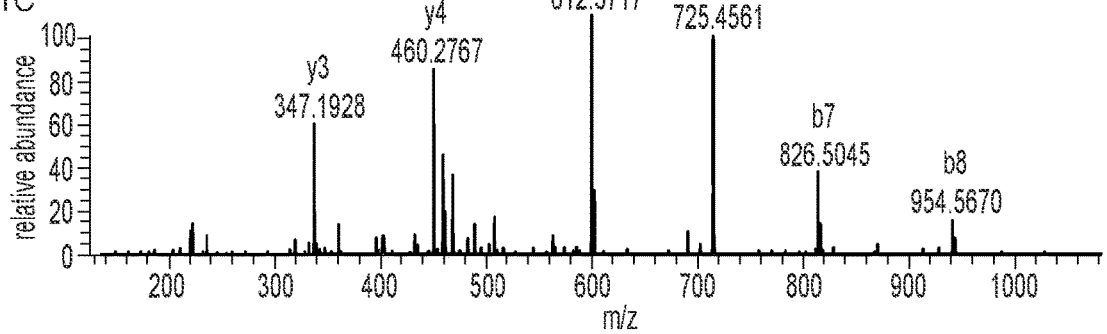
Figure 1D:
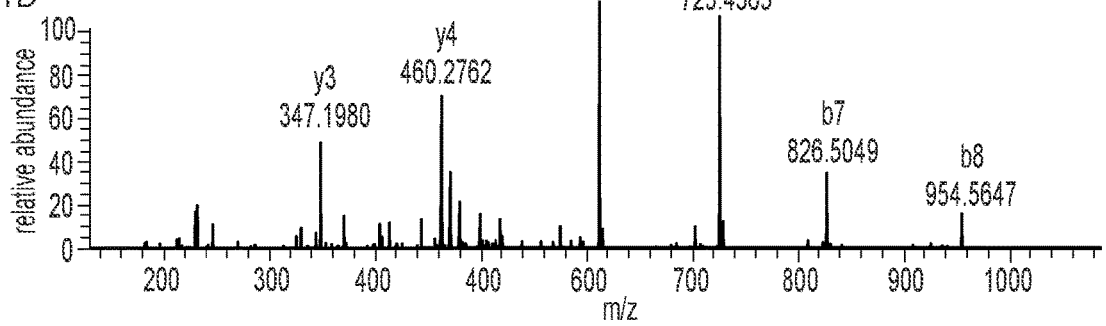

The following tables show the peptides according to the present invention, their respective SEQ ID NO, and the prospective source proteins for these peptides. All peptides in Tables 1a, 1b and 1c bind to the HLA-A*02 allele, peptides in Table 1d and 1e bind to HLA-DR alleles.

The class II peptides in table 1d and 1e are particularly useful in the treatment of cancers over-expressing and/or over-presenting the polypeptides BCAN, BIRC5 and/or PTPRZ1.

TABLE 1a

Peptides of the present invention

| SEQ ID NO: | Peptide Code | Sequence | Source Protein(s) |
|---|---|---|---|
| 1 | CSRP2-001 | RLGIKPESV | CSRP2 |
| 2 | SLC10A4-001 | ALAFKLDEV | SLC10A4 |
| 3 | ELOVL2-001 | YLPTFFLTV | ELOVL2 |
| 4 | MTSS1L-001 | GLPSGAPPGV | MTSS1L |
| 5 | PTP-013 | MIWEHNVEV | PTPRZ1 |
| 6 | KIF1A-001 | LLWGNAIFL | KIF1A |
| 7 | PCDHGC5-001 | GLDPSSGAIHV | PCDHGC5 |
| 8 | GRIK3-001 | LLYDAVHIV | GRIK3 |
| 9 | SEZ6L-001 | LLLGSPAAA | SEZ6L |
| 10 | ANKRD40-001 | ALGDIREV | ANKRD40 |
| 11 | NLGN4Y-001 | SLDTLMTYV | NLGN4Y |
| 12 | KCN-002 | ALSVRISNV | KCNJ10 |
| 13 | BCA-003 | FLWSDGVPL | BCAN |
| 14 | MAGI2-001 | AVAPGPWKV | MAGI2 |
| 15 | PTP-012 | FLLPDTDGLTAL | PTPRZ1 |
| 16 | SCARA3-001 | SLGLFLAQV | SCARA3 |
| 17 | GRI-002 | VLIQDVPTL | GRIA4 |
| 18 | CLU-001 | KLFDSDPITVTV | CLU |
| 19 | CERS1-001 | FLHDISDVQL | CERS1 |
| 20 | SLC10A4-002 | RVADYIVKV | SLC10A4 |
| 21 | GPR98-001 | ALFNKGGSVFL | GPR98 |
| 22 | GYG2-001 | KVFDEVIEV | GYG2 |
| 23 | CPT1C-001 | GLMEKIKEL | CPT1C |
| 24 | SLC35E1-002 | GMMTAILGV | SLC35E1 |
| 25 | PTP-002 | FLYKVILSL | PTPRZ1 |
| 26 | PTP-001 | ALTTLMHQL | PTPRZ1 |
| 27 | ASIC4-001 | EILDYIYEV | ASIC4 |
| 28 | COL20-001 | FLVDGSWSI | COL20A1 |
| 29 | EGFR-008 | YQDPHSTAV | EGFR |
| 30 | JAK-001 | KLTDIQIEL | JAKMIP2/JAKMIP3 |
| 31 | WLS-002 | TMMSRPPVL | WLS/MIER1 |
| 32 | IRS-001 | RVAS*PTSGV | IRS2 |
| 33 | NAT8L-001 | SLAERLFFQV | NAT8L |
| 34 | TNC-001 | AMTQLLAGV | TNC |
| 35 | MAP1B-002 | GLSEFTEYL | MAP1B |
| 36 | NC AN-001 | VLCGPPPAV | NCAN |
| 37 | ADORA3-001 | ALADIAVGV | ADORA3 |
| 38 | NPAS3-001 | LLYTGDLEAL | NPAS3 |
| 39 | NLGN4X-002 | GLLDQIQAL | NLGN4Y/NLGN3/NLGN4X/NLGN2 |
| 40 | GRI-001 | NILEQIVSV | GRIA4 |
| 41 | DPP3-001 | FLYNEALYSL | DPP3/BBS1 |

S* = optionally phosphorylated serine

TABLE 1b

Additional peptides of the present invention

| SEQ ID NO: | Peptide Code | Sequence | Source Protein(s) |
|---|---|---|---|
| 42 | USP11-001 | MLFGHPLLVSV | USP11 |
| 43 | EIF4E-001 | RLISKFDTV | EIF4E |

TABLE 1b-continued

Additional peptides of the present invention

| SEQ ID NO: | Peptide Code | Sequence | Source Protein(s) |
|---|---|---|---|
| 44 | PLEKHA4-001 | LLQDRLVSV | PLEKHA4 |
| 45 | CCT-001 | TLLAAEFLKQV | CCT7 |
| 46 | NOC4-001 | LTAPPEALLMV | NOC4L |
| 47 | MAP1B-001 | FLDSKFYLL | MAP1B |
| 48 | CHCHD2-005 | KLCEGFNEV | CHCHD2 |
| 49 | SOX-001 | KLADQYPHL | SOX8/SOX9/SOX10 |

TABLE 1c

Additional peptides that are over-expressed in glioblastoma

| SEQ ID NO: | Peptide Code | Sequence | Source Protein(s) |
|---|---|---|---|
| 50 | PTP-005 | KVFAGIPTV | PTPRZI |
| 51 | BCA-002 | ALWAWPSEL | BCAN |
| 52 | CDK4-001 | TLWYRAPEV | CDK4/CDK6 |
| 53 | MAGEF1-001 | ILFPDIIARA | MAGEF1 |
| 54 | PTP-003 | AIIDGVESV | PTPRZI |
| 55 | NLGN4X-001 | NLDTLMTYV | NLGN4X |
| 56 | VPS13B-001 | SLWGGDVVL | VPS13B |
| 57 | NRC AM-001 | GLWHHQTEV | NRCAM |
| 58 | RAD54B-001 | SLYKGLLSV | RAD54B |
| 59 | FABP7-001 | LTFGDVVAV | FABP7 |
| 60 | CSP-001 | TMLARLASA | CSPG4 |
| 61 | ORMDL1-002 | TLTNIIHNL | ORMDL1 |
| 62 | TACC3-001 | KLVEFDFLGA | TACC3 |
| 63 | DCA-001 | KLGDFGLATVV | DCLK2 |
| 64 | PCNXL3-001 | GVLENIFGV | PCNXL3 |
| 65 | DPYSL4-001 | NLLAEIHGV | DPYSL4 |
| 66 | IGF2BP3-001 | KIQEILTQV | IGF2BP3 |
| 67 | DROSHA-001 | AVVEFLTSV | DROSHA |
| 68 | ABCA13-001 | ILFEINPKL | ABCA13 |
| 69 | CCNB1-002 | ILIDWLVQV | CCNB1 |
| 70 | CNOT1-002 | SLADFMQEV | CNOT1 |

TABLE 1d

MHC class 11 peptides of the present invention

| SEQ ID NO: | Peptide Code | Sequence | Source Protein(s) |
|---|---|---|---|
| 71 | BCA-005 | VKVNEAYRFRVALPAYPA | BCAN |

TABLE 1e

Additional MHC class 11 peptides

| SEQ ID NO: | Peptide Code | Sequence | Source Protein(s) |
|---|---|---|---|
| 72 | BIR-002 | TLGEFLKLDRERAKN | BIRC5 |
| 73 | PTP-010 | EIGWSYTGALNQKN | PTPRZI |

Tables 2a and b show additional peptides according to the present invention, their respective SEQ ID NO, and the source proteins from which these peptides may arise. All peptides in tables 2 bind to the HLA A*24 alleles.

TABLE 2a

Additional peptides of the present invention

| SEQ ID NO: | Peptide Code | Sequence | Source Protein(s) |
|---|---|---|---|
| 74 | TMEM255A-001 | YYPGVILGF | TMEM255A |
| 75 | ST8SIA5-001 | VYYFHPQYL | ST8SIA5 |
| 76 | FAM120C-001 | MYPYIYHVL | FAM120C |
| 77 | GRIK3-002 | YYHFIFTTL | GRIK3 |
| 78 | PTP-014 | YYTVRNFTL | PTPRZ1 |
| 79 | PTP-019 | NYTSLLVTW$^{+4}$ | PTPRZ1 |
| 80 | FABP7-002 | EYMKALGVGF | FABP7 |
| 81 | ZNF3-001 | KYNDFGNSF | ZNF3 |
| 82 | DOCK7-002 | LYIYPQSLNF | DOCK7 |
| 83 | LOC72839-001 | IFTYIHLQL | LOC728392 |
| 84 | PJA2-001 | RYQESLGNTVF | PJA2 |
| 85 | HEATR1-001 | KYNEFSVSL | HEATR1 |
| 86 | GPM-002 | TYNYAVLKF | GPM6B |
| 87 | CRB1-001 | SYFENVHGF | CRB1 |
| 88 | PTP-016 | VYDTMIEKF | PTPRZ1 |
| 89 | PTP-015 | QYVFIHDTL | PTPRZ1 |
| 90 | PTP-018 | NYTSLLVTW | PTPRZ1 |
| 91 | OLIG2-001 | IYGGHHAGF | OLIG2 |
| 92 | VCAN-003 | TYVDSSHTI | VCAN |
| 93 | SMOX-001 | VYNLTQEFF | SMOX |
| 94 | EXOC7-001 | YYQIRSSQL | EXOC7 |
| 95 | LZTS1-001 | RYSDGLLRF | LZTS1 |
| 96 | FADS2-003 | QYQIIMTMI | FADS2 |
| 97 | TMEM231-001 | TYIPPLLVAF | TMEM231 |
| 98 | ASCL1-001 | EYIRALQQL | ASCL1 |
| 99 | UNKN-003 | TYIIKSVGF | TXN2 |
| 100 | NKA-001 | QWAPILANF | NKAINI/NKAIN2/NKAIN4 |
| 101 | PCD-002 | RYGPQFTL | PCDHG-Family |
| 102 | ARHGAP21-001 | RYIPLIVDI | ARHGAP21 |
| 103 | PNMA2-001 | AYVLRLETL | PNMA2 |
| 104 | FADS2-002 | PYNHQHEYF | FADS2 |
| 105 | APC-001 | VLPDADTLLHF | APC |
| 106 | WASL-001 | FYGPQVNNI | WASL/ASB15 |
| 107 | SLC-002 | KYFSFPGEL | SLC1A3/SLC1A6 |
| 108 | TENM4-001 | AYSDGHFLF | TENM4 |
| 109 | ZNF749-001 | RYLPSSVFL | ZNF749 |
| 110 | EFCAB7-001 | VYLTIKPLNL | EFCAB7 |
| 111 | DOCK7-003 | PYLDKFFAL | DOCK7 |
| 112 | BMP7-001 | VYQVLQEHL | BMP7 |
| 113 | ITGA7-001 | AFSPDSHYLLF | ITGA7 |
| 114 | RPL-001 | NYNDRYDEI | RPL7A |
| 115 | HS2-001 | KYNLINEYF | HS2ST1 |
| 116 | VIM-002 | NYQDTIGRL | VIM |
| 117 | IFT17-001 | AYLIDIKTI | IFT172 |
| 118 | GAB-001 | AYPRLSLSF | GABRB1/GABRB3 |
| 119 | CDCA7L-001 | KFAEEFYSF | CDCA7L |
| 120 | SCARA3-002 | YYLDKSVSI | SCARA3 |
| 121 | SSR1-001 | NYKDLNGNVF | SSR1 |
| 122 | NR0B1-001 | AYLKGTVLF | NR0B1 |
| 123 | LNX1-001 | NYIDNVGNLHF | LNX1 |
| 124 | EP4-001 | PFAKPLPTF | EP400 |
| 125 | KIF1B-001 | VYLKEANAI | KIF1B |
| 126 | RHOBTB3-001 | KYFGGVLEYF | RHOBTB3 |
| 127 | KIF7-001 | KYFDKVVTL | KIF7 |
| 128 | KIF1B-002 | VYNDIGKEMLL | KIF1B |
| 129 | MAPK6-001 | TYTSYLDKF | MAPK6 |

The peptide according to SEQ ID NO 101 can be derived from any of the following proteins: PCDHGA12, PCDHGC3, PCDHGC5, PCDHGC4, PCDHGB7, PCDHGB6, PCDHGB5, PCDHGB3, PCDHGB2, PCDHGB1, PCDHGA11, PCDHGA10, PCDHGA9, PCDHGA7, PCDHGA6, PCDHGA5, PCDHGA4, PCDHGA3, PCDHGA2, PCDHGA, PCDHGB4, or PCDHGA8. The peptide according to SEQ ID NO 109 is a frameshift of EVPSKQCVS; chr 19, 2+ frame: 57954686-57954712. W$^{+4}$: Kynurenine ((S)-2-amino-4-(2-aminophenyl)-4-oxo-butanoic acid). The peptide according to SEQ ID NO: 99 is part of the first intron of TXN2 (supported by a matching EST, BG169743.1).

TABLE 2b

Additional peptides that are over-expressed in glioblastoma

| SEQ ID NO: | Peptide Code | Sequence | Source Protein(s) |
|---|---|---|---|
| 130 | ASPM-002 | SYNPLWLRI | ASPM |
| 131 | SMC4-001 | HYKPTPLYF | SMC4 |

TABLE 2c

Additional indications (e.g. cancers to be treated) based on the peptides according to the invention overexpressed and/or overpresented in said indications

| SEQ ID NO | Sequence | Peptide Code | Additional Indication(s) |
|---|---|---|---|
| 1 | RLGIKPESV | CSRP2-001 | Liver, Prostate |
| 2 | ALAFKLDEV | SLC10A4-001 | Lung |
| 3 | YLPTFFLTV | ELOVL2-001 | Kidney, Liver |
| 4 | GLPSGAPPGV | MTSS1L-001 | Kidney, Liver |
| 8 | LLYDAVHIV | GRIK3-001 | Leukaemia |
| 9 | LLLGSPAAA | SEZ6L-001 | Pancreas |
| 10 | ALGDIREV | ANKRD40-001 | Kidney, Colon, Rectum, Liver |
| 11 | SLDTLMTYV | NLGN4Y-001 | Colon, Rectum, Prostate, Leukaemia |
| 12 | ALSVRISNV | KCN-002 | Kidney, Liver, Pancreas |
| 14 | AVAPGPWKV | MAGI2-001 | Liver |
| 18 | KLFDSDPITVTV | CLU-001 | Liver |
| 24 | GMMTAILGV | SLC35E1-002 | Liver |
| 29 | YQDPHSTAV | EGFR-008 | Kidney, Liver |
| 30 | KLTDIQIEL | JAK-001 | Prostate |
| 32 | RVASPTSGV | IRS-001 | Liver |
| 34 | AMTQLLAGV | TNC-001 | Lung, Colon, Rectum |
| 35 | GLSEFTEYL | MAP1B-002 | Kidney, Prostate |
| 37 | ALADIAVGV | ADORA3-001 | Lung, Kidney, Pancreas, Prostate |
| 40 | NILEQIVSV | GRI-001 | Kidney |
| 42 | MLFGHPLLVSV | USP11-001 | Lung, Kidney, Liver, Pancreas, Prostate |
| 43 | RLISKFDTV | EIF4E-001 | Lung, Colon, Rectum, Liver, Prostate |
| 44 | LLQDRLVSV | PLEKHA4-001 | Colon, Rectum, Liver |
| 45 | TLLAAEFLKQV | CCT-001 | Lung, Liver |
| 46 | LTAPPEALLMV | NOC4-001 | Lung, Kidney, Colon, Rectum, Liver, Pancreas |
| 47 | FLDSKFYLL | MAP1B-001 | Kidney, Liver, Prostate |
| 48 | KLCEGFNEV | CHCHD2-005 | Colon, Rectum, Liver |
| 52 | TLWYRAPEV | CDK4-001 | Lung, Kidney, Stomach, Colon, Rectum, Liver |
| 53 | ILFPDIIARA | MAGEF1-001 | Lung, Kidney, Colon, Rectum, Liver, Leukaemia |
| 56 | SLWGGDVVL | VPS13B-001 | Lung, Colon, Rectum, Liver, Prostate |
| 58 | SLYKGLLSV | RAD54B-001 | Lung, Kidney, Colon, Rectum, Prostate |
| 59 | LTFGDVVAV | FABP7-001 | Stomach |
| 60 | TMLARLASA | CSP-001 | Kidney |
| 61 | TLTNIIHNL | ORMDL1-002 | Lung, Kidney, Liver, Leukaemia |
| 62 | KLVEFDFLGA | TACC3-001 | Lung, Stomach, Colon, Rectum, Liver |
| 64 | GVLENIFGV | PCNXL3-001 | Lung, Kidney, Stomach, Colon, Rectum, Liver, Prostate |
| 65 | NLLAEIHGV | DPYSL4-001 | Kidney |
| 66 | KIQEILTQV | IGF2BP3-001 | Lung, Kidney, Stomach, Colon, Rectum, Liver, Pancreas, Leukaemia |
| 67 | AVVEFLTSV | DROSHA-001 | Lung, Kidney, Stomach, Colon, Rectum, Liver, Pancreas |
| 68 | ILFEINPKL | ABCA13-001 | Lung, Leukaemia |
| 69 | ILIDWLVQV | CCNB1-002 | Lung, Kidney, Stomach, Colon, Rectum, Liver, Pancreas |
| 70 | SLADFMQEV | CNOT1-002 | Lung, Kidney, Colon, Rectum, Pancreas |
| 74 | YYPGVILGF | TMEM255A-001 | Lung |
| 81 | KYNDFGNSF | ZNF3-001 | Lung, Liver |
| 82 | LYIYPQSLNF | DOCK7-002 | Lung, Kidney, Liver |
| 83 | IFTYIHLQL | LOC72839-001 | Liver |
| 92 | TYVDSSHTI | VCAN-003 | Lung, Stomach, Liver |
| 93 | VYNLTQEFF | SMOX-001 | Lung, Kidney, Stomach |
| 94 | YYQIRSSQL | EXOC7-001 | Lung, Stomach, Liver |
| 96 | QYQIIMTMI | FADS2-003 | Liver |
| 97 | TYIPPLLVAF | TMEM231-001 | Lung, Kidney, Stomach, Liver |
| 103 | AYVLRLETL | PNMA2-001 | Lung |
| 104 | PYNHQHEYF | FADS2-002 | Lung, Liver |
| 105 | VLPDADTLLHF | APC-001 | Liver |
| 108 | AYSDGHFLF | TENM4-001 | Lung, Kidney, Stomach, Prostate |
| 109 | RYLPSSVFL | ZNF749-001 | Lung, Stomach, Liver |
| 110 | VYLTIKPLNL | EFCAB7-001 | Lung, Stomach, Liver |
| 112 | VYQVLQEHL | BMP7-001 | Stomach |
| 113 | AFSPDSHYLLF | ITGA7-001 | Lung, Kidney, Liver |

TABLE 2c-continued

Additional indications (e.g. cancers to be treated) based on the peptides according to the invention overexpressed and/or overpresented in said indications

| SEQ ID NO | Sequence | Peptide Code | Additional Indication(s) |
|---|---|---|---|
| 115 | KYNLINEYF | HS2-001 | Lung, Kidney, Liver |
| 116 | NYQDTIGRL | VIM-002 | Kidney |
| 117 | AYLIDIKTI | IFT17-001 | Lung, Kidney, Liver |
| 118 | AYPRLSLSF | GAB-001 | Liver |
| 119 | KFAEEFYSF | CDCA7L-001 | Lung, Kidney, Stomach |
| 122 | AYLKGTVLF | NR0B1-001 | Lung |
| 124 | PFAKPLPTF | EP4-001 | Lung, Kidney, Stomach, Liver |
| 126 | KYFGGVLEYF | RHOBTB3-001 | Lung, Stomach, Liver |
| 127 | KYFDKVVTL | KIF7-001 | Lung, Liver, Prostate |
| 129 | TYTSYLDKF | MAPK6-001 | Lung, Liver |
| 130 | SYNPLWLRI | ASPM-002 | Lung, Stomach, Liver |
| 131 | HYKPTPLYF | SMC4-001 | Lung, Stomach, Liver, Prostate |

Thus, another preferred aspect of the present invention relates to the use of the peptides according to the present invention for the—preferably combined—preferred immunotherapy of cancerous diseases according to the table 2c as above in analogy to the uses as described herein for, e.g., glioblastoma.

The peptides according to the present invention have the ability to bind to a molecule of the human major histocompatibility complex (WIC) class-I or -II.

The present invention further relates to the peptides according to the present invention wherein said peptides consist or consist essentially of an amino acid sequence according to SEQ ID No. 1 to SEQ ID No. 49, SEQ ID No. 71, and SEQ IDs No. 74 to 129.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii) according to SEQ ID No. 133.

The present invention further relates to a nucleic acid, encoding the peptides according to the present invention.

The present invention further relates to the nucleic acid according to the present invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine.

The present invention further relates to antibodies according to the present invention.

The present invention further relates to sTCRs according to the present invention.

The present invention further relates to a host cell comprising a nucleic acid according to the present invention or an expression vector as described before.

The present invention further relates to the host cell according to the present invention that is an antigen presenting cell. The present invention further relates to the host cell according to the present invention wherein the antigen presenting cell is a dendritic cell.

The present invention further relates to a method of producing a peptide according to the present invention, the method comprising culturing the host cell according to the present invention, and isolating the peptide from the host cell or its culture medium.

The present invention further relates to an in vitro method for producing activated cytotoxic T lymphocytes (CTL), the method comprising contacting in vitro CTL with antigen loaded human class I or II WIC molecules expressed on the surface of a suitable antigen-presenting cell for a period of time sufficient to activate said CTL in an antigen specific manner, wherein said antigen is any peptide according to the present invention.

The present invention further relates to the method according to the present invention, wherein the antigen is loaded onto class I or II WIC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129, or said variant amino acid sequence.

The present invention further relates to activated cytotoxic T lymphocytes (CTL), produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of cytotoxic T lymphocytes (CTL) as according to the present invention.

The present invention further relates to the use of any peptide described, a nucleic acid according to the present invention, an expression vector according to the present invention, a cell according to the present invention, an antibody according to the present invention, or an activated cytotoxic T lymphocyte according to the present invention as a medicament or in the manufacture of a medicament.

The present invention further relates to a use according to the present invention, wherein said medicament is a vaccine.

The present invention further relates to a use according to the present invention, wherein the medicament is active against cancer.

The present invention further relates to particular marker proteins and biomarkers based on the peptides according to the present invention that can be used in the diagnosis and/or prognosis of glioblastoma.

Further, the present invention relates to the use of these novel targets for cancer treatment.

Further, the present invention relates to a method for providing and producing vaccines for patient pool with a specific set of alleles and/or patient specific.

That is, the present invention further relates to a peptide according to the present invention according to SEQ ID No. 1 to SEQ ID No. 49, SEQ ID No. 71, and SEQ ID No. 74 to 129, a nucleic acid according to the present invention or an expression vector according to the present invention for use in medicine.

The present invention also relates to antibodies as described herein according to the present invention that are specific for a peptide according to a sequence selected from SEQ ID No. 1 to SEQ ID No. 49, SEQ ID No. 71, and SEQ ID No. 74 to 129, and methods of making these.

The present invention further relates to T-cell receptors (TCR), in particular soluble TCR (sTCRs) targeting, in particularly specifically targeting, a peptide according to a sequence selected from SEQ ID No. 1 to SEQ ID No. 49, SEQ ID No. 71, and SEQ ID No. 74 to 129 and/or complexes of said peptides according to the present invention with MHC, and methods of making these TCRs.

The present invention further relates to a host cell comprising a nucleic acid according to the present invention or an expression vector as described before. The present invention further relates to the host cell according to the present invention that is an antigen presenting cell. The present invention further relates to the host cell according to the present invention wherein the antigen presenting cell is a dendritic cell.

The present invention further relates to a method of producing a peptide according to the present invention, the method comprising culturing the host cell according to the present invention, and isolating the peptide from the host cell or its culture medium.

The present invention further relates to an in vitro method for producing activated cytotoxic T lymphocytes (CTL), the method comprising contacting in vitro CTL with antigen loaded human class I or II WIC molecules expressed on the surface of a suitable antigen-presenting cell for a period of time sufficient to activate said CTL in an antigen specific manner, wherein said antigen is any peptide according to the present invention.

The present invention further relates to the method according to the present invention, wherein the antigen is loaded onto class I or II WIC molecules expressed on the surface of a suitable antigen-presenting cell by contacting a sufficient amount of the antigen with an antigen-presenting cell. The present invention further relates to the method according to the present invention, wherein said antigen-presenting cell comprises an expression vector capable of expressing said peptide containing at least one sequence selected from SEQ ID No. 1 to SEQ ID No. 49, SEQ ID No. 71, and SEQ ID No. 74 to 129, or a variant amino acid sequence thereof.

The present invention further relates to activated cytotoxic T lymphocytes (CTL) as described herein, produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention (i.e. at least one sequence selected from SEQ ID No. 1 to SEQ ID No. 49, SEQ ID No. 71, and SEQ ID No. 74 to 129), the method comprising administering to the patient an effective number of cytotoxic T lymphocytes (CTL) as according to the present invention.

The present invention further relates to the use of any peptide according to the present invention, the nucleic acid according to the present invention, the expression vector according to the present invention, the host cell or cell according to the present invention, or the activated cytotoxic T lymphocyte according to the present invention as a medicament or in the manufacture of a medicament. The present invention further relates to the use according to the present invention, wherein said medicament is a vaccine.

The present invention further relates to particular marker proteins and biomarkers based on the peptides according to the present invention that can be used in the diagnosis and/or prognosis of haematological malignancies, in particular chronic lymphoid leukemia (CLL) cells.

Further, the present invention relates to the use of these novel targets for cancer treatment.

Further, the present invention relates to a method for producing a personalized anti-cancer vaccine comprising at least one peptide according to the present invention, a nucleic acid according to the present invention, an expression vector according to the present invention, a host cell or cell according to the present invention, or an activated cytotoxic T lymphocyte according to the present invention which has been designed and formulated for use in an individual patient, wherein said design comprises the use of a database ("warehouse") of pre-selected and/or pre-screened tumour associated peptides that are patient- and/or patient-group and/or cancer-specific.

The peptides of the present invention can be used to generate, produce and develop specific antibodies against the WIC/peptide complexes of the present invention (i.e. comprising at least one sequence selected from SEQ ID No. 1 to SEQ ID No. 49, SEQ ID No. 71, and SEQ ID No. 74 to 129). These antibodies can be used for therapy, targeting toxins or radioactive substances to a diseased tissue, e.g. a tumour. Another use of these antibodies can be targeting radionuclides to the diseased tissue for imaging purposes such as PET.

Therefore, it is a further aspect of the invention to provide a method for producing a recombinant antibody specifically binding to a human major histocompatibility complex (MHC) class I or II being complexed with an HLA-restricted antigen (i.e. comprising at least one sequence selected from SEQ ID No. 1 to SEQ ID No. 49, SEQ ID No. 71, and SEQ ID No. 74 to 129), the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bispecific antibody and/or a chimeric antibody.

Yet another aspect of the present invention then relates to a method of producing an antibody that specifically binds to a human major histocompatibility complex (MHC) class I or II being complexed with an HLA-restricted antigen (i.e. comprising at at least one sequence selected from SEQ ID No. 1 to SEQ ID No. 49, SEQ ID No. 71, and SEQ ID No. 74 to 129), the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools.

It is a further aspect of the invention to provide a method for producing a soluble T-cell receptor recognizing a specific peptide-MHC complex according to the invention. Such soluble T-cell receptors can be generated from specific T-cell clones, and their affinity can be increased by mutagenesis targeting the complementarity-determining regions.

Stimulation of an immune response is dependent upon the presence of antigens recognised as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognising and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognise Class I molecules of the major histocompatibility complex (MHC)-bearing peptides of usually 8 to 10 amino acid residues derived from proteins or defect ribosomal products (DRIPS) located in the cytosol, play an important role in this response. The WIC-molecules of the human are also designated as human leukocyte-antigens (HLA).

There are two classes of WIC-molecules: WIC class I molecules that can be found on most cells having a nucleus. MHC molecules are composed of an alpha heavy chain and beta-2-microglobulin (WIC class I receptors) or an alpha and a beta chain (WIC class II receptors), respectively. Their three-dimensional conformation results in a binding groove, which is used for non-covalent interaction with peptides. WIC class I present peptides that result from proteolytic cleavage of predominantly endogenous proteins, DRIPs and larger peptides. WIC class II molecules can be found predominantly on professional antigen presenting cells (APCs), and primarily present peptides of exogenous or transmembrane proteins that are taken up by APCs during the course of endocytosis, and are subsequently processed. Complexes of peptide and WIC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells (Wang and Livingstone, 2003; Sun and Bevan, 2003; Shedlock and Shen, 2003). The identification of CD4-positive T-cell epitopes derived from tumor associated antigens (TAA) is of great importance for the development of pharmaceutical products for triggering anti-tumor immune responses (Kobayashi et al., 2002; Qin et al., 2003; Gnjatic et al., 2003). At the tumor site, T helper cells, support a CTL friendly cytokine milieu (Qin and Blankenstein, 2000; Mortara et al., 2006) and attract effector cells, e.g. CTLs, NK cells, macrophages, (Marzo et al., 2000; Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel et al., 2006).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ).

Additionally, it was shown that CD4-positive T cells recognizing peptides from tumor-associated antigens presented by HLA class II molecules can counteract tumor progression via the induction of antibody (Ab) responses (Kennedy et al., 2003).

In contrast to tumor-associated peptides binding to HLA class I molecules, only a small number of class II ligands of tumor associated antigens (TAA) have been described to date.

Since the constitutive expression of HLA class II molecules is usually limited to cells of the immune system, the possibility of isolating class II peptides directly from primary tumors was not considered possible. However, Dengjel et al. were recently successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines.

The present invention also relates to a very useful MHC class II peptide (see SEQ ID NO 71). This peptide is useful against glioblastoma and other cancers over-expressing and/ or over—presenting BCAN.

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not or in comparably small amounts by normal healthy tissues or in another embodiment the peptide should be over-presented by tumor cells as compared to normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, downstream targets of the proteins directly causative for a transformation may be upregulated and thus may be indirectly tumor-associated. Such indirect tumor-associated antigens may also be targets of a vaccination approach. In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of TCRs and antibodies according to the invention the immunogenicity of the underlying peptides is secondary. For TCRs and antibodies according to the invention the presentation is the determining factor.

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Uses against additional cancers are disclosed in the following description of the underlying polypeptides of the peptides according to the invention.

Cysteine and Glycine-Rich Protein 2 (CSRP2)

CSRP2 is a member of the CSRP family of genes, encoding a group of LEVI domain proteins, which may be involved in regulatory processes important for development and cellular differentiation. CSRP2 was mapped to chromosome subband 12q21.1, a region frequently affected by deletion or breakage events in various tumor types (Weiskirchen et al., 1997). Expression of CSRP2 is significantly elevated in moderately differentiated tumor of hepatocellular carcinoma (HCC). CSRP2 is likely to be associated with dedifferentiation of HCC (Midorikawa et al., 2002).

Solute Carrier Family 10 (Sodium/Bile Acid Cotransporter Family), Member 4 (SLC10A4)

The gene SLC10A4 encodes a recently described carrier protein present in pre-synaptic terminals of cholinergic and monoaminergic neurons (Zelano et al., 2013). SLC10A4 mRNA is ubiquitously expressed in human tissues with the highest levels of mRNA expression in brain, placenta, and liver. In SLC10A4-transfected CHO cells, immunoblotting analysis and immunofluorescence staining demonstrated a 49-kDa protein that is expressed at the plasma membrane and intracellular compartments (Splinter et al., 2006). SLC10A4 may participate in vesicular storage or exocytosis of neurotransmitters or mastocyte mediators (Claro da et al., 2013).

ELOVL Fatty Acid Elongase 2 (ELOVL2)

ELOVL2 is a member of the mammalian microsomal ELOVL fatty acid enzyme family, which is involved in oxidative stress induction and lipid biosynthesis and is responsible for the elongation of very long-chain fatty acids including polyunsaturated fatty acids (PUFAs) required for various cellular functions in mammals (Aslibekyan et al., 2012; Zadravec et al., 2011). Specifically, ELOVL2 is an essential enzyme for the formation of very-long PUFA in testis (Casado et al., 2013). A lack of ELOVL2 has been shown to be associated with a complete arrest of spermatogenesis, with seminiferous tubules displaying only spermatogonia and primary spermatocytes without further germinal cells (Zadravec et al., 2011). ELOVL2 shows a progressive increase in methylation that begins since the very first stage of life and appears to be a very promising biomarker of aging (Garagnani et al., 2012). Its upregulation has been reported from hepatocellular carcinoma (Zekri et al., 2012).

Metastasis Suppressor 1-Like (MTSS1L)

Radial glias play key roles in neuronal migration, axon guidance, and neurogenesis during development of the central nervous system. A recent study identified MTSS1L (alias ABBA) as a novel regulator of actin and plasma membrane dynamics in radial glial cells. Interestingly, ABBA localizes to the interface between the plasma membrane and the actin cytoskeleton in radial-glia-like C6-R cells, and its depletion results in defects in plasma membrane dynamics and process extension (Saarikangas et al., 2008). Overexpression of GFP-tagged Abba in murine fibroblasts (NIH3T3 cells) potentiated PDGF-mediated formation of membrane ruffles and lamellipodia. Some data indicates that the interaction between full-length Abba and Rac1 is implicated in membrane deformation (Zheng et al., 2010).

Protein Tyrosine Phosphatase, Receptor-Type, Z Polypeptide 1 (PTPRZ1)

PTPRZ1 (protein tyrosine phosphatase, receptor-type, Z polypeptide 1) is a member of the receptor type protein tyrosine phosphatase family and encodes a single-pass type I membrane protein with two cytoplasmic tyrosine-protein phosphatase domains, an alpha-carbonic anhydrase domain and a fibronectin type-III domain. PTPRZ1 is expressed primarily in the nervous system and is synthesized by glial progenitors, and astrocytes (Canoll et al., 1993; Milev et al., 1994; Engel et al., 1996; Meyer-Puttlitz et al., 1996; Sakurai et al., 1996). PTPRZ1 is over-expressed in GBM and is thought to be involved in GBM cell motility (Muller et al., 2003; Ulbricht et al., 2003; Lu et al., 2005; Wellstein, 2012). Furthermore, PTRPZ1 is frequently amplified at the genomic DNA level in glioblastoma (Mulholland et al., 2006). In astrocytomas, the increased expression level of PTPRZ1 also correlates with a poor clinical prognosis (Ulbricht et al., 2003). Antagonization of PTPRZ1 expression by siRNA transfection inhibits glioma growth in vitro and in vivo (Ulbricht et al., 2006).

Kinesin Family Member 1A (KIF1A)

KIF1A is a monomeric motor protein of the kinesin 3 family. It is regarded as brain-specific protein, whose basic function concerns the fast anterograde axonal transport of synaptic vesicles in neurons. KIF1A is vital for neuronal function and survival (Hirokawa and Noda, 2008). Aberrant hypermethylation of KIF1A is a frequent event in different types of cancer, such as head and neck squamous cell carcinoma (Demokan et al., 2010; Kaur et al., 2010; Loyo et al., 2011; Pattani et al., 2010; Guerrero-Preston et al., 2011), lung cancer (Loyo et al., 2011), thyroid cancer and breast cancer (Brait et al., 2012; Ostrow et al., 2009). KIF1A was found as one of eight markers for minimal residual disease (MRD) and abundantly expressed in stage IV neuroblastoma tumors and had low to no detection in normal bone marrow/blood samples. In stage IV patients, expression levels of KIF1A in bone marrow were highly prognostic for progression-free and overall survival (Cheung et al., 2008). Concerning minimal residual disease in neuroblastoma, KIF1A was one of 11 genes, whose over-expression in tumor-initiating cells correlates with MRD (Hartomo et al., 2013).

Protocadherin Gamma Subfamily C, 5 (PCDHGC5)

Protocadherin γ-C5 (PCDHGC5) is one of the 22 members of the PCDHG family. The protocadherins (PCDH) are a subgroup of cadherins, which are predominantly expressed in the central nervous system (Kallenbach et al., 2003; Hirayama and Yagi, 2006). The gamma gene cluster is organized similar to an immunoglobulin cluster: 22 variable exons, which encode the ectodomain (cadherin repeats, transmembrane and proximal intracellular domain), and 3 constant exons, which encode the common distal moiety of the cytoplasmic domain, are joined by RNA splicing (Morishita and Yagi, 2007; Wang et al., 2002). PCDHs are involved in developmental tissue morphogenesis and in synapse formation and modulation (Frank and Kemler, 2002) and the production of cerebrospinal fluid in the postnatal brain (Lobas et al., 2012). It was shown that several PCDHGs, such as PCDHGC5, interact with the intracellular adaptor protein PDCD10 (programmed cell death 10), which mediates apoptosis in neurons (Lin et al., 2010a).

Glutamate Receptor, Ionotropic, Kainate 3 (GRIK3)

Glutamate receptors are the predominant excitatory neurotransmitter receptors in the mammalian brain and are activated in a variety of normal neurophysiologic processes. GRIK3 (GluR7) belongs to the kainate family of glutamate receptors, which are composed of four subunits and function as ligand-activated ion channels (Pinheiro et al., 2007). GluR5-7 subunits are expressed in human glioneuronal tumors (Aronica et al., 2001). In glioblastomas GluR7 was expressed at levels higher than in human brain (Brocke et al., 2010). GluR7 was also found to be differentially expressed in several human tumor cell lines (rhabdomyosarcoma/medulloblastoma, neuroblastoma, thyroid carcinoma, lung carcinoma, astrocytoma, multiple myeloma, glioma, lung carcinoma, colon adenocarcinoma, T cell leukemia cells, breast carcinoma and colon adenocarcinoma) (Stepulak et al., 2009).

Seizure Related 6 Homolog (Mouse)-Like (SEZ6L)

The SEZ6L cDNA contains a 3,072-bp open reading frame encoding a 1,024-amino acid transmembrane protein with multiple domains involved in protein-protein interaction and signal transduction. SEZ6L was abundantly expressed in the brain, and also expressed in a variety of human tissues, including lung epithelial cells. Therefore, SEZ6L protein is considered to be a transmembrane protein functioning as an intracellular signal transducer via protein-protein interactions in a variety of human cells (Nishioka et al., 2000). Genetic variants in the SEZ6L gene are associated with bipolar disorder I in female patients (Xu et al., 2013). A polymorphic variant of SEZ6L might be linked with an increased risk of lung cancer (Raji et al., 2010; Gorlov et al., 2007). Methylation status of SEZ6L might also be a marker of gastric carcinoma (Kang et al., 2008). A study conducted by Suzuki at al. (2002) suggests that SEZ6L gene may also influence development and progression of colorectal cancer. The authors found that SEZ6L was one of the few genes highly hypermethylated in primary colorectal tumors (Suzuki et al., 2002).

Ankyrin Repeat Domain 40 (ANKRD40)

ANKRD40 is a member of the ankyrin repeat protein family. ANKRD40 is localized on chromosome 17q21.33. The function of ANKRD40 is unknown. However the ankyrin repeat is a 33-residue motif in proteins consisting of two alpha helices separated by loops, first discovered in signaling proteins in yeast Cdc10 and *Drosophila* Notch (Breeden and Nasmyth, 1987). Domains consisting of ankyrin repeats mediate protein-protein interactions and are among the most common structural motifs in known proteins (Mosavi et al., 2004). Ankyrin-repeat proteins have been associated with a number of human diseases. These proteins include the cell cycle inhibitor p16, which is associated with cancer, and the Notch protein (a key component of cell signalling pathways) which can cause the neurological disorder CADASIL when the repeat domain is disrupted by mutations. (Mosavi et al., 2004)

Neuroligin 4, Y-Linked (NLGN4Y)

Neuroligins, such as NLGN4Y, are cell adhesion molecules present at the postsynaptic side of the synapse and may be essential for the formation of functional synapses (Jamain et al., 2003). Skaletsky et al. (2003) determined that NLGN4Y, the Y-chromosomal homolog of NLGN4, was expressed in fetal and adult brain, prostate, and testis (Skaletsky et al., 2003). Some data suggested that sequence variants in NLGN4Y might be associated with autism or mental retardation (Ylisaukko-oja et al., 2005; Yan et al., 2008).

Potassium Inwardly-Rectifying Channel, Subfamily J, Member 10 (KCNJ10)

KCNJ10 encodes one of 16 inward rectifier-type potassium (Kir) channel subunits, which are grouped in 7 subfamilies by homology. KCNJ10 is the major pore forming subunit in glial cells and most data suggest homomeric channels. Mutations in KCNJ10 have been associated with seizure susceptibility of common idiopathic generalized epilepsy syndromes (Olsen and Sontheimer, 2008). In normal brain, KCNJ10 was detected by IHC around microvessels, in the glia limitans/pia, and in occasional neurons (Saadoun et al., 2003). In various human brain tumors (low- and high-grade astrocytomas and oligodendrogliomas), KCNJ10 is mislocalized as compared to healthy tissue, which may impair the buffering capacity of glial cells and thereby to water influx, leading to water influx (cytotoxic edema) (Warth et al., 2005). KCNJ10 was also upregulated in astrocytes in damaged brain (carcinoma, oligodendroglioma, and glioblastoma cells). It was hypothesized that this is a response to the up-regulation of Aquaporin 4 (Saadoun et al., 2003). KCNJ10 may be used as a new biomarker and as therapeutic target with astrocytoma (Tan et al., 2008).

Brevican (BCAN)

Brevican (BCAN) is a brain-specific member of the lectican family of chondroitin sulfate proteoglycans. Two BCAN isoforms have been reported: a full-length isoform that is secreted into the extracellular matrix and a shorter isoform with a sequence that predicts a glycophosphatidylinositol (GPI) anchor (Gary et al., 2000). BCAN shows dramatic upregulation in gliomas, where an approximately seven-fold increase in expression over normal levels can be detected (Gary et al., 2000; Gary et al., 1998). BCAN has also been validated as upregulated in the biologically more aggressive grade II oligodendrogliomas (Rostomily et al., 2010). Furthermore, BCAN has been described as selectively over-expressed in a type of GBM cancer stem cells which show the highest pluripotency and tumorigenicity in vivo (Gunther et al., 2008). Clinically, BCAN upregulation correlates with poor survival of patients with high-grade gliomas (Liang et al., 2005).

Membrane Associated Guanylate Kinase, WW and PDZ Domain Containing 2 (MAGI2)

MAGI2 has been localized to chromosome 7q21, a region that is deleted in uterine leiomyomas, prostate cancer and glioblastoma (Cui et al., 1998; Cunningham et al., 1996; Ishwad et al., 1995; Kim et al., 1995). MAGI2 is brain-specific (Shoji et al., 2000; Wood et al., 1998; Yamada et al., 2003) and has been shown to interact with NMDA receptors at excitatory synapses (Hirao et al., 1998). MAGI2 is involved in recruitment of neurotransmitter receptors such as AMPA- and NMDA-type glutamate receptors (Koide et al., 2012). MAGI2 interacts with several different ligands in brain, including PTEN (Deng et al., 2006). Binding of the tumor suppressor PTEN to the PDZ-2 domain from MAGI2 increased PTEN protein stability (Valiente et al., 2005). MAGI2 overexpression enhances the sensitivity of cancer cells harboring ectopic PTEN to STS-induced apoptosis (Li et al., 2013b). Significant associations of MAGI2 with the risk for developing Alzheimer's disease have been found (Kohannim et al., 2012).

Scavenger Receptor Class A, Member 3 (SCARA3)

Using predicted exonic sequences from a cosmid mapping to chromosome 8p21, Han et al. (1998) screened a human fetal brain library and isolated a novel macrophage scavenger receptor-like gene, SCARA3, which they called CSR1 (Han et al., 1998). CSR1 is located at 8p21-22, a locus that is frequently deleted in several human malignancies, including prostate cancer, head and neck squamous cell carcinoma and lung cancer (Coon et al., 2004; Gallucci et al., 2006; Kurimoto et al., 2001). High SCARA3 levels in primary ovarian carcinomas and its up-regulation along disease progression from diagnosis to recurrence, suggested a role in ovarian cancer biology (Bock et al., 2012). One study suggested that CSR1 (SCARA3) protects cells from mutational damage of oxidative-free radicals by increasing their metabolism (Han et al., 1998). Furthermore, CSR1, a newly characterized tumor-suppressor gene, undergoes hypermethylation in over 30% of prostate cancers and induce cell death through a novel mechanism by hijacking a critical RNA processing enzyme (Zhu et al., 2009).

Glutamate Receptor, Ionotropic, AMPA 4 (GRIA4)

GRIA4 (also called GLUR4) belongs to a family of AMPA (alpha-amino-3-hydroxy-5-methyl-4-isoxazole propionate)-sensitive glutamate receptors, and is subject to RNA editing (AGA→GGA; R→G). The GluR4 subunit (GRIA4) may play a pivotal role in regulating channel properties as well as trafficking of AMPA receptors in the adult human brain (Kawahara et al., 2004). Emerging evidence supports a role for glutamate in the biology of cancer. Knockdown of GLUR4 influenced the expression and function of genes involved in invasion and metastasis, tumor suppressor genes, oncogenes and adhesion genes (Luksch et al., 2011). GRIA4 has crucial roles in growth of glioblastoma. Blockage of Ca(2+)-permeable receptors containing GRIA4 subunits may be a useful therapeutic strategy for the prevention of glioblastoma invasion (Ishiuchi et al., 2002). Glioblastoma cells express Ca(2+)-permeable AMPARs assembled from the GluR1 and/or GluR4 subunits. The overexpression of Ca(2+)-permeable AMPA receptors facilitated migration and proliferation of the tumor cells (Ishiuchi, 2009).

Clusterin (CLU)

Clusterin is an enigmatic heterodimeric glycoprotein with a nearly ubiquitous tissue distribution. It plays important roles in various pathophysiological processes, including tissue remodeling, reproduction, lipid transport, complement regulation and apoptosis (Li et al., 2010; Niu et al., 2012). The product of the CLU gene promotes or inhibits tumorigenesis in a context-dependent manner. It has been hypothesized that different CLU isoforms have different and even opposing biological functions (Chaiwatanasirikul and Sala, 2011). The pro-apoptotic CLU appears to be a nuclear isoform (nuclear clusterin; nCLU), and the secretory CLU (sCLU) is thought to be anti-apoptotic (Kim et al., 2012b). As a pleiotropic molecular chaperone, Clusterin confers survival and proliferative advantage to cancer cells (Shiota et al., 2012) and as a membrane-stabilizing protein it appears to be involved in limiting the autophagic lysis of epithelial cells during apoptosis (Bruchovsky et al., 1996). Overexpression of sCLU was detected in primary gastric cancer (Bi et al., 2010), ovarian cancer (Yang et al., 2009), breast cancer (Niu et al., 2012), lung cancer (Panico et al., 2013), hepatocellular carcinoma (Chen et al., 2012a) and was associated with poor survival and metastasis.

Ceramide Synthase 1 (CERS1)

Ceramide, a bioactive sphingolipid, is now at the forefront of cancer research. Classically, ceramide is thought to induce death, growth inhibition, and senescence in cancer cells (Saddoughi and Ogretmen, 2013). Ceramide synthase 1 (CerS1) acylates sphinganine (dihydrosphingosine) to form dihydroceramide and sphingosine to form ceramide (Futerman and Riezman, 2005). Jiang et al. (1998) analyzed the human tissue expression of CerS1 by Northern blotting and found the highest expression in brain, skeletal muscle and testis (Jiang et al., 1998). C(18)-pyridinium ceramide treatment or endogenous C(18)-ceramide generation by CerS1 expression mediates autophagic cell death, independent of apoptosis in human cancer cells (Sentelle et al., 2012). Several lines of evidence point to a role for CerS1 in regulating the sensitivity to cancer chemotherapeutic agents and radiation (Min et al., 2007; Separovic et al., 2012). Further experiments demonstrated a growth-inhibiting and pro-apoptotic effect of overexpression of CerS1 and production of C18:0-ceramide in HNSCC cells (Senkal et al., 2007).

G Protein-Coupled Receptor 98 (GPR98)

G protein-coupled receptors (GPCRs) are the largest superfamily of related proteins. The GPR98 gene encodes a member of the G-protein coupled receptor superfamily. The encoded protein contains a 7-transmembrane receptor domain, binds calcium and is expressed in the central nervous system. By linkage analysis of YAC clones, FISH, and radiation hybrid analysis, Nikkila et al. (2000) mapped the GPR98 gene to chromosome 5q14.1 (Nikkila et al., 2000). By genomic sequence analysis, McMillan et al. (2002) determined that the GPR98 gene contains 90 exons and spans at least 600 kb (McMillan et al., 2002). Mutations in the large GPR98 gene are associated with Usher syndrome type 2C (Ebermann et al., 2009) and familial febrile seizures (Nakayama et al., 2000). In a study, GPR98 was associated with glioblastoma multiforme patient survival (Sadeque et al., 2012).

Glycogenin 2 (GYG2)

Glycogenin is a self-glucosylating protein involved in the initiation phase of glycogen biosynthesis. It acts as a primer, by polymerizing the first few glucose molecules, after which other enzymes take over. Cloning of the human glycogenin-2 gene GYG2, has revealed the presence of 11 exons and a gene of more than 46 kb in size (Zhai et al., 2000). By FISH, Mu and Roach (1998) mapped the GYG2 gene to Xp22.3. The level of glycogenin-2 can determine glycogen accumulation and hence has the potential to control glycogen synthesis (Mu and Roach, 1998).

Carnitine Palmitoyltransferase 1C (CPT1C)

The CPT1C gene encodes a member of the carnitine/choline acetyltransferase family (Jogl and Tong, 2003). The encoded protein regulates the beta-oxidation and transport of long-chain fatty acids into mitochondria, and may play a role in the regulation of feeding behavior and whole-body energy homeostasis (Bonnefont et al., 2004), (Wolfgang et al., 2006). CPT1C is a newly identified and poorly understood brain-specific CPT1 homologue (Reamy and Wolfgang, 2011). Recent preclinical studies suggest that a gene usually expressed only in the brain, CPT1C, promotes cancer cell survival and tumor growth. Because of CPT1C's normally brain-restricted expression and the inability of most drugs to pass the blood-brain barrier, CPT1C may be an ideal candidate for specific small-molecule inhibition (Reilly and Mak, 2012).

Solute Carrier Family 35, Member E1 (SLC35E1)

The solute carrier family SLC35 consists of at least 17 molecular species in humans. The family members so far characterized encode nucleotide sugar transporters localizing at the Golgi apparatus and/or the endoplasmic reticulum (ER) (Ishida and Kawakita, 2004). SLC35E1 was mapped on chromosome 19p13.11 (Gerhard et al., 2004). For patients with locally advanced rectal cancer a gene expression signature of 42 genes, which includes SLC35E1, might discriminate responders from non-responders. Thus, pretherapeutic prediction of response of rectal carcinomas to neoadjuvant chemoradiotherapy is feasible, and may represent a new valuable and practical tool of therapeutic stratification (Rimkus et al., 2008).

Acid-Sensing (Proton-Gated) Ion Channel Family Member 4 (ASIC4)

ASIC4 belongs to the super-gene family of amiloride-sensitive sodium channels. So far five different ASICs have been cloned from mammalian tissues. ASIC4 is expressed throughout the brain, in spinal cord, and inner ear (Grunder et al., 2000). ASICs have been implicated with synaptic transmission, pain perception as well as mechanoperception. ASIC4 shows expression throughout the central nervous system with strongest expression in pituitary gland. ASIC4 is inactive by itself and its function is unknown. Mutations in ion channel subunits, which are homologues of ASICs lead to neurodegeneration in *Caenorhabditis elegans*. It has, therefore, been speculated that similar mutations in ASICs may be responsible for neurodegeneration in humans (Grunder et al., 2001). Furthermore, in bone ASIC4 expression was always very low abundant (Jahr et al., 2005).

Collagen, Type XX, Alpha 1 (COL20A1)

COL20A1 is a collagen gene. The COL20A1 gene was mapped to the chromosome 20q13.33 (Deloukas et al., 2001). The function of this gene is still unknown. Recently, a study identified subsets of the concurrent genes associated with breast cancer recurrence, metastases, or mortality in survival analyses. A 16-gene signature, including COL20A1, was established for disease-free survival in Han Chinese breast cancer patients (Huang et al., 2013a).

Epidermal Growth Factor Receptor (EGFR)

EGFR is the proto-oncogene of erbB. EGFR is involved in the activation of a number of pathways that regulate the phenotype of progenitor cells. Activated EGFR tyrosine kinase activity enhances neural stem cell migration, proliferation and survival. Overexpression of EGFR can augment cell growth because of increased formation of active ligand:receptor complexes. Gene amplification is the mechanism underlying overexpression of EGF receptors in GBM tumors (Thompson and Gill, 1985). As EGFR signaling is also known to play a role in glioblastoma, it can be concluded that glioblastoma derives from a cancer stem cell and that EGFR signals are commonly altered in these precursor cells (yuso-Sacido et al., 2006). A range of potential therapies that target EGFR or its mutant constitutively active form, ΔEGFR, including tyrosine kinase inhibitors (TKIs), monoclonal antibodies, vaccines, and RNA-based agents, are currently in development or in clinical trials for the treatment of GBM. Data from experimental studies evaluating these therapies have been very promising; however, their efficacy in the clinic has so far been limited by both upfront and acquired drug resistance. Many studies indicate that a multiple target approach will provide a more favorable future for these types of targeted therapies in GBM (Taylor et al., 2012).

Janus Kinase and Microtubule Interacting Protein 2 (JAKMIP2)/Janus Kinase and Microtubule Interacting Protein 3 (JAKMIP3)

JAKMIP2 has been identified in 2012 (Cruz-Garcia et al., 2012) as a member of the family of long α-helical coiled-coil proteins or golgins, which have diverse biological functions as motor proteins, membrane tethering and vesicle transport proteins (Rose and Meier, 2004; Rose et al., 2005). JAKMIP2 is a peripheral membrane protein, which distributes across the Golgi apparatus and post-Golgi carriers in neuroendocrine cells and may act as a negative modulator of the regulated trafficking of secretory cargo in neuroendocrine cells (Cruz-Garcia et al., 2012). JAKMIP3 was identified as a paralogue of JAKMIP2 (Cruz-Garcia et al., 2012) and a member of the family of long α-helical coiled-coil proteins or golgins, which have diverse biological functions as motor proteins, membrane tethering and vesicle transport proteins (Rose and Meier, 2004; Rose et al., 2005). JAKMIP3 displays a long coiled-coil region highly similar to that of JAKMPI2 and an identical C-terminal transmembrane domain. As JAKMIP2, it is predominantly expressed in tissues containing cells with regulated secretory pathway, that is, endocrine and neural tissues. Both are peripheral membrane proteins are located to the Golgi apparatus and post-Golgi carriers and may act as negative modulators of the regulated trafficking of secretory cargo in neuroendocrine cells (Cruz-Garcia et al., 2007; Cruz-Garcia et al., 2012; Malagon et al., 2009).

Wntless Homolog (*Drosophila*) (WLS)/Mesoderm Induction Early Response 1 Homolog (*Xenopus laevis*) (MIER1)

WLS is a transmembrane sorting receptor, which recycles between the trans-Golgi network and the cell surface. WLS is required for efficient secretion of Wnt signaling proteins (Gasnereau et al., 2011). Loss of WLS in the follicular epithelium resulted in a profound hair cycle arrest (Myung et al., 2013). WLS functions as a negative regulator of melanoma proliferation and spontaneous metastasis by activating WNT/β-catenin signaling (Yang et al., 2012b). WLS is overexpressed in astrocytic glioma. Depletion of WLS in glioma and glioma-derived stem-like cells led to decreased cell proliferation and apoptosis. WLS silencing in glioma cells reduced cell migration and the capacity to form tumors in vivo. WLS is an essential regulator of glioma tumorigenesis (Augustin et al., 2012). MIER1 is a fibroblast growth factor (FGF)-activated transcriptional regulator (Paterno et al., 1997). Alternatively spliced transcript variants encode multiple isoforms, some of which lack a C-terminal nuclear localization signal (Paterno et al., 2002). The oestrogen receptor-alpha (ER alpha) plays a key role in breast development and tumorigenesis and inhibiting its activity remains a prime strategy in the treatment of ER alpha-positive breast cancers. Differential splicing alters subcellular localization of the alpha but not beta isoform of the MIER1 transcriptional regulator in breast cancer cells (Clements et al., 2012). It was suggested that loss of nuclear MI-ER1 alpha might contribute to the development of invasive breast carcinoma (McCarthy et al., 2008).

Insulin Receptor Substrate 2 (IRS2) Insulin-like growth factors (IGFs) are thought to promote tumor progression and metastasis in part by stimulating cell migration. The IRS proteins play a central role in mediating the signals from the IR/IGF-1R that control tumor cell metabolism (Shaw, 2011). Insulin receptor substrate-1 (IRS-1) and IRS-2 are multisite docking proteins positioned immediately downstream from the type IIGF and insulin receptors. IRS-2 is ubiquitously expressed and is the primary mediator of insulin-dependent mitogenesis and regulation of glucose metabolism in most cell types (White, 2002). IRS-2 is also ubiquitously expressed in many types of cancer (Mardilovich et al., 2009). IRS-2 but not IRS-1 has been reported to be involved in the migratory response of breast cancer cells to IGFs (de Blaquiere et al., 2009). IRS-2 is often associated with tumor motility and invasion (Mardilovich et al., 2009). Some data show that IRS2 is expressed in the kidney epithelium. The specific up-regulation of IRS2 in the kidney tubules of diabetic nephropathy (DN) patients indicates a novel role for IRS2 as a marker and/or mediator of human DN progression (Hookham et al., 2013).

N-Acetyltransferase 8-Like (GCN5-Related, Putative) (NAT8L)

NAT8L (N-acetyltransferase 8-like) was recently identified as aspartate N-acetyltransferase, the enzyme that makes N-acetylaspartate, the second most abundant metabolite in mammalian brain. The NAT8L protein is a neuron-specific protein and is the N-acetylaspartate (NAA) biosynthetic enzyme, catalyzing the NAA synthesis from L-aspartate and acetyl-CoA (Wiame et al., 2010), (Ariyannur et al., 2010). NAT8L, a neuron-specific protein, is mutated in primary NAA deficiency (hypoacetylaspartia) (Wiame et al., 2010).

Tenascin C (TNC)

Tenascin-C(TNC) is an extracellular matrix protein that is highly up-regulated in processes that are closely associated with elevated migratory activity such as embryonic development (Bartsch et al., 1992), wound healing (Mackie et al., 1988) and neoplastic processes (Chiquet-Ehrismann, 1993; Chiquet-Ehrismann and Chiquet, 2003). Furthermore, TNC is over-expressed in tumor vessels that have a high proliferative index, which indicates that TNC is involved in neoplastic angiogenesis (Kim et al., 2000). In normal human brain, the expression of TNC is detected only rarely whereas it is expressed at high levels in malignant gliomas (Bourdon et al., 1983). Recently, TNC was identified as target gene of Notch signalling in malignant gliomas as well as in GBM cell lines (Sivasankaran et al., 2009). Overexpression of TNC has further been reported from colon cancer (De et al., 2013), adenoid cystic carcinoma, where it has been associated with worst prognosis (Siu et al., 2012), juvenile nasopharyngeal angiofibroma, where it possibly promotes angiogenesis (Renkonen et al., 2012), advanced melanoma (Fukunaga-Kalabis et al., 2010), pancreatic cancer, where it plays a role in proliferation, migration and metastasis (Paron et al., 2011).

Microtubule-Associated Protein 1B (MAP1B)

The MAP1B gene encodes a protein that belongs to the microtubule-associated protein family. The proteins of this family are thought to be involved in microtubule assembly, which is an essential step in neurogenesis. MAP1B regulates tyrosination of alpha-tubulin in neuronal microtubules which may be important for general processes involved in nervous system development such as axonal guidance and neuronal migration (Utreras et al., 2008). MAP 1B was strongly and diffusely expressed in neuroblastomas, it was also focally or multifocally expressed in rhabdomyosarcomas and in stroma of Wilms tumors (Willoughby et al., 2008). Further, microtubule-associated protein 1B light chain (MAP1B-LC1) negatively regulates the activity of tumor suppressor p53 in neuroblastoma cells (Lee et al., 2008a).

Neurocan (NCAN)

Neurocan is a nervous system-specific CSPG, which belongs to the aggrecan/versican proteoglycan family. It is an important component of the extracellular matrix of the brain especially during development and is down-regulated in most areas of the brain during maturation (Rauch, 2004; Zimmermann et al., 1994). NCAN has several binding partners including the ECM components tenascin C (Grumet et al., 1994), hyaluronan (Melrose et al., 1996; Zhang et al., 2004) and the membrane proteins L1CAM (Grumet et al., 1994) and heparin sulfate proteoglycans (Akita et al., 2004). Several studies consider a correlation of NCAN with tumor invasiveness. In a comparison of locally infiltrative glioblastoma and well-confined intracerebral metastasis of lung adenocarcinoma, NCAN showed a higher expression on mRNA and protein (IHC) level in glioblastoma (Klekner et al., 2010; Varga et al., 2010). NCAN and 3 other genes were found to correlate with the invasive phenotype of low-grade astrocytoma (Varga et al., 2012).

Adenosine A3 Receptor (ADORA3)

ADORA3 encodes a protein that belongs to the family of adenosine receptors, which are G-protein-coupled receptors that are involved in a variety of intracellular signaling pathways and physiological functions. It has been accepted that A3ARs (ADORA3) are highly expressed in tumor cells showing an important role in the development of cancer (Fishman et al., 2002), (Merighi et al., 2003), (Gessi et al., 2008), (Bar-Yehuda et al., 2008). For the human A3AR, potent and selective agonists as well as selective A3AR antagonists have been identified. Cl-IB-MECA, an agonist of A3AR (ADORA3), has been reported to induce cell death in various cancer cells. Cl-IB-MECA induce a caspase-dependent cell death through suppression of ERK and Akt mediated by an increase in intracellular Ca(2+) and ROS generation in human glioma cells (Kim et al., 2012a) and in human bladder cancer cells (Kim et al., 2010). The A3AR agonist, IB-MECA, inhibits in vivo tumor growth and metastasis of prostate cancer in mice, in addition to inhibition of in vitro cell proliferation and invasion of prostate cancer cells (Jajoo et al., 2009).

Neuronal PAS Domain Protein 3 (NPAS3)

NPAS3 is a member of the basic helix-loop-helix PAS domain class of transcription factors expressed in the brain, that have diverse roles including cancer development and neurobehavior (Brunskill et al., 1999), (Erbel-Sieler et al., 2004), (Kamnasaran et al., 2003), (Lavedan et al., 2009). Furthermore, deletion of chromosome 14 with NPAS3 has been reported in numerous tumors including oligodendrogliomas, melanomas, and carcinomas of the breast, prostate gland, and urogenital tract, as compared with normal non-neoplastic tissues (Schaefer et al., 2001), (Kimchi et al., 2005), (Turashvili et al., 2007), (Harada et al., 2008). NPAS3 exhibits features of a tumor-suppressor, which drives the progression of astrocytomas by modulating the cell cycle, proliferation, apoptosis, and cell migration/invasion and has a further influence on the viability of endothelial cells. Of clinical importance, absence of NPAS3 expression in glioblastomas was a significantly negative prognostic marker of survival. While overexpressed NPAS3 in malignant glioma cell lines significantly suppressed transformation, the converse decreased expression considerably induced more aggressive growth (Moreira et al., 2011). NPAS3 drives the progression of human malignant astrocytomas as a tumor suppressor and is a negative prognostication marker for survival (Moreira et al., 2011).

Neuroligin 4, X-Linked (NLGN4X)/Neuroligin 4, Y-Linked (NLGN4Y)/Neuroligin 2 (NLGN2)/Neuroligin 3 (NLGN3)

The neuroligin gene family consists of five members: NLGN1 at 3q26, NLGN2 at 17p13, NLGN3 at Xq13, NLGN4 at Xp22, and NLGN4Y at Yq11 (Ylisaukko-oja et al., 2005). Neuroligin 4, X-linked is a member of a cell adhesion protein family that appears to play a role in the maturation and function of neuronal synapses. One paper describes the detection of NLGN4X mRNA in the brain of healthy adults by RT-PCR (Jamain et al., 2003). Furthermore, an upregulation of NLGN4X has been described from human embryonic neural stem cells and adult human olfactory bulb-derived neural stem cells (Marei et al., 2012). Mutations in the X-linked NLGN4 gene are a potential cause of autistic spectrum disorders, and mutations have been reported in several patients with autism, Asperger syndrome, and mental retardation (Jamain et al., 2003; Laumonnier et al., 2004; Lawson-Yuen et al., 2008). Few associations of NLGN4X with cancer have been described. In gastrointestinal stromal tumors, over-expression of NLGN4X has been found in paediatric and young adult versus older adult cases (Prakash et al., 2005).

Neuroligins, such as NLGN4Y, are cell adhesion molecules present at the postsynaptic side of the synapse and may be essential for the formation of functional synapses (Jamain et al., 2003). Skaletsky et al. (2003) determined that NLGN4Y, the Y-chromosomal homolog of NLGN4, was expressed in fetal and adult brain, prostate, and testis (Skaletsky et al., 2003). Some data suggested that sequence variants in NLGN4Y might be associated with autism or mental retardation (Ylisaukko-oja et al., 2005; Yan et al., 2008). NLGN2 is highly expressed in cultured neurons (Chubykin et al., 2007). Among NLGN family proteins, NLGN2 is critical for inhibitory synaptic transmission (Chubykin et al., 2007) and defects in inhibitory circuit function contribute to the working memory impairments that represent major clinical features of schizophrenia (Lewis et al., 2005). Mutations of the neuroligin-2 gene (NLGN2) were associated with schizophrenia (Sun et al., 2011).

In cultured hippocampal neurons, endogenous NLGN3 was highly expressed and was localized at both glutamatergic and GABAergic synapses (Budreck and Scheiffele, 2007). Recently, point mutations in a family of neuronal cell adhesion molecules called neuroligins have been linked to autism-spectrum disorders and mental retardation. Overexpression of wild-type NLGN3 protein in hippocampal neurons stimulates the formation of presynaptic terminals, whereas the disease-associated mutations result in a loss of this synaptic function (Chih et al., 2004). Further, mutations in the NLGN3 gene affect cell-adhesion molecules localized at the synapse and suggest that a defect of synaptogenesis may predispose to autism (Jamain et al., 2003).

Dipeptidyl-Peptidase 3 (DPP3)/Bardet-Biedl Syndrome 1 (BBS1)

The DPP3 gene encodes a protein that is a member of the S9B family in clan SC of the serine proteases. DPP3 was mapped to the chromosome 11q12-q13.1 (Fukasawa et al., 2000). DPP3 is a cytosolic zinc-exopeptidase involved in the intracellular protein catabolism of eukaryotes (Abramic et al., 2004). Tumor cytosol DPP3 activity is increased in primary ovarian carcinomas (Simaga et al., 2003) and the proteolytic activity of DPP3 might be a biochemical indicator of endometrial or ovarian malignancies (Simaga et al., 2008), (Simaga et al., 1998). Altered expression of DPP3 suggests involvement in primary ovarian carcinoma, oxidative stress, pain, inflammation and cataractogenesis (Prajapati and Chauhan, 2011). Bardet-Biedl syndrome (BBS) is a genetic disorder with the primary features of obesity, pigmentary retinopathy, polydactyly, renal malformations, mental retardation, and hypogenitalism. Patients with BBS are also at increased risk for diabetes mellitus, hypertension, and congenital heart disease. BBS is known to map to at least six loci: 11q13 (BBS1), 16q21 (BBS2), 3p13-p12 (BBS3), 15q22.3-q23 (BBS4), 2q31 (BBS5), and 20p12 (BBS6) (Mykytyn et al., 2003). The BBS1 protein may play a role in eye, limb, cardiac and reproductive system development. Mutations in this gene have been observed in patients with the major form (type 1) of Bardet-Biedl syndrome (Harville et al., 2010). Experimental studies have demonstrated that BBS1 expression is strictly limited to ciliated cells, including photoreceptors which are the primary ciliated cells in the retina (Azari et al., 2006).

Ubiquitin Specific Peptidase 11 (USP11)

Ubiquitination of chromosome-associated proteins is important for many aspects of DNA repair and transcriptional regulation (Vissers et al., 2008; Weake and Workman, 2008). The full-length cDNA of USP11 was cloned from a Jurkat cell library. By immunofluorescence assay, USP11 primarily was localized in the nucleus of non-dividing cells (Ideguchi et al., 2002). USP-11, a member of the ubiquitin-specific protease family, has emerged as an essential regulator of double-strand break repair (Bayraktar et al., 2013; Wiltshire et al., 2010). USP11 might participate in DNA damage repair within the BRCA2 pathway (Schoenfeld et al., 2004), but had no apparent effect on p53 (Li et al., 2002). Low USP-11 expression correlated with better survival outcomes in women with breast cancer (Bayraktar et al., 2013). Increased endogenous USP11 mRNA levels in pancreatic ductal adenocarcinoma (PDA) cells were associated with increased sensitivity to mitoxantrone, a USP11 inhibitor. Interestingly, USP11 silencing in PDA cells also enhanced sensitivity to gemcitabine (Burkhart et al., 2013).

Eukaryotic Translation Initiation Factor 4E (EIF4E)

EIF4E is a eukaryotic translation initiation factor involved in directing ribosomes to the cap structure of mRNAs. EIF4E, an important regulator of translation, plays a crucial role in the malignant transformation, progression and radioresistance of many human solid tumors. The overexpression of eIF4E has been associated with tumor formation in a wide range of human malignancies (Yang et al., 2012a; Nasr et al., 2013; Wheater et al., 2010). Levels of EIF4E have also been associated with poor prognosis and outcome (Carroll and Borden, 2013). EIF4E regulates the translation of multiple oncogenic networks that control cell survival, proliferation, metastasis, and angiogenesis. EIF4E is a potent oncogene that promotes the nuclear export and translation of specific transcripts (Culjkovic-Kraljacic et al., 2012).

Pleckstrin Homology Domain Containing, Family A (Phosphoinositide Binding Specific) Member 4 (PLEKHA4)

By searching EST databases for proteins containing a putative phosphatidylinositol 3,4,5-trisphosphate-binding motif (PPBM), followed by screening a human universal cDNA library, Dowler et al. (2000) obtained a full-length cDNA encoding PLEKHA4, which they designated PEPP1. Northern blot analysis did not detect expression in any normal tissue, but a 3-kb transcript was detected at high levels in a melanoma cancer cell line. The PLEKHA4 gene was mapped to chromosome 19q13.33 (Dowler et al., 2000). Pleckstrin homology domain (PH domain) is a protein domain of approximately 120 amino acids that occurs in a wide range of proteins involved in intracellular signaling or as constituents of the cytoskeleton (Musacchio et al., 1993). PH domains play a role in recruiting proteins to different membranes, thus targeting them to appropriate cellular compartments or enabling them to interact with other components of the signal transduction pathways (Ingley and Hemmings, 1994). The PH domain of PEPP1 is located at the N-terminal region of PEPP1, and there are no other obvious functional motifs (Dowler et al., 2000).

Chaperonin Containing TCP1, Subunit 7 (Eta) (CCT7)

The chaperonin-containing t-complex polypeptide 1 (CCT) is a cytosolic molecular chaperone composed of eight subunits, CCT1-CCT8, that assists in the folding of actin, tubulin and other cytosolic proteins (Yokota et al., 2001). By FISH, Edwards et al. (1997) mapped the CCT7 gene to chromosome 2p13 (Edwards et al., 1997). Some observations suggest that increased expression of CCT-eta appears to be a marker for latent and active disease in Dupuytren's contracture patients and to be essential for the increased contractility exhibited by the fibroblasts (Satish et al., 2013). CCT7 was shown to be different between of late stage colon cancers versus control (Nibbe et al., 2009).

Nucleolar Complex Associated 4 Homolog (*S. cerevisiae*) (NOC4L)

NOC4L was mapped on chromosome 12q24.33 (Milkereit et al., 2003). The function of NOC4L is still unknown and the protein has not been biologically characterized.

Coiled-Coil-Helix-Coiled-Coil-Helix Domain Containing 2 (CHCHD2)

CHCHD2 was identified as a novel cell migration determinant. Intracellular localization and further functional studies suggested that CHCHD2 and HABP1 may mutually regulate each other to balance cell migration (Seo et al., 2010). CHCHD2 is involved in mitochondrial function and PKIB in protein kinase A-dependent pathway regulation (Feyeux et al., 2012). In patients with Huntington's disease CHCHD2 expression differs from normal cells (Feyeux et al., 2012).

SRY (Sex Determining Region Y)-Box 8 (50X8)/SRY (Sex Determining Region Y)-Box 9 (SOX9)/SRY (Sex Determining Region Y)-Box 10 (SOX10)

Sox8 is a transcription factor and belongs besides Sox9 and Sox10 to group E of the Sox gene family. It is involved in the regulation of embryonic development and in the determination of the cell fate. The protein may be involved in brain development and function. Sox8 is strongly expressed in the embryonic and adult brain, in immature glia in the developing cerebellum. It is also expressed in medulloblastoma and provides an early glial marker (Cheng et al., 2001). It was shown, that Sox8 was able to form DNA-dependent heterodimers with Sox10 (Stolt et al., 2004).

Sox9 is implicated in melanogenesis in the adult and associated with cancerous transformation (Harris et al., 2010), (Flammiger et al., 2009), (Rao et al., 2010). Furthermore it was described as regulating cartilage extracellular matrix (ECM) production and cell proliferation, and it is expressed in a wide range of cancers, where it regulates cell proliferation (Pritchett et al., 2011). Over-expression of SOX9 mRNA is closely associated with poor clinical outcome of patients with malignant gliomas (Wang et al., 2012a). The Sox10 protein acts as a nucleocytoplasmic shuttle protein and is important for neural crest and peripheral nervous system development. Sox10 was restricted to later stages of oligodendrocyte development (Kordes et al., 2005) and it was described as an oligodendroglial lineage marker (Rousseau et al., 2006). Sox10 was consistently expressed in RIGs (Radiation-induced glioblastomas) but rarely in pediatric GBMs (Donson et al., 2007).

Cyclin-Dependent Kinase 4 (CDK4)/Cyclin-Dependent Kinase 6 (CDK6)

CDK4 is a member of the Ser/Thr protein kinase family. It is a catalytic subunit of the protein kinase complex that is important for cell cycle G1 phase progression. The activity of this kinase is restricted to the G1-to S phase transition during the cell cycle and its expression is primarily controlled at the transcriptional level (Xiao et al., 2007). CDK4 and CDK6 enzymes and their regulators, e.g., cyclins, play critical roles in embryogenesis, homeostasis, and cancerogenesis (Graf et al., 2010). In lung cancer tissues, the expression level of CDK4 protein was significantly increased compared to normal tissues (P<0.001). Patients with higher CDK4 expression had a markedly shorter overall survival time than patients with low CDK4 expression. Multivariate analysis suggested the level of CDK4 expression was an independent prognostic indicator (P<0.001) for the survival of patients with lung cancer. Furthermore, suppressing CDK4 expression also significantly elevated the expression of cell cycle regulator p21 (Wu et al., 2011). In lung cells that express an endogenous K-Ras oncogene, ablation of Cdk4, but not Cdk2 or Cdk6, induces an immediate senescence response. No such response occurs in lungs expressing a single Cdk4 allele or in other K-Ras-expressing tissues. Targeting Cdk4 alleles in advanced tumors detectable by computed tomography scanning also induces senescence and prevents tumor progression (Puyol et al., 2010).

Melanoma Antigen Family F, 1 (MAGEF1)

Most known members of the MAGE (melanoma-associated antigen) superfamily are expressed in tumors, testis and fetal tissues, which has been described as a cancer/testis expression pattern (MAGE subgroup I). Peptides of MAGE subgroup I have been successfully used in peptide and DC vaccination (Nestle et al., 1998; Marchand et al., 1999; Marchand et al., 1999; Marchand et al., 1995; Thurner et al., 1999). In contrast, some MAGE genes (MAGE subgroup II), such as MAGEF1, are expressed ubiquitously in all adult and fetal tissues tested and also in many tumor types including ovarian, breast, cervical, melanoma and leukemia (Nestle et al., 1998; Marchand et al., 1999; Marchand et al., 1999; Marchand et al., 1995; Thurner et al., 1999). Nevertheless, overexpression of MAGEF1 could be detected in glioblastoma (Tsai et al., 2007) and in 79% of a cohort of Taiwanese colorectal cancer patients (Chung et al., 2010).

Neuroligin 4, X-Linked (NLGN4X)

Neuroligin 4, X-linked is a member of a cell adhesion protein family that appears to play a role in the maturation and function of neuronal synapses. One paper describes the detection of NLGN4X mRNA in the brain of healthy adults by RT-PCR (Jamain et al., 2003). Furthermore, an upregulation of NLGN4X has been described from human embryonic neural stem cells and adult human olfactory bulb-derived neural stem cells (Marei et al., 2012). Mutations in the X-linked NLGN4 gene are a potential cause of autistic spectrum disorders, and mutations have been reported in several patients with autism, Asperger syndrome, and mental retardation (Jamain et al., 2003; Laumonnier et al., 2004; Lawson-Yuen et al., 2008). Few associations of NLGN4X with cancer have been described. In gastrointestinal stromal tumors, over-expression of NLGN4X has been found in paediatric and young adult versus older adult cases (Prakash et al., 2005).

Vacuolar Protein Sorting 13 Homolog B (VPS13B)

VPS13B was identified as a peripheral membrane protein localized to the Golgi complex, where it overlaps with the cis-Golgi matrix protein GM130. Consistent with its subcellular localization, VPS13B depletion using RNAi causes fragmentation of the Golgi ribbon into ministacks (Seifert et al., 2011). Kolehmainen et al. (2003) identified the COH1 gene, also known as VPS13B, within the Cohen syndrome critical region on chromosome 8q22 (Kolehmainen et al., 2003). Loss-of-function mutations in the gene VPS13B lead to autosomal recessive Cohen syndrome (Seifert et al., 2011). Mutations of VPS13B and other genes were described in gastric and colorectal cancers with microsatellite instability (An et al., 2012).

Neuronal Cell Adhesion Molecule (NRCAM)

NRCAM (neuronal cell adhesion molecule) is a neuronal transmembrane cell adhesion molecule with multiple immunoglobulin-like C2-type and fibronectin type-III domains. It is involved in the guidance, outgrowth, and fasciculation of neuronal cells (Grumet et al., 1991; Morales et al., 1993; Stoeckli and Landmesser, 1995; Perrin et al., 2001; Sakurai et al., 2001) by forming homophilic, as well as heterophilic interactions with other IgCAMs (Volkmer et al., 1996; Sakurai et al., 1997; Zacharias et al., 1999). NRCAM is upregulated in anaplastic astrocytomas and GBM tumor tissues as compared to normal brain, and increased levels are correlated with the invasive behaviour (Sehgal et al., 1998). Antisense RNA against NRCAM decreases the tumorigenic capacity of human GBM cells (Sehgal et al., 1999). NRCAM is also overexpressed in human papillary thyroid carcinomas at the mRNA and protein levels (Gorka et al., 2007). Overexpression of NRCAM mRNA in tumors is associated with high proliferation indices and was associated with a poor outcome in ependymomas (Zangen et al., 2007). In colon cancer as well, overexpression of NRCAM was associated with poor prognosis in advanced patients (Chan et al., 2011), while in prostate cancer, a high level of NRCAM expression was associated with favorable tumor phenotype and reduced risk of PSA recurrence (Tsourlakis et al., 2013).

RAD54 Homolog B (S. cerevisiae) (RAD54B)

DNA repair and recombination protein RAD54B is a protein that in humans is encoded by the RAD54B gene. RAD54 binds to double-stranded DNA, and displays ATPase activity in the presence of DNA. The human RAD54B protein is a paralog of the RAD54 protein, which plays important roles in homologous recombination. Homologous recombination (HR) is essential for the accurate repair of DNA double-strand breaks (DSBs) (Sarai et al., 2008). Knockdown of RAD54B, a gene known to be somatically mutated in cancer, causes chromosome instability (CIN) in mammalian cells (McManus et al., 2009). RAD54B elevated gene expression is significantly associated with shorter time-to-progression and poor OS in GBM patients (Grunda et al., 2010).

Fatty Acid Binding Protein 7, Brain (FABP7)

Fatty acid-binding proteins (FABPs) are cytosolic 14-15 kDa proteins, which are supposed to be involved in fatty acid (FA) uptake, transport, and targeting. FABP7 is highly expressed in the developing brain and retina and its expression decreases significantly in the adult CNS (Godbout et al., 1998). Based on in vitro results, it has been suggested that FABP7 is required for the establishment of the radial glial system of the developing brain (Mita et al., 2007). In normal brain FABP7 protein is barely detectable but shows moderate to strong nuclear and cytoplasmic expression in several GBMs. FABP7-transfected cells display 5-fold greater migration than control cells. Thus, the shorter overall survival associated with FABP7 overexpression especially in glioblastoma may be due to increased migration and invasion of tumor cells into the surrounding brain parenchyma (Liang et al., 2005). Further analysis of FABP7 distribution in astrocytoma tumors indicates elevated levels of FABP7 in infiltrating regions of the tumors proposing an important role for FABP7 in driving the infiltration of malignant cells into adjacent brain tissues (Mita et al., 2007; De et al., 2012). The FABP7 promoter was shown to be hypomethylated consistent with its overexpression in GMB (Etcheverry et al., 2010).

Chondroitin Sulfate Proteoglycan 4 (CSPG4)

CSPG4 (chondroitin sulfate proteoglycan) represents an integral membrane chondroitin sulfate proteoglycan on nascent pericytes with a functional role in neovascularization (Ozerdem, 2006). There is accumulating evidence from in vitro data that CSPG4 plays an important role in tumor angiogenesis. Thus, CSPG4-positive tumors have been found to have significantly increased neovascularization rates and vascular volumes, and CSPG4 has been shown to sequester angiostatin, which normally inhibits endothelial cell proliferation and angiogenesis (Chekenya et al., 2002). CSPG4 is over-expressed by both tumor cells and pericytes on the blood vessels of malignant brain tumors (Chekenya and Pilkington, 2002). CSPG4 is differentially expressed in human gliomas with higher expression in high compared to low-grade gliomas (Chekenya et al., 1999). High CSPG4 levels on tumor cells and associated vessels were associated with significantly shorter survival in GBM (Svendsen et al., 2011). Targeting CSPG4 in two heterogeneous GBM xenografts significantly reduced tumor growth and oedema levels, angiogenesis and normalised vascular function (Wang et al., 2011a). Recently, CSPG4 has even been reported to be up-regulated in a glioblastoma-derived stem-like cell line (He et al., 2010). High expression of CSPG4 correlates with multidrug resistance mediated by increased activation of α3β1 integrin/PI3K signaling and their downstream targets, promoting cell survival (Chekenya et al., 2008).

ORM1-Like 1 (S. cerevisiae) (ORMDL1)

The human genes (ORMDL1, ORMDL2 and ORMDL3) are expressed ubiquitously in adult and fetal tissues, they encode transmembrane proteins anchored in the endoplasmic reticulum which are likely involved in protein folding in the ER. By genomic sequence analysis, Hjelmqvist et al. (2002) mapped the ORMDL1 gene to chromosome 2q32.2 (Hjelmqvist et al., 2002). ORMDL proteins are the primary regulators of ceramide biosynthesis in mammalian cells (Siow and Wattenberg, 2012). ORMDL1 is specifically down-regulated in association with presenilin 1 (PS1) mutations (Araki et al., 2008).

Transforming, Acidic Coiled-Coil Containing Protein 3 (TACC3)

TACC3 exists in a complex with ch-TOG (colonic and hepatic tumor over-expressed gene) and clathrin that crosslinks microtubules in kinetochore fibers. TACC3 is expressed in certain proliferative tissues including testis, lung, spleen, bone marrow, thymus and peripheral blood leukocytes. TACC3 expression is altered in some human tumor types. In cells, TACC3 is localized to both centrosomes and spindle microtubules but not at astral microtubules (Hood and Royle, 2011). TACC3 expression was correlated with p53 expression, and patient whose tumors highly expressed TACC3 and p53 had a significantly poorer prognosis than patients whose tumors had low-level expression for both immunostainings (P=0.006). It is suggested that increase in TACC3 may impart a proliferative advantage to glioblastoma and contribute to tumor progression, and that TACC3 expression is a strong prognostic indicator of clinical outcome in glioblastoma (Jung et al., 2006). Tacc3 may be a negative regulator of the Notch signaling pathway (Bargo et al., 2010).

Doublecortin-Like Kinase 2 (DCLK2)

The microtubule (MT)-associated DCX protein plays an essential role in the development of the mammalian cerebral cortex. Identification of a protein kinase, doublecortin kinase-2 (DCAMKL2), with a domain (DC) highly homologous to DCX was reported. Overexpression of DCAMKL2 stabilizes the MT cytoskeleton against cold-induced depolymerization. Autophosphorylation of DCAMKL2 strongly reduces its affinity for MTs (Edelman et al., 2005). DCLK2 is a member of the CaMK Ser/Thr protein kinase family, which is not calcium- or CaM-dependent, and rather inhibits CRE-dependent gene expression (Ohmae et al., 2006). DCLK2 is highly expressed in the central nervous system (Edelman et al., 2005) in a neuron-specific manner (Ohmae et al., 2006). It is expressed in proliferating neurons during development and persists in post-mitotic neurons in adulthood. In sympathetic neurons, DCLK2 is localized to the cell body and to the terminal segments of axons and dendrites (Tuy et al., 2008; Edelman et al., 2005).

Pecanex-Like 3 (*Drosophila*) (PCNXL3)

Pecanex-like protein 3 (PCNXL3) is a multi-pass membrane protein; it belongs to the pecanex family. The PCNXL3 gene was mapped to the chromosomal region 11q12.1-q13. Three novel human tumor-associated translocation breakpoints were located in the chromosome 11q13 region between the markers D11S4933 and D11S546. Thus PCNXL3 might be an 11q13-associated disease gene (van et al., 2000).

Dihydropyrimidinase-Like 4 (DPYSL4)

Dihydropyrimidinase-related protein 4 (DPYSL4) is a known regulator of hippocampal neuron development. DPYSL4 is involved in growth regulation, polarization and differentiation of dental epithelial cells during tooth germ morphogenesis (Yasukawa et al., 2013). Some studies showed DPYSL4's role in attenuating neurite outgrowth possibility through inhibiting microtubule polymerization, and also revealed its novel association with vimentin during nuclear condensation prior to neuronal death (Aylsworth et al., 2009). The p53 tumor suppressor gene, which is frequently mutated in a wide variety of tumors, plays an important role in maintaining genomic integrity. Both mRNA and protein expressions of DPYSL4 were specifically induced by anticancer agents in p53-proficient cells. DPYSL4 is an apoptosis-inducible factor controlled by p53 in response to DNA damage (Kimura et al., 2011).

Insulin-Like Growth Factor 2 mRNA Binding Protein 3 (IGF2BP3)

IGF2BP3 is a member of the insulin-like growth factor-II mRNA-binding protein family, implicated in mRNA localization, turnover and translational control. The protein contains several KH (K-homologous) domains, which are important in RNA binding and are known to be involved in RNA synthesis and metabolism. Expression occurs mainly during embryonic development and has been described for some tumors. Thus, IGF2BP3 is considered to be an oncofoetal protein (Liao et al., 2005). IGF2BP3 may promote tumor cell proliferation by enhancing IGF-II protein synthesis and by inducing cell adhesion and invasion through stabilization of CD44 mRNA (Findeis-Hosey and Xu, 2012). Moreover, IGF2BP3 expression has been studied in many human neoplasms with growing evidence that it mediates migration, invasion, cell survival and tumor metastasis (Jeng et al., 2009; Kabbarah et al., 2010; Li et al., 2011a; Liao et al., 2011; Lu et al., 2011; Hwang et al., 2012; Samanta et al., 2012) and it might also be implicated in angiogenesis (Suvasini et al., 2011; Chen et al., 2012b). In lung adenocarcinomas, a higher frequency of IGF2BP3 expression can be detected in moderately or poorly differentiated adenocarcinomas, which may be associated with an aggressive biological behavior (Findeis-Hosey et al., 2010; Beljan et al., 2012; Findeis-Hosey and Xu, 2012).

Drosha, Ribonuclease Type III (DROSHA)

Drosha is a Class 2 RNase III enzyme responsible for initiating the processing of microRNA (miRNA), or short RNA molecules naturally expressed by the cell that regulate a wide variety of other genes by interacting with the RNA-induced silencing complex (RISC) to induce cleavage of complementary messenger RNA (mRNA) as part of the RNAi pathway. A microRNA molecule is synthesized as a long RNA primary transcript known as a pri-miRNA, which is cleaved by Drosha to produce a characteristic stem-loop structure of about 70 base pairs long, known as a pre-miRNA (Lee et al., 2003). Drosha exists as part of a protein complex called the Microprocessor complex, which also contains the double-stranded RNA binding protein Pasha (also called DGCR8) (Denli et al., 2004), which is essential for Drosha activity and is capable of binding single-stranded fragments of the pri-miRNA that are required for proper processing (Han et al., 2006). Human Drosha was cloned in 2000, when it was identified as a nuclear dsRNA ribonuclease involved in the processing of ribosomal RNA precursors (Wu et al., 2000). Drosha was the first human RNase III enzyme identified and cloned. The other two human enzymes that participate in the processing and activity of miRNA are the Dicer and Argonaute proteins. Both Drosha and Pasha are localized to the cell nucleus, where processing of pri-miRNA to pre-miRNA occurs. This latter molecule is then further processed by the RNase Dicer into mature miRNAs in the cell cytoplasm (Lee et al., 2003). Drosha and other miRNA processing enzymes may be important in cancer prognosis (Slack and Weidhaas, 2008).

ATP-Binding Cassette, Sub-Family A (ABC1), Member 13 (ABCA13)

In human, the ATP-binding cassette (ABC) family of transmembrane transporters has at least 48 genes and 7 gene subfamilies. The predicted ABCA13 protein consists of 5,058 amino acid residues making it the largest ABC protein described to date (Prades et al., 2002). Knight et al. determined that ABCA13 protein is expressed in mouse and human hippocampus and cortex, both regions relevant to schizophrenia and bipolar disorder (Knight et al., 2009). The ABCA13 gene maps to chromosome 7p12.3, a region that contains an inherited disorder affecting the pancreas (Shwachman-Diamond syndrome) as well as a locus involved in T-cell tumor invasion and metastasis (INM7), and therefore is a positional candidate for these pathologies (Prades et al., 2002).

Cyclin B1 (CCNB1)

CCNB1 is a regulatory protein involved in mitosis. The gene product complexes with p34(cdc2) to form the maturation-promoting factor (MPF) (Zhao et al., 2006; Gong and Ferrell, Jr., 2010). In collaboration with p53, cyclins B1 and G1 regulate the G2/M transition, a key checkpoint in the active cell cycle (Li et al., 2003). Subsequent independent investigations identified in a variety of cancers a CCNB1 (over-)expression which was associated with a tendency to tumor progression and/or poor clinical prognosis e.g. in colorectal carcinoma (Li et al., 2003), RCC (Tsavachidou-Fenner et al., 2010), breast cancer (Aaltonen et al., 2009; Agarwal et al., 2009; Suzuki et al., 2007; Chae et al., 2011), medulloblastoma (de et al., 2008), squamous cell lung cancer (Kettunen et al., 2004), gastrointestinal stromal tumors (Koon et al., 2004), esophageal squamous cell carcinoma (Song et al., 2008), laryngeal squamous cell carcinoma (Dong et al., 2002), oral tongue squamous cell carcinoma (Harada et al., 2006), adrenocortical carcinomas (Soon et al., 2009), pulmonary adenocarcinoma (Wikman et al., 2002), non-small cell lung cancer (Cooper et al., 2009), cervical cancer (Zhao et al., 2006), prolactin pituitary tumors (Raverot et al., 2010) and renal cell carcinoma (Ikuerowo et al., 2006).

CCR4-NOT Transcription Complex, Subunit 1 (CNOT1)

The human CCR4-NOT deadenylase complex consists of at least nine enzymatic and non-enzymatic subunits. CNOT1 has an important role in exhibiting enzymatic activity of the CCR4-NOT complex, and thus is critical in control of mRNA deadenylation and mRNA decay. CNOT1 depletion structurally and functionally deteriorates the CCR4-NOT-complex and induces stabilization of mRNAs, which results in the increment of translation causing ER stress-mediated apoptosis. Ito et al. conclude that CNOT1 contributes to cell viability by securing the activity of the CCR4-NOT deadenylase (Ito et al., 2011). siRNA-mediated depletion of endogenous CNOT1 or other Ccr4-Not subunits in breast cancer cells results in deregulation of ERalpha target genes (increased induction of ERα target genes TTF1 and c-Myc). These findings define a function for the human Ccr4-Not complex as a transcriptional repressor of nuclear receptor signaling that is relevant for the understanding of molecular pathways involved in cancer (Winkler et al., 2006).

Baculoviral IAP Repeat-Containing 5 (Survivin) (BIRC5)

BIRC5 (Survivin) is a member of the inhibitor of apoptosis protein (IAP) family. Survivin is overexpressed in a multitude of cancer entities. Thus, in general, overexpression of survivin is thought to be associated with shorter overall-survival and higher malignancy grades.

Elevated levels of survivin have been reported from cancer stem cells isolated from GBM and astrocytoma (Jin et al., 2008). It is suggested that survivin overexpression in brain gliomas might play an important role in malignant proliferation, anti-apoptosis and angiogenesis (Zhen et al., 2005; Liu et al., 2006). Several analyses were performed to study survivin expression and its impact on survival in glioblastoma. To summarize, survivin expression, especially the simultaneous expression in nucleus and cytoplasm in astrocytic tumors was significantly associated with malignancy grade (with highest survivin expression in glioblastoma) and shorter overall survival times compared with patients who had survivin-negative tumors (Kajiwara et al., 2003; Saito et al., 2007; Uematsu et al., 2005; Mellai et al., 2008; Grunda et al., 2006; Xie et al., 2006; Sasaki et al., 2002b; Chakravarti et al., 2002). Additionally, Survivin expression was significantly increased in recurrent GBM compared with newly diagnosed tumors (Guvenc et al., 2013). As survivin is such a promising target for cancer therapy, studies using survivin-derived peptides showed that survivin is immunogenic in tumor patients by eliciting CD8+ T cell-mediated responses. In addition, surviving specifically stimulated CD4+ T-cell reactivity in peripheral blood lymphocytes from the same patients (Casati et al., 2003; Piesche et al., 2007).

Transmembrane Protein 255A (TMEM255A)

The TMEM255A gene (alias FAM70A) was located on chromosome Xq24 (Ross et al., 2005). The function of TMEM255A is still unknown. But the chromosome Xq24, were TMEM255A was mapped, is also the location for some cancer/testis (CT) genes, which are expressed in some tumors (Chen et al., 2006). Furthermore, in 80% of HER2-positive breast tumors deletion at Xq24 was observed, covering both previously known genes as well as novel genes in relation to cancer (Tina et al., 2012).

ST8 Alpha-N-Acetyl-Neuraminide Alpha-2,8-Sialyltransferase 5 (ST8SIA5)

By screening a human brain cDNA library with a DNA probe generated from the cDNA sequence of mouse Siat8e, followed by 5-prime RACE of mRNA from human brain tissue, Kim et al. (1997) cloned human SIAT8E (alpha-2,8-sialyltransferase V, ST8SIA5). Northern blot analysis detected expression of 11- and 2.5-kb transcripts in fetal and adult brain (Kim et al., 1997). ST8SIA5 is a type II membrane protein that may be present in the Golgi apparatus. The encoded protein, which is a member of glycosyltransferase family 29, may be involved in the synthesis of gangliosides GD1c, GT1a, GQ1b, and GT3 from GD1a, GT1b, GM1b, and GD3, respectively (Kim et al., 1997). Gangliosides play an important role in neuronal differentiation processes. The regulation of ganglioside levels is related to the induction of neuronal cell differentiation. Some results suggest that the ST8Sia5 gene increases ganglioside GQ1b and improves neuronal differentiation via the ERK1/2 MAP kinase pathway (Kwak et al., 2011).

Family with Sequence Similarity 120C (FAM120C)

Family with sequence similarity 120C is a protein in humans that is encoded by the FAM120C gene. FAM120C encodes a potential transmembrane protein and lies in a region where mutations and deletions have been associated with intellectual disability and autism (Qiao et al., 2008). FAM120C seems to be expressed at low levels in several adult and fetal human tissues. It consists of 16 coding exons and maps to Xp11.22. The 5-prime end of the FAM120C gene lies within a CpG island (Holden and Raymond, 2003).

Fatty Acid Binding Protein 7, Brain (FABP7)

Fatty acid-binding proteins (FABPs) are cytosolic 14-15 kDa proteins, which are supposed to be involved in fatty acid (FA) uptake, transport, and targeting. FABP7 is highly expressed in the developing brain and retina and its expression decreases significantly in the adult CNS (Godbout et al., 1998). Based on in vitro results, it has been suggested that FABP7 is required for the establishment of the radial glial system of the developing brain (Mita et al., 2007). In normal brain FABP7 protein is barely detectable but shows moderate to strong nuclear and cytoplasmic expression in several GBMs. FABP7-transfected cells display 5-fold greater migration than control cells. Thus, the shorter overall survival associated with FABP7 overexpression especially in glioblastoma may be due to increased migration and invasion of tumor cells into the surrounding brain parenchyma (Liang et al., 2005). Further analysis of FABP7 distribution in astrocytoma tumors indicates elevated levels of FABP7 in infiltrating regions of the tumors proposing an important role for FABP7 in driving the infiltration of malignant cells into adjacent brain tissues (Mita et al., 2007; De et al., 2012). The FABP7 promoter was shown to be hypomethylated consistent with its overexpression in GMB (Etcheverry et al., 2010).

Zinc Finger Protein 3 (ZNF3)

The ZNF family represents a large group of molecules which are involved in various aspects of transcriptional regulation. The ZNF3 gene was mapped to chromosome 7q22.1. Northern blot analysis of mRNA from cell lines of various tissue origins showed ubiquitous expression of a 3.5-kb transcript (Pannuti et al., 1988). Multiple mutations in the zinc finger (ZNF) family genes, including ZNF3, were found in HNSCC (head and neck squamous cell carcinoma) tumors (Nichols et al., 2012; Nichols et al., 2012). In HRneg/Tneg breast cancer ZNF3 was identified as an outcome predictor regarding metastatic outcome of early stage (Yau et al., 2010).

Dedicator of Cytokinesis 7 (DOCK7)

DOCK7 (Dedicator of cytokinesis 7), also known as Zir2, is a large (~240 kDa) protein involved in intracellular signalling networks. It is a member of the DOCK-C subfamily of the DOCK family of guanine nucleotide exchange factors (GEFs) which function as activators of small G proteins.

DOCK7 expression has been reported in neurons (Watabe-Uchida et al., 2006), (Yamauchi et al., 2008). DOCK7 functions as an essential and downstream regulator of receptor for advanced glycation end products (RAGE)-mediated cellular migration (Yamamoto et al., 2013). DOCK7 also functions as an intracellular substrate for ErbB2 to promote Schwann cell migration (Yamauchi et al., 2008). Furthermore, DOCK7 induces multiple axon formation when over-expressed and prevents axon formation when it is knocked down (Watabe-Uchida et al., 2006).

DOCK7 interaction with TACC3 controls interkinetic nuclear migration and the genesis of neurons from radial glial progenitor cells (RGCs) during cortical development (Yang et al., 2012b).

Uncharacterized LOC728392 (LOC728392)

LOC728392 is an uncharacterized protein located on chromosome 17p13.2 (Kim et al., 2006), (Zody et al., 2006). To this date, there was no further characterization of the protein LOC728392.

Praja Ring Finger 2, E3 Ubiquitin Protein Ligase (PJA2)

PJA2 is a widely expressed RING (Really Interesting New Gene) protein. RING-finger proteins contain cysteine-rich, zinc-binding domains and are involved in the formation of macromolecular scaffolds important for transcriptional repression and ubiquitination (Sasaki et al., 2002a). In nervous tissue, PJA2 is distributed mainly on the cytoplasmic side of the membranes constituting endoplasmic reticulum and Golgi apparatus, but also to the postsynaptic density region of axosomatic synapses (Nakayama et al., 1995). In human GBM samples, high protein and mRNA expression of PJA2 was detected, whereas expression in human astrocytomas was low. This suggests that PJA2 expression correlates with malignancy, which is based on the inhibition of the Hippo tumor suppressor pathway by accumulated PJA2 (Lignitto et al., 2013).

HEAT Repeat Containing 1 (HEATR1)

Human HEATR1, also called UTP10, had been identified as an uncharacterized protein termed BAP28. Zebrafish embryos homozygous for a mutant bap28 allele display excess apoptosis primarily in the central nervous system (Azuma et al., 2006). Human HEATR1 (UTP10) was mapped to chromosome 1q43. Endogenous human UTP10 is clearly enriched in nucleoli as revealed by staining of HeLa cells with affinity-purified antibodies raised against recombinant protein. It has been suggested, that UTP10 binds to chromatin throughout the rDNA repeat (Prieto and McStay, 2007).

Glycoprotein M6B (GPM6B)

GPM6B belongs to a proteolipid protein family, which is expressed in neurons and in oligodendrocytes in the brain. The knowledge of the biological function of this protein family is sparse, but their expression in most brain regions have led to the hypothesis that they are involved in cellular housekeeping functions such as membrane trafficking and cell-to-cell communication (Fjorback et al., 2009). Taken together, GPM6B is thought to have a function in the development of the nervous system (Mobius et al., 2008). GPM6B was firstly described as a brain specific protein expressed mainly in neurons and oligodendrocytes (Werner et al., 2001; Yan et al., 1993), but several recent studies demonstrate its broad distribution throughout many cell types and tissues (Charfi et al., 2011). GPM6B expression has been described in some tumor entities. For example, it is expected to be B leukemia-specific and showed significant overexpression in these tumors (Charfi et al., 2011). In ovarian cancer, GPM6B is detectable from patients serum and is among the most promising candidates for an early stage marker (Urban et al., 2011).

Crumbs Homolog 1 (*Drosophila*) (CRB1)

The CRB1 gene encodes a protein which is similar to the *Drosophila* crumbs protein and localizes to the inner segment of mammalian photoreceptors. CRB1 mapped to 1q31-q32.1, a region harboring a gene involved in a severe form of autosomal recessive retinitis pigmentosa (den Hollander et al., 1999). Pellikka et al. (2002) showed that CRB1 localizes to corresponding subdomains of the photoreceptor apical plasma membrane (Pellikka et al., 2002). CRB1 may organize an intracellular protein scaffold in the human retina (den Hollander et al., 2001). Mutations in the CRB1 gene are associated with a severe form of retinitis pigmentosa, RP12, and with Leber congenital amaurosis; (Coppieters et al., 2010); (Walia et al., 2010); (van de Pavert et al., 2007). Jacobson et al. (2003) suggested that the CRB1 disease pathway disturbs the development of normal human retinal organization by interrupting naturally occurring apoptosis (Jacobson et al., 2003).

Oligodendrocyte Lineage Transcription Factor 2 (OLIG2)

Oligodendrocyte lineage transcription factor 2 (OLIG2) is a member of the OLIG family of basic helix-loop-helix transcription factors. It plays a key role in the cell fate specification of oligodendrocytes and motor neurons in the dorsal spinal cord during development (Lu et al., 2000), (Takebayashi et al., 2000). OLIG2 is a universal marker of diffuse gliomas (oligodendroglioma, astrocytoma, glioblastoma, and mixed glioma) (Lu et al., 2001), (Marie et al., 2001). Olig2 is strictly required to maintain the malignancy of oligodendroglioma cells, since its silencing by interfering RNA abrogates tumor propagation (Appolloni et al., 2012). It has been proposed that OLIG2 transcript level may correlate with malignant progression of astrocytoma (Bozinov et al., 2008). Furthermore, OLIG2-positive glioma-initiating cells were proposed as therapeutic target (Fu et al., 2013). Recent studies have identified stem cells in brain cancer. In this study they observe expression of the CNS-restricted transcription factor, OLIG2, in human glioma stem and progenitor cells reminiscent of type C transit-amplifying cells in germinal zones of the adult brain. These findings identify an Olig2-regulated lineage-restricted pathway critical for proliferation of normal and tumorigenic CNS stem cells (Ligon et al., 2007).

Versican (VCAN)

VCAN gene is a member of the aggrecan/versican proteoglycan family. The protein encoded is a large chondroitin sulfate proteoglycan and is a major component of the extracellular matrix. This protein is involved in cell adhesion, proliferation, migration and angiogenesis and plays a central role in tissue morphogenesis and maintenance.

VCAN is expressed in a variety of tissues. It is highly expressed in the early stages of tissue development, and its expression decreases after tissue maturation. Its expression is also elevated during wound repair and tumor growth. In the adult human brain, VCAN is expressed mainly in the white matter of the frontal lobe, cerebellum, brainstem, and spinal cord, in close association with astrocytes and oligodendrocytes (Ghosh et al., 2010). VCAN has been found in many malignancies including melanomas and prostate and in multiple human cancers its isoforms has been shown a differential expression (Ghosh et al., 2010; Zheng et al., 2004). A higher VCAN expression in tumor tissue than in the surrounding normal tissues was observed analysing three high-grade human brain tumors (Zheng et al., 2004).

Spermine Oxidase (SMOX)

SMOX is an inducible FAD-dependent polyamine oxidase, which oxidizes spermine, to produce spermidine, $H_2O_2$, and 3-aminopropanal (Wang et al., 2001). SMOX is located on chromosome 20p13 and encodes for several splice variants (Murray-Stewart et al., 2002). SMOX is a highly inducible enzyme, its deregulation can alter polyamine homeostasis, and dysregulation of polyamine catabolism is often associated with several disease states. SMOX participates in drug response, apoptosis, response to stressful stimuli and etiology of several pathological conditions, including cancer (Cervelli et al., 2012). Elevated cellular polyamine levels are a common feature of cancer cells, including GBM cells, and the polyamine pathway has been explored as a potential therapeutic target to inhibit polyamine biosynthesis or activate polyamine catabolism inhibitor (Jiang et al., 2007).

Exocyst Complex Component 7 (EXOC7)

EXOC7 is a component of the exocyst, which is an evolutionarily conserved octameric protein complex essential for exocytosis (Kee et al., 1997). The exocyst targets secretory vesicles at specific domains of the plasma membrane for cell surface expansion and protein secretion (Zuo et al., 2006). By analysis of a human-rodent hybrid panel, Kikuno et al. (1999) mapped the EXOC7 gene to chromosome 17q25 (Kikuno et al., 1999). The exocyst is involved in vesicle trafficking, specifically the tethering and spatial targeting of post-Golgi vesicles to the plasma membrane prior to vesicle fusion. It is implicated in a number of cell processes, including exocytosis and also cell migration and growth (Zuo et al., 2006). The exocyst plays important roles in cell invasion by mediating the secretion of MMPs at focal degrading sites and regulating actin dynamic (Liu et al., 2009). A set of 14 genes, including EXOC7, might be an outcome predictor in early stage hormone receptor-negative and triple-negative breast cancer (Yau et al., 2010).

Leucine Zipper, Putative Tumor Suppressor 1 (LZTS1)

The FEZ1/LZTS1 gene was identified as a candidate tumor suppressor gene at 8p22 by Ishii et al in 1999 (Ishii et al., 1999). LZTS1 has been shown to regulate growth of human tumor cell lines and physically interacts with cell-cycle regulators in that context (Cabeza-Arvelaiz et al., 2001); (Ishii et al., 2001); (Vecchione et al., 2002). Introduction of LZTS1 into LZTS1-negative cancer cells resulted in suppression of tumorigenicity and reduced cell growth with accumulation of cells at the late S-G2/M stage of the cell cycle (Ishii et al., 2001). The FEZ1/LZTS1 (FEZ1) gene is frequently altered in human cancer, including prostate (Hawkins et al., 2002), lung (Lin et al., 2013), bladder (Abraham et al., 2007) and breast (Chen et al., 2009) cancer. Frequent reduction in expression and infrequent mutations were reported. Hypermethylation of a CpG island in the LZTS1 promoter appeared to be frequent and could be responsible for the reduced expression of LZTS1 in cancer cells (Toyooka et al., 2002), (Vecchione et al., 2001).

Fatty Acid Desaturase 2 (FADS2)

Fatty acid desaturase 2 (FADS2) also known as delta(6) fatty acid desaturase (D6D) is an enzyme that in humans is encoded by the FADS2 gene. Fatty acid desaturase 2 is a member of the fatty acid desaturase (FADS) gene family. Marquardt et al. (2000) identified the FADS2 gene on chromosome 11q12-q13.1 (Marquardt et al., 2000). FADS2 is the rate-limiting enzyme in mammalian synthesis of long-chain polyunsaturated fatty acids (Nwankwo et al., 2003). FADS2 function loss at the cancer hotspot 11q13 locus diverts lipid signaling precursor synthesis to unusual eicosanoid fatty acids (Park et al., 2011). FADS2 is upregulated in hepatocellular carcinoma (Muir et al., 2013). FADS2 may be involved in the pathogenesis of breast cancer (Pender-Cudlip et al., 2013) and the expression of delta-6-desaturase is associated with aggressiveness of breast cancer (Lane et al., 2003). Furthermore, inhibiting delta-6 desaturase activity suppresses tumor growth in mice (He et al., 2012).

Transmembrane Protein 231 (TMEM231)

TMEM231 encodes a transmembrane protein, which is a component of the B9 complex involved in the formation of the diffusion barrier between the cilia and plasma membrane. TMEM231 localizes to the basal body before and independently of intraflagellar transport in a Septin 2 (Sept2)-regulated fashion (Chih et al., 2012). Mutations in TMEM231 cause several ciliopathies. These are multiorgan system disorders caused by dysfunction of the primary cilium, a cytoskeletal appendage which plays essential roles in cellular homeostasis and organ development (Nigg and Raff, 2009; Hildebrandt et al., 2011). Very recently, compound heterozygosity for two mutations in TMEM231 was identified in three patients with Joubert syndrome, a predominantly autosomal recessive disorder characterised by a distinctive midhindbrain malformation, oculomotor apraxia, breathing abnormalities and developmental delay. JBTS is genetically heterogeneous, involving genes required for formation and function of non-motile cilia (Parisi and Glass, 1993; Srour et al., 2012).

Achaete-Scute Complex Homolog 1 (*Drosophila*) (ASCL1)

Achaete-scute homolog-1 ASCL1 (also termed hASH1 in humans) is a basic helix-loop-helix transcription factor important in early development of neural and neuroendocrine (NE) progenitor cells in multiple tissues including the CNS, autonomic nervous system, adrenal medulla, thyroid, lung, and prostate, among others (Guillemot et al., 1993; Borges et al., 1997; Fode et al., 2000; Ball, 2004; Nakada et al., 2004; Pattyn et al., 2006; Miki et al., 2012; Righi et al., 2012). As it is crucial for early development of the sympathetic nervous system, it is transiently expressed in sympathetic neuroblasts during embryogenesis (Soderholm et al., 1999). Furthermore, ASCL1 is expressed in immature olfactory neurons and is required for their development (Carney et al., 1995). ASCL1 is essential for the maintenance and in vivo tumorigenicity of GBM CSCs (Rheinbay et al., 2013). An efficient generation of induced neuronal (iN) cells from glioma cells could be achieved by the infection with three transcription factors: Asc1, Brn2 and Ngn2 (ABN). This causes glioma cell death, decreased tumor growth and conversion of human glioma cells to functional neurons (Zhao et al., 2012b). ASCL1 upregulation in progressive astrocytoma is accompanied by inhibition of Notch signaling (Somasundaram et al., 2005). ASCL1 is expressed in a majority of primary neuroblastomas and neuroblastoma cell lines (Axelson, 2004). During neuroblastoma differentiation, the ASCL1-pathway is responsible for the up-regulation of IGF2 (Li et al., 2011b).

Na+/K+ Transporting ATPase Interacting 1 (NKAIN1)/Na+/K+ Transporting ATPase Interacting 2 (NKAIN2)/Na+/K+ Transporting ATPase Interacting 4 (NKAIN4)

NKAIN proteins 1-4 are a family of evolutionary conserved transmembrane proteins that localize to neurons and interact with the Na,K-ATPase β1 subunit. There are three splice variants of NKAIN2, 3 and 4, whereas only a single form of NKAIN1 was found. All four family members are highly expressed in mouse brain with distinct and overlapping expression in different brain regions. Interestingly, a short splice variant of NKAIN4 is brain- and testis-specific, whereas a longer splice variant of NKAIN4 is expressed ubiquitously (Gorokhova et al., 2007). The genomic region NKAIN1-SERINC2 harbors SNPs, which are causally associated with alcohol dependence in Europeans (Zuo et al., 2013). Disruption of the NKAIN2 gene has been implicated in neurological disorders, e.g. in a child with developmental delay and recurrent infections (Bocciardi et al., 2005; Yue et al., 2006). In addition, SNPs in NKAIN2 have been associated with neuroticism (Calboli et al., 2010) and alcohol dependence (Wang et al., 2011b). Human NKAIN2 was identified first as gene, which is disrupted within the breakpoint region 6q21-22 in the T-cell lymphoma/leukemia cell lines HT-1 and ATN-1 (Tagawa et al., 2002). It may also be a candidate tumor suppressor gene in prostate cancer, although no functional experimental data are available for that idea (Mao et al., 2011).

Protocadherin Gamma Family (PCDHG-Family)

The protocadherins (PCDH) are a subgroup of cadherins, which are predominantly expressed in the central nervous system (Kallenbach et al., 2003; Hirayama and Yagi, 2006). The gamma gene cluster (PCDHG-) includes 22 genes divided into 3 subfamilies. The gamma gene cluster is organized similar to an immunoglobulin cluster: 22 variable exons, which encode the ectodomain (cadherin repeats, transmembrane and proximal intracellular domain), and 3 constant exons, which encode the common distal moiety of the cytoplasmic domain, are joined by RNA splicing (Morishita and Yagi, 2007; Wang et al., 2002). PCDHs are involved in developmental tissue morphogenesis and in synapse formation and modulation (Frank and Kemler, 2002) and the production of cerebrospinal fluid in the postnatal brain (Lobas et al., 2012). It was shown that several PCDHGs interact with the intracellular adaptor protein PDCD10 (programmed cell death 10), which mediates apoptosis in neurons (Lin et al., 2010a). Agglomerative epigenetic aberrations—for example of the protocadherin gene family clusters on chromosome 5 (PCDHA, PCDHB, and PCDHG)—are a common event in human breast cancer (Novak et al., 2008).

Rho GTPase Activating Protein 21 (ARHGAP21)

ARHGAP21 functions preferentially as a GTPase-activating protein (GAP) for CDC42 and regulates the ARP2/3 complex and F-actin dynamics at the Golgi through control of CDC42 activity (Dubois et al., 2005). Several Rho GTPase-activating proteins (RhoGAPs) are implicated in tumor progression through their effects on Rho GTPase activity. ARHGAP21 is a RhoGAP with increased expression in head and neck squamous cell carcinoma and with a possible role in glioblastoma tumor progression (Lazarini et al., 2013). ARHGAP21 modulate cell migration through the control of Cdc42 and FAK activities (Bigarella et al., 2012). ARHGAP21 is expressed in the nuclear and perinuclear regions of several glioblastoma derived cell lines. ARHGAP21 might act as a tumor suppressor gene and might be a master regulator of migration having a crucial role in controlling the progression of different tumor types (Bigarella et al., 2009).

Paraneoplastic Ma Antigen 2 (PNMA2)

Human PNMA2 encodes the paraneoplastic antigen Ma2 which belongs to the human PNMA family (Schuller et al., 2005). In healthy persons, PNMA2 expression is restricted to neuronal tissue. In the CNS, neuronal cells show discrete subnuclear and cytoplasmic immunostaining (Gultekin et al., 2000; Voltz et al., 1999). In cancer tissue, PNMA2 expression has been shown for testicular cancer (Voltz et al., 1999; Leja et al., 2009), breast cancer (Sahashi et al., 2003), lung cancer (Barnett et al., 2001), small intestine neuroendocrine tumors and liver metastasis (Leja et al., 2009). PNMA2 was identified as novel marker gene for neuroendocrine carcinoma cells (Leja et al., 2009). Patients with PNMA2-positive tumors may develop anti-PNMA2 antibodies, which induce neurological degenerative syndromes, such as paraneoplastic encephalitis (PNE) (Sahashi et al., 2003). As the neurological symptoms of PNE strongly affect the patient's condition and may be fatal (Barnett et al., 2001), cancer treatment should be forced in such patients (Kraker, 2009).

Adenomatous Polyposis Coli (APC)

Adenomatous polyposis coli (APC) also known as deleted in polyposis 2.5 (DP2.5) is a protein that in humans is encoded by the APC gene. The APC protein plays a critical role in several cellular processes that determine whether a cell may develop into a tumor. The APC protein helps control how often a cell divides, how it attaches to other cells within a tissue, or whether a cell moves within or away from a tissue. APC is a key tumor suppressor gene that acts as a gatekeeper of intestinal epithelial homeostasis by restraining cytoplasmic cellular levels of β-catenin, the central activator of transcription in the Wnt signaling pathway (Minde et al., 2011). Mutations in the human APC gene are linked to familial adenomatous polyposis and to the progression of sporadic colorectal and gastric tumors (Rubinfeld et al., 1993). APC gene is also a candidate susceptibility gene for attenuated polypotic syndromes (Zhou et al., 2001). The association between brain tumors and multiple colorectal adenomas can result from two distinct types of germ-line defects: mutation of the APC gene or mutation of a mismatch-repair gene (Hamilton et al., 1995).

Wiskott-Aldrich Syndrome-Like (WASL)

Neural Wiskott-Aldrich syndrome protein is a protein that in humans is encoded by the WASL gene. The Wiskott-Aldrich syndrome (WAS) family of proteins share similar domain structure, and are involved in transduction of signals from receptors on the cell surface to the actin cytoskeleton (Kovacs et al., 2011). WASL associates with Cdc42, known to regulate formation of actin filaments, and the cytoskeletal organizing complex Arp2/3 and is ubiquitously expressed and shows highest expression in neural tissues (Kovacs et al., 2011). WASL and the arp2/3 complex are critical regulators of actin in the development of dendritic spines and synapses (Wegner et al., 2008). The Arp2/3 complex with the associated protein WASL mediates multigeneration dendritic protrusions for efficient 3-dimensional cancer cell migration (Giri et al., 2013). WASL is involved in the metastasis of human breast cancer (Escudero-Esparza et al., 2012) and in primary brain tumors (Khalil and El-Sibai, 2012).

Solute Carrier Family 1 (Glial High Affinity Glutamate Transporter), Member 3 (SLC1A3)/Solute Carrier Family 1 (High Affinity Aspartate/Glutamate Transporter), Member 6 (SLC1A6)

SLC1A3 encodes a member of a member of a high affinity glutamate transporter family. SLC1A3 is also often called the GLutamate ASpartate Transporter (GLAST) or Excitatory Amino Acid Transporter 1 (EAAT1). GLAST is predominantly expressed in the plasma membrane, allowing it to remove glutamate from the extracellular space (Langley et al., 2009). Various acute and chronic brain diseases result in disturbed expression of the glial glutamate transporters, GLAST/EAAT-1 and GLT-1/EAAT-2, and subsequent secondary neuronal cell death (Unger et al., 2012). The expression of glutamate transporters (GLT-1 and GLAST) in astrocytes and microglia are differentially regulated following nerve injury (Xin et al., 2009). Autoantigen specific T cells inhibit glutamate uptake in astrocytes by decreasing expression of astrocytic glutamate transporter GLAST (Korn et al., 2005). SLC1A3 might be associated with glioma cell motility (Tatenhorst et al., 2004). Inhibition of glutamate transporter enhances the therapeutic efficacy of doxorubicin (Sugiyama et al., 2001).

The glutamate transporter gene SLC1A6 encodes the glutamate transporter EAAT4. It is thought, that at least one susceptibility locus for schizophrenia may be located within or nearby SLC1A6 in the Japanese population (Deng et al., 2007). Furthermore, it is localized neuronal in the mammalian central nervous system (Jackson et al., 2001) and expressed predominantly in the cerebellum (Need et al., 2009).

Teneurin Transmembrane Protein 4 (TENM4)

Teneurin-4 (Ten-4/Odz4) is a type II transmembrane protein that is highly expressed in the CNS. Ten-4 is also expressed in developing eyes and somites, as well as in tail bud and limbs (Tucker and Chiquet-Ehrismann, 2006); (Kenzelmann-Broz et al., 2010). Ten-4 expression is induced in response to endoplasmic reticulum (ER) stress (Wang et al., 1998), and an involvement of Ten-4 has been suggested in mouse gastrulation (Lossie et al., 2005) and bipolar disorder in humans (2011). However, the biological function of Ten-4 remains unknown. Some findings suggest that teneurin-4 is a novel regulator of oligodendrocyte differentiation and that it plays a critical role in the myelination of small-diameter axons in the CNS (Suzuki et al., 2012).

Zinc Finger Protein 749 (ZNF749)

ZNF749 was mapped on chromosome 19q13.43 (Grimwood et al., 2004), (Tsuritani et al., 2007). This gene has 4 transcripts (splice variants). To date, the ZNF749 has not been characterized and the function of this gene is unknown.

EF-Hand Calcium Binding Domain 7 (EFCAB7)

EFCAB7 was mapped on chromosome 1p31.3 (Mehrle et al., 2006), (Wiemann et al., 2004). EFCAB7 is an uncharacterized protein with unknown biological function.

Bone Morphogenetic Protein 7 (BMP7)

BMP7/OP-1 belongs together with other BMPs to the transforming growth factor (TGF) β family. BMP7 is a very pleiotropic growth factor. Bone morphogenic proteins (BMPs) play a key role in bone formation. In recent years, recombinant BMPs, particularly BMP2 and BMP7/OP-1, have been used therapeutically in patients with large bone defects or delayed or impaired fracture healing, with the notion that locally applied BMP would promote bone repair (Geesink et al., 1999), (Donati et al., 2008), (Zimmermann et al., 2006), (Garrison et al., 2010). BMP-7 belongs to the superfamily of transforming growth factor (3-like cytokines, which can act either as tumor suppressors or as tumor promoters depending on cell type and differentiation. BMP7 expression have been reported to be involved in the growth of several cancer cells, such as osteosarcoma, malignant melanoma, prostate cancer, breast cancer, renal cell cancer, colorectal cancer, and gastric cancer, causing increased aggression or suppression (Motoyama et al., 2008), (Kwak et al., 2007), (Sulzbacher et al., 2002), (Rothhammer et al., 2007), (Masuda et al., 2004), (Alarmo et al., 2006). Endogenous neural precursor cells protect the young brain from glioblastoma by releasing BMP7, which acts as a paracrine tumor suppressor that represses proliferation, self-renewal and tumor-initiation of stem-like glioblastoma cells (Chirasani et al., 2010).

Integrin, Alpha 7 (ITGA7)

Integrins are heterodimeric proteins, which mediate interactions between cells and ECM or other cells. ITGA7 encodes the integrin alpha 7, which forms a heterodimer with the integrin beta 1 chain (Vignier et al., 1999). The beta 1 chain interacts with the cytoskeletal component α-actinin, thus ensuring signaling between the cytoskeleton and the basal lamina (Otey et al., 1990). ITGA7 is mainly and abundantly expressed in skeletal and cardiac muscle (Pegoraro et al., 2002; Leung et al., 1998). In human, mutation, deletion or reduced expression of ITGA7 is strongly correlated with muscular dystrophy and myopathy (Pegoraro et al., 2002; Hayashi et al., 1998). ITGA7 was associated with malignant transformation in melanoma (Kramer et al., 1991b; Kramer et al., 1991a; Kramer et al., 1989). In line with this, enhanced ITGA7 expression in squamous cell carcinoma of the tongue suggested ITGA7 as a potential marker of metastases (Carinci et al., 2005). Some results suggest that blocking of ITGA7 may be an important step during carcinogenesis. However, the authors noted that the role of ITGA7 in tumor growth remains unclear and may depend on the cell type involved (Ren et al., 2007).

Ribosomal Protein L7a (RPL7A)

Cytoplasmic ribosomes, organelles that catalyze protein synthesis, consist of a small 40S subunit and a large 60S subunit. The RPL7A gene encodes a ribosomal protein that is a component of the 60S subunit. Many ribosomal proteins, particularly those of the large subunit, including ribosomal protein L7a (RPL7a), are composed of a globular surface-exposed RNA-binding domain that binds to the rRNA core to stabilize its structure. Although the critical activities of decoding and peptide transfer are rRNA-based, ribosomal proteins also play an important role in the process of protein synthesis (Wool, 1996). RPL7a plays a critical role in stabilizing ribosomes by binding to rRNA (De et al., 1993; Huxley and Fried, 1990). In addition to its function in the ribosome, RPL7a may also be involved in cell growth and differentiation by interacting with human thyroid hormone receptor (THR) and retinoic acid receptor (RAR) and in turn inhibiting the activities of the two nuclear hormone receptors (Burris et al., 1995). In osteosarcoma, RPL7a mRNA and protein expression was significantly down-regulated compared with samples from normal bone and benign bone lesion tissues and low RPL7A mRNA expression was a significant poor prognostic indicator for overall survival in patients with high grade lesion developed lung metastasis at the time of diagnosis of the primary osteosarcoma (Zheng et al., 2009). On the other hand, RPL7a is reported to be up-regulated in colorectal cancer (Wang et al., 2000). An over-expression of RPL7a mRNA was also confirmed in prostate-cancer tissue samples by in situ hybridization (Vaarala et al., 1998). Furthermore, ribosomal proteins L7a might be associated with malignant brain tumor formation (Kroes et al., 2000).

Heparan Sulfate 2-O-Sulfotransferase 1 (HS2ST1)

Heparan sulfate 2-O-sulfotransferase 1 is an enzyme that in humans is encoded by the HS2ST1 gene. Heparan sulfate biosynthetic enzymes are key components in generating a myriad of distinct heparan sulfate fine structures that carry out multiple biologic activities. HS2ST1 transfer sulfate to the 2 position of the iduronic acid residue of heparan sulfate. The disruption of the HS2ST1 gene resulted in no kidney formation in knockout embryonic mice, indicating that the absence of this enzyme may interfere with the signaling required for kidney formation (Seki et al., 1997). HS2ST1 is involved in prostate cancer cell proliferation, invasion, and growth factor signalling (Ferguson and Datta, 2011). Increased gene expression of HS2ST1 in malignant compared to normal plasma cells was associated with a good prognosis (Bret et al., 2009).

Vimentin (VIM)

Vimentin, a major constituent of the intermediate filament (IF) family of proteins, is ubiquitously expressed in normal mesenchymal cells and is known to maintain cellular integrity and provide resistance against stress (Schietke et al., 2006). In recent years, vimentin has been recognized as a marker for epithelial-mesenchymal transition (EMT) (Thomson et al., 2005). Various reports show that vimentin plays an important role in cell migration (Eckes et al., 1998), (Eckes et al., 2000), (Kang and Massague, 2004). Vimentin has also been indicated in regulation of cell survival, cell adhesion and lipid transport (Sarria et al., 1992), (McInroy and Maatta, 2007), (Mendez et al., 2010). Increased vimentin expression has been reported in various tumor cell lines and tissues including prostate cancer, breast cancer, endometrial cancer, CNS tumors, malignant melanoma and gastrointestinal tumors including pancreatic, colorectal and hepatic cancers. Vimentin's overexpression in cancer correlates well with accelerated tumor growth, invasion, and poor prognosis.

Vimentin has been used as a molecular marker for GBM and astrocytomas (Shiras et al., 2003), (Yang et al., 1994). Further, a novel cell-penetrating peptide derived from the intermediate filament protein vimentin, called Vim-TBS.58-81 has recently been described. The authors show that it enters cells from a glioblastoma line via endocytosis where it distributes throughout the cytoplasm and nucleus (Balzeau et al., 2012).

Intraflagellar Transport 172 Homolog (*Chlamydomonas*) (IFT172)

IFT172, also known as Selective Lim-domain Binding protein (SLB), is a component of the Intraflagellar Transport (IFT) complex. Mutations that affect components of the IFT machinery are known to compromise the formation and function of cilia. Cilia play essential roles in the differentiation and survival of olfactory and retinal neurons and auditory hair cells (Scholey and Anderson, 2006). IFT172, a complex B subunit, plays an essential role in the flagellar entry of IFT-dynein (Williamson et al., 2012). Further, IFT172 is potentially required for early regulation of FGF8 at the midbrain-hindbrain boundary and maintenance of the isthmic organizer (Gorivodsky et al., 2009).

Gamma-Aminobutyric Acid (GABA) A Receptor, Beta 1 (GABRB1)/Gamma-Aminobutyric Acid (GABA) A Receptor, Beta 3 (GABRB3)

Gamma-aminobutyric acid receptor subunit beta-1 is a protein that in humans is encoded by the GABRB1 gene. The gamma-aminobutyric acid (GABA) A receptor is a multisubunit chloride channel that mediates the fastest inhibitory synaptic transmission in the central nervous system. This gene encodes GABA A receptor, beta 1 subunit. It is mapped to chromosome 4p12 in a cluster of genes encoding alpha 4, alpha 2 and gamma 1 subunits of the GABA A receptor. Alteration of this gene is implicated in the pathogenetics of schizophrenia (Vasquez et al., 2013). Gamma-aminobutyric acid receptor subunit beta-3 is a protein that in humans is encoded by the GABRB3 gene. This gene is located on the long arm of chromosome 15 in a cluster with two genes encoding related subunits of the family. Mutations in this gene may be associated with the pathogenesis of Angelman syndrome, Prader-Willi syndrome, and autism (Nurmi et al., 2003).

Cell Division Cycle Associated 7-Like (CDCA7L)

Cell division cycle-associated 7-like protein is a protein that in humans is encoded by the CDCA7L gene (Ou et al., 2006). CDCA7L shows nuclear colocalization with c-Myc, and interacts with c-Myc both in vitro and in mammalian cells (Huang et al., 2005). CDCA7L inhibited the MAOA promoter and MAOA enzymatic activity and acted as a repressor in apoptotic signaling pathways (Ou et al., 2006). CDCA7L is a Myc interactor associated with metastatic medulloblastoma (Zhou et al., 2010).

Signal Sequence Receptor, Alpha (SSR1)

Translocon-associated protein subunit alpha is a protein that in humans is encoded by the SSR1 gene. The signal sequence receptor (SSR) is a glycosylated endoplasmic reticulum (ER) membrane receptor associated with protein translocation across the ER membrane. The SSR consists of 2 subunits, a 34-kD glycoprotein encoded by this gene and a 22-kD glycoprotein (Hirama et al., 1999). SSR1 was detected in 50% of medulloblastomas and in 78% of primitive neuroectodermal tumors (Johnson et al., 2013).

Nuclear Receptor Subfamily 0, Group B, Member 1 (NR0B1)

NR0B1 (also called dosage-sensitive sex reversal/adrenal hypoplasia congenital critical region on the X chromosome 1; DAX1) acts as a negative regulator of steroid production, and is expressed in the reproductive and endocrine systems (Niakan and McCabe, 2005). NR0B1 is highly expressed in several kinds of cancers, such as endometrial carcinoma (Saito et al., 2005), ovarian carcinoma (Abd-Elaziz et al., 2003), prostatic carcinoma (Nakamura et al., 2009), and Ewing's sarcoma (Mendiola et al., 2006; Camoes et al., 2012; Kinsey et al., 2006). In lung adenocarcinoma, higher levels of NR0B1 expression correlated with higher rates of lymph node metastasis and recurrence (Oda et al., 2009).

Ligand of Numb-Protein X 1, E3 Ubiquitin Protein Ligase (LNX1)

E3 ubiquitin-protein ligase LNX is an enzyme that in humans is encoded by the LNX1 gene. Studies have approved that LNX1 could participate in signal transduction, such as Notch pathway, and play an important role in tumorigenesis. Some results suggested that down-regulation of LNX1 could result in cell cycle arrest in G0/G1 phase through inhibition of β-catenin, MAPK, NFκB, c-Myc-dependent pathway and activation of p53, TGF-β-dependent pathway (Zheng et al., 2011). Gene sequence alterations and amplifications of LNX1 are present in a subset of human gliomas (Blom et al., 2008; Holtkamp et al., 2007). Human LNX1 was downregulated in gliomas including low- and high-grade ones (Chen et al., 2005).

E1A Binding Protein p400 (EP400)

E1A-binding protein p400 is a protein that in humans is encoded by the EP400 gene. p400 is a mediator of E1A-induced downregulation of epidermal growth factor receptor and of apoptosis (Flinterman et al., 2007; Samuelson et al., 2005). Mutations in the EP400 Gene were described for near haploid lymphoblastic leukemia patients (Chen et al., 2013a). Further, a genome-wide siRNA screen identified EP400 as a regulator of human papillomavirus oncogene expression (Smith et al., 2010). The p400/Tip60 ratio is critical for colon cancer cells proliferation and response to therapeutic drugs through the control of stress-response pathways (Mattera et al., 2009).

Kinesin Family Member 1B (KIF1B)

The KIF1B gene on 1p36, a region commonly deleted in neural crest cancers, was found to be a proapoptotic factor for sympathetic precursors. KIF1B beta mutations were detected in pheochromocytomas and neuroblastomas, two sympathetic lineage tumors, suggesting a role for this gene in cancer (Yeh et al., 2008). The KIF1B-related pathway might be involved in the pathogenesis of hepatitis B virus-related hepatocellular carcinoma (Casper et al., 2011). KIF1B is down-regulated in high stage neuroblastomas (Caren et al., 2005; Ohira et al., 2000; Nagai et al., 2000). Cell surface localization of MT1-MMP is dependent on KIF1B, which consequently plays a critical role in gastric cancer invasion (Dong et al., 2013). KIF1B is associated with pheochromocytomas, a neuroendocrine tumor (Galan and Kann, 2013).

Rho-Related BTB Domain Containing 3 (RHOBTB3)

Rho-related BTB domain-containing protein 3 is a protein that in humans is encoded by the RHOBTB3 gene. RHOBTB3 is a member of the evolutionarily conserved RhoBTB subfamily of Rho GTPases (Rivero et al., 2001; Boureux et al., 2007). RHOBTB genes are upregulated in some cancer cell lines, suggesting that these proteins might participate in tumorigenesis (Ramos et al., 2002). Berthold et al. (2008) also described a potential role of the RhoBTB subfamily in tumorigenesis (Berthold et al., 2008b). A decreased expression of RHOBTB and CUL3 genes in kidney and breast tumor samples was observed (Berthold et al., 2008a).

Kinesin Family Member 7 (KIF7)

The KIF7 gene encodes a cilia-associated protein belonging to the kinesin family. This protein plays a role in the sonic hedgehog (SHH) signaling pathway through the regulation of GLI transcription factors (Li et al., 2012b). It functions as a negative regulator of the SHH pathway by preventing inappropriate activation of GLI2 in the absence of ligand, and as a positive regulator by preventing the processing of GLI3 into its repressor form. KIF7 is implicated in a variety of diseases including Joubert, hydrolethalus and acrocallosal syndromes. It is also involved in primary cilium formation and the Hedgehog signalling pathway and may play a role in cancer (Klejnot and Kozielski, 2012). Aberrant activation of Hedgehog signaling pathway leads to pathological consequences in a variety of human tumors, such as gastric cancer and pancreatic cancer. KIF7 is implicated in the Hedgehog signaling (Katoh and Katoh, 2005).

Mitogen-Activated Protein Kinase 6 (MAPK6)

Mitogen-activated protein kinase 6 (MAPK6, also called ERK3) is an enzyme that in humans is encoded by the MAPK6 gene. MAPK6 is a member of the Ser/Thr protein kinase family, and is most closely related to mitogen-activated protein kinases (MAP kinases). There is an increase in ERK3 transcripts in oral cancer tissue compared to healthy tissue; colorectal cancer tissues had higher ERK3 expression levels that adjacent normal mucosa. Elevated ERK3 protein levels are also associated with gastric cancer. Increased ERK3 transcripts or protein levels have also been observed in breast cancer, melanoma and non-small cancer lung cells (Kostenko et al., 2012). Certain observations suggest that ERK3 may play some roles in tumor suppression, including its apparent negative regulatory effect on cell cycle progression, cell proliferation, and migration (Cargnello and Roux, 2011).

Asp (Abnormal Spindle) Homolog, Microcephaly Associated (*Drosophila*) (ASPM)

Abnormal spindle-like microcephaly associated (ASPM) is the human orthologue of the *Drosophila* abnormal spindle (asp). ASPM have been implicated in spindle organization, spindle orientation, mitotic progression, and cytokinesis (Van et al., 2009); (Higgins et al., 2010). ASPM overexpression, like many Wnt-activating components, is associated with increased cell proliferation and tumor development, supporting a common effect on proliferation (Lin et al., 2008); (Bikeye et al., 2010); (Vulcani-Freitas et al., 2011). As overexpression of ASPM was observed in several tumor cells lines and reduction of ASPM levels inhibited cellular proliferation, most publications suggest ASPM as novel target in cancer therapy. In glioblastoma multiforme, ASPM is highly overexpressed as compared to normal brain and other body tissues (Horvath et al., 2006). Several studies have found that ASPM expression levels have a strong positive correlation with the malignant phenotype and WHO grade of glioma, as ASPM was overexpressed in GBM as compared to astrocytomas and expression increased at recurrence (Bikeye et al., 2010; Bikeye et al., 2011; Hagemann et al., 2008; Marie et al., 2008). It was suggested that ASPM is involved in the malignant progression of glioma and represents an attractive therapeutic target. ASPM expression negatively correlates with clinical outcome in GBM (Horvath et al., 2006; Visnyei et al., 2011).

Structural Maintenance of Chromosomes 4 (SMC4)

Structural maintenance of chromosomes (SMC) proteins are chromosomal ATPases, highly conserved from bacteria to humans, that play fundamental roles in many aspects of higher-order chromosome organization and dynamics (Losada and Hirano, 2005). The SMC4 protein is a core component of the condensin complex that plays a role in chromatin condensation and has also been associated with nucleolar segregation, DNA repair, and maintenance of the chromatin scaffold (Cervantes et al., 2006). SMC2 and SMC4 function as the core of the condensin complexes that are essential for chromosome assembly and segregation (Losada and Hirano, 2005). RT-PCR studies on human cancer samples show that the RNA is expressed highly in many cancer cell lines and cancer specimens, including human breast cancers, prostate cancers, colon cancers, and pancreatic cancers (Egland et al., 2006).

Thioredoxin 2 (TXN2)

TXN2 encodes a mitochondrial member of the thioredoxin family, a group of small multifunctional redox-active proteins. The encoded protein may play important roles in the regulation of the mitochondrial membrane potential and in protection against oxidant-induced apoptosis (Tanaka et al., 2002). TXN and TXN2 regulate the proliferation and survival of adipose tissue-derived mesenchymal stem cells, and these processes are mediated by the activation of ERK1/2 (Song et al., 2011). Because of its role in stimulating cancer cell growth and as an inhibitor of apoptosis, thioredoxin offers a target for the development of drugs to treat and prevent cancer. The protein TXN2 is linked to breast cancer (Seibold et al., 2011) and therefore the peptide SEQ ID No 99 is also useful in this indication.

The protein CSRP2 is linked to hepatocellular carcinoma (Midorikawa et al., 2002) and therefore the peptide SEQ ID No 1 is also useful in this indication.

The protein ELOVL2 is linked to hepatocellular carcinoma (Zekri et al., 2012) and therefore the peptide SEQ ID No 3 is also useful in this indication.

The protein KIF1A is linked to head and neck squamous cell carcinoma (Demokan et al., 2010; Kaur et al., 2010; Loyo et al., 2011; Pattani et al., 2010; Guerrero-Preston et al., 2011), neuroblastoma (Hartomo et al., 2013), lung cancer (Loyo et al., 2011), thyroid cancer and breast cancer (Brait et al., 2012; Ostrow et al., 2009) and therefore the peptide SEQ ID No 6 is also useful in these indications.

The protein GRIK3 is linked to rhabdomyosarcoma/medulloblastoma, neuroblastoma, thyroid carcinoma, lung cancer, astrocytoma, multiple myeloma, T cell leukemia cells, breast cancer and colon adenocarcinoma (Stepulak et al., 2009) and therefore the peptide SEQ ID No 8 is also useful in these indications.

The protein SEZ6L is linked to lung cancer (Raji et al., 2010; Gorlov et al., 2007), gastric carcinoma (Kang et al., 2008), colorectal cancer (Suzuki et al., 2002) and therefore the peptide SEQ ID No 9 is also useful in these indications.

The protein KCNJ10 is linked to astrocytoma (Tan et al., 2008) and therefore the peptide SEQ ID No 12 is also useful in this indication.

The protein SCARA3 is linked to ovarian cancer (Bock et al., 2012), prostate cancer (Zhu et al., 2009) and therefore the peptide SEQ ID No 16 is also useful in this indication.

The protein CLU is linked to primary gastric cancer (Bi et al., 2010), ovarian cancer (Yang et al., 2009), breast cancer (Niu et al., 2012), lung cancer (Panico et al., 2013), hepatocellular carcinoma (Chen et al., 2012a), colorectal cancer (Rodriguez-Pineiro et al., 2012), prostate cancer (Ammar and Closset, 2008), pancreatic cancer (Jin et al., 2012) and therefore the peptide SEQ ID No 18 is also useful in these indications.

The protein CERS1 is linked to head-and-neck squamous cell carcinoma (Senkal et al., 2007) and therefore the peptide SEQ ID No 19 is also useful in this indication.

The protein SLC35E1 is linked to rectal carcinoma (Rimkus et al., 2008) and therefore the peptide SEQ ID No 24 is also useful in this indication.

The protein COL20A1 is linked to breast cancer (Huang et al., 2013b) and therefore the peptide SEQ ID No 28 is also useful in this indication.

The protein EGFR is linked to renal cell carcinoma (Lee et al., 2008b), prostate cancer (Wang et al., 2013), lung cancer (Bivona et al., 2011), melanoma (Girotti et al., 2013), head and neck squamous cell carcinoma (Deng et al., 2013), breast cancer (Li et al., 2009), colon cancer (Yokoi et al., 2005), and therefore the peptide SEQ ID No 29 is also useful in these indications.

The protein WLS is linked to melanoma (Yang et al., 2012b) and the protein MIER1 is linked to breast cancer (McCarthy et al., 2008) and therefore the peptide SEQ ID No 31 is also useful in these indications.

The protein IRS2 is linked to breast cancer (Clark et al., 2011), prostate cancer (Heni et al., 2012), gastric cancer (Zhao et al., 2012a), ovarian cancer (Meunier et al., 2010), endometrial cancer (Cayan et al., 2010) and therefore the peptide SEQ ID No 32 is also useful in these indications.

The protein TNC is linked to colon cancer (De et al., 2013), adenoid cystic carcinoma (Siu et al., 2012), juvenile nasopharyngeal angiofibroma (Renkonen et al., 2012), advanced melanoma (Fukunaga-Kalabis et al., 2010), pancreatic cancer (Paron et al., 2011) and therefore the peptide SEQ ID No 34 is also useful in these indications.

The protein MAP1B is linked to neuroblastoma (Willoughby et al., 2008) and therefore the peptides SEQ ID No 35 and No 47 is also useful in this indication.

The protein ADORA3 is linked to prostate cancer (Jajoo et al., 2009), hepatocellular carcinoma (Bar-Yehuda et al., 2008), primary thyroid cancer (Morello et al., 2008), colon carcinoma (Gessi et al., 2004), bladder cancer (Kim et al., 2010) and therefore the peptide SEQ ID No 37 is also useful in this indication.

The protein NLGN4X is linked to gastrointestinal stromal tumor (Prakash et al., 2005) and therefore the peptide SEQ ID No 39 is also useful in this indication.

The protein DPP3 is linked to primary ovarian carcinoma (Simaga et al., 2003) and therefore the peptide SEQ ID No 41 is also useful in this indication.

The protein USP11 is linked to breast cancer (Bayraktar et al., 2013), pancreatic ductal adenocarcinoma (Burkhart et al., 2013) and therefore the peptide SEQ ID No 42 is also useful in this indication.

The protein EIF4E is linked to breast cancer (Zindy et al., 2011), cervical cancer (Wang et al., 2013), nasopharyngeal carcinoma (Wu et al., 2013), gastric cardiac adenocarcinoma (Yang et al., 2013), liver cancer (Wang et al., 2012b), laryngeal carcinoma (Yi et al., 2012), pancreatic cancer (Martineau et al., 2013), melanoma (Populo et al., 2012), NSCLC (Li et al., 2012a), head and neck squamous cell carcinoma (Sunavala-Dossabhoy et al., 2011), liver cancer (Cillo et al., 2011), prostate cancer (Hay, 2010; Furic et al., 2010), endometrial cancer (Choi et al., 2011) and therefore the peptide SEQ ID No 43 is also useful in these indications.

The protein CCT7 is linked to colon cancer (Nibbe et al., 2009) and therefore the peptide SEQ ID No 45 is also useful in this indication.

The protein SOX9 is linked to metastatic melanoma (Rao et al., 2010) and the protein SOX10 is linked to melanoma (Mohamed et al., 2012), salivary gland cancer (Ohtomo et al., 2013), breast carcinoma (Cimino-Mathews et al., 2013), and therefore the peptide SEQ ID No 49 is also useful in these indications.

The protein CDK4 is linked to lung cancer (Puyol et al., 2010), oral squamous cell carcinoma (Poomsawat et al., 2010), hepatocellular carcinoma (Chen et al., 2013b), breast cancer (Harrison Pitner and Saavedra, 2013) and therefore the peptide SEQ ID No 52 is also useful in this indication.

The protein CDK6 is linked to oral squamous cell carcinoma (Poomsawat et al., 2010), hepatocellular carcinoma (Chen et al., 2013b) and therefore the peptide SEQ ID No 52 is also useful in this indication.

The protein MAGEF1 is linked to lung cancer (Tsai et al., 2007), colorectal cancer patients (Chung et al., 2010) and therefore the peptide SEQ ID No 53 is also useful in these indications. The protein NLGN4X is linked to gastrointestinal stromal cancer (Prakash et al., 2005) and therefore the peptide SEQ ID No 55 is also useful in this indication.

The protein VPS13B is linked to gastric and colorectal cancer (An et al., 2012) and therefore the peptide SEQ ID No 56 is also useful in this indication.

The protein NRCAM is linked to papillary thyroid carcinoma (Gorka et al., 2007), colon cancer (Chan et al., 2011), prostate cancer (Tsourlakis et al., 2013) and therefore the peptide SEQ ID No 57 is also useful in these indications.

The protein RAD54B is linked to esophageal squamous cell carcinoma (Li et al., 2013a) and therefore the peptide SEQ ID No 58 is also useful in this indication.

The protein FABP7 is linked to renal cell carcinoma (Teratani et al., 2007), melanoma (Goto et al., 2006), breast cancer (Liu et al., 2012a) and therefore the peptides SEQ ID No 59 and No 80 are also useful in these indications.

The protein TACC3 is linked to lung cancer (Jung et al., 2006) and therefore the peptide SEQ ID No 62 is also useful in this indication.

The protein IGF2BP3 is linked to gastric cancer (Wang et al., 2010; Okada et al., 2012), hepatocellular carcinoma (Wachter et al., 2012), tongue squamous cell carcinoma (Li et al., 2011a), oral cancer (Hwang et al., 2012), and renal cell carcinoma (Jiang et al., 2006), hepatocellular carcinoma (Riener, 2011), invasive squamous cell carcinoma (Lu et al., 2011), neuroblastoma (Chen et al., 2011), squamous cell carcinoma of the lung (Kobayashi et al., 2004; Findeis-Hosey and Xu, 2012), glioblastoma (Suvasini et al., 2011), pancreatic ductal adenocarcinoma (Yantiss et al., 2008; Schaeffer et al., 2010; Wachter et al., 2011), primary adenoid cystic carcinomas of the breast (Vranic et al., 2011), prostate carcinomas (Ikenberg et al., 2010), thyroid carcinomas (Jin et al., 2010), endometrioid adenocarcinoma (Li et al., 2007), melanoma (Pryor et al., 2008) and ovarian cancer (Gu et al., 2004) and therefore the peptide SEQ ID No 66 is also useful in these indications.

The protein DROSHA is linked to breast cancer (Passon et al., 2012), with ovarian cancer (Merritt et al., 2008), endometrial cancer (Torres et al., 2011), cervical cancer (Zhou et al., 2013), gastric cancer (Tchernitsa et al., 2010), colorectal carcinoma (Papachristou et al., 2011), bladder cancer (Han et al., 2013), esophageal cancers (Sugito et al., 2006), renal cell carcinoma (Lin et al., 2010b), lung cancer survival (Rotunno et al., 2010), and therefore the peptide SEQ ID No 67 is also useful in these indications.

The protein ABCA13 is linked to breast carcinoma (Hlavac et al., 2013), colorectal carcinoma (Hlavata et al., 2012) and therefore the peptide SEQ ID No 68 is also useful in these indications.

The protein CCNB1 is linked to colorectal carcinoma (Li et al., 2003), RCC (Tsavachidou-Fenner et al., 2010), breast cancer (Aaltonen et al., 2009; Agarwal et al., 2009; Suzuki et al., 2007; Chae et al., 2011), medulloblastoma (de et al., 2008), squamous cell lung cancer (Kettunen et al., 2004), gastrointestinal stromal tumors (Koon et al., 2004), esophageal squamous cell carcinoma (Song et al., 2008), laryngeal squamous cell carcinoma (Dong et al., 2002), oral tongue squamous cell carcinoma (Harada et al., 2006), adrenocortical carcinomas (Soon et al., 2009), pulmonary adenocarcinoma (Wikman et al., 2002), non-small cell lung cancer (Cooper et al., 2009), cervical cancer (Zhao et al., 2006), prolactin pituitary tumors (Raverot et al., 2010) and renal cell carcinoma (Ikuerowo et al., 2006) and therefore the peptide SEQ ID No 69 is also useful in these indications.

The protein CNOT1 is linked to breast cancer (Winkler et al., 2006) and therefore the peptide SEQ ID No 70 is also useful in this indication.

The protein BIRC5 is linked to breast cancer (Yamashita et al., 2007; Al-Joudi et al., 2007; Span et al., 2004), esophageal cancer (Sato et al., 2006), colorectal cancer (Tan et al., 2005), clear cell renal cell carcinoma (Kosari et al., 2005), pancreatic cancer (Mahlamaki et al., 2002), squamous cell carcinoma (Lo et al., 2001), lung cancer (Krepela et al., 2009) and in neuroblastoma (Lamers et al., 2011) and therefore the peptide SEQ ID No 72 is also useful in these indications.

The protein ZNF3 is linked to head and neck squamous cell carcinoma (Nichols et al., 2012) and therefore the peptide SEQ ID No 81 is also useful in this indication.

The protein PJA2 is linked to thyroid cancer (Cantara et al., 2012) and therefore the peptide SEQ ID No 84 is also useful in this indication.

The protein GPM6B is linked to ovarian cancer (Urban et al., 2011) and therefore the peptide SEQ ID No 86 is also useful in this indication.

The protein OLIG2 is linked to breast cancer (Kamalakaran et al., 2011) and therefore the peptide SEQ ID No 91 is also useful in this indication.

The protein VCAN is linked to ovarian cancer (Zhang et al., 2012), breast cancer (Nara et al., 1997), colon cancer (Yoon et al., 2002), skin cancer (Kunisada et al., 2011), lung cancer (Rotunno et al., 2011), renal cell carcinoma (Dondeti et al., 2012) and therefore the peptide SEQ ID No 92 is also useful in these indications.

The protein SMOX is linked to prostate cancer (Goodwin et al., 2008), breast cancer (Cervelli et al., 2010) and therefore the peptide SEQ ID No 93 is also useful in these indications.

The protein EXOC7 is linked to breast cancer (Yau et al., 2010) and therefore the peptide SEQ ID No 94 is also useful in this indication.

The protein LZTS1 is linked to prostate cancer (Hawkins et al., 2002), lung cancer (Lin et al., 2013), bladder cancer (Abraham et al., 2007) and breast cancer (Chen et al., 2009) and therefore the peptide SEQ ID No 95 is also useful in these indications.

The protein FADS2 is linked to hepatocellular carcinoma (Muir et al., 2013), breast cancer (Pender-Cudlip et al., 2013) and therefore the peptide SEQ ID No 96 is also useful in this indication.

The protein ASCL1 is linked to lung cancer (Borges et al., 1997; Jiang et al., 2004; Osada et al., 2005), neuroblastomas (Singh et al., 2004), medullary thyroid carcinomas (Kastan et al., 1990), breast cancer (Righi et al., 2012), prostate cancer (Rapa et al., 2008), gastrointestinal NECs (Shida et al., 2005) and therefore the peptide SEQ ID No 98 is also useful in these indications.

The protein NKAIN2 is linked to prostate cancer (Mao et al., 2011) and therefore the peptide SEQ ID No 100 is also useful in this indication.

The protein PCDHG A12 is linked to bladder cancer (Reinert et al., 2011), lung cancer (Lu et al., 2006), the protein PCDHGC3 is linked to colorectal carcinoma (Dallosso et al., 2012), the protein PCDHGC4 is linked to neuroblastoma (Abe et al., 2008), the protein PCDHGB6 is linked to breast cancer (Miyamoto et al., 2005), and therefore the peptide SEQ ID No 101 is also useful in these indications.

The protein ARHGAP21 is linked to head and neck squamous cell carcinoma (Lazarini et al., 2013) and therefore the peptide SEQ ID No 102 is also useful in this indication.

The protein PNMA2 is linked to testicular cancer (Mathew et al., 2007), breast cancer (Sahashi et al., 2003), lung cancer (Barnett et al., 2001), small intestine neuroendocrine tumors and liver metastasis (Leja et al., 2009) and therefore the peptide SEQ ID No 103 is also useful in these indications.

The protein APC is linked to sporadic colorectal and gastric cancers (Rubinfeld et al., 1993), lung cancer (Usadel et al., 2002), breast cancer (Van, I et al., 2008), bladder cancer (Ellinger et al., 2008), prostate cancer (Richiardi et al., 2013), and therefore the peptide SEQ ID No 105 is also useful in these indications.

The protein WASL is linked to breast cancer (Escudero-Esparza et al., 2012), esophageal squamous cell carcinomas (Li et al., 2013a), hepatocellular carcinoma (Jin et al., 2013) and therefore the peptide SEQ ID No 106 is also useful in these indications.

The protein BMP7 is linked to esophageal squamous cell carcinoma (Megumi et al., 2012), gastric cancer (Aoki et al., 2011), hepatocellular carcinoma (Li et al., 2013a), CRC (Motoyama et al., 2008), lung cancer (Liu et al., 2012b), prostate cancer (Kobayashi et al., 2011), breast cancer (Rodriguez-Martinez et al., 2011), melanoma (Na et al., 2009), and therefore the peptide SEQ ID No 112 is also useful in these indications.

The protein ITGA7 is linked to melanoma (Kramer et al., 1989), squamous cell carcinoma of the tongue (Carinci et al., 2005), oral squamous cell carcinoma (Richter et al., 2011), hepatocellular carcinoma (Ren et al., 2007) and therefore the peptide SEQ ID No 113 is also useful in these indications.

The protein RPL7A is linked to colorectal cancer (Wang et al., 2000), prostate cancer (Vaarala et al., 1998) and therefore the peptide SEQ ID No 114 is also useful in these indications.

The protein HS2ST1 is linked to prostate cancer (Ferguson and Datta, 2011) and therefore the peptide SEQ ID No 115 is also useful in this indication.

The protein VIM is linked to prostate cancer (Burch et al., 2013), gastric cancer (Zhao et al., 2013), esophageal squamous cell carcinoma (Jin et al., 2010), hepatocellular carcinoma (Hu et al., 2004), colorectal cancer (Shirahata et al., 2009), pancreatic cancer (Zou et al., 2007), breast cancer (Gilles et al., 2003), melanoma (Hendrix et al., 1992), lung cancer (Upton et al., 1986), cervical cancer (Gilles et al., 1996), clear cell renal cell carcinoma (Williams et al., 2009), certain type of lymphomas (Gustmann et al., 1991), papillary thyroid carcinoma (Yamamoto et al., 1992) and endometrial carcinomas (Coppola et al., 1998) and therefore the peptide SEQ ID No 116 is also useful in these indications.

The protein CDCA7L is linked to metastatic medulloblastoma (Zhou et al., 2010) and therefore the peptide SEQ ID No 119 is also useful in this indication.

The protein SCARA3 is linked to ovarian cancer (Bock et al., 2012) and therefore the peptide SEQ ID No 120 is also useful in this indication.

The protein SSR1 is linked to neuroectodermal tumors (Johnson et al., 2013) and therefore the peptide SEQ ID No 121 is also useful in this indication.

The protein NR0B1 is linked to endometrial carcinoma (Saito et al., 2005), ovarian carcinoma (Abd-Elaziz et al., 2003), prostatic carcinoma (Nakamura et al., 2009), and Ewing's sarcoma (Mendiola et al., 2006; Camoes et al., 2012; Kinsey et al., 2006), lung adenocarcinoma (Oda et al., 2009) and therefore the peptide SEQ ID No 122 is also useful in these indications.

The protein EP400 is linked to colon cancer (Mattera et al., 2009) and therefore the peptide SEQ ID No 124 is also useful in this indication.

The protein KIF1B is linked to hepatocellular carcinoma (Casper et al., 2011), neuroblastomas (Caren et al., 2005; Ohira et al., 2000; Nagai et al., 2000), gastric cancer invasion (Dong et al., 2013) and therefore the peptides SEQ ID No 125 and No 128 are also useful in these indications.

The protein RHOBTB3 is linked to in kidney and breast cancers (Berthold et al., 2008a) and therefore the peptide SEQ ID No 126 is also useful in these indications.

The protein KIF7 is linked to gastric cancer and pancreatic cancer (Katoh and Katoh, 2005) and therefore the peptide SEQ ID No 127 is also useful in these indications.

The protein MAPK6 is linked to oral cancer, colorectal cancer, gastric cancer, breast cancer, melanoma and lung cancer (Kostenko et al., 2012) and therefore the peptide SEQ ID No 129 is also useful in these indications.

The protein ASPM is linked to hepatocellular carcinoma (Lin et al., 2008), medulloblastoma (Vulcani-Freitas et al., 2011; Salsano et al., 2012), lung cancer (Jung et al., 2009), ovarian cancer (Bruning-Richardson et al., 2011), and therefore the peptide SEQ ID No 130 is also useful in these indications.

The protein SMC4 is linked to breast cancers, prostate cancers, colon cancers, and pancreatic cancers (Egland et al., 2006) and therefore the peptide SEQ ID No 131 is also useful in these indications.

Preferred is the use of a peptide according to the present invention, the nucleic acid, the TCR, the antibody or the expression vector according to the present invention, the cell according to the present invention, or an activated cytotoxic T lymphocyte produced according to the present invention for the treatment of cancer or for the manufacture of a medicament against cancer, wherein said medicament preferably is a vaccine. Preferably, said cancer is selected from astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, gangliogliomas, gangliocytoma, central gangliocytoma, primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma), glioblastoma prostate tumor, breast cancer, esophageal cancer, colon cancer, colorectal cancer, renal cell carcinoma, clear cell renal cell carcinoma, lung cancer, CNS, ovarian, melanoma pancreatic cancer, squamous cell carcinoma, leukemia and medulloblastoma, and other tumors or cancers showing an overexpression of survivin and/or the other proteins as described herein.

Another aspect of the present invention relates to a kit, comprising: (a) a container that contains a pharmaceutical composition containing a peptide according to the present invention, the nucleic acid or the expression vector according to the present invention, a cell according to the present invention, or an activated cytotoxic T lymphocyte according to the present invention, in solution or in lyophilized form; (b) optionally, a second container containing a diluent or reconstituting solution for the lyophilized formulation; (c) optionally, at least one peptide selected from the group consisting of the peptides according to SEQ ID NOs 1 to 131, and (d) optionally, instructions for the use of the solution and/or the reconstitution and/or use of the lyophilized formulation.

Yet another aspect of the present invention relates to a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen.

Yet another aspect of the present invention relates to an antibody that specifically binds to a peptide according to the present invention, preferably that specifically binds to a human major histocompatibility complex (MHC) class I or II being complexed with the HLA-restricted antigen and/or the peptide according to the present invention, wherein the antibody preferably is a polyclonal antibody, monoclonal antibody and/or a chimeric antibody.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 and in case of MHC class II peptides they can be as long as 15, 16, 17, 18, 19, 20, 21, 22 or 23 amino acids in length.

Furthermore, the term "peptide" shall include salts of a series of amino acid residues, connected one to the other typically by peptide bonds between the alpha-amino and carbonyl groups of the adjacent amino acids. Preferably the salts are pharmaceutical acceptable salts.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8 to 14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

For therapeutic and diagnostic purposes, a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a non-mutated ("normal"), mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for a peptide" refers to a nucleotide sequence coding for the peptide including artificial (man-made) start and stop codons compatible for the biological system the sequence is going to be expressed.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated. The polypeptides can be in aqueous solution and the purity is than defined by compound purity not taking in account water and determinants used for the solution.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endo-nucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[I-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated. Preferably these substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The peptides of the invention can be elongated by up to four amino acids, meaning 1, 2, 3 or 4 amino acids can be added to either end in any combination between 4:0 and 0:4. Combinations of the elongations according to the invention can be depicted from the following table 3:

| C-terminus | N-terminus |
| --- | --- |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation can be the peptides of the original sequence of the protein or any other amino acid. The elongation can be used to enhance the stability or solubility of the peptides.

The term "T-cell response" means the specific proliferation and activation of effector functions induced by a peptide in vitro or in vivo. For WIC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the CTLs specific for a peptide of SEQ ID No. 1 to SEQ ID No. 49, SEQ ID No. 71, and SEQ IDs No. 74 to 129 are tested against (compared with) the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity. Substantially identical antigenic activity means stimulation of T cells in comparable frequencies or numbers with comparable avidity, effector or memory phenotype, similar response pattern.

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

Since both types of response, CD8 and CD4 dependent, contribute jointly and synergistically to the anti-tumor effect, the identification and characterization of tumor-associated antigens recognized by either CD8-positive CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and glioblastoma in particular. Furthermore, there is a need to identify factors that can be used in the treatment of cancer in general and glioblastoma in particular.

The present invention provides peptides that are useful in treating cancers/tumors, preferably brain cancers, even more preferably glioblastoms that over- or exclusively present the peptides of the invention. These peptides were shown by mass spectrometry to be naturally presented by HLA molecules on primary human glioblastoma samples (see example 1, and FIG. 1).

The source gene/protein (also designated "full-length protein" or "underlying protein") from which the peptides are derived were shown to be highly overexpressed in glioblastoma compared with normal tissues (see example 2, and FIG. 2 for glioblastoma) demonstrating a high degree of tumor association of the source genes. Moreover, the peptides themselves are strongly over-presented on tumor tissue but not on normal tissues (see example 1 and FIG. 3).

HLA-bound peptides can be recognized by the immune system, specifically T lymphocytes/T cells. T cells can destroy the cells presenting the recognized HLA/peptide complex, e.g. glioblastoma cells presenting the derived peptides.

Figure 3B:
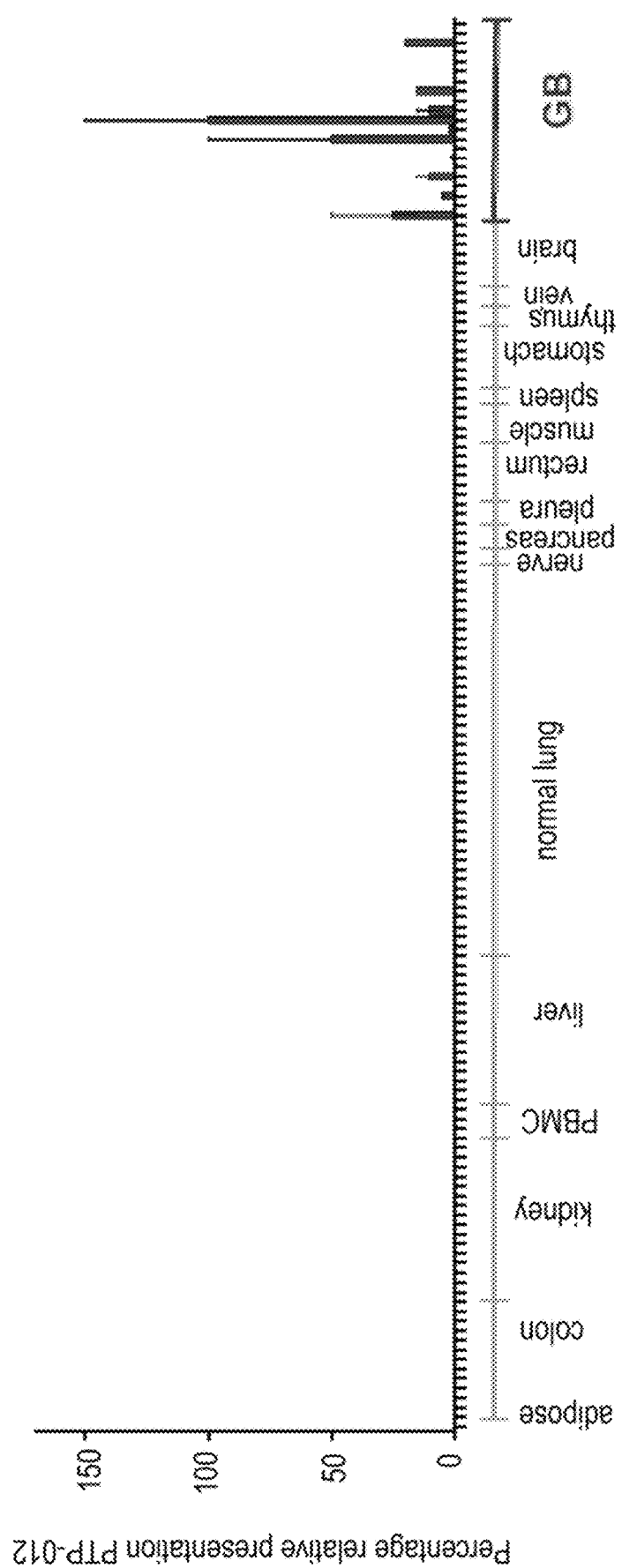
Figure 3C:
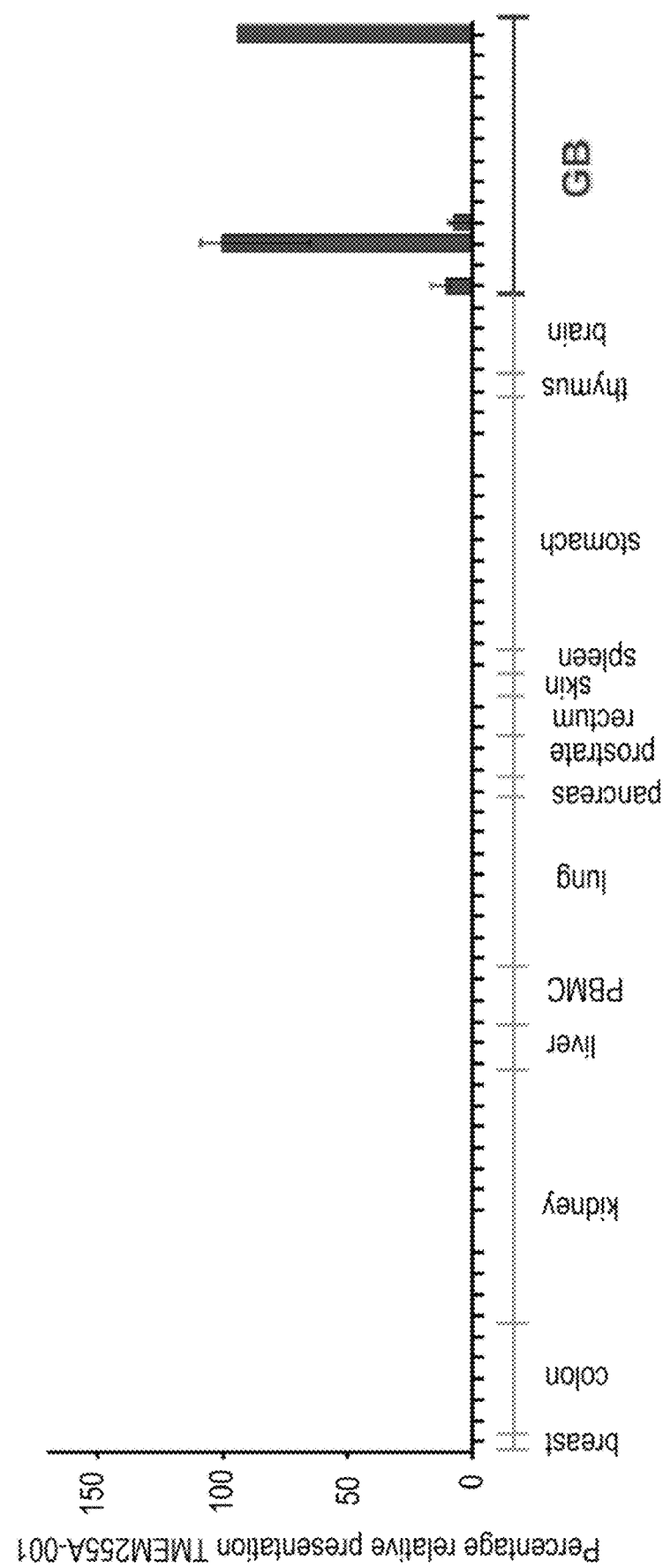
Figure 3D:
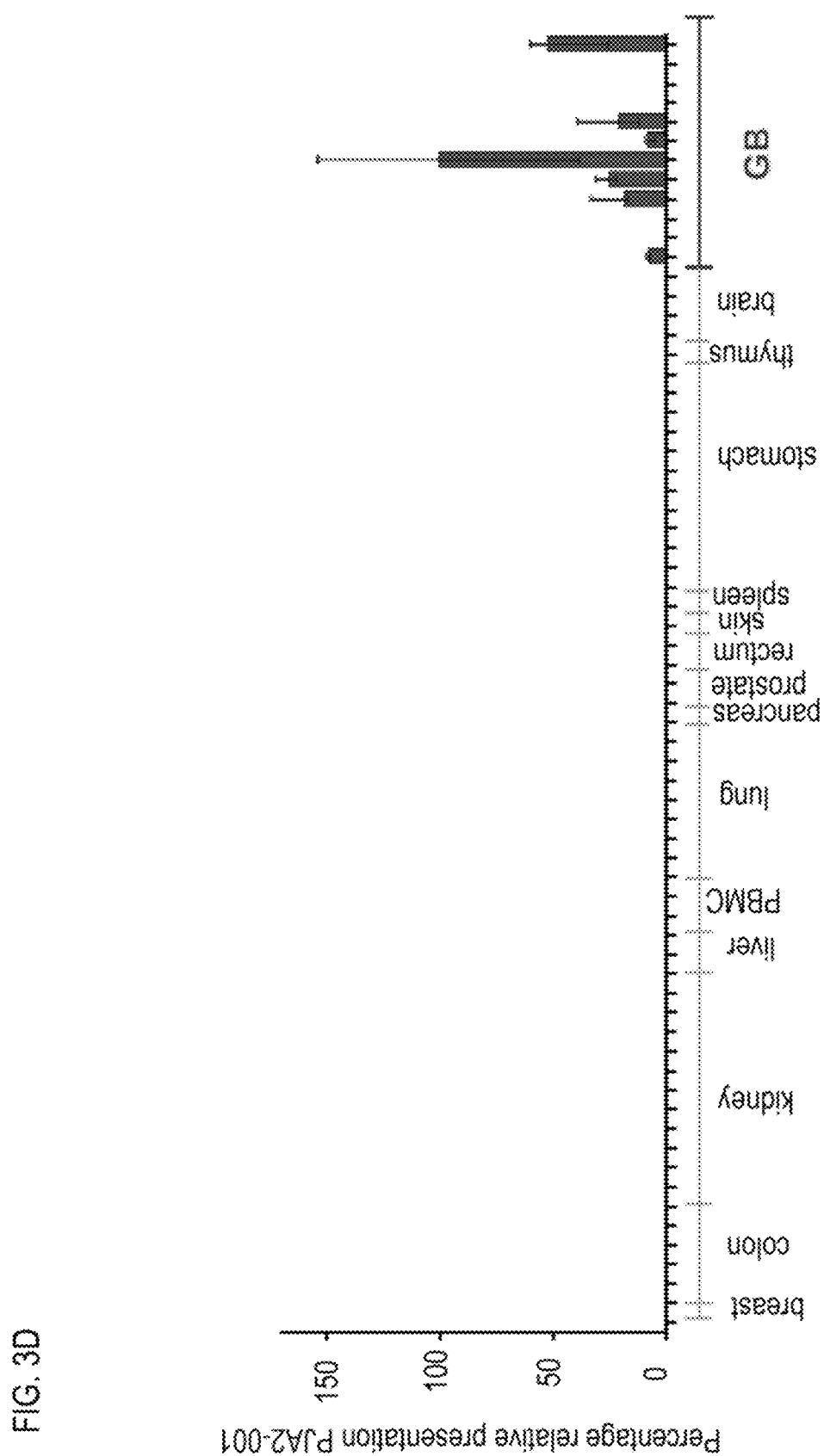
Figure 4:
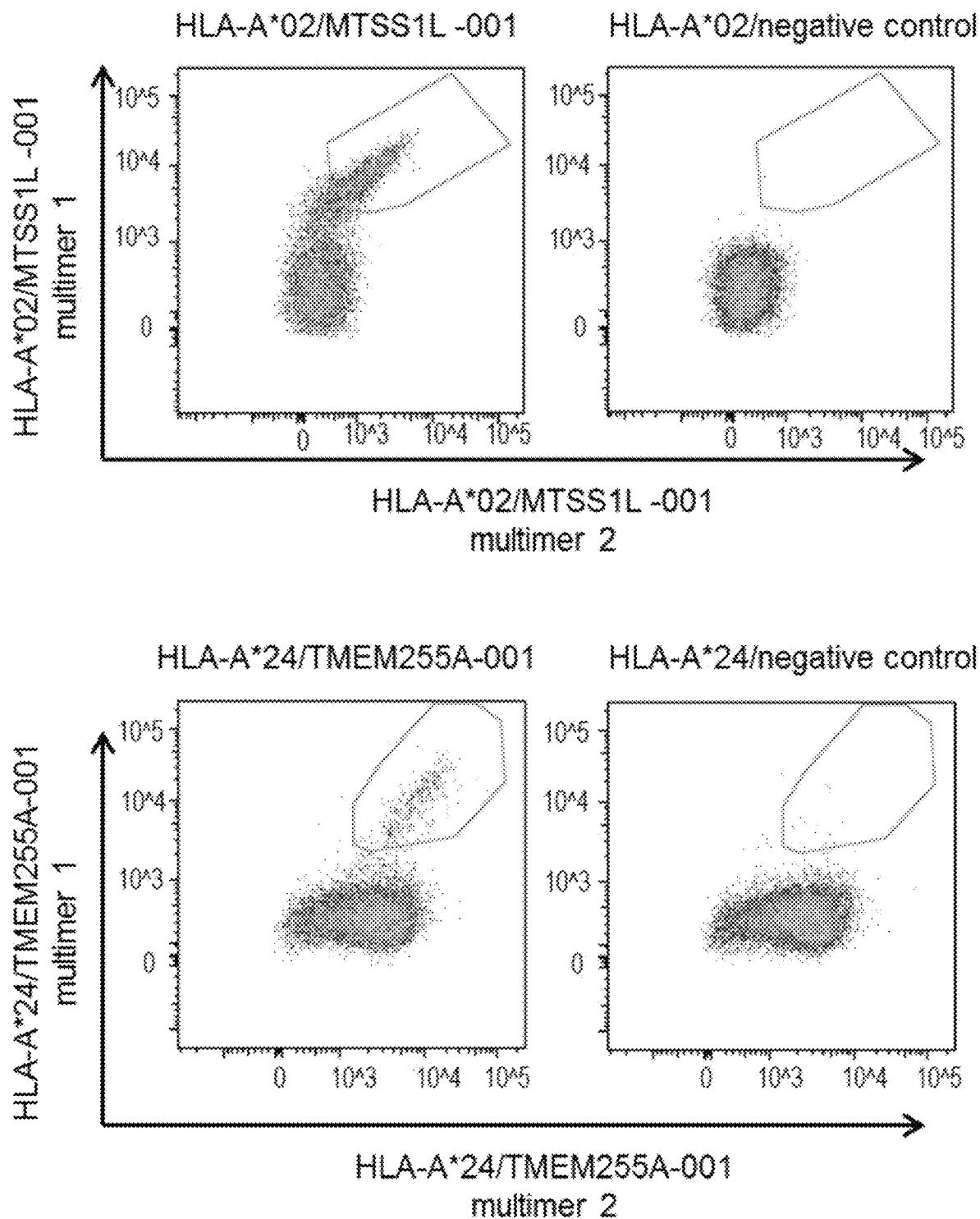
FIG. 4: Exemplary results of peptide-specific in vitro immunogenicity of class I TUMAPs for HLA*A02 and HLA*A24. Specific CD8+ T cells were stained with HLA multimers each linked to two different fluorochromes. Dot plots show MHC multimer-double-positive populations for the stimulating peptides (left panels) and the respective negative control stimulations (right panels).

The peptides of the present invention have been shown to be capable of stimulating T cell responses and/or are over-presented and can be used for the production of antibodies and/or sTCRs according to the present invention (see example 3 and 1 and FIGS. 4 and 3). Thus, the peptides are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt. As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), tri-fluor acetates or hydrochloric acid (chlorides).

In addition to being useful for treating cancer, the peptides of the present invention are also useful as diagnostics. Since the peptides were generated-from brain cancer cells and since it was determined that these peptides are not or at lower levels present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or sub-classification of diseased tissues. The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immunosurveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bispecific antibody and/or a chimeric antibody.

Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, Denkberg G, Lev A, Epel M, Reiter Y. Recombinant antibodies with WIC-restricted, peptide-specific, T-cell receptor-like specificity: new tools to study antigen presentation and TCR-peptide-WIC interactions. J Mol Recognit. 2003 September-October; 16(5):324-32.; Denkberg G, Lev A, Eisenbach L, Benhar I, Reiter Y. Selective targeting of melanoma and APCs using a recombinant antibody with TCR-like specificity directed toward a melanoma differentiation antigen. J Immunol. 2003 Sep. 1; 171(5):2197-207; and Cohen C J, Sarig O, Yamano Y, Tomaru U, Jacobson S, Reiter Y. Direct phenotypic analysis of human WIC class I antigen presentation: visualization, quantitation, and in situ detection of human viral epitopes using peptide-specific, WIC-restricted human recombinant antibodies. J Immunol. 2003 Apr. 15; 170(8):4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

It is a further aspect of the invention to provide a method for producing a soluble T-cell receptor recognizing a specific peptide-WIC complex. Such soluble T-cell receptors can be generated from specific T-cell clones, and their affinity can be increased by mutagenesis targeting the complementarity-determining regions. For the purpose of T-cell receptor selection, phage display can be used (US 2010-0113300, Liddy N, Bossi G, Adams K J, Lissina A, Mahon T M, Hassan N J, et al. Monoclonal TCR-redirected tumor cell killing. *Nat Med* 2012 June; 18(6):980-987). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (see Boulter J M, et al. Stable, soluble T-cell receptor molecules for crystallization and therapeutics. Protein Eng 2003 September; 16(9):707-711.; Card K F, Price-Schiavi S A, Liu B, Thomson E, Nieves E, Belmont H, et al. A soluble single-chain T-cell receptor IL-2 fusion protein retains MHC-restricted peptide specificity and IL-2 bioactivity. Cancer Immunol Immunother 2004 April; 53(4):345-357; and Willcox B E, Gao G F, Wyer J R, O'Callaghan C A, Boulter J M, Jones E Y, et al. Production of soluble alphabeta T-cell receptor heterodimers suitable for biophysical analysis of ligand binding. Protein Sci 1999 November; 8(11):2418-2423). The T-cell receptor can be linked to toxins, drugs, cytokines (see US20130115191), domains recruiting effector cells such as an anti-CD3 domain, etc., in order to execute particular functions on target cells. Moreover, it could be expressed in T cells used for adoptive transfer. Further information can be found in WO2004033685A1 and WO2004074322A1. A combination of sTCRs is described in WO2012056407A1. Further methods for the production are disclosed in WO2013057586A1.

In addition, they can be used to verify a pathologist's diagnosis of a cancer based on a biopsied sample.

To select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, D. Bates, S. DebRoy, Sarkar D., R Core team. nlme: Linear and Nonlinear Mixed Effects Models. 2008) adjusting for multiple testing by False Discovery Rate (Y. Benjamini and Y. Hochberg. Controlling the False Discovery Rate: A Practical and Powerful Approach to Multiple Testing. *Journal of the Royal Statistical Society. Series B (Methodological)*, Vol. 57 (No. 1):289-300, 1995).

In order to identify and to relatively quantify HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from glioblastoma samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary tumor tissue obtained from glioblastoma patients.

The proprietary discovery pipeline XPRESIDENT® v2.1 (see for example U.S. patent application Ser. No. 13/640,989 which is hereby incorporated in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from 32 HLA-A*02-restricted and 13 HLA-A*24-restricted shock-frozen glioblastoma tumor tissue samples were purified and HLA-associated peptides were isolated and analyzed by LC-MS.

All TUMAPs contained in the application at hand were identified with this approach on primary glioblastoma tumor samples confirming their presentation on primary glioblastoma.

TUMAPs identified on multiple glioblastoma tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention therefore relates to a peptide comprising a sequence that is selected from the group consisting of SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129 or a variant thereof that induces T cells cross-reacting with said peptide, wherein said peptide is not a full-length polypeptide.

The present invention further relates to a peptide comprising a sequence that is selected from the group consisting of SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129, wherein said peptide or variant has an overall length of between 8 and 100, preferably between 8 and 30, and most preferred between 8 and 14 amino acids.

The present invention further relates to the peptides previously described, having the ability to bind to a molecule of the human major histocompatibility complex (MHC) class-I or -II.

The present invention further relates to the peptides previously described wherein the peptide consists or consists essentially of an amino acid sequence according to SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129.

The present invention further relates to the peptides previously described, wherein the peptide is modified and/or includes non-peptide bonds.

The present invention further relates to the peptides previously described, wherein the peptide is a fusion protein, in particular comprising N-terminal amino acids of the HLA-DR antigen-associated invariant chain (Ii) according to SEQ ID No. 133.

The present invention further relates to a nucleic acid, encoding the peptides previously described, provided, that the peptide is not the full human protein.

The present invention further relates to the nucleic acid previously described that is DNA, cDNA, PNA, RNA or combinations thereof The present invention further relates to an expression vector capable of expressing a nucleic acid previously described.

The present invention further relates to a peptide as described before, a nucleic acid as described before or an expression vector as described before for use in medicine.

The present invention further relates to a host cell comprising a nucleic acid as described before or an expression vector as described before.

The present invention further relates to the host cell described that is an antigen presenting cell.

The present invention further relates to the host cell described wherein the antigen presenting cell is a dendritic cell.

The present invention further relates to a method of producing a peptide described, the method comprising culturing the host cell described and isolating the peptide from the host cell or its culture medium.

The present invention further relates to an in vitro method for producing activated cytotoxic T lymphocytes (CTL), the method comprising contacting in vitro CTL with antigen loaded human class I or II WIC molecules expressed on the surface of a suitable antigen-presenting cell for a period of time sufficient to activate said CTL in an antigen specific manner, wherein said antigen is any peptide described.

The present invention further relates to the method as described, wherein the antigen is loaded onto class I or II WIC molecules expressed on the surface of a suitable antigen-presenting cell by contacting a sufficient amount of the antigen with an antigen-presenting cell.

The present invention further relates to the method as described, wherein the antigen-presenting cell comprises an expression vector capable of expressing said peptide containing SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129 or said variant amino acid sequence.

The present invention further relates to activated cytotoxic T lymphocytes (CTL), produced by the method described, which selectively recognise a cell which aberrantly expresses a polypeptide comprising an amino acid sequence described.

The present invention further relates to a method of killing target cells in a patient which target cells aberrantly express a polypeptide comprising any amino acid sequence described, the method comprising administering to the patient an effective number of cytotoxic T lymphocytes (CTL) as defined.

The present invention further relates to the use of any peptide described, a nucleic acid as described, an expression vector as described, a cell as described, or an activated cytotoxic T lymphocyte as described as a medicament or in the manufacture of a medicament.

The present invention further relates to a use as described, wherein the medicament is a vaccine.

The present invention further relates to a use as described, wherein the medicament is active against cancer.

The present invention further relates to a use as described, wherein said cancer cells are glioblastoma or other brain tumor.

Furthermore, the present invention relates to a method for producing a personalized anti-cancer vaccine for an individual patient using a warehouse of prescreened tumor associated peptides, preferably according to the present invention and/or as described herein.

The present invention further relates to particular marker proteins and biomarkers that can be used in the prognosis of glioblastoma.

Furthermore, the present invention relates to the use of these novel targets for cancer treatment.

The term "antibodies" is used herein in a broad sense and includes both polyclonal and monoclonal antibodies. In addition to intact immunoglobulin molecules, also included in the term "antibodies" are fragments or polymers of those immunoglobulin molecules and humanized versions of immunoglobulin molecules, so long as they exhibit any of the desired properties (e.g., specific binding of an glioblastoma marker polypeptide, delivery of a toxin to an glioblastoma cell expressing a glioblastoma marker gene at an increased level, and/or inhibiting the activity of a glioblastoma marker polypeptide) described herein.

Whenever possible, the antibodies of the invention may be purchased from commercial sources. The antibodies of the invention may also be generated using well-known methods. The skilled artisan will understand that either full length glioblastoma marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding PTPRZ1, BCAN, and FABP7, or any other polypeptide according to SEQ ID No. 1 to SEQ ID No. 49, SEQ ID No. 71, and SEQ IDs No. 74 to 129 or a variant sequence thereof which is at least 90% homolog to SEQ ID No. 1 to SEQ ID No. 49, SEQ ID No. 71, and SEQ IDs No. 74 to 129, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the glioblastoma marker polypeptide used to generate the antibody.

One of skill in the art will know that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988). For example, the antibodies may be tested in ELISA assays, Western blots, immunohistochemical staining of formalin-fixed glioblastoma or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fe fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody for treating glioblastoma, the efficacy of the therapeutic antibody can be assessed in various ways well known to the skilled practitioner. For instance, the size, number, and/or distribution of glioblastoma in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of glioblastoma.

Because the glioblastoma markers PTPRZ1, BCAN, FABP7 and others of the invention are highly expressed in glioblastoma cells and are expressed at extremely low levels in normal cells, inhibition of PTPRZ1, BCAN, FABP7 expression or polypeptide activity may be integrated into any therapeutic strategy for treating or preventing glioblastoma.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of lung tumor marker function by antisense gene therapy may be accomplished by direct administration of antisense lung tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of gastric tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more antigenic (epitope) targets, and the affinity value (Kd) is less than 10 μM, preferably less than $10^{-3}$ μM, more preferably less than 10–6 μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the respective epitopes of peptides, polypeptides and/or MHC complexes in situ.

The present invention thus provides a peptide comprising a sequence that is selected from the group of consisting of SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129 or a variant thereof that will induce T cells cross-reacting with said peptide.

The peptides of the invention have the ability to bind to a molecule of the human major histocompatibility complex (MHC) class-I and/or class II.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm. Commonly available sequence analysis software, more specifically, Vector NTI, GENETYX or analysis tools provided by public databases.

A person skilled in the art will be able to assess, whether T cells induced by a variant of a specific peptide will be able to cross-react with the peptide itself (Fong et al., 2001); (Zaremba et al., 1997; Colombetti et al., 2006; Appay et al., 2006).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL.

These CTL can subsequently cross-react with cells and kill cells that express a polypeptide that contains the natural amino acid sequence of the cognate peptide as defined in the aspects of the invention. As can be derived from the scientific literature (Rammensee et al., 1997) and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129, by maintaining the known anchor residues, and would be able to determine whether such variants maintain the ability to bind MHC class I or II molecules. The variants of the present invention retain the ability to bind to the TCR of activated CTL, which can subsequently cross-react with- and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MEW. Thus, apart from the proviso given, the peptide of the invention may be any peptide (by which term the inventors include oligopeptide or polypeptide), which includes the amino acid sequences or a portion or variant thereof as given.

TABLE 4

Variants and motif of the peptides according to SEQ ID NO: 1, 2, 4, 51, 56 (A*02), 74, 75, 76, 80, 81, 84 (A*24)

| | | Position | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| CSRP2-001 SEQ ID 1 | Peptide Code Variant | | R | L | G | I | K | P | E | S | V | | | | | |
| | | | | | | | | | | | I | | | | | |
| | | | | | | | | | | | L | | | | | |
| | | | | | | | | | | | A | | | | | |
| | | | | M | | | | | | | | | | | | |
| | | | | M | | | | | | | I | | | | | |
| | | | | M | | | | | | | L | | | | | |
| | | | | M | | | | | | | A | | | | | |
| | | | | A | | | | | | | | | | | | |
| | | | | A | | | | | | | I | | | | | |
| | | | | A | | | | | | | L | | | | | |
| | | | | A | | | | | | | A | | | | | |
| | | | | V | | | | | | | | | | | | |
| | | | | V | | | | | | | I | | | | | |
| | | | | V | | | | | | | L | | | | | |
| | | | | V | | | | | | | A | | | | | |
| | | | | T | | | | | | | | | | | | |
| | | | | T | | | | | | | I | | | | | |
| | | | | T | | | | | | | L | | | | | |
| | | | | T | | | | | | | A | | | | | |
| | | | | Q | | | | | | | | | | | | |
| | | | | Q | | | | | | | I | | | | | |
| | | | | Q | | | | | | | L | | | | | |
| | | | | Q | | | | | | | A | | | | | |
| SLC10A4-001 SEQ ID 2 | Peptide Code Variant | | A | L | A | F | K | L | D | E | V | | | | | |
| | | | | | | | | | | | I | | | | | |
| | | | | | | | | | | | L | | | | | |
| | | | | | | | | | | | A | | | | | |
| | | | | M | | | | | | | | | | | | |
| | | | | M | | | | | | | I | | | | | |
| | | | | M | | | | | | | L | | | | | |
| | | | | M | | | | | | | A | | | | | |
| | | | | A | | | | | | | | | | | | |
| | | | | A | | | | | | | I | | | | | |
| | | | | A | | | | | | | L | | | | | |
| | | | | A | | | | | | | A | | | | | |
| | | | | V | | | | | | | | | | | | |

TABLE 4-continued

Variants and motif of the peptides according to SEQ ID NO: 1, 2, 4, 51, 56 (A*02), 74, 75, 76, 80, 81, 84 (A*24)

| | | Position | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | | | V | | | | | | | I | | | | | |
| | | | | V | | | | | | | L | | | | | |
| | | | | V | | | | | | | A | | | | | |
| | | | | T | | | | | | | | | | | | |
| | | | | T | | | | | | | I | | | | | |
| | | | | T | | | | | | | L | | | | | |
| | | | | T | | | | | | | A | | | | | |
| | | | | Q | | | | | | | | | | | | |
| | | | | Q | | | | | | | I | | | | | |
| | | | | Q | | | | | | | L | | | | | |
| | | | | Q | | | | | | | A | | | | | |
| MTSS1L-001 SEQ ID 4 | Peptide Code G Variant | | | L | P | S | G | A | P | P | G | V | | | | |
| | | | | | | | | | | | | I | | | | |
| | | | | | | | | | | | | L | | | | |
| | | | | | | | | | | | | A | | | | |
| | | | | M | | | | | | | | | | | | |
| | | | | M | | | | | | | I | | | | | |
| | | | | M | | | | | | | L | | | | | |
| | | | | M | | | | | | | A | | | | | |
| | | | | A | | | | | | | | | | | | |
| | | | | A | | | | | | | I | | | | | |
| | | | | A | | | | | | | L | | | | | |
| | | | | A | | | | | | | A | | | | | |
| | | | | V | | | | | | | | | | | | |
| | | | | V | | | | | | | I | | | | | |
| | | | | V | | | | | | | L | | | | | |
| | | | | V | | | | | | | A | | | | | |
| | | | | T | | | | | | | | | | | | |
| | | | | T | | | | | | | I | | | | | |
| | | | | T | | | | | | | L | | | | | |
| | | | | T | | | | | | | A | | | | | |
| | | | | Q | | | | | | | | | | | | |
| | | | | Q | | | | | | | I | | | | | |
| | | | | Q | | | | | | | L | | | | | |
| | | | | Q | | | | | | | A | | | | | |
| BCA-002 SEQID51 | Peptide Code A Variant | | | L | W | A | W | P | S | E | L | | | | | |
| | | | | | | | | | | | | V | | | | |
| | | | | | | | | | | | | I | | | | |
| | | | | | | | | | | | | A | | | | |
| | | | | M | | | | | | | V | | | | | |
| | | | | M | | | | | | | I | | | | | |
| | | | | M | | | | | | | | | | | | |
| | | | | M | | | | | | | A | | | | | |
| | | | | A | | | | | | | V | | | | | |
| | | | | A | | | | | | | I | | | | | |
| | | | | A | | | | | | | | | | | | |
| | | | | A | | | | | | | A | | | | | |
| | | | | V | | | | | | | V | | | | | |
| | | | | V | | | | | | | I | | | | | |
| | | | | V | | | | | | | | | | | | |
| | | | | V | | | | | | | A | | | | | |
| | | | | T | | | | | | | V | | | | | |
| | | | | T | | | | | | | I | | | | | |
| | | | | T | | | | | | | | | | | | |
| | | | | T | | | | | | | A | | | | | |
| | | | | Q | | | | | | | V | | | | | |
| | | | | Q | | | | | | | I | | | | | |
| | | | | Q | | | | | | | | | | | | |
| | | | | Q | | | | | | | A | | | | | |
| VPS13B-001 SEQ ID 56 | Peptide Code S Variant | | | L | W | G | G | D | V | V | L | | | | | |
| | | | | | | | | | | | | V | | | | |
| | | | | | | | | | | | | I | | | | |
| | | | | | | | | | | | | A | | | | |
| | | | | M | | | | | | | V | | | | | |
| | | | | M | | | | | | | I | | | | | |
| | | | | M | | | | | | | | | | | | |
| | | | | M | | | | | | | A | | | | | |
| | | | | A | | | | | | | V | | | | | |
| | | | | A | | | | | | | I | | | | | |
| | | | | A | | | | | | | | | | | | |
| | | | | A | | | | | | | A | | | | | |
| | | | | V | | | | | | | V | | | | | |
| | | | | V | | | | | | | I | | | | | |
| | | | | V | | | | | | | | | | | | |
| | | | | V | | | | | | | A | | | | | |

TABLE 4-continued

Variants and motif of the peptides according to SEQ ID NO: 1, 2, 4, 51, 56 (A*02), 74, 75, 76, 80, 81, 84 (A*24)

| | | Position | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | | | T | | | | | | | V | | | | | |
| | | | | T | | | | | | | I | | | | | |
| | | | | T | | | | | | | | | | | | |
| | | | | T | | | | | | | A | | | | | |
| | | | | Q | | | | | | | V | | | | | |
| | | | | Q | | | | | | | I | | | | | |
| | | | | Q | | | | | | | | | | | | |
| | | | | Q | | | | | | | A | | | | | |
| TMEM255A-001 SEQ ID 74 | Peptide Code Y | | Y | P | G | V | 1 | L | G | F | | | | | | |
| | Variant | | | | | | | | | | I | | | | | |
| | | | | | | | | | | | L | | | | | |
| | | | | F | | | | | | | I | | | | | |
| | | | | F | | | | | | | L | | | | | |
| | | | | F | | | | | | | | | | | | |
| ST8SIA5-001 SEQ ID 75 | Peptide Code V | | Y | Y | F | H | P | Q | Y | L | | | | | | |
| | Variant | | | | | | | | | | I | | | | | |
| | | | | | | | | | | | F | | | | | |
| | | | | F | | | | | | | I | | | | | |
| | | | | F | | | | | | | | | | | | |
| | | | | F | | | | | | | | | | | | |
| FAM120C-001 SEQ ID 76 | Peptide Code M | | Y | P | Y | 1 | Y | H | V | L | F | | | | | |
| | Variant | | | | | | | | | | I | | | | | |
| | | | | | | | | | | | F | | | | | |
| | | | | F | | | | | | | I | | | | | |
| | | | | F | | | | | | | | | | | | |
| | | | | F | | | | | | | F | | | | | |
| FABP7-002 SEQ ID 80 | Peptide Code E | | Y | M | K | A | L | G | V | G | F | | | | | |
| | Variant | | | | | | | | | | I | | | | | |
| | | | | | | | | | | | L | | | | | |
| | | | | F | | | | | | | I | | | | | |
| | | | | F | | | | | | | L | | | | | |
| | | | | F | | | | | | | | | | | | |
| ZNF3-001 SEQ ID 81 | Peptide Code K | | Y | N | D | F | G | N | S | F | | | | | | |
| | Variant | | | | | | | | | | I | | | | | |
| | | | | | | | | | | | L | | | | | |
| | | | | F | | | | | | | I | | | | | |
| | | | | F | | | | | | | L | | | | | |
| | | | | F | | | | | | | | | | | | |
| PJA2-001 SEQ ID 84 | Peptide Code R | | Y | Q | E | S | L | G | N | T | V | F | | | | |
| | Variant | | | | | | | | | | | I | | | | |
| | | | | | | | | | | | | L | | | | |
| | | | | F | | | | | | | | I | | | | |
| | | | | F | | | | | | | | L | | | | |
| | | | | F | | | | | | | | | | | | |

Longer peptides may also be suitable. It is also possible, that MHC class I epitopes, although usually between 8-11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 14, namely 8, 9, 10, 11, 12, 13, 14 amino acids, in case of the class II binding peptides the length can also be 15, 16, 17, 18, 19, 20, 21, 22 or 23 amino acids.

Of course, the peptide or variant according to the present invention will have the ability to bind to a molecule of the human major histocompatibility complex (MHC) class I. Binding of a peptide or a variant to a MHC complex may be tested by methods known in the art.

In a particularly preferred embodiment of the invention the peptide consists or consists essentially of an amino acid sequence according SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129.

"Consisting essentially of" shall mean that a peptide according to the present invention, in addition to the sequence according to any SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii"; SEQ ID No. 133) as derived from the NCBI, GenBank Accession number X00497.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins.

Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lu et al (1981) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example (Bruckdorfer et al., 2004) and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, CNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by (Saiki et al., 1988)). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275,104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Small et al., 2006; Rini et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Brunsvig et al., 2006; Staehler et al., 2007).

Another aspect of the present invention includes an in vitro method for producing activated T cells, the method comprising contacting in vitro T cells with antigen loaded human MEW molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre et al 1985.

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the costimulator molecules are publicly available from the GenBank and EMBL databases.

In case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129.

A number of other methods may be used for generating CTL in vitro. For example, the methods described in Peoples et al (1995) and Kawakami et al (1992) use autologous tumor-infiltrating lymphocytes in the generation of CTL. Plebanski et al (1995) makes use of autologous peripheral blood lymphocytes (PLBs) in the preparation of CTL. Jochmus et al (1997) describes the production of autologous CTL by pulsing dendritic cells with peptide or polypeptide, or via infection with recombinant virus. Hill et al (1995) and Jerome et al (1993) make use of B cells in the production of autologous CTL. In addition, macrophages pulsed with peptide or polypeptide, or infected with recombinant virus, may be used in the preparation of autologous CTL. S. Walter et al. 2003 describe the in vitro priming of T cells by using artificial antigen presenting cells (aAPCs), which is also a suitable way for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al (1994)) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID No. 1 to SEQ ID No. 49, SEQ ID No. 71 and SEQ IDs No. 74 to 129.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in (Gattinoni et al., 2006) and (Morgan et al., 2006).

Any molecule of the invention, i.e. the peptide, nucleic acid, antibody, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker 1993). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth in SEQ ID No. 1 to SEQ ID No. 49, SEQ ID No. 71 and SEQ IDs No. 74 to 129 or a variant sequence thereof which is at least 90% homolog to SEQ ID No. 1 to SEQ ID No. 49, SEQ ID No. 71 and SEQ IDs No. 74 to 129 and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. (Pascolo et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T (Tx) cells to an antigen, and would thus be considered useful in the medicament of the present invention. Suitable adjuvants include, but are not limited to, 1018 ISS, aluminium salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995; Allison and Krummel, 1995). Also cytokines may be used. Several cytokines have been directly linked to influencing dendritic cell migration to lymphoid tissues (e.g., TNF-), accelerating the☐ maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immuno-adjuvants (e.g., IL-12, IL-15, IL-23, IL-7, IFN-alpha. IFN-beta) [Gabrilovich 1996].

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), immiquimod and resimiquimod.

In a preferred embodiment of the pharmaceutical composition according to the invention, the adjuvant is imiquimod or resiquimod.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed. 2000, American Pharmaceutical Association and pharmaceutical press. The composition can be used for a prevention, prophylaxis and/or therapy of adenomateous or cancerous diseases. Exemplary formulations can be found in EP2113253.

Nevertheless depending on the number and the physicochemical characteristics of the peptides of the invention further research is needed to provide formulations for specific combinations of peptides that are stable for more than 12-18 months.

The present invention provides a medicament that useful in treating cancer, in particular non-small cell lung carcinoma, gastric cancer, renal cell carcinoma, colon cancer, adenocarcinoma, prostate cancer, benign neoplasm and malignant melanoma.

The present invention further includes a kit comprising:
(a) a container that contains a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

Another aspect of the invention then relates to a method for distinguishing glioblastoma from other forms of cancer comprising analyzing the expression of PTPRZ1, BCAN, and/or FABP7 in a sample obtained from the brain or another tumorous specimen from a subject to be diagnosed, either alone or in addition to the therapy based on the methods herein (e.g. for a monitoring). For this, another aspect of the invention relates to s kit for measuring expression level of PTPRZ1, BCAN, and/or FABP7 as (a) glioblastoma marker gene(s), comprising at least one antibody that specifically binds a chosen glioblastoma marker polypeptide, or one or more nucleic acids that specifically hybridize with PTPRZ1, BCAN, and/or FABP7 mRNA, and, optionally, a control (e.g., a specific amount of a particular glioblastoma marker polypeptide), primary and secondary antibodies when appropriate, and optionally other reagents, such as detectable moieties, enzyme substrates, and/or colour reagents.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

Since the peptides of the invention derived from SEQ ID No. 1 to SEQ ID No. 49, SEQ ID No. 71, and SEQ IDs No. 74 to 129 were isolated from glioblastoma, the medicament of the invention is preferably used to treat glioblastoma.

The present invention further includes a method for producing a personalized pharmaceutical for an individual patient comprising manufacturing a pharmaceutical composition comprising at least one peptide selected from a warehouse of pre-screened TUMAPs, such as, for example the peptides according to SEQ ID No. 1 to SEQ ID No. 131, or the peptides of the invention derived from SEQ ID No. 1 to SEQ ID No. 49, SEQ ID No. 71, and SEQ IDs No. 74 to 129 and/or other suitable tumor associated peptides; wherein the at least one peptide used in the pharmaceutical composition is selected for suitability in the individual patient or a small group of patients. Preferably, the pharmaceutical composition is a vaccine. The method could also be adapted to produce T cell clones for down-stream applications such as TCR isolations.

A "personalized pharmaceutical" shall mean specifically tailored therapies for one individual patient or a small group of patients (i.e. less than 100, preferably less than 10, more preferably less than 5, most preferred one) that will only be used for therapy in such individual or small group of patients, including actively personalized cancer vaccines and adoptive cellular therapies using autologous patient tissue.

As used herein, the term "warehouse" shall refer to a group of peptides that have been pre-screened for immunogenicity and over-presentation in a particular tumor type or group of tumor types. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored.

The warehouse is preferably composed of tumor-associated peptides which were highly overexpressed in the tumor tissue of several HLA-A*02 or HLA-A*24 positive GBM patients analyzed. It contains MHC class I and MHC class II peptides. In addition to the tumor associated peptides collected from several GBM tissues, the warehouse contains an HLA-A*02 and an HLA-A*24 marker peptide. These peptides allow comparison of the magnitude of T-cell immunity induced by TUMAPS in a quantitative manner and hence allow important conclusion to be drawn on the capacity of the vaccine to elicit anti-tumor responses. Secondly, it functions as an important positive control peptide derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient population.

HLA class I and II TUMAPs for the warehouse are identified by using an integrated functional genomics approach combining gene expression analysis, mass spectrometry, and T-cell immunology. This methodology has been the basis for selection of the TUMAPs included in IMA901, IMA910 or IMA950 and the approach assures that only TUMAPs truly present on a high percentage of tumors but not or only minimally expressed on normal tissue, are chosen for further analysis. For peptide selection, glioblastoma samples from surgically removed malignant tissue from GBM patients and blood from healthy donors were analyzed in a stepwise approach:

1. HLA ligands from the malignant material were identified by mass spectrometry
2. Genome-wide messenger ribonucleic acid (mRNA) expression analysis by microarrays was used to identify genes over-expressed in the malignant tissue (GBM) compared with a range of normal organs and tissues
3. Identified HLA ligands were compared to gene expression data. Peptides encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. To assess whether an induction of in vivo T-cell responses by the selected peptides may be feasible, in vitro immunogenicity assays were performed using human T cells from healthy donors as well as from GBM patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/WIC complexes and anti-CD28 antibody, as described in detail below in EXAMPLE 3.

This method is preferred for rare cancers and patients with a rare expression profile. In contrast to multi-peptide cocktails with a fixed composition as currently developed the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 2 million possible drug product (DP) compositions.

The HLA phenotype, transcriptomic and peptidomic data will be gathered from the patient's tumor material and blood samples to identify the most suitable peptides for each patient containing warehouse and patient-unique (i.e. mutated) TUMAPs. Those peptides will be chosen, which are selectively or over-expressed in the patients tumor and, where possible, showed strong in vitro immunogenicity if tested with the patients individual PBMCs.

In one embodiment, the warehouse comprises and/or consists of the peptides according to SEQ ID No. 1 to 131, preferably of the peptides according to the invention. Preferred additional TUMAPs presented by a tumor sample from an individual patient or small group of patients are selected from the peptides described and claimed in EP1806358, EP1806359, EP1760088, EP1922335, EP2135878, EP2119726, EP2291395, GB1313987, and/or EP2138509.

Preferably, the peptides included in the vaccine are identified by a method comprising: (a) identifying tumor-associated peptides (TUMAPs) presented by a tumor sample from the individual patient; (b) comparing the peptides identified in (a) with a warehouse of peptides as described above; and (c) selecting at least one peptide from the warehouse that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

The peptides are selected for inclusion in the vaccine based on their suitability for the individual patient based on the immunogenicity, which can be determined by a method comprising in vitro immunogenicity assays, based on their level of overpresentation on the peptide level, or based on the level of overexpression of the mRNA encoding the peptide. Preferably, the in vitro immunogenicity is determined on cells of the individual patient.

In addition to, or as an alternative to, selecting peptides using a warehousing model, TUMAPs may be identified in the patient de novo and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides may then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the methods described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides are selected, the vaccine is manufactured. The vaccine is a liquid formulation consisting of the individual peptides dissolved in 33% DMSO. Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 μm sterile filter. The final bulk solution is obtained. Final bulk solution is filled into vials and stored at −20° C. until use. One vial contains 7004, solution containing 0.578 mg of each peptide. Thereof 500 μL (approx. 400 μg per peptide) will be applied for intradermal injection.

The present invention will now be described in the following examples that describe preferred embodiments thereof, nevertheless, without being limited thereto. For the purposes of the present invention, all references as cited herein are incorporated by reference in their entireties.

EXAMPLES

Example 1

Identification and Quantitation of Tumor Associated Peptides Presented on the Cell Surface Tissue Samples Patients' tumor tissues were provided by Universities of Heidelberg, University of Tubingen, both Germany, University of Geneva, Switzerland. Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, -C-specific antibody W6/32, CNBr-activated sepharose, acid treatment, and ultrafiltration.

Methods

The HLA peptide pools as obtained were separated according to their hydrophobicity by reversed-phase chromatography (Acquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 μm i.d.×250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometer was operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIG. 1 shows an exemplary spectrum obtained from tumor tissue for the MHC class I associated peptide IGF2BP3-001 and its elution profile on the UPLC system.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2007). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profile juxtaposes glioblastoma samples to a baseline of normal tissue samples.

Presentation profiles of exemplary over-presented peptides are shown in FIG. 3.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by several institutions as listed in Example 1 after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalisation, 100 housekeeping genes provided by Affymetrix were used. Relative expression values were calculated from the signal log ratios given by the software and the normal kidney sample was arbitrarily set to 1.0.

Figure 2A:
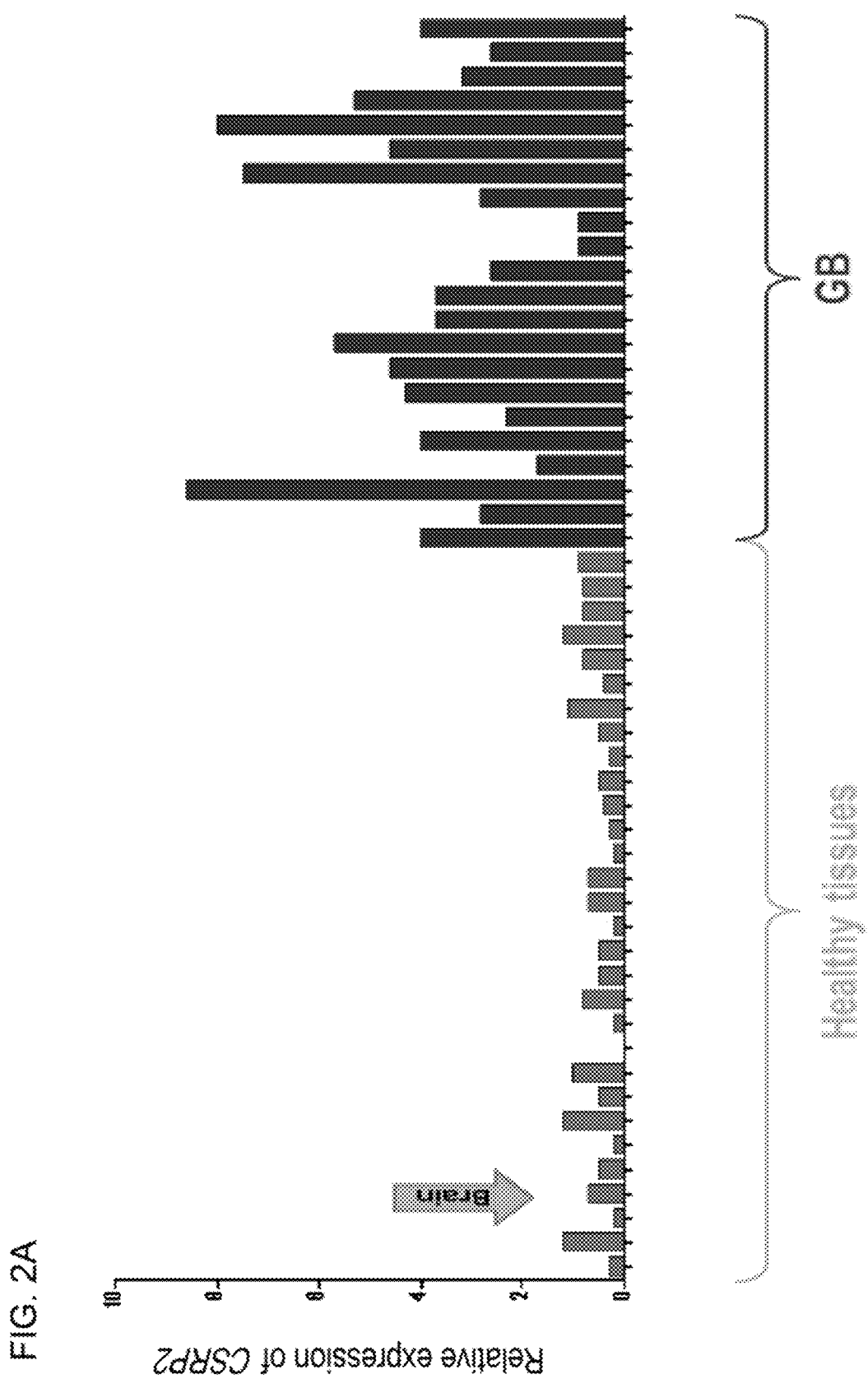
FIGS. 2A-2B: Expression profiles of mRNA of selected proteins in normal tissues and in 22 glioblastoma cancer samples.
Figure 2B:
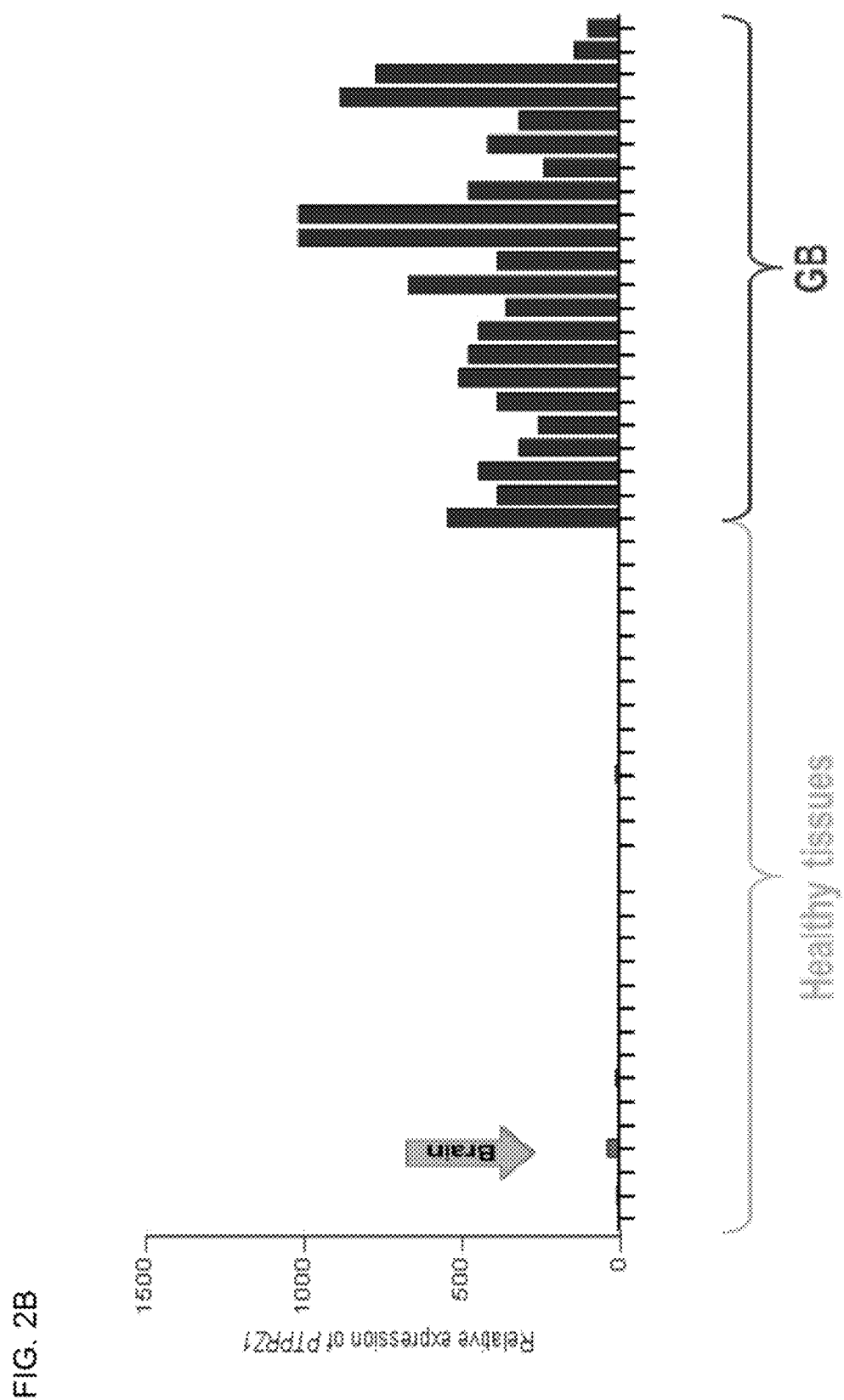

Exemplary expression profiles of source genes of the present invention that are highly over-expressed or exclusively expressed in glioblastoma are shown in FIG. 2.

Example 3

In Vitro Immunogenicity for Glioblastoma MHC Class I Presented Peptides

In order to obtain information regarding the immunogenicity of the TUMAPs of the present invention, we performed investigations using an in vitro T-cell priming assay based on repeated stimulations of CD8+ T cells with artificial antigen presenting cells (aAPCs) loaded with peptide/MHC complexes and anti-CD28 antibody. This way we could show immunogenicity for 69 HLA-A*0201 and 58 HLA-A*24 restricted TUMAPs of the invention so far, demonstrating that these peptides are T-cell epitopes against which CD8+ precursor T cells exist in humans.

In Vitro Priming of CD8+ T Cells

In order to perform in vitro stimulations by artificial antigen presenting cells loaded with peptide-MHC complex (pMHC) and anti-CD28 antibody, we first isolated CD8+ T cells from fresh HLA-A*02 leukapheresis products via positive selection using CD8 microbeads (Miltenyi Biotec, Bergisch-Gladbach, Germany) of healthy donors obtained from the Transfusion Medicine Tuebingen after informed consent.

Isolated CD8+ lymphocytes or PBMCs were incubated until use in T-cell medium (TCM) consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nurnberg, Germany) were also added to the TCM at this step. Generation of pMHC/anti-CD28 coated beads, T-cell stimulations and readout was performed in a highly defined in vitro system using four different pMHC molecules per stimulation condition and 8 different pMHC molecules per readout condition. All pMHC complexes used for aAPC loading and cytometric readout were derived from UV-induced MHC ligand exchange with minor modifications. In order to determine the amount of pMHC monomer obtained by exchange we performed streptavidin-based sandwich ELISAs according to (Rodenko et al., 2006). The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used as controls for high immunogenic and low immunogenic stimulations were A*0201/MLA-001 (peptide ELAGIGILTV from modified Melan-A/MART-1) and A*0201/DDX5-001 (YLLPAIVHI from DDX5), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times, with 12 individual wells per condition For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+ CD8+ lymphocytes was detected by comparison to irrelevant control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the irrelevant control stimulations).

In Vitro Immunogenicity for Glioblastoma Peptides

For tested HLA class I peptides, in vitro immunogenicity could be demonstrated by generation of peptide specific T-cell lines. Exemplary flow cytometry results after TUMAP-specific multimer staining for two peptides of the invention are shown in FIG. 4 together with corresponding negative controls. Results for 69 HLA-A*0201 and 58 HLA-A*24 peptides from the invention are summarized in Table 5a and b.

TABLE 5a

In vitro immunogenicity of HLA-A*02class I peptides of the invention
Exemplary results of in vitro immunogenicity experiments conducted by the applicant for the peptides of the invention.

| SEQ ID NO: | Peptide Code | Wells | Donors |
|---|---|---|---|
| 68 | ABCA13-001 | + | ++ |
| 37 | ADORA3-001 | + | ++ |
| 10 | ANKRD40-001 | + | +++ |
| 27 | ASIC4-001 | + | ++ |
| 51 | BCA-002 | ++++ | ++++(100%) |
| 13 | BCA-003 | + | ++ |
| 69 | CCNB1-002 | + | +++ |
| 45 | CCT-001 | + | +++ |
| 52 | CDK4-001 | ++ | ++++ |
| 48 | CHCHD2-005 | + | +++ |
| 18 | CLU-001 | + | ++ |
| 70 | CNOT1-002 | + | ++ |
| 28 | COL20-001 | + | ++ |
| 23 | CPT1C-001 | + | ++ |
| 60 | CSP-001 | + | +++ |
| 1 | CSRP2-001 | ++ | ++++(100%) |
| 63 | DCA-001 | + | ++ |
| 41 | DPP3-001 | + | +++ |
| 65 | DPYSL4-001 | + | ++ |
| 67 | DROSHA-001 | + | ++ |
| 29 | EGFR-008 | + | ++ |
| 43 | EIF4E-001 | + | +++ |
| 3 | ELOVL2-001 | + | ++++ |
| 59 | FABP7-001 | + | ++++ |
| 21 | GPR98-001 | + | ++ |
| 40 | GRI-001 | + | ++ |
| 17 | GRI-002 | + | ++ |
| 8 | GRIK3-001 | + | ++++ |
| 22 | GYG2-001 | + | ++ |
| 66 | IGF2BP3-001 | + | +++ |
| 32 | IRS-001 | + | +++ |
| 30 | JAK-001 | + | ++ |
| 12 | KCN-002 | + | +++ |
| 6 | KIF1A-001 | ++ | +++ |
| 53 | MAGEF1-001 | ++ | ++++ |
| 14 | MAGI2-001 | + | ++ |
| 47 | MAP1B-001 | + | +++ |
| 35 | MAP1B-002 | + | ++ |
| 4 | MTSS1L-001 | +++ | ++++(100%) |
| 33 | NAT8L-001 | + | ++++ |
| 36 | NC AN-001 | + | ++++(100%) |
| 55 | NLGN4X-001 | ++ | ++++(100%) |
| 39 | NLGN4X-002 | + | ++ |
| 11 | NLGN4Y-001 | + | ++++ |
| 46 | NOC4-001 | + | +++ |
| 33 | NPAS3-001 | + | ++ |
| 57 | NRCAM-001 | + | ++++(100%) |
| 61 | ORMDL1-002 | + | +++ |
| 7 | PCDHGC5-001 | + | ++++(100%) |
| 64 | PCNXL3-001 | + | ++ |
| 44 | PLEKHA4-001 | + | +++ |
| 26 | PTP-001 | + | ++ |
| 25 | PTP-002 | + | +++ |
| 54 | PTP-003 | + | ++++ |
| 50 | PTP-005 | ++ | ++++ |
| 15 | PTP-012 | + | ++ |
| 5 | PTP-013 | + | ++++ |

TABLE 5a-continued

In vitro immunogenicity of HLA-A*02class I peptides of the invention
Exemplary results of in vitro immunogenicity experiments conducted by the applicant for the peptides of the invention.

| SEQ ID NO: | Peptide Code | Wells | Donors |
|---|---|---|---|
| 58 | RAD54B-001 | ++ | ++++(100%) |
| 16 | SCARA3-001 | + | ++ |
| 9 | SEZ6L-001 | + | ++++ |
| 2 | SLC10A4-001 | ++ | +++ |
| 20 | SLC10A4-002 | + | +++ |
| 24 | SLC35E1-002 | + | ++ |
| 49 | SOX-001 | + | ++++ |
| 62 | TACC3-001 | + | ++ |
| 34 | TNC-001 | + | ++ |
| 42 | USP11-001 | ++ | ++++ |
| 56 | VPS13B-001 | ++ | ++++(100%) |
| 31 | WLS-002 | + | +++ |

<20% = +; 20%-49% = ++; 50%-70% = +++; >70% = ++++

TABLE 5b

In vitro immunogenicity of HLA-A*24 class I peptides of the invention
Exemplary results of in vitro immunogenicity experiments conducted by the inventors for the peptides of the invention.

| SEQ ID NO: | Peptide Code | Wells | Donors |
|---|---|---|---|
| 74 | TMEM255A-001 | + | ++ |
| 75 | ST8SIA5-001 | ++ | ++++ |
| 76 | FAM120C-001 | ++ | ++++(100%) |
| 77 | GRIK3-002 | + | ++++ |
| 78 | PTP-014 | + | ++ |
| 79 | PTP-019 | + | ++ |
| 80 | FABP7-002 | + | ++ |
| 81 | ZNF749-001 | + | ++ |
| 82 | DOCK7-002 | + | +++ |
| 83 | LOC72839-001 | + | +++ |
| 84 | PJA2-001 | + | ++ |
| 85 | HEATR1-001 | + | +++ |
| 86 | GPM-002 | + | +++ |
| 87 | CRB1-001 | + | ++ |
| 88 | PTP-016 | + | ++ |
| 89 | PTP-015 | + | ++ |
| 90 | PTP-018 | + | ++++ |
| 91 | OLIG2-001 | + | ++ |
| 92 | VCAN-003 | + | +++ |
| 93 | SMOX-001 | + | ++ |
| 94 | EXOC7-001 | + | ++ |
| 95 | LZTS1-001 | + | ++ |
| 96 | FADS2-003 | + | +++ |
| 97 | TMEM231-001 | + | +++ |
| 98 | ASCL1-001 | + | ++ |
| 99 | UNKN-003 | + | ++ |
| 100 | NKA-001 | + | ++ |
| 101 | PCD-002 | + | ++ |
| 102 | ARHGAP21-001 | + | ++ |
| 103 | PNMA2-001 | + | ++ |
| 104 | FADS2-002 | + | ++++ |
| 105 | APC-001 | + | ++ |
| 106 | WASL-001 | + | ++++ |
| 107 | SLC-002 | + | ++ |
| 108 | TENM4-001 | + | ++ |
| 109 | ZNFS3-001 | ++ | +++ |
| 110 | EFCAB7-001 | + | ++ |
| 111 | DOCK7-003 | + | ++ |
| 112 | BMP7-001 | + | ++ |
| 113 | ITGA7-001 | + | ++ |
| 114 | RPL-001 | + | ++ |
| 115 | HS2-001 | + | ++ |
| 116 | VIM-002 | + | ++ |
| 117 | IFT17-001 | + | +++ |
| 118 | GAB-001 | + | ++ |
| 119 | CDCA7L-001 | + | ++ |
| 120 | SCARA3-002 | + | ++ |
| 121 | SSR1-001 | + | ++ |
| 122 | NROB1-001 | + | ++ |
| 123 | LNX1-001 | + | ++ |
| 124 | EP4-001 | + | ++ |
| 125 | KIF1B-001 | + | ++ |
| 126 | RHOBTB3-001 | + | ++ |
| 127 | KIF7-001 | + | ++ |
| 128 | KIF1B-002 | + | ++ |
| 129 | MAPK6-001 | + | ++ |
| 130 | ASPM-002 | + | +++ |
| 131 | SMC4-001 | + | ++ |

<20% = +; 20%-49% = ++; 50%-70% = +++; >70% = ++++

REFERENCE LIST

An C H, et al. (2012). Frameshift mutations of vacuolar protein sorting genes in gastric and colorectal cancers with microsatellite instability. Hum. Pathol. 43, 40-47.

Araki W, et al. (2008). A family of membrane proteins associated with presenilin expression and gamma-secretase function. FASEB J 22, 819-827.

Aronica E, et al. (2001). Ionotropic and metabotropic glutamate receptor protein expression in glioneuronal tumors from patients with intractable epilepsy. Neuropathol. Appl. Neurobiol. 27, 223-237.

Aslibekyan S, et al. (2012). Genetic variation in fatty acid elongases is not associated with intermediate cardiovascular phenotypes or myocardial infarction. Eur. J Clin Nutr. 66, 353-359.

Aylsworth A, Jiang S X, Desbois A, Hou S T (2009). Characterization of the role of full-length CRMP3 and its calpain-cleaved product in inhibiting microtubule polymerization and neurite outgrowth. Exp. Cell Res. 315, 2856-2868.

Bargo S, et al. (2010). Transforming acidic coiled-coil protein-3 (Tacc3) acts as a negative regulator of Notch signaling through binding to CDC10/Ankyrin repeats. Biochem. Biophys. Res Commun. 400, 606-612.

Bayraktar S, et al. (2013). USP-11 as a predictive and prognostic factor following neoadjuvant therapy in women with breast cancer. Cancer J 19, 10-17.

Bi J, et al. (2010). Overexpression of clusterin correlates with tumor progression, metastasis in gastric cancer: a study on tissue microarrays. Neoplasma 57, 191-197.

Bock A J, et al. (2012). SCARA3 mRNA is overexpressed in ovarian carcinoma compared with breast carcinoma effusions. Hum. Pathol. 43, 669-674.

Brait M, et al. (2012). Correlation between BRAF mutation and promoter methylation of TIMP3, RARbeta2 and RASSF1A in thyroid cancer. Epigenetics. 7, 710-719.

Breeden L, Nasmyth K (1987). Similarity between cell-cycle genes of budding yeast and fission yeast and the Notch gene of Drosophila. Nature 329, 651-654.

Brocke K S, et al. (2010). Glutamate receptors in pediatric tumors of the central nervous system. Cancer Biol. Ther. 9, 455-468.

Bruchovsky N, et al. (1996). Control of tumor progression by maintenance of apoptosis. Prostate Suppl 6, 13-21.

Burkhart R A, et al. (2013). Mitoxantrone Targets Human Ubiquitin-Specific Peptidase 11 (USP11) and Is a Potent Inhibitor of Pancreatic Cancer Cell Survival. Mol. Cancer Res. 11, 901-911.

Canoll P D, et al. (1993). The expression of a novel receptor-type tyrosine phosphatase suggests a role in morphogenesis and plasticity of the nervous system. Brain Res. Dev. Brain Res. 75, 293-298.

Carroll M, Borden K L (2013). The Oncogene eIF4E: Using Biochemical Insights to Target Cancer. J Interferon Cytokine Res. 33, 227-238.

Casado M E, et al. (2013). Hormone-sensitive lipase deficiency disturbs the fatty acid composition of mouse testis. Prostaglandins Leukot. Essent. Fatty Acids 88, 227-233.

Casati C, et al. (2003). The apoptosis inhibitor protein survivin induces tumor-specific CD8+ and CD4+ T cells in colorectal cancer patients. Cancer Res. 63, 4507-4515.

Chaiwatanasirikul K A, Sala A (2011). The tumour-suppressive function of CLU is explained by its localisation and interaction with HSP60. Cell Death. Dis. 2, e219.

Chakravarti A, et al. (2002). Quantitatively determined survivin expression levels are of prognostic value in human gliomas. J Clin Oncol 20, 1063-1068.

Chan J Y, Ong C W, Salto-Tellez M (2011). Overexpression of neurone glial-related cell adhesion molecule is an independent predictor of poor prognosis in advanced colorectal cancer. Cancer Sci. 102, 1855-1861.

Chekenya M, et al. (2002). NG2 proteoglycan promotes angiogenesis-dependent tumor growth in CNS by sequestering angiostatin. FASEB J 16, 586-588.

Chekenya M, et al. (2008). The progenitor cell marker NG2/MPG promotes chemoresistance by activation of integrin-dependent PI3K/Akt signaling. Oncogene 27, 5182-5194.

Chekenya M, Pilkington G J (2002). NG2 precursor cells in neoplasia: functional, histogenesis and therapeutic implications for malignant brain tumours. J Neurocytol. 31, 507-521.

Chekenya M, et al. (1999). The NG2 chondroitin sulfate proteoglycan: role in malignant progression of human brain tumours. Int J Dev. Neurosci. 17, 421-435.

Chen D, et al. (2012). Antisense oligonucleotide against clusterin regulates human hepatocellular carcinoma invasion through transcriptional regulation of matrix metalloproteinase-2 and e-cadherin. Int. J Mol. Sci. 13, 10594-10607.

Cheung I Y, et al. (2008). Exploiting gene expression profiling to identify novel minimal residual disease markers of neuroblastoma. Clin Cancer Res. 14, 7020-7027.

Chung F Y, et al. (2010). Differential gene expression profile of MAGE family in taiwanese patients with colorectal cancer. J Surg. Oncol 102, 148-153.

Claro da S T, Polli J E, Swaan P W (2013). The solute carrier family 10 (SLC10): beyond bile acid transport. Mol. Aspects Med. 34, 252-269.

Coon S W, et al. (2004). Prognostic implications of loss of heterozygosity at 8p21 and 9p21 in head and neck squamous cell carcinoma. Int. J Cancer 111, 206-212.

Cui J, et al. (1998). Chromosome 7 abnormalities in prostate cancer detected by dual-color fluorescence in situ hybridization. Cancer Genet. Cytogenet. 107, 51-60.

Culjkovic-Kraljacic B, et al. (2012). The oncogene eIF4E reprograms the nuclear pore complex to promote mRNA export and oncogenic transformation. Cell Rep. 2, 207-215.

Cunningham J M, et al. (1996). Allelic imbalance and microsatellite instability in prostatic adenocarcinoma. Cancer Res. 56, 4475-4482.

De R A, et al. (2012). A Radial Glia Gene Marker, Fatty Acid Binding Protein 7 (FABP7), Is Involved in Proliferation and Invasion of Glioblastoma Cells. PLoS. ONE. 7, e52113.

Demokan S, et al. (2010). KIF1A and EDNRB are differentially methylated in primary HNSCC and salivary rinses. Int. J Cancer 127, 2351-2359.

Deng F, et al. (2006). Stargazin and other transmembrane AMPA receptor regulating proteins interact with synaptic scaffolding protein MAGI-2 in brain. J Neurosci. 26, 7875-7884.

Dowler S, et al. (2000). Identification of pleckstrin-homology-domain-containing proteins with novel phosphoinositide-binding specificities. Biochem. J 351, 19-31.

Edelman A M, et al. (2005). Doublecortin kinase-2, a novel doublecortin-related protein kinase associated with terminal segments of axons and dendrites. J Biol Chem. 280, 8531-8543.

Engel M, et al. (1996). Chondroitin sulfate proteoglycans in the developing central nervous system. I. cellular sites of synthesis of neurocan and phosphacan. J Comp Neurol. 366, 34-43.

Etcheverry A, et al. (2010). DNA methylation in glioblastoma: impact on gene expression and clinical outcome. BMC. Genomics 11, 701.

Frank M, Kemler R (2002). Protocadherins. Curr. Opin. Cell Biol. 14, 557-562.

Futerman A H, Riezman H (2005). The ins and outs of sphingolipid synthesis. Trends Cell Biol. 15, 312-318.

Gallucci M, et al. (2006). Cytogenetic profiles as additional markers to pathological features in clinically localized prostate carcinoma. Cancer Lett. 237, 76-82.

Garagnani P, et al. (2012). Methylation of ELOVL2 gene as a new epigenetic marker of age. Aging Cell 11, 1132-1134.

Gary S C, Kelly G M, Hockfield S (1998). BEHAB/brevican: a brain-specific lectican implicated in gliomas and glial cell motility. Curr. Opin. Neurobiol. 8, 576-581.

Gary S C, et al. (2000). cDNA cloning, chromosomal localization, and expression analysis of human BEHAB/brevican, a brain specific proteoglycan regulated during cortical development and in glioma. Gene 256, 139-147.

Godbout R, Bisgrove D A, Shkolny D, Day R S, III (1998). Correlation of B-FABP and GFAP expression in malignant glioma. Oncogene 16, 1955-1962.

Gorka B, et al. (2007). NrCAM, a neuronal system cell-adhesion molecule, is induced in papillary thyroid carcinomas. Br. J Cancer 97, 531-538.

Gorlov I P, et al. (2007). Seizure 6-like (SEZ6L) gene and risk for lung cancer. Cancer Res. 67, 8406-8411.

Graf F, et al. (2010). Cyclin-dependent kinase 4/6 (cdk4/6) inhibitors: perspectives in cancer therapy and imaging. Mini. Rev. Med. Chem. 10, 527-539.

Grumet M, et al. (1991). Structure of a new nervous system glycoprotein, Nr-CAM, and its relationship to subgroups of neural cell adhesion molecules. J Cell Biol. 113, 1399-1412.

Grunda J M, et al. (2010). Rationally designed pharmacogenomic treatment using concurrent capecitabine and radiotherapy for glioblastoma; gene expression profiles associated with outcome. Clin Cancer Res. 16, 2890-2898.

Grunda J M, et al. (2006). Increased expression of thymidylate synthetase (TS), ubiquitin specific protease 10

(USP10) and survivin is associated with poor survival in glioblastoma multiforme (GBM). J Neurooncol. 80, 261-274.

Guerrero-Preston R, et al. (2011). NID2 and HOXA9 promoter hypermethylation as biomarkers for prevention and early detection in oral cavity squamous cell carcinoma tissues and saliva. Cancer Prev. Res. (Phila) 4, 1061-1072.

Gunther H S, et al. (2008). Glioblastoma-derived stem cell-enriched cultures form distinct subgroups according to molecular and phenotypic criteria. Oncogene 27, 2897-2909.

Guvenc H, et al. (2013). Impairment of Glioma Stem Cell Survival and Growth by a Novel Inhibitor for Survivin-Ran Protein Complex. Clin Cancer Res.

Han H J, Tokino T, Nakamura Y (1998). CSR, a scavenger receptor-like protein with a protective role against cellular damage caused by UV irradiation and oxidative stress. Hum. Mol. Genet. 7, 1039-1046.

Hartomo T B, et al. (2013). Minimal residual disease monitoring in neuroblastoma patients based on the expression of a set of real-time RT-PCR markers in tumor-initiating cells. Oncol Rep. 29, 1629-1636.

He J, et al. (2010). Identification of cell surface glycoprotein markers for glioblastoma-derived stem-like cells using a lectin microarray and LC-MS/MS approach. J Proteome. Res 9, 2565-2572.

Hirao K, et al. (1998). A novel multiple PDZ domain-containing molecule interacting with N-methyl-D-aspartate receptors and neuronal cell adhesion proteins. J Biol. Chem. 273, 21105-21110.

Hirayama T, Yagi T (2006). The role and expression of the protocadherin-alpha clusters in the CNS. Curr. Opin. Neurobiol. 16, 336-342.

Hirokawa N, Noda Y (2008). Intracellular transport and kinesin superfamily proteins, KIFs: structure, function, and dynamics. Physiol Rev. 88, 1089-1118.

Hjelmqvist L, et al. (2002). ORMDL proteins are a conserved new family of endoplasmic reticulum membrane proteins. Genome Biol. 3, RESEARCH0027.

Hood F E, Royle S J (2011). Pulling it together: The mitotic function of TACC3. Bioarchitecture. 1, 105-109.

Ideguchi H, et al. (2002). Structural and functional characterization of the USP11 deubiquitinating enzyme, which interacts with the RanGTP-associated protein RanBPM. Biochem. J 367, 87-95.

Ingley E, Hemmings B A (1994). Pleckstrin homology (PH) domains in signal transduction. J Cell Biochem. 56, 436-443.

Ishiuchi S (2009). [New roles of glutamate receptors in glias and gliomas]. Brain Nerve 61, 753-764.

Ishiuchi S, et al. (2002). Blockage of Ca(2+)-permeable AMPA receptors suppresses migration and induces apoptosis in human glioblastoma cells. Nat. Med 8, 971-978.

Ishwad C S, et al. (1995). Molecular and cytogenetic analysis of chromosome 7 in uterine leiomyomas. Genes Chromosomes. Cancer 14, 51-55.

Jamain S, et al. (2003). Mutations of the X-linked genes encoding neuroligins NLGN3 and NLGN4 are associated with autism. Nat. Genet. 34, 27-29.

Jiang J C, Kirchman P A, Zagulski M, Hunt J, Jazwinski S M (1998). Homologs of the yeast longevity gene LAG1 in Caenorhabditis elegans and human. Genome Res. 8, 1259-1272.

Jin F, et al. (2008). Comparison between cells and cancer stem-like cells isolated from glioblastoma and astrocytoma on expression of anti-apoptotic and multidrug resistance-associated protein genes. Neuroscience 154, 541-550.

Jung C K, Jung J H, Park G S, Lee A, Kang C S, Lee K Y (2006). Expression of transforming acidic coiled-coil containing protein 3 is a novel independent prognostic marker in non-small cell lung cancer. Pathol. Int 56, 503-509.

Kajiwara Y, et al. (2003). Expression of survivin in astrocytic tumors: correlation with malignant grade and prognosis. Cancer 97, 1077-1083.

Kallenbach S, et al. (2003). Changes in subcellular distribution of protocadherin gamma proteins accompany maturation of spinal neurons. J Neurosci. Res. 72, 549-556.

Kang G H, Lee S, Cho N Y, Gandamihardja T, Long T I, Weisenberger D J, Campan M, Laird P W (2008). DNA methylation profiles of gastric carcinoma characterized by quantitative DNA methylation analysis. Lab Invest 88, 161-170.

Kaur J, Demokan S, Tripathi S C, Macha M A, Begum S, Califano J A, Ralhan R (2010). Promoter hypermethylation in Indian primary oral squamous cell carcinoma. Int. J Cancer 127, 2367-2373.

Kawahara Y, Ito K, Sun H, Ito M, Kanazawa I, Kwak S (2004). GluR4c, an alternative splicing isoform of GluR4, is abundantly expressed in the adult human brain. Brain Res. Mol. Brain Res. 127, 150-155.

Kim D H, Mohapatra G, Bollen A, Waldman F M, Feuerstein B G (1995). Chromosomal abnormalities in glioblastoma multiforme tumors and glioma cell lines detected by comparative genomic hybridization. Int. J Cancer 60, 812-819.

Kim N, Yoo J C, Han J Y, Hwang E M, Kim Y S, Jeong E Y, Sun C H, Yi G S, Roh G S, Kim H J, Kang S S, Cho G J, Park J Y, Choi W S (2012). Human nuclear clusterin mediates apoptosis by interacting with Bcl-XL through C-terminal coiled coil domain. J Cell Physiol 227, 1157-1167.

Kimura J, Kudoh T, Miki Y, Yoshida K (2011). Identification of dihydropyrimidinase-related protein 4 as a novel target of the p53 tumor suppressor in the apoptotic response to DNA damage. Int. J Cancer 128, 1524-1531.

Kohannim O, et al. (2012). Discovery and Replication of Gene Influences on Brain Structure Using LASSO Regression. Front Neurosci. 6, 115.

Koide T, et al. N (2012). Common variants in MAGI2 gene are associated with increased risk for cognitive impairment in schizophrenic patients. PLoS. ONE. 7, e36836.

Kolehmainen J, et al. (2003). Cohen syndrome is caused by mutations in a novel gene, COH1, encoding a transmembrane protein with a presumed role in vesicle-mediated sorting and intracellular protein transport. Am. J Hum. Genet. 72, 1359-1369.

Kurimoto F, et al. (2001). Unchanged frequency of loss of heterozygosity and size of the deleted region at 8p21-23 during metastasis of lung cancer. Int. J Mol. Med. 8, 89-93.

Laumonnier F, et al. (2004). X-linked mental retardation and autism are associated with a mutation in the NLGN4 gene, a member of the neuroligin family. Am J Hum. Genet. 74, 552-557.

Lawson-Yuen A, Saldivar J S, Sommer S, Picker J (2008). Familial deletion within NLGN4 associated with autism and Tourette syndrome. Eur. J Hum. Genet. 16, 614-618.

Li H, Liu S, Zhu X, Yang S, Xiang J, Chen H (2010). Clusterin immunoexpression and its clinical significance in patients with non-small cell lung cancer. Lung 188, 423-431.

Li M, Chen D, Shiloh A, Luo J, Nikolaev A Y, Qin J, Gu W (2002). Deubiquitination of p53 by HAUSP is an important pathway for p53 stabilization. Nature 416, 648-653.

Li X, et al. (2013). MAGI2 enhances the sensitivity of BEL-7404 human hepatocellular carcinoma cells to staurosporine-induced apoptosis by increasing PTEN stability. Int. J Mol. Med.

Liang Y, et al. (2005). Gene expression profiling reveals molecularly and clinically distinct subtypes of glioblastoma multiforme. Proc. Natl. Acad. Sci. U.S.A 102, 5814-5819.

Lin C, Meng S, Zhu T, Wang X (2010). PDCD10/CCM3 acts downstream of {gamma}-protocadherins to regulate neuronal survival. J Biol. Chem. 285, 41675-41685.

Liu X, Chen N, Wang X, He Y, Chen X, Huang Y, Yin W, Zhou Q (2006). Apoptosis and proliferation markers in diffusely infiltrating astrocytomas: profiling of 17 molecules. J Neuropathol. Exp. Neurol. 65, 905-913.

Lobas M A, et al. (2012). Molecular heterogeneity in the choroid plexus epithelium: the 22-member gamma-protocadherin family is differentially expressed, apically localized, and implicated in CSF regulation. J Neurochem. 120, 913-927.

Loyo M, et al. (2011). A survey of methylated candidate tumor suppressor genes in nasopharyngeal carcinoma. Int. J Cancer 128, 1393-1403.

Lu K V, et al. (2005). Differential induction of glioblastoma migration and growth by two forms of pleiotrophin. J Biol Chem. 280, 26953-26964.

Luksch H, et al. (2011). Silencing of selected glutamate receptor subunits modulates cancer growth. Anticancer Res. 31, 3181-3192.

Marchand M, et al. (1999). Tumor regressions observed in patients with metastatic melanoma treated with an antigenic peptide encoded by gene MAGE-3 and presented by HLA-A1. Int. J. Cancer 80, 219-230.

Marchand M, et al. (1995). Tumor regression responses in melanoma patients treated with a peptide encoded by gene MAGE-3. Int. J Cancer 63, 883-885.

Marei H E, et al. (2012). Gene expression profile of adult human olfactory bulb and embryonic neural stem cell suggests distinct signaling pathways and epigenetic control. PLoS. ONE. 7, e33542.

McManus K J, Barrett I J, Nouhi Y, Hieter P (2009). Specific synthetic lethal killing of RAD54B-deficient human colorectal cancer cells by FEN1 silencing. Proc. Natl. Acad. Sci. U.S.A 106, 3276-3281.

Mellai M, Caldera V, Patrucco A, Annovazzi L, Schiffer D (2008). Survivin expression in glioblastomas correlates with proliferation, but not with apoptosis. Anticancer Res. 28, 109-118.

Meyer-Puttlitz B, Junker E, Margolis R U, Margolis R K (1996). Chondroitin sulfate proteoglycans in the developing central nervous system. II. Immunocytochemical localization of neurocan and phosphacan. J Comp Neurol. 366, 44-54.

Midorikawa Y, et al. (2002). Identification of genes associated with dedifferentiation of hepatocellular carcinoma with expression profiling analysis. Jpn. J Cancer Res. 93, 636-643.

Miley P, et al. (1994). Interactions of the chondroitin sulfate proteoglycan phosphacan, the extracellular domain of a receptor-type protein tyrosine phosphatase, with neurons, glia, and neural cell adhesion molecules. J Cell Biol. 127, 1703-1715.

Min J, et al. (2007). (Dihydro)ceramide synthase 1 regulated sensitivity to cisplatin is associated with the activation of p38 mitogen-activated protein kinase and is abrogated by sphingosine kinase 1. Mol. Cancer Res. 5, 801-812.

Mita R, Coles J E, Glubrecht D D, Sung R, Sun X, Godbout R (2007). B-FABP-expressing radial glial cells: the malignant glioma cell of origin? Neoplasia. 9, 734-744.

Morales G, et al. (1993). Induction of axonal growth by heterophilic interactions between the cell surface recognition proteins F11 and Nr-CAM/Bravo. Neuron 11, 1113-1122.

Morishita H, Yagi T (2007). Protocadherin family: diversity, structure, and function. Curr. Opin. Cell Biol. 19, 584-592.

Mosavi L K, Cammett T J, Desrosiers D C, Peng Z Y (2004). The ankyrin repeat as molecular architecture for protein recognition. Protein Sci. 13, 1435-1448.

Mulholland P J, et al. (2006). Genomic profiling identifies discrete deletions associated with translocations in glioblastoma multiforme. Cell Cycle 5, 783-791.

Muller S, et al. (2003). A role for receptor tyrosine phosphatase zeta in glioma cell migration. Oncogene 22, 6661-6668.

Musacchio A, Gibson T, Rice P, Thompson J, Saraste M (1993). The PH domain: a common piece in the structural patchwork of signalling proteins. Trends Biochem. Sci. 18, 343-348.

Nasr Z, Robert F, Porco J A, Jr., Muller W J, Pelletier J (2013). eIF4F suppression in breast cancer affects maintenance and progression. Oncogene 32, 861-871.

Nestle F O, et al. (1998). Vaccination of melanoma patients with peptide- or tumor lysate-pulsed dendritic cells. Nat Med. 4, 328-332.

Nishioka M, Kohno T, Takahashi M, Niki T, Yamada T, Sone S, Yokota J (2000). Identification of a 428-kb homozygously deleted region disrupting the SEZ6L gene at 22q12.1 in a lung cancer cell line. Oncogene 19, 6251-6260.

Niu Z, Li X, Hu B, Li R, Wang L, Wu L, Wang X (2012). Small interfering RNA targeted to secretory clusterin blocks tumor growth, motility, and invasion in breast cancer. Acta Biochim. Biophys. Sin. (Shanghai) 44, 991-998.

Ohmae S, et al. (2006). Molecular identification and characterization of a family of kinases with homology to Ca2+/calmodulin-dependent protein kinases UIV. J Biol. Chem. 281, 20427-20439.

Olsen M L, Sontheimer H (2008). Functional implications for Kir4.1 channels in glial biology: from K+ buffering to cell differentiation. J Neurochem. 107, 589-601.

Ostrow K L, et al. (2009). Pharmacologic unmasking of epigenetically silenced genes in breast cancer. Clin Cancer Res. 15, 1184-1191.

Ozerdem U (2006). Targeting of pericytes diminishes neovascularization and lymphangiogenesis in prostate cancer. Prostate 66, 294-304.

Panico F, et al. (2013). Prognostic role of clusterin in resected adenocarcinomas of the lung. Lung Cancer 79, 294-299.

Pattani K M, et al. (2010). Endothelin receptor type B gene promoter hypermethylation in salivary rinses is independently associated with risk of oral cavity cancer and premalignancy. Cancer Prev. Res. (Phila) 3, 1093-1103.

Perrin F E, Rathjen F G, Stoeckli E T (2001). Distinct subpopulations of sensory afferents require F11 or axonin-1 for growth to their target layers within the spinal cord of the chick. Neuron 30, 707-723.

Piesche M, Hildebrandt Y, Zettl F, Chapuy B, Schmitz M, Wulf G, Trumper L, Schroers R (2007). Identification of a promiscuous HLA DR-restricted T-cell epitope derived from the inhibitor of apoptosis protein survivin. Hum. Immunol. 68, 572-576.

Pinheiro P S, Perrais D, Coussen F, Barhanin J, Bettler B, Mann J R, Malva J O, Heinemann S F, Mulle C (2007). GluR7 is an essential subunit of presynaptic kainate autoreceptors at hippocampal mossy fiber synapses. Proc. Natl. Acad. Sci. U.S.A 104, 12181-12186.

Prakash S, et al. (2005). Gastrointestinal stromal tumors in children and young adults: a clinicopathologic, molecular, and genomic study of 15 cases and review of the literature. J Pediatr. Hematol. Oncol 27, 179-187.

Puyol M, et al. (2010). A synthetic lethal interaction between K-Ras oncogenes and Cdk4 unveils a therapeutic strategy for non-small cell lung carcinoma. Cancer Cell 18, 63-73.

Raji O Y, Agbaje O F, Duffy S W, Cassidy A, Field J K (2010). Incorporation of a genetic factor into an epidemiologic model for prediction of individual risk of lung cancer: the Liverpool Lung Project. Cancer Prev. Res. (Phila) 3, 664-669.

Rostomily R C, et al. (2010). Quantitative proteomic analysis of oligodendrogliomas with and without 1p/19q deletion. J Proteome. Res. 9, 2610-2618.

Saadoun S, Papadopoulos M C, Krishna S (2003). Water transport becomes uncoupled from K+ siphoning in brain contusion, bacterial meningitis, and brain tumours: immunohistochemical case review. J Clin Pathol. 56, 972-975.

Saarikangas J, Hakanen J, Mattila P K, Grumet M, Salminen M, Lappalainen P (2008). ABBA regulates plasma-membrane and actin dynamics to promote radial glia extension. J Cell Sci. 121, 1444-1454.

Saddoughi S A, Ogretmen B (2013). Diverse functions of ceramide in cancer cell death and proliferation. Adv. Cancer Res. 117, 37-58.

Saito T, et al. (2007). Survivin subcellular localization in high-grade astrocytomas: simultaneous expression in both nucleus and cytoplasm is negative prognostic marker. J Neurooncol. 82, 193-198.

Sakurai T, Friedlander D R, Grumet M (1996). Expression of polypeptide variants of receptor-type protein tyrosine phosphatase beta: the secreted form, phosphacan, increases dramatically during embryonic development and modulates glial cell behavior in vitro. J Neurosci. Res. 43, Sakurai T, et al. (2001). Overlapping functions of the cell adhesion molecules Nr-CAM and L1 in cerebellar granule cell development. J Cell Biol. 154, 1259-1273.

Sakurai T, Lustig M, Nativ M, Hemperly J J, Schlessinger J, Peles E, Grumet M (1997). Induction of neurite outgrowth through contactin and Nr-CAM by extracellular regions of glial receptor tyrosine phosphatase beta. J Cell Biol. 136, 907-918.

Sarai N, et al. (2008). Biochemical analysis of the N-terminal domain of human RAD54B. Nucleic Acids Res. 36, 5441-5450.

Sasaki T, Lopes M B, Hankins G R, Helm G A (2002). Expression of survivin, an inhibitor of apoptosis protein, in tumors of the nervous system. Acta Neuropathol. 104, 105-109.

Schoenfeld A R, Apgar S, Dolios G, Wang R, Aaronson S A (2004). BRCA2 is ubiquitinated in vivo and interacts with USP11, a deubiquitinating enzyme that exhibits prosurvival function in the cellular response to DNA damage. Mol. Cell Biol. 24, 7444-7455.

Sehgal A, et al. (1998). Cell adhesion molecule Nr-CAM is over-expressed in human brain tumors. Int J Cancer 76, 451-458.

Sehgal A, Ricks S, Warrick J, Boynton A L, Murphy G P (1999). Antisense human neuroglia related cell adhesion molecule hNr-CAM, reduces the tumorigenic properties of human glioblastoma cells. Anticancer Res. 19, 4947-4953.

Seifert W, Kuhnisch J, Maritzen T, Horn D, Haucke V, Hennies H C (2011). Cohen syndrome-associated protein, COH1, is a novel, giant Golgi matrix protein required for Golgi integrity. J Biol. Chem. 286, 37665-37675.

Senkal C E, et al. (2007). Role of human longevity assurance gene 1 and C18-ceramide in chemotherapy-induced cell death in human head and neck squamous cell carcinomas. Mol. Cancer Ther. 6, 712-722.

Sentelle R D, et al. (2012). Ceramide targets autophagosomes to mitochondria and induces lethal mitophagy. Nat Chem. Biol. 8, 831-838.

Separovic D, Breen P, Joseph N, Bielawski J, Pierce J S, VAN B E, Gudz T I (2012). siRNA-mediated down-regulation of ceramide synthase 1 leads to apoptotic resistance in human head and neck squamous carcinoma cells after photodynamic therapy. Anticancer Res. 32, 2479-2485.

Shiota M, et al. (2012). Clusterin mediates TGF-beta-induced epithelial-mesenchymal transition and metastasis via Twist1 in prostate cancer cells. Cancer Res. 72, 5261-5272.

Shoji H, Tsuchida K, Kishi H, Yamakawa N, Matsuzaki T, Liu Z, Nakamura T, Sugino H (2000). Identification and characterization of a PDZ protein that interacts with activin type II receptors. J Biol. Chem. 275, 5485-5492.

Siow D L, Wattenberg B W (2012). Mammalian ORMDL proteins mediate the feedback response in ceramide biosynthesis. J Biol. Chem. 287, 40198-40204.

Skaletsky H et al (2003). The male-specific region of the human Y chromosome is a mosaic of discrete sequence classes. Nature 423, 825-837.

Splinter P L, Lazaridis K N, Dawson P A, LaRusso N F (2006). Cloning and expression of SLC10A4, a putative organic anion transport protein. World J Gastroenterol. 12, 6797-6805.

Stepulak A, et al. (2009). Expression of glutamate receptor subunits in human cancers. Histochem. Cell Biol. 132, 435-445.

Stoeckli E T, Landmesser L T (1995). Axonin-1, Nr-CAM, and Ng-CAM play different roles in the in vivo guidance of chick commissural neurons. Neuron 14, 1165-1179.

Suzuki H, Gabrielson E, Chen W, Anbazhagan R, Van E M, Weijenberg M P, Herman J G, Baylin S B (2002). A genomic screen for genes upregulated by demethylation and histone deacetylase inhibition in human colorectal cancer. Nat Genet. 31, 141-149.

Svendsen A et al (2011). Expression of the progenitor marker NG2/CSPG4 predicts poor survival and resistance to ionising radiation in glioblastoma. Acta Neuropathol. 122, 495-510.

Tan G, Sun S Q, Yuan D L (2008). Expression of Kir 4.1 in human astrocytic tumors: correlation with pathologic grade. Biochem. Biophys. Res. Commun. 367, 743-747.

Thurner B et al (1999). Vaccination with mage-3A1 peptide-pulsed mature, monocyte-derived dendritic cells expands specific cytotoxic T cells and induces regression of some metastases in advanced stage IV melanoma. J Exp. Med 190, 1669-1678.

Tsai J R, et al. (2007). Differential expression profile of MAGE family in non-small-cell lung cancer. Lung Cancer 56, 185-192.

Tsourlakis M C, et al. (2013). High Nr-CAM expression is associated with favorable phenotype and late PSA recurrence in prostate cancer treated by prostatectomy. Prostate Cancer Prostatic. Dis.

Tuy F P, Saillour Y, Kappeler C, Chelly J, Francis F (2008). Alternative transcripts of Dclk1 and Dclk2 and their expression in doublecortin knockout mice. Dev. Neurosci. 30, 171-186.

Uematsu M, et al. (2005). Prognostic significance of the immunohistochemical index of survivin in glioma: a comparative study with the MIB-1 index. J Neurooncol. 72, 231-238.

Ulbricht U, et al. (2003). Expression and function of the receptor protein tyrosine phosphatase zeta and its ligand pleiotrophin in human astrocytomas. J Neuropathol. Exp. Neurol. 62, 1265-1275.

Ulbricht U, Eckerich C, Fillbrandt R, Westphal M, Lamszus K (2006). RNA interference targeting protein tyrosine phosphatase zeta/receptor-type protein tyrosine phosphatase beta suppresses glioblastoma growth in vitro and in vivo. J Neurochem. 98, 1497-1506.

Valiente M, et al. (2005). Binding of PTEN to specific PDZ domains contributes to PTEN protein stability and phosphorylation by microtubule-associated serine/threonine kinases. J Biol. Chem. 280, 28936-28943.

van A M, Schepens M, de B D, Janssen B, Merkx G, Geurts van K A (2000). Construction of a 350-kb sequence-ready 11q13 cosmid contig encompassing the markers D11S4933 and D11S546: mapping of 11 genes and 3 tumor-associated translocation breakpoints. Genomics 66, 35-42.

Vissers J H, Nicassio F, van L M, Di Fiore P P, Citterio E (2008). The many faces of ubiquitinated histone H2A: insights from the DUBs. Cell Div. 3, 8.

Volkmer H, Leuschner R, Zacharias U, Rathjen F G (1996). Neurofascin induces neurites by heterophilic interactions with axonal NrCAM while NrCAM requires F11 on the axonal surface to extend neurites. J Cell Biol. 135, 1059-1069.

Wang J, et al. (2011). Targeting the NG2/CSPG4 proteoglycan retards tumour growth and angiogenesis in preclinical models of GBM and melanoma. PLoS. ONE. 6, e23062.

Wang X, Su H, Bradley A (2002). Molecular mechanisms governing Pcdh-gamma gene expression: evidence for a multiple promoter and cis-alternative splicing model. Genes Dev. 16, 1890-1905.

Warth A, Mittelbronn M, Wolburg H (2005). Redistribution of the water channel protein aquaporin-4 and the K+ channel protein Kir4.1 differs in low- and high-grade human brain tumors. Acta Neuropathol. (Berl) 109, 418-426.

Weake V M, Workman J L (2008). Histone ubiquitination: triggering gene activity. Mol. Cell 29, 653-663.

Weiskirchen R, Erdel M, Utermann G, Bister K (1997). Cloning, structural analysis, and chromosomal localization of the human CSRP2 gene encoding the LIM domain protein CRP2. Genomics 44, 83-93.

Wellstein A (2012). ALK receptor activation, ligands and therapeutic targeting in glioblastoma and in other cancers. Front Oncol 2, 192.

Wheater M J, Johnson P W, Blaydes J P (2010). The role of MNK proteins and eIF4E phosphorylation in breast cancer cell proliferation and survival. Cancer Biol. Ther. 10, 728-735.

Wiltshire T D, Lovejoy C A, Wang T, Xia F, O'Connor M J, Cortez D (2010). Sensitivity to poly(ADP-ribose) polymerase (PARP) inhibition identifies ubiquitin-specific peptidase 11 (USP11) as a regulator of DNA double-strand break repair. J Biol. Chem. 285, 14565-14571.

Wood J D, Yuan J, Margolis R L, Colomer V, Duan K, Kushi J, Kaminsky Z, Kleiderlein J J, Sharp A H, Ross C A (1998). Atrophin-1, the DRPLA gene product, interacts with two families of W W domain-containing proteins. Mol. Cell Neurosci. 11, 149-160.

Wu A, et al. (2011). Elevated expression of CDK4 in lung cancer. J Transl. Med. 9, 38.

Xiao L, Rao J N, Zou T, Liu L, Marasa B S, Chen J, Turner D J, Passaniti A, Wang J Y (2007). Induced JunD in intestinal epithelial cells represses CDK4 transcription through its proximal promoter region following polyamine depletion. Biochem. J 403, 573-581.

Xie D, Zeng Y X, Wang H J, Wen J M, Tao Y, Sham J S, Guan X Y (2006). Expression of cytoplasmic and nuclear Survivin in primary and secondary human glioblastoma. Br. J Cancer 94, 108-114.

Xu C, et al. (2013). Polymorphisms in seizure 6-like gene are associated with bipolar disorder I: evidence of gene x gender interaction. J Affect. Disord. 145, 95-99.

Yamada A, Irie K, Deguchi-Tawarada M, Ohtsuka T, Takai Y (2003). Nectin-dependent localization of synaptic scaffolding molecule (S-SCAM) at the puncta adherentia junctions formed between the mossy fibre terminals and the dendrites of pyramidal cells in the CA3 area of the mouse hippocampus. Genes Cells 8, 985-994.

Yan J, Feng J, Schroer R, Li W, Skinner C, Schwartz C E, Cook E H, Jr., Sommer S S (2008). Analysis of the neuroligin 4Y gene in patients with autism. Psychiatr. Genet. 18, 204-207.

Yang G F, Li X M, Xie D (2009). Overexpression of clusterin in ovarian cancer is correlated with impaired survival. Int. J Gynecol. Cancer 19, 1342-1346.

Yang H, et al. (2012). In vivo study of breast carcinoma radiosensitization by targeting eIF4E. Biochem. Biophys. Res. Commun. 423, 878-883.

Yasukawa M, et al. (2013). Dpys14 is involved in tooth germ morphogenesis through growth regulation, polarization and differentiation of dental epithelial cells. Int. J Biol. Sci. 9, 382-390.

Ylisaukko-oja T, et al. (2005). Analysis of four neuroligin genes as candidates for autism. Eur. J Hum. Genet. 13, 1285-1292.

Zacharias U, Norenberg U, Rathjen F G (1999). Functional interactions of the immunoglobulin superfamily member F11 are differentially regulated by the extracellular matrix proteins tenascin-R and tenascin-C. J Biol. Chem. 274, 24357-24365.

Zadravec D, et al. (2011). ELOVL2 controls the level of n-6 28:5 and 30:5 fatty acids in testis, a prerequisite for male fertility and sperm maturation in mice. J Lipid Res. 52, 245-255.

Zangen I, et al. (2007). Ependymoma gene expression profiles associated with histological subtype, proliferation, and patient survival. Acta Neuropathol. 113, 325-337.

Zekri A R, et al. (2012). Molecular prognostic profile of Egyptian HCC cases infected with hepatitis C virus. Asian Pac. J Cancer Prev. 13, 5433-5438.

Zelano J, et al. (2013). The synaptic protein encoded by the gene Slc10A4 suppresses epileptiform activity and regulates sensitivity to cholinergic chemoconvulsants. Exp. Neurol. 239, 73-81.

Zhen H N, et al. (2005). Survivin expression and its relation with proliferation, apoptosis, and angiogenesis in brain gliomas. Cancer 104, 2775-2783.

Zheng D, et al. (2010). Abba promotes PDGF-mediated membrane ruffling through activation of the small GTPase Rac1. Biochem. Biophys. Res. Commun. 401, 527-532.

Zhu Z H, Yu Y P, Shi Y K, Nelson J B, Luo J H (2009). CSR1 induces cell death through inactivation of CPSF3. Oncogene 28, 41-51.

Aaltonen K, et al. (2009). High cyclin B1 expression is associated with poor survival in breast cancer. Br. J Cancer 100, 1055-1060.

Abd-Elaziz M, Akahira J, Moriya T, Suzuki T, Yaegashi N, Sasano H (2003). Nuclear receptor DAX-1 in human common epithelial ovarian carcinoma: an independent prognostic factor of clinical outcome. Cancer Sci. 94, 980-985.

Abe M, Watanabe N, McDonell N, Takato T, Ohira M, Nakagawara A, Ushijima T (2008). Identification of genes targeted by CpG island methylator phenotype in neuroblastomas, and their possible integrative involvement in poor prognosis. Oncology 74, 50-60.

Abraham R, Pagano F, Gomella L G, Baffa R (2007). Chromosomal deletions in bladder cancer: shutting down pathways. Front Biosci. 12, 826-838.

Abramic M, Simaga S, Osmak M, Cicin-Sain L, Vukelic B, Vlahovicek K, Dolovcak L (2004). Highly reactive cysteine residues are part of the substrate binding site of mammalian dipeptidyl peptidases III. Int. J Biochem. Cell Biol. 36, 434-446.

Agarwal R, et al. (2009). Integrative analysis of cyclin protein levels identifies cyclin b 1 as a classifier and predictor of outcomes in breast cancer. Clin Cancer Res 15, 3654-3662.

Akita K, et al. (2004). Heparan sulphate proteoglycans interact with neurocan and promote neurite outgrowth from cerebellar granule cells. Biochem. J 383, 129-138.

Al-Joudi F S, Iskandar Z A, Imran A K (2007). Survivin expression correlates with unfavourable prognoses in invasive ductal carcinoma of the breast. Med J Malaysia 62, 6-8.

Alarmo E L, Rauta J, Kauraniemi P, Karhu R, Kuukasjarvi T, Kallioniemi A (2006). Bone morphogenetic protein 7 is widely overexpressed in primary breast cancer. Genes Chromosomes. Cancer 45, 411-419.

Allison J P, Krummel M F (1995). The Yin and Yang of T cell costimulation. Science 270, 932-933.

Ammar H, Closset J L (2008). Clusterin activates survival through the phosphatidylinositol 3-kinase/Akt pathway. J Biol. Chem. 283, 12851-12861.

An C H, Kim Y R, Kim H S, Kim S S, Yoo N J, Lee S H (2012). Frameshift mutations of vacuolar protein sorting genes in gastric and colorectal cancers with microsatellite instability. Hum. Pathol. 43, 40-47.

Andersen R S, et al. (2012). Parallel detection of antigen-specific T cell responses by combinatorial encoding of MHC multimers. Nat. Protoc. 7, 891-902.

Aoki M, et al. (2011). Expression of BMP-7 in human gastric cancer and its clinical significance. Br. J Cancer 104, 714-718.

Appay V, et al. (2006). Decreased specific CD8+ T cell cross-reactivity of antigen recognition following vaccination with Melan-A peptide. Eur. J Immunol. 36, 1805-1814.

Appolloni I, Calzolari F, Barilari M, Terrile M, Daga A, Malatesta P (2012). Antagonistic modulation of gliomagenesis by Pax6 and Olig2 in PDGF-induced oligodendroglioma. Int. J Cancer 131, E1078-E1087.

Araki W, Takahashi-Sasaki N, Chui D H, Saito S, Takeda K, Shirotani K, Takahashi K, Murayama K S, Kametani F, Shiraishi H, Komano H, Tabira T (2008). A family of membrane proteins associated with presenilin expression and gamma-secretase function. FASEB J 22, 819-827.

Ariyannur P S, et al. (2010). Methamphetamine-induced neuronal protein NAT8L is the NAA biosynthetic enzyme: implications for specialized acetyl coenzyme A metabolism in the CNS. Brain Res. 1335, 1-13.

Aronica E, et al. (2001). Ionotropic and metabotropic glutamate receptor protein expression in glioneuronal tumours from patients with intractable epilepsy. Neuropathol. Appl. Neurobiol. 27, 223-237.

Aslibekyan S, et al. (2012). Genetic variation in fatty acid elongases is not associated with intermediate cardiovascular phenotypes or myocardial infarction. Eur. J Clin Nutr. 66, 353-359.

Augustin I, et al. (2012). The Wnt secretion protein Evi/Gpr177 promotes glioma tumourigenesis. EMBO Mol. Med. 4, 38-51.

Axelson H (2004). The Notch signaling cascade in neuroblastoma: role of the basic helix-loop-helix proteins HASH-1 and HES-1. Cancer Lett. 204, 171-178.

Aylsworth A, Jiang S X, Desbois A, Hou S T (2009). Characterization of the role of full-length CRMP3 and its calpain-cleaved product in inhibiting microtubule polymerization and neurite outgrowth. Exp. Cell Res. 315, 2856-2868.

Azari A A et al (2006). Retinal disease expression in Bardet-Biedl syndrome-1 (BBS1) is a spectrum from maculopathy to retina-wide degeneration. Invest Ophthalmol. Vis. Sci. 47, 5004-5010.

Azuma M, Toyama R, Laver E, Dawid I B (2006). Perturbation of rRNA synthesis in the bap28 mutation leads to apoptosis mediated by p53 in the zebrafish central nervous system. J Biol. Chem. 281, 13309-13316.

Ball D W (2004). Achaete-scute homolog-1 and Notch in lung neuroendocrine development and cancer. Cancer Lett. 204, 159-169.

Balzeau J, Peterson A, Eyer J (2012). The vimentin-tubulin binding site peptide (Vim-TBS.58-81) crosses the plasma membrane and enters the nuclei of human glioma cells. Int. J Pharm. 423, 77-83.

Bar-Yehuda S, Stemmer S M, Madi L, Castel D, Ochaion A, Cohen S, Barer F, Zabutti A, Perez-Liz G, Del V L, Fishman P (2008). The A3 adenosine receptor agonist CF102 induces apoptosis of hepatocellular carcinoma via de-regulation of the Wnt and NF-kappaB signal transduction pathways. Int. J Oncol 33, 287-295.

Bargo S, Raafat A, McCurdy D, Amirjazil I, Shu Y, Traicoff J, Plant J, Vonderhaar B K, Callahan R (2010). Transforming acidic coiled-coil protein-3 (Tacc3) acts as a negative regulator of Notch signaling through binding to CDC10/Ankyrin repeats. Biochem. Biophys. Res Commun. 400, 606-612.

Barnett M, et al. (2001). Paraneoplastic brain stem encephalitis in a woman with anti-Ma2 antibody. J Neurol. Neurosurg. Psychiatry 70, 222-225.

Bartsch S, et al. (1992). Expression of tenascin in the developing and adult cerebellar cortex. J Neurosci. 12, 736-749.

Bayraktar S, Gutierrez Barrera A M, Liu D, Pusztai L, Litton J, Valero V, Hunt K, Hortobagyi G N, Wu Y, Symmans F, Arun B (2013). USP-11 as a predictive and prognostic factor following neoadjuvant therapy in women with breast cancer. Cancer J 19, 10-17.

Beljan P R, Durdov M G, Capkun V, Ivcevic V, Pavlovic A, Soljic V, Peric M (2012). IMP3 can predict aggressive behaviour of lung adenocarcinoma. Diagn. Pathol. 7, 165.

Berthold J, Schenkova K, Ramos S, Miura Y, Furukawa M, Aspenstrom P, Rivero F (2008a). Characterization of RhoBTB-dependent Cul3 ubiquitin ligase complexes—evidence for an autoregulatory mechanism. Exp. Cell Res. 314, 3453-3465.

Berthold J, Schenkova K, Rivero F (2008b). Rho GTPases of the RhoBTB subfamily and tumorigenesis. Acta Pharmacol. Sin. 29, 285-295.

Bi J, et al. (2010). Overexpression of clusterin correlates with tumor progression, metastasis in gastric cancer: a study on tissue microarrays. Neoplasma 57, 191-197.

Bigarella C L, Borges L, Costa F F, Saad S T (2009). ARHGAP21 modulates FAK activity and impairs glioblastoma cell migration. Biochim. Biophys. Acta 1793, 806-816.

Bigarella et al. (2012). Post-translational modification of the RhoGTPase activating protein 21, ARHGAP21, by SUMO2/3. FEBS Lett. 586, 3522-3528.

Bikeye S N, et al. (2010). ASPM-associated stem cell proliferation is involved in malignant progression of gliomas and constitutes an attractive therapeutic target. Cancer Cell Int 10, 1.

Bikeye S N, et al. (2011). Correction: ASPM-associated stem cell proliferation is involved in malignant progression of gliomas and constitutes an attractive therapeutic target. Cancer Cell Int. 11, 10.

Bivona T G, et al. (2011). FAS and NF-kappaB signalling modulate dependence of lung cancers on mutant EGFR. Nature 471, 523-526.

Blom T, Roselli A, Tanner M, Nupponen N N (2008). Mutation and copy number analysis of LNX1 and Numbl in nervous system tumors. Cancer Genet. Cytogenet. 186, 103-109.

Bocciardi R, et al. (2005). Molecular characterization of a t(2; 6) balanced translocation that is associated with a complex phenotype and leads to truncation of the TCBA1 gene. Hum. Mutat. 26, 426-436.

Bock A J, Nymoen D A, Brenne K, Kaern J, Davidson B (2012). SCARA3 mRNA is overexpressed in ovarian carcinoma compared with breast carcinoma effusions. Hum. Pathol. 43, 669-674.

Bonnefont J P, Djouadi F, Prip-Buus C, Gobin S, Munnich A, Bastin J (2004). Carnitine palmitoyltransferases 1 and 2: biochemical, molecular and medical aspects. Mol. Aspects Med. 25, 495-520.

Borges M, Linnoila R I, van de Velde H J, Chen H, Nelkin B D, Mabry M, Baylin S B, Ball D W (1997). An achaete-scute homologue essential for neuroendocrine differentiation in the lung. Nature 386, 852-855.

Bourdon M A, Wikstrand C J, Furthmayr H, Matthews T J, Bigner D D (1983). Human glioma-mesenchymal extracellular matrix antigen defined by monoclonal antibody. Cancer Res. 43, 2796-2805.

Boureux A, Vignal E, Faure S, Fort P (2007). Evolution of the Rho family of ras-like GTPases in eukaryotes. Mol. Biol. Evol. 24, 203-216.

Bozinov O, Kohler S, Samans B, Benes L, Miller D, Ritter M, Sure U, Bertalanffy H (2008). Candidate genes for the progression of malignant gliomas identified by microarray analysis. Neurosurg. Rev. 31, 83-89.

Brait M, et al. (2012). Correlation between BRAF mutation and promoter methylation of TIMP3, RARbeta2 and RASSF1A in thyroid cancer. Epigenetics. 7, 710-719.

Breeden L, Nasmyth K (1987). Similarity between cell-cycle genes of budding yeast and fission yeast and the Notch gene of Drosophila. Nature 329, 651-654.

Bret C, et al. (2009). Expression of genes encoding for proteins involved in heparan sulphate and chondroitin sulphate chain synthesis and modification in normal and malignant plasma cells. Br. J Haematol. 145, 350-368.

Brocke K S, et al. (2010). Glutamate receptors in pediatric tumors of the central nervous system. Cancer Biol. Ther. 9, 455-468.

Bruchovsky N, Snoek R, Rennie P S, Akakura K, Goldenberg L S, Gleave M (1996). Control of tumor progression by maintenance of apoptosis. Prostate Suppl 6, 13-21.

Bruckdorfer T, Marder O, Albericio F (2004). From production of peptides in milligram amounts for research to multi-tons quantities for drugs of the future. Curr. Pharm. Biotechnol. 5, 29-43.

Bruning-Richardson A, et al. (2011). ASPM and microcephalin expression in epithelial ovarian cancer correlates with tumour grade and survival. Br. J Cancer 104, 1602-1610.

Brunskill E W, Witte D P, Shreiner A B, Potter S S (1999). Characterization of npas3, a novel basic helix-loop-helix PAS gene expressed in the developing mouse nervous system. Mech. Dev. 88, 237-241.

Brunsvig P F, et al. (2006). Telomerase peptide vaccination: a phase I/II study in patients with non-small cell lung cancer. Cancer Immunol. Immunother. 55, 1553-1564.

Budreck E C, Scheiffele P (2007). Neuroligin-3 is a neuronal adhesion protein at GABAergic and glutamatergic synapses. Eur. J Neurosci. 26, 1738-1748.

Burch T C, Watson M T, Nyalwidhe J O (2013). Variable metastatic potentials correlate with differential plectin and vimentin expression in syngeneic androgen independent prostate cancer cells. PLoS. ONE. 8, e65005.

Burkhart R A, et al. (2013). Mitoxantrone Targets Human Ubiquitin-Specific Peptidase 11 (USP11) and Is a Potent Inhibitor of Pancreatic Cancer Cell Survival. Mol. Cancer Res. 11, 901-911.

Burris T P, Nawaz Z, Tsai M J, O'Malley B W (1995). A nuclear hormone receptor-associated protein that inhibits transactivation by the thyroid hormone and retinoic acid receptors. Proc. Natl. Acad. Sci. U.S.A 92, 9525-9529.

Cabeza-Arvelaiz Y, Sepulveda J L, Lebovitz R M, Thompson T C, Chinault A C (2001). Functional identification of LZTS1 as a candidate prostate tumor suppressor gene on human chromosome 8p22. Oncogene 20, 4169-4179.

Calboli F C, et al. (2010). A genome-wide association study of neuroticism in a population-based sample. PLoS. ONE. 5, e11504.

Camoes M J, et al. (2012). Potential downstream target genes of aberrant ETS transcription factors are differentially affected in Ewing's sarcoma and prostate carcinoma. PLoS. ONE. 7, e49819.

Canoll P D, Barnea G, Levy J B, Sap J, Ehrlich M, Silvennoinen O, Schlessinger J, Musacchio J M (1993). The expression of a novel receptor-type tyrosine phosphatase suggests a role in morphogenesis and plasticity of the nervous system. Brain Res. Dev. Brain Res. 75, 293-298.

Cantara S, D'Angeli F, Toti P, Lignitto L, Castagna M G, Capuano S, Prabhakar B S, Feliciello A, Pacini F (2012). Expression of the ring ligase PRAJA2 in thyroid cancer. J Clin Endocrinol. Metab 97, 4253-4259.

Caren H, Ejeskar K, Fransson S, Hesson L, Latif F, Sjoberg R M, Krona C, Martinsson T (2005). A cluster of genes located in 1p36 are down-regulated in neuroblastomas with poor prognosis, but not due to CpG island methylation. Mol. Cancer 4, 10.

Cargnello M, Roux P P (2011). Activation and function of the MAPKs and their substrates, the MAPK-activated protein kinases. Microbiol. Mol. Biol. Rev. 75, 50-83.

Carinci F, et al. (2005). Potential markers of tongue tumor progression selected by cDNA microarray. Int. J Immunopathol. Pharmacol. 18, 513-524.

Carney M E, O'Reilly R C, Sholevar B, Buiakova O I, Lowry L D, Keane W M, Margolis F L, Rothstein J L (1995). Expression of the human Achaete-scute 1 gene in olfactory neuroblastoma (esthesioneuroblastoma). J Neurooncol. 26, 35-43.

Carroll M, Borden K L (2013). The Oncogene eIF4E: Using Biochemical Insights to Target Cancer. J Interferon Cytokine Res. 33, 227-238.

Casado M E, et al. (2013). Hormone-sensitive lipase deficiency disturbs the fatty acid composition of mouse testis. Prostaglandins Leukot. Essent. Fatty Acids 88, 227-233.

Casati C, et al. (2003). The apoptosis inhibitor protein survivin induces tumor-specific CD8+ and CD4+ T cells in colorectal cancer patients. Cancer Res. 63, 4507-4515.

Casper M, Grunhage F, Lammert F (2011). Cancer risk in chronic hepatitis B: Do genome-wide association studies hit the mark? Hepatology 53, 1390-1392.

Cayan F, Tok E, Aras-Ates N, Ayaz L, Akbay E, Gen R, Karakas S, Dilek S (2010). Insulin receptor substrate-2 gene polymorphism: is it associated with endometrial cancer? Gynecol. Endocrinol. 26, 378-382.

Cervantes M D, Coyne R S, Xi X, Yao M C (2006). The condensin complex is essential for amitotic segregation of bulk chromosomes, but not nucleoli, in the ciliate Tetrahymena thermophila. Mol. Cell Biol. 26, 4690-4700.

Cervelli M, Amendola R, Polticelli F, Mariottini P (2012). Spermine oxidase: ten years after. Amino. Acids 42, 441-450.

Cervelli M et al (2010). Spermine oxidase (SMO) activity in breast tumor tissues and biochemical analysis of the anticancer spermine analogues BENSpm and CPENSpm. BMC. Cancer 10, 555.

Chae S W, Sohn J H, Kim D H, Choi Y J, Park Y L, Kim K, Cho Y H, Pyo J S, Kim J H (2011). Overexpressions of Cyclin B1, cdc2, p16 and p53 in human breast cancer: the clinicopathologic correlations and prognostic implications. Yonsei Med. J 52, 445-453.

Chaiwatanasirikul K A, Sala A (2011). The tumour-suppressive function of CLU is explained by its localisation and interaction with HSP60. Cell Death. Dis. 2, e219.

Chakravarti A, Noll E, Black P M, Finkelstein D F, Finkelstein D M, Dyson N J, Loeffler J S (2002). Quantitatively determined survivin expression levels are of prognostic value in human gliomas. J Clin Oncol 20, 1063-1068.

Chan J Y, Ong C W, Salto-Tellez M (2011). Overexpression of neurone glial-related cell adhesion molecule is an independent predictor of poor prognosis in advanced colorectal cancer. Cancer Sci. 102, 1855-1861.

Chanock S J, Foster C B, Miller F W, O'Hanlon T P (2004). HLA-A, -B, -Cw, -DQA1 and -DRB1 Alleles in a Caucasian Population from Bethesda, USA. Hum. Immunol. 65, 1211-1223.

Charfi C, Voisin V, Levros L C, Jr., Edouard E, Rassart E (2011). Gene profiling of Graffi murine leukemia virus-induced lymphoid leukemias: identification of leukemia markers and Fmn2 as a potential oncogene. Blood 117, 1899-1910.

Chekenya M, Hjelstuen M, Enger P O, Thorsen F, Jacob A L, Probst B, Haraldseth O, Pilkington G, Butt A, Levine J M, Bjerkvig R (2002). NG2 proteoglycan promotes angiogenesis-dependent tumor growth in CNS by sequestering angiostatin. FASEB J 16, 586-588.

Chekenya M, et al. (2008). The progenitor cell marker NG2/MPG promotes chemoresistance by activation of integrin-dependent PI3K/Akt signaling. Oncogene 27, 5182-5194.

Chekenya M, Pilkington G J (2002). NG2 precursor cells in neoplasia: functional, histogenesis and therapeutic implications for malignant brain tumours. J Neurocytol. 31, 507-521.

Chekenya M, Rooprai H K, Davies D, Levine J M, Butt A M, Pilkington G J (1999). The NG2 chondroitin sulfate proteoglycan: role in malignant progression of human brain tumours. Int J Dev. Neurosci. 17, 421-435.

Chen C, Bartenhagen C, Gombert M, Okpanyi V, Binder V, Rottgers S, Bradtke J, Teigler-Schlegel A, Harbott J, Ginzel S, Thiele R, Fischer U, Dugas M, Hu J, Borkhardt A (2013a). Next-generation-sequencing-based risk stratification and identification of new genes involved in structural and sequence variations in near haploid lymphoblastic leukemia. Genes Chromosomes. Cancer 52, 564-579.

Chen D, Wang Y, Zhang K, Jiao X, Yan B, Liang J (2012a). Antisense oligonucleotide against clusterin regulates human hepatocellular carcinoma invasion through transcriptional regulation of matrix metalloproteinase-2 and e-cadherin. Int. J Mol. Sci. 13, 10594-10607.

Chen J, Xu J, Zhao W, Hu G, Cheng H, Kang Y, Xie Y, Lu Y (2005). Characterization of human LNX, a novel ligand of Numb protein X that is downregulated in human gliomas. Int. J Biochem. Cell Biol. 37, 2273-2283.

Chen J C, Chen Y, Wu J M, Su Y H, Tai K F, Tseng S H (2006). Effects of irradiated tumor vaccine and infusion of granulocyte-macrophage colony-stimulating factor and interleukin-12 on established gliomas in rats. Cancer Immunol. Immunother. 55, 873-883.

Chen L, Zhu Y Y, Zhang X J, Wang G L, Li X Y, He S, Zhang J B, Zhu J W (2009). TSPAN1 protein expression: a significant prognostic indicator for patients with colorectal adenocarcinoma. World J Gastroenterol. 15, 2270-2276.

Chen P, Wang S J, Wang H B, Ren P, Wang X Q, Liu W G, Gu W L, Li D Q, Zhang T G, Zhou C J (2012b). The distribution of IGF2 and IMP3 in osteosarcoma and its relationship with angiogenesis. J Mol. Histol. 43, 63-70.

Chen S T, et al. (2011). Insulin-like growth factor II mRNA-binding protein 3 expression predicts unfavorable prognosis in patients with neuroblastoma. Cancer Sci. 102, 2191-2198.

Chen Y W, Chu H C, Ze-Shiang L, Shiah W J, Chou C P, Klimstra D S, Lewis B C (2013b). p16 Stimulates CDC42-dependent migration of hepatocellular carcinoma cells. PLoS. ONE. 8, e69389.

Cheng Y C, Lee C J, Badge R M, Orme A T, Scotting P J (2001). Sox8 gene expression identifies immature glial cells in developing cerebellum and cerebellar tumours. Brain Res. Mol. Brain Res. 92, 193-200.

Cheung I Y, Feng Y, Gerald W, Cheung N K (2008). Exploiting gene expression profiling to identify novel minimal residual disease markers of neuroblastoma. Clin Cancer Res. 14, 7020-7027.

Chih B, Afridi S K, Clark L, Scheiffele P (2004). Disorder-associated mutations lead to functional inactivation of neuroligins. Hum. Mol. Genet. 13, 1471-1477.

Chih B, Liu P, Chinn Y, Chalouni C, Komuves L G, Hass P E, Sandoval W, Peterson A S (2012). A ciliopathy complex at the transition zone protects the cilia as a privileged membrane domain. Nat Cell Biol. 14, 61-72.

Chiquet-Ehrismann R (1993). Tenascin and other adhesion-modulating proteins in cancer. Semin. Cancer Biol. 4, 301-310.

Chiquet-Ehrismann R, Chiquet M (2003). Tenascins: regulation and putative functions during pathological stress. J Pathol. 200, 488-499.

Chirasani S R, et al. (2010). Bone morphogenetic protein-7 release from endogenous neural precursor cells suppresses the tumourigenicity of stem-like glioblastoma cells. Brain 133, 1961-1972.

Choi C H, Lee J S, Kim S R, Lee Y Y, Kim C J, Lee J W, Kim T J, Lee J H, Kim B G, Bae D S (2011). Direct inhibition of eIF4E reduced cell growth in endometrial adenocarcinoma. J Cancer Res. Clin Oncol 137, 463-469.

Chubykin A A, Atasoy D, Etherton M R, Brose N, Kavalali E T, Gibson J R, Sudhof T C (2007). Activity-dependent validation of excitatory versus inhibitory synapses by neuroligin-1 versus neuroligin-2. Neuron 54, 919-931.

Chung F Y, et al. (2010). Differential gene expression profile of MAGE family in taiwanese patients with colorectal cancer. J Surg. Oncol 102, 148-153.

Cillo C, et al. (2011). The HOX gene network in hepatocellular carcinoma. Int. J Cancer 129, 2577-2587.

Cimino-Mathews A, Subhawong A P, Elwood H, Warzecha H N, Sharma R, Park B H, Taube J M, Illei P B, Argani P (2013). Neural crest transcription factor Sox10 is preferentially expressed in triple-negative and metaplastic breast carcinomas. Hum. Pathol. 44, 959-965.

Clark J L, Dresser K, Hsieh C C, Sabel M, Kleer C G, Khan A, Shaw L M (2011). Membrane localization of insulin receptor substrate-2 (IRS-2) is associated with decreased overall survival in breast cancer. Breast Cancer Res. Treat. 130, 759-772.

Claro da S T, Polli J E, Swaan P W (2013). The solute carrier family 10 (SLC10): beyond bile acid transport. Mol. Aspects Med. 34, 252-269.

Clements J A, Mercer F C, Paterno G D, Gillespie L L (2012). Differential splicing alters subcellular localization of the alpha but not beta isoform of the MIER1 transcriptional regulator in breast cancer cells. PLoS. ONE. 7, e32499.

Colombetti S, Basso V, Mueller D L, Mondino A (2006). Prolonged TCR/CD28 engagement drives IL-2-independent T cell clonal expansion through signaling mediated by the mammalian target of rapamycin. J Immunol. 176, 2730-2738.

Coon S W, Savera A T, Zarbo R J, Benninger M S, Chase G A, Rybicki B A, Van Dyke D L (2004). Prognostic implications of loss of heterozygosity at 8p21 and 9p21 in head and neck squamous cell carcinoma. Int. J Cancer 111, 206-212.

Cooper W A, Kohonen-Corish M R, McCaughan B, Kennedy C, Sutherland R L, Lee C S (2009). Expression and prognostic significance of cyclin B1 and cyclin A in non-small cell lung cancer. Histopathology 55, 28-36.

Coppieters F, Casteels I, Meire F, De J S, Hooghe S, van R N, Van E H, Matuleviciene A, Nunes L, Meersschaut V, Walraedt S, Standaert L, Coucke P, Hoeben H, Kroes H Y, Vande W J, de R T, Leroy B P, De B E (2010). Genetic screening of LCA in Belgium: predominance of CEP290 and identification of potential modifier alleles in AHI1 of CEP290-related phenotypes. Hum. Mutat. 31, E1709-E1766.

Coppola D, Fu L, Nicosia S V, Kounelis S, Jones M (1998). Prognostic significance of p53, bcl-2, vimentin, and S100 protein-positive Langerhans cells in endometrial carcinoma. Hum. Pathol. 29, 455-462.

Cruz-Garcia D, Diaz-Ruiz A, Rabanal-Ruiz Y, Peinado J R, Gracia-Navarro F, Castano J P, Montero-Hadjadje M, Tonon M C, Vaudry H, Anouar Y, Vazquez-Martinez R, Malagon M M (2012). The Golgi-associated long coiled-coil protein NECC1 participates in the control of the regulated secretory pathway in PC12 cells. Biochem. J 443, 387-396.

Cruz-Garcia D, Vazquez-Martinez R, Peinado J R, Anouar Y, Tonon M C, Vaudry H, Castano J P, Malagon M M (2007). Identification and characterization of two novel (neuro)endocrine long coiled-coil proteins. FEBS Lett. 581, 3149-3156.

Cui J, Deubler D A, Rohr L R, Zhu X L, Maxwell T M, Changus J E, Brothman A R (1998). Chromosome 7 abnormalities in prostate cancer detected by dual-color fluorescence in situ hybridization. Cancer Genet. Cytogenet. 107, 51-60.

Culjkovic-Kraljacic B, Baguet A, Volpon L, Amri A, Borden K L (2012). The oncogene eIF4E reprograms the nuclear pore complex to promote mRNA export and oncogenic transformation. Cell Rep. 2, 207-215.

Cunningham J M, Shan A, Wick M J, McDonnell S K, Schaid D J, Tester D J, Qian J, Takahashi S, Jenkins R B, Bostwick D G, Thibodeau S N (1996). Allelic imbalance and microsatellite instability in prostatic adenocarcinoma. Cancer Res. 56, 4475-4482.

Dallosso A R, Oster B, Greenhough A, Thorsen K, Curry T J, Owen C, Hancock A L, Szemes M, Paraskeva C, Frank M, Andersen C L, Malik K (2012). Long-range epigenetic silencing of chromosome 5q31 protocadherins is involved in early and late stages of colorectal tumorigenesis through modulation of oncogenic pathways. Oncogene 31, 4409-4419.

de Blaquiere G E, May F E, Westley B R (2009). Increased expression of both insulin receptor substrates 1 and 2 confers increased sensitivity to IGF-1 stimulated cell migration. Endocr. Relat Cancer 16, 635-647.

De B A, Hendrix A, Maynard D, Van B M, Daniels A, Pauwels P, Gespach C, Bracke M, De W O (2013). Differential secretome analysis of cancer-associated fibroblasts and bone marrow-derived precursors to identify microenvironmental regulators of colon cancer progression. Proteomics. 13, 379-388.

De F S, Russo G, Angiolillo A, Pietropaolo C (1993). Human L7a ribosomal protein: sequence, structural organization, and expression of a functional gene. Gene 126, 227-235.

de H T, Hasselt N, Troost D, Caron H, Popovic M, Zadravec-Zaletel L, Grajkowska W, Perek M, Osterheld M C, Ellison D, Baas F, Versteeg R, Kool M (2008). Molecular risk stratification of medulloblastoma patients based on immunohistochemical analysis of MYC, LDHB, and CCNB1 expression. Clin Cancer Res 14, 4154-4160.

De R A, Pellegatta S, Rossi M, Tunici P, Magnoni L, Speranza M C, Malusa F, Miragliotta V, Mori E, Finocchiaro G, Bakker A (2012). A Radial Glia Gene Marker, Fatty Acid Binding Protein 7 (FABP7), Is Involved in Proliferation and Invasion of Glioblastoma Cells. PLoS. ONE. 7, e52113.

Deloukas P et al (2001). The DNA sequence and comparative analysis of human chromosome 20. Nature 414, 865-871.

Demokan S, Chang X, Chuang A, Mydlarz W K, Kaur J, Huang P, Khan Z, Khan T, Ostrow K L, Brait M, Hoque M O, Liegeois N J, Sidransky D, Koch W, Califano J A (2010). KIF1A and EDNRB are differentially methylated in primary HNSCC and salivary rinses. Int. J Cancer 127, 2351-2359.

den Hollander A I, Johnson K, de Kok Y J, Klebes A, Brunner H G, Knust E, Cremers F P (2001). CRB1 has a cytoplasmic domain that is functionally conserved between human and Drosophila. Hum. Mol. Genet. 10, 2767-2773.

den Hollander A I, van Driel M A, de Kok Y J, van de Pol D J, Hoyng C B, Brunner H G, Deutman A F, Cremers F P (1999). Isolation and mapping of novel candidate genes for retinal disorders using suppression subtractive hybridization. Genomics 58, 240-249.

Deng F, Price M G, Davis C F, Mori M, Burgess D L (2006). Stargazin and other transmembrane AMPA receptor regulating proteins interact with synaptic scaffolding protein MAGI-2 in brain. J Neurosci. 26, 7875-7884.

Deng R, Wang X, Liu Y, Yan M, Hanada S, Xu Q, Zhang J, Han Z, Chen W, Zhang P (2013). A new gamboge derivative Compound 2 inhibits cancer stem-like cells via suppressing EGFR tyrosine phosphorylation in head and neck squamous cell carcinoma. J Cell Mol. Med.

Deng X, Shibata H, Takeuchi N, Rachi S, Sakai M, Ninomiya H, Iwata N, Ozaki N, Fukumaki Y (2007). Association study of polymorphisms in the glutamate transporter genes SLC1A1, SLC1A3, and SLC1A6 with schizophrenia. Am. J Med. Genet. B Neuropsychiatr. Genet. 144B, 271-278.

Dengjel J, Nastke M D, Gouttefangeas C, Gitsioudis G, Schoor O, Altenberend F, Muller M, Kramer B, Missiou A, Sauter M, Hennenlotter J, Wernet D, Stenzl A, Rammensee H G, Klingel K, Stevanovic S (2006). Unexpected Abundance of HLA Class II Presented Peptides in Primary Renal Cell Carcinomas. Clin Cancer Res. 12, 4163-4170.

Denli A M, Tops B B, Plasterk R H, Ketting R F, Hannon G J (2004). Processing of primary microRNAs by the Microprocessor complex. Nature 432, 231-235.

Donati D, Di B C, Lucarelli E, Dozza B, Frisoni T, Aldini N N, Giardino R (2008). OP-1 application in bone allograft integration: preliminary results in sheep experimental surgery. Injury 39 Suppl 2, S65-S72.

Dondeti V R, Wubbenhorst B, Lal P, Gordan J D, D'Andrea K, Attiyeh E F, Simon M C, Nathanson K L (2012). Integrative genomic analyses of sporadic clear cell renal cell carcinoma define disease subtypes and potential new therapeutic targets. Cancer Res. 72, 112-121.

Dong Y, Sui L, Watanabe Y, Sugimoto K, Tokuda M (2002). Clinical relevance of cyclin B1 overexpression in laryngeal squamous cell carcinoma. Cancer Lett. 177, 13-19.

Dong Z, Xu X, Du L, Yang Y, Cheng H, Zhang X, LI Z, Wang L, Li J, Liu H, Qu X, Wang C (2013). Leptin-mediated regulation of MT1-MMP localization is KIF1B dependent and enhances gastric cancer cell invasion. Carcinogenesis 34, 974-983.

Donson A M, Erwin N S, Kleinschmidt-DeMasters B K, Madden J R, Addo-Yobo S O, Foreman N K (2007). Unique molecular characteristics of radiation-induced glioblastoma. J Neuropathol. Exp. Neurol. 66, 740-749.

Dowler S, Currie R A, Campbell D G, Deak M, Kular G, Downes C P, Alessi D R (2000). Identification of pleckstrin-homology-domain-containing proteins with novel phosphoinositide-binding specificities. Biochem. J 351, 19-31.

Dubois T, Paleotti O, Mironov A A, Fraisier V, Stradal T E, De Matteis M A, Franco M, Chavrier P (2005). Golgi-localized GAP for Cdc42 functions downstream of ARF1 to control Arp2/3 complex and F-actin dynamics. Nat Cell Biol. 7, 353-364.

Ebermann I, Wiesen M H, Zrenner E, Lopez I, Pigeon R, Kohl S, Lowenheim H, Koenekoop R K, Bolz H J (2009). GPR98 mutations cause Usher syndrome type 2 in males. J Med. Genet. 46, 277-280.

Eckes B, Dogic D, Colucci-Guyon E, Wang N, Maniotis A, Ingber D, Merckling A, Langa F, Aumailley M, Delouvee A, Koteliansky V, Babinet C, Krieg T (1998). Impaired mechanical stability, migration and contractile capacity in vimentin-deficient fibroblasts. J Cell Sci. 111 (Pt 13), 1897-1907.

Eckes B, Zigrino P, Kessler D, Holtkotter O, Shephard P, Mauch C, Krieg T (2000). Fibroblast-matrix interactions in wound healing and fibrosis. Matrix Biol. 19, 325-332.

Edelman A M, Kim W Y, Higgins D, Goldstein E G, Oberdoerster M, Sigurdson W (2005). Doublecortin kinase-2, a novel doublecortin-related protein kinase associated with terminal segments of axons and dendrites. J Biol Chem. 280, 8531-8543.

Edwards M C, Liegeois N, Horecka J, Depinho R A, Sprague G F, Jr., Tyers M, Elledge S J (1997). Human CPR (cell cycle progression restoration) genes impart a Far-phenotype on yeast cells. Genetics 147, 1063-1076.

Egland K A, Liu X F, Squires S, Nagata S, Man Y G, Bera T K, Onda M, Vincent J J, Strausberg R L, Lee B, Pastan I (2006). High expression of a cytokeratin-associated protein in many cancers. Proc Natl. Acad. Sci. U.S.A 103, 5929-5934.

Ellinger J, El K N, Heukamp L C, Matthews S, Cubukluoz F, Kahl P, Perabo F G, Muller S C, Von R A, Bastian P J (2008). Hypermethylation of cell-free serum DNA indicates worse outcome in patients with bladder cancer. J Urol. 179, 346-352.

Engel M, Maurel P, Margolis R U, Margolis R K (1996). Chondroitin sulfate proteoglycans in the developing central nervous system. I. cellular sites of synthesis of neurocan and phosphacan. J Comp Neurol. 366, 34-43.

Erbel-Sieler C, Dudley C, Zhou Y, Wu X, Estill S J, Han T, Diaz-Arrastia R, Brunskill E W, Potter S S, McKnight S L (2004). Behavioral and regulatory abnormalities in mice deficient in the NPAS1 and NPAS3 transcription factors. Proc. Natl. Acad. Sci. U.S.A 101, 13648-13653.

Escudero-Esparza A, Jiang W G, Martin T A (2012). Claudin-5 is involved in breast cancer cell motility through the N-WASP and ROCK signalling pathways. J Exp. Clin Cancer Res. 31, 43.

Etcheverry A, Aubry M, de T M, Vauleon E, Boniface R, Guenot F, Saikali S, Hamlat A, Riffaud L, Menei P, Quillien V, Mosser J (2010). DNA methylation in glioblastoma: impact on gene expression and clinical outcome. BMC. Genomics 11, 701.

Falk K, Rotzschke O, Stevanovic S, Jung G, Rammensee H G (1991). Allele-specific motifs revealed by sequencing of self-peptides eluted from MHC molecules. Nature 351, 290-296.

Ferguson B W, Datta S (2011). Role of heparan sulfate 2-o-sulfotransferase in prostate cancer cell proliferation, invasion, and growth factor signaling. Prostate Cancer 2011, 893208.

Feyeux M, Bourgois-Rocha F, Redfern A, Giles P, Lefort N, Aubert S, Bonnefond C, Bugi A, Ruiz M, Deglon N, Jones L, Peschanski M, Allen N D, Perrier A L (2012). Early transcriptional changes linked to naturally occurring Huntington's disease mutations in neural derivatives of human embryonic stem cells. Hum. Mol. Genet. 21, 3883-3895.

Findeis-Hosey J J, Xu H (2012). Insulin-like growth factor II-messenger RNA-binding protein-3 and lung cancer. Biotech. Histochem. 87, 24-29.

Findeis-Hosey J J, Yang Q, Spaulding B O, Wang H L, Xu H (2010). IMP3 expression is correlated with histologic grade of lung adenocarcinoma. Hum. Pathol. 41, 477-484.

Fishman P, Bar-Yehuda S, Madi L, Cohn I (2002). A3 adenosine receptor as a target for cancer therapy. Anticancer Drugs 13, 437-443.

Fjorback A W, Muller H K, Wiborg O (2009). Membrane glycoprotein M6B interacts with the human serotonin transporter. J Mol. Neurosci. 37, 191-200.

Flammiger A, Besch R, Cook A L, Maier T, Sturm R A, Berking C (2009). SOX9 and SOX10 but not BRN2 are required for nestin expression in human melanoma cells. J Invest Dermatol. 129, 945-953.

Flinterman M B, Mymryk J S, Klanrit P, Yousef A F, Lowe S W, Caldas C, Gaken J, Farzaneh F, Tavassoli M (2007). p400 function is required for the adenovirus E1A-mediated suppression of EGFR and tumour cell killing. Oncogene 26, 6863-6874.

Fode C, Ma Q, Casarosa S, Ang S L, Anderson D J, Guillemot F (2000). A role for neural determination genes in specifying the dorsoventral identity of telencephalic neurons. Genes Dev. 14, 67-80.

Fong L, Hou Y, Rivas A, Benike C, Yuen A, Fisher G A, Davis M M, Engleman E G (2001). Altered peptide ligand vaccination with Flt3 ligand expanded dendritic cells for tumor immunotherapy. Proc. Natl. Acad. Sci. U.S.A 98, 8809-8814.

Frank M, Kemler R (2002). Protocadherins. Curr. Opin. Cell Biol. 14, 557-562.

Fu J, Koul D, Yao J, Wang S, Yuan Y, Colman H, Sulman E P, Lang F F, Yung W K (2013). Novel HSP90 inhibitor NVP-HSP990 targets cell-cycle regulators to ablate Olig2-positive glioma tumor-initiating cells. Cancer Res. 73, 3062-3074.

Fukasawa K M, Fukasawa K, Harada M (2000). Assignment of the dipeptidyl peptidase III gene (DPP3) to human chromosome 11 band q12→q13.1 by in situ hybridization. Cytogenet. Cell Genet. 88, 99-100.

Fukunaga-Kalabis M, Martinez G, Nguyen T K, Kim D, Santiago-Walker A, Roesch A, Herlyn M (2010). Tenascin-C promotes melanoma progression by maintaining the ABCB5-positive side population. Oncogene 29, 6115-6124.

Furic L, Rong L, Larsson O, Koumakpayi I H, Yoshida K, Brueschke A, Petroulakis E, Robichaud N, Pollak M, Gaboury L A, Pandolfi P P, Saad F, Sonenberg N (2010). eIF4E phosphorylation promotes tumorigenesis and is associated with prostate cancer progression. Proc. Natl. Acad. Sci. U.S.A 107, 14134-14139.

Futerman A H, Riezman H (2005). The ins and outs of sphingolipid synthesis. Trends Cell Biol. 15, 312-318.

Galan S R, Kann P H (2013). Genetics and molecular pathogenesis of pheochromocytoma and paraganglioma. Clin Endocrinol. (Oxf) 78, 165-175.

Gallucci M, Merola R, Farsetti A, Orlandi G, Sentinelli S, De C P, Leonardo C, Carlini P, Guadagni F, Sperduti I, Cianciulli A M (2006). Cytogenetic profiles as additional markers to pathological features in clinically localized prostate carcinoma. Cancer Lett. 237, 76-82.

Garagnani P, Bacalini M G, Pirazzini C, Gori D, Giuliani C, Mari D, Di Blasio A M, Gentilini D, Vitale G, Collino S, Rezzi S, Castellani G, Capri M, Salvioli S, Franceschi C (2012). Methylation of ELOVL2 gene as a new epigenetic marker of age. Aging Cell 11, 1132-1134.

Garrison K R, Shemilt I, Donell S, Ryder J J, Mugford M, Harvey I, Song F, Alt V (2010). Bone morphogenetic protein (BMP) for fracture healing in adults. Cochrane. Database. Syst. Rev. CD006950.

Gary S C, Kelly G M, Hockfield S (1998). BEHAB/brevican: a brain-specific lectican implicated in gliomas and glial cell motility. Curr. Opin. Neurobiol. 8, 576-581.

Gary S C, Zerillo C A, Chiang V L, Gaw J U, Gray G, Hockfield S (2000). cDNA cloning, chromosomal localization, and expression analysis of human BEHAB/brevican, a brain specific proteoglycan regulated during cortical development and in glioma. Gene 256, 139-147.

Gasnereau I, Herr P, Chia P Z, Basler K, Gleeson P A (2011). Identification of an endocytosis motif in an intracellular loop of Wntless protein, essential for its recycling and the control of Wnt protein signaling. J Biol. Chem. 286, 43324-43333.

Gattinoni L, Powell D J, Jr., Rosenberg S A, Restifo N P (2006). Adoptive immunotherapy for cancer: building on success. Nat. Rev. Immunol. 6, 383-393.

Geesink R G, Hoefnagels N H, Bulstra S K (1999). Osteogenic activity of OP-1 bone morphogenetic protein (BMP-7) in a human fibular defect. J Bone Joint Surg. Br. 81, 710-718.

Gerhard D S et al (2004). The status, quality, and expansion of the NIH full-length cDNA project: the Mammalian Gene Collection (MGC). Genome Res. 14, 2121-2127.

Gessi S, Cattabriga E, Avitabile A, Gafa' R, Lanza G, Cavazzini L, Bianchi N, Gambari R, Feo C, Liboni A, Gullini S, Leung E, Mac-Lennan S, Borea P A (2004). Elevated expression of A3 adenosine receptors in human colorectal cancer is reflected in peripheral blood cells. Clin Cancer Res. 10, 5895-5901.

Gessi S, Merighi S, Varani K, Leung E, Mac L S, Borea P A (2008). The A3 adenosine receptor: an enigmatic player in cell biology. Pharmacol. Ther. 117, 123-140.

Ghosh S, Albitar L, LeBaron R, Welch W R, Samimi G, Birrer M J, Berkowitz R S, Mok S C (2010). Up-regulation of stromal versican expression in advanced stage serous ovarian cancer. Gynecol. Oncol 119, 114-120.

Gilles C, Polette M, Mestdagt M, Nawrocki-Raby B, Ruggeri P, Birembaut P, Foidart J M (2003). Transactivation of vimentin by beta-catenin in human breast cancer cells. Cancer Res. 63, 2658-2664.

Gilles C, Polette M, Piette J, Delvigne A C, Thompson E W, Foidart J M, Birembaut P (1996). Vimentin expression in cervical carcinomas: association with invasive and migratory potential. J Pathol. 180, 175-180.

Giri A, Bajpai S, Trenton N, Jayatilaka H, Longmore G D, Wirtz D (2013). The Arp2/3 complex mediates multigeneration dendritic protrusions for efficient 3-dimensional cancer cell migration. FASEB J.

Girotti M R, Pedersen M, Sanchez-Laorden B, Viros A, Turajlic S, Niculescu-Duvaz D, Zambon A, Sinclair J, Hayes A, Gore M, Lorigan P, Springer C, Larkin J, Jorgensen C, Marais R (2013). Inhibiting EGF receptor or SRC family kinase signaling overcomes BRAF inhibitor resistance in melanoma. Cancer Discov. 3, 158-167.

Gnjatic S, Atanackovic D, Jager E, Matsuo M, Selvakumar A, Altorki N K, Maki R G, Dupont B, Ritter G, Chen Y T, Knuth A, Old L J (2003). Survey of naturally occurring CD4+ T cell responses against N Y-ESO-1 in cancer patients: correlation with antibody responses. Proc Natl. Acad. Sci. U.S.A 100, 8862-8867.

Godbout R, Bisgrove D A, Shkolny D, Day R S, III (1998). Correlation of B-FABP and GFAP expression in malignant glioma. Oncogene 16, 1955-1962.

Gong D, Ferrell J E, Jr. (2010). The roles of cyclin A2, B1, and B2 in early and late mitotic events. Mol. Biol. Cell 21, 3149-3161.

Goodwin A C, Jadallah S, Toubaji A, Lecksell K, Hicks J L, Kowalski J, Bova G S, De Marzo A M, Netto G J, Casero R A, Jr. (2008). Increased spermine oxidase expression in human prostate cancer and prostatic intraepithelial neoplasia tissues. Prostate 68, 766-772.

Gorivodsky M, Mukhopadhyay M, Wilsch-Braeuninger M, Phillips M, Teufel A, Kim C, Malik N, Huttner W, Westphal H (2009). Intraflagellar transport protein 172 is essential for primary cilia formation and plays a vital role in patterning the mammalian brain. Dev. Biol. 325, 24-32.

Gorka B, Skubis-Zegadlo J, Mikula M, Bardadin K, Paliczka E, Czarnocka B (2007). NrCAM, a neuronal system cell-adhesion molecule, is induced in papillary thyroid carcinomas. Br. J Cancer 97, 531-538.

Gorlov I P, Meyer P, Liloglou T, Myles J, Boettger M B, Cassidy A, Girard L, Minna J D, Fischer R, Duffy S, Spitz M R, Haeussinger K, Kammerer S, Cantor C, Dierkesmann R, Field J K, Amos C I (2007). Seizure 6-like (SEZ6L) gene and risk for lung cancer. Cancer Res. 67, 8406-8411.

Gorokhova S, Bibert S, Geering K, Heintz N (2007). A novel family of transmembrane proteins interacting with beta subunits of the Na,K-ATPase. Hum. Mol. Genet. 16, 2394-2410.

Goto Y, Matsuzaki Y, Kurihara S, Shimizu A, Okada T, Yamamoto K, Murata H, Takata M, Aburatani H, Hoon D S, Saida T, Kawakami Y (2006). A new melanoma antigen fatty acid-binding protein 7, involved in proliferation and invasion, is a potential target for immunotherapy and molecular target therapy. Cancer Res. 66, 4443-4449.

Graf F, Mosch B, Koehler L, Bergmann R, Wuest F, Pietzsch J (2010). Cyclin-dependent kinase 4/6 (cdk4/6) inhibitors: perspectives in cancer therapy and imaging. Mini. Rev. Med. Chem. 10, 527-539.

Grimwood J et al (2004). The DNA sequence and biology of human chromosome 19. Nature 428, 529-535.

Grumet M, Mauro V, Burgoon M P, Edelman G M, Cunningham B A (1991). Structure of a new nervous system glycoprotein, Nr-CAM, and its relationship to subgroups of neural cell adhesion molecules. J Cell Biol. 113, 1399-1412.

Grumet M, Milev P, Sakurai T, Karthikeyan L, Bourdon M, Margolis R K, Margolis R U (1994). Interactions with tenascin and differential effects on cell adhesion of neurocan and phosphacan, two major chondroitin sulfate proteoglycans of nervous tissue. J Biol. Chem. 269, 12142-12146.

Grunda J M, Fiveash J, Palmer C A, Cantor A, Fathallah-Shaykh H M, Nabors L B, Johnson M R (2010). Rationally designed pharmacogenomic treatment using concurrent capecitabine and radiotherapy for glioblastoma; gene expression profiles associated with outcome. Clin Cancer Res. 16, 2890-2898.

Grunda J M, Nabors L B, Palmer C A, Chhieng D C, Steg A, Mikkelsen T, Diasio R B, Zhang K, Allison D, Grizzle W E, Wang W, Gillespie G Y, Johnson M R (2006). Increased expression of thymidylate synthetase (T S), ubiquitin specific protease 10 (USP10) and survivin is associated with poor survival in glioblastoma multiforme (GBM). J Neurooncol. 80, 261-274.

Grunder S, Geisler H S, Rainier S, Fink J K (2001). Acid-sensing ion channel (ASIC) 4 gene: physical mapping, genomic organisation, and evaluation as a candidate for paroxysmal dystonia. Eur. J Hum. Genet. 9, 672-676.

Grunder S, Geissler H S, Bassler E L, Ruppersberg J P (2000). A new member of acid-sensing ion channels from pituitary gland. Neuroreport 11, 1607-1611.

Gu L, Shigemasa K, Ohama K (2004). Increased expression of IGF II mRNA-binding protein 1 mRNA is associated with an advanced clinical stage and poor prognosis in patients with ovarian cancer. Int. J Oncol 24, 671-678.

Guerrero-Preston R, et al (2011). NID2 and HOXA9 promoter hypermethylation as biomarkers for prevention and early detection in oral cavity squamous cell carcinoma tissues and saliva. Cancer Prev. Res. (Phila) 4, 1061-1072.

Guillemot F, Lo L C, Johnson J E, Auerbach A, Anderson D J, Joyner A L (1993). Mammalian achaete-scute homolog 1 is required for the early development of olfactory and autonomic neurons. Cell 75, 463-476.

Gultekin S H, Rosenfeld M R, Voltz R, Eichen J, Posner J B, Dalmau J (2000). Paraneoplastic limbic encephalitis: neurological symptoms, immunological findings and tumour association in 50 patients. Brain 123 (Pt 7), 1481-1494.

Gunther H S, Schmidt N O, Phillips H S, Kemming D, Kharbanda S, Soriano R, Modrusan Z, Meissner H, Westphal M, Lamszus K (2008). Glioblastoma-derived stem cell-enriched cultures form distinct subgroups according to molecular and phenotypic criteria. Oncogene 27, 2897-2909.

Gustmann C, Altmannsberger M, Osborn M, Griesser H, Feller A C (1991). Cytokeratin expression and vimentin content in large cell anaplastic lymphomas and other non-Hodgkin's lymphomas. Am. J Pathol. 138, 1413-1422.

Guvenc H, Pavlyukov M S, Joshi K, Kurt H, Banasavadi-Siddegowda Y K, Mao P, Hong C, Yamada R, Kwon C H, Bhasin D, Chettiar S, Kitange G, Park I H, Sarkaria J N, Li C, Shakhparonov M I, Nakano I (2013). Impairment of Glioma Stem Cell Survival and Growth by a Novel Inhibitor for Survivin-Ran Protein Complex. Clin Cancer Res.

Hagemann C, Anacker J, Gerngras S, Kuhnel S, Said H M, Patel R, Kammerer U, Vordermark D, Roosen K, Vince G H (2008). Expression analysis of the autosomal recessive primary microcephaly genes MCPH1 (microcephalin) and MCPHS (ASPM, abnormal spindle-like, microcephaly associated) in human malignant gliomas. Oncol Rep. 20, 301-308.

Hamilton S R, Liu B, Parsons R E, Papadopoulos N, Jen J, Powell S M, Krush A J, Berk T, Cohen Z, Tetu B, (1995). The molecular basis of Turcot's syndrome. N. Engl. J Med. 332, 839-847.

Han H J, Tokino T, Nakamura Y (1998). CSR, a scavenger receptor-like protein with a protective role against cellular damage caused by UV irradiation and oxidative stress. Hum. Mol. Genet. 7, 1039-1046.

Han J, Lee Y, Yeom K H, Nam J W, Heo I, Rhee J K, Sohn S Y, Cho Y, Zhang B T, Kim V N (2006). Molecular basis for the recognition of primary microRNAs by the Drosha-DGCR8 complex. Cell 125, 887-901.

Han Y, Liu Y, Gui Y, Cai Z (2013). Inducing cell proliferation inhibition and apoptosis via silencing Dicer, Drosha, and Exportin 5 in urothelial carcinoma of the bladder. J Surg. Oncol 107, 201-205.

Harada H, Omura K, Nakajima Y, Hasegawa S, Mogi S (2006). Cyclin B1 is useful to predict occult cervical lymph node metastases in tongue carcinoma. J Exp. Clin Cancer Res. 25, 351-356.

Harada T, Chelala C, Bhakta V, Chaplin T, Caulee K, Baril P, Young B D, Lemoine N R (2008). Genome-wide DNA copy number analysis in pancreatic cancer using high-density single nucleotide polymorphism arrays. Oncogene 27, 1951-1960.

Harris M L, Baxter L L, Loftus S K, Pavan W J (2010). Sox proteins in melanocyte development and melanoma. Pigment Cell Melanoma Res. 23, 496-513.

Harrison Pitner M K, Saavedra H I (2013). Cdk4 and nek2 signal binucleation and centrosome amplification in a her2+ breast cancer model. PLoS. ONE. 8, e65971.

Hartomo T B, Kozaki A, Hasegawa D, Van Huyen P T, Yamamoto N, Saitoh A, Ishida T, Kawasaki K, Kosaka Y, Ohashi H, Yamamoto T, Morikawa S, Hirase H, Kubokawa I, Mori T, Yanai T, Hayakawa A, Takeshima Y, Iijima K, Matsuo M, Nishio H, Nishimura N (2013). Minimal residual disease monitoring in neuroblastoma patients based on the expression of a set of real-time R T-PCR markers in tumor-initiating cells. Oncol Rep. 29, 1629-1636.

Harville H M, Held S, Diaz-Font A, Davis E E, Diplas B H, Lewis R A, Borochowitz Z U, Zhou W, Chaki M, Mac-Donald J, Kayserili H, Beales P L, Katsanis N, Otto E, Hildebrandt F (2010). Identification of 11 novel mutations in eight BBS genes by high-resolution homozygosity mapping. J Med. Genet. 47, 262-267.

Hawkins G A, Mychaleckyj J C, Zheng S L, Faith D A, Kelly B, Isaacs S D, Wiley K E, Chang B L, Ewing C M, Bujnovszky P, Bleecker E R, Walsh P C, Meyers D A, Isaacs W B, Xu J (2002). Germline sequence variants of the LZTS1 gene are associated with prostate cancer risk. Cancer Genet. Cytogenet. 137, 1-7.

Hay N (2010). Mnk earmarks eIF4E for cancer therapy. Proc. Natl. Acad. Sci. U.S.A 107, 13975-13976.

Hayashi Y K, Chou F L, Engvall E, Ogawa M, Matsuda C, Hirabayashi S, Yokochi K, Ziober B L, Kramer R H, Kaufman S J, Ozawa E, Goto Y, Nonaka I, Tsukahara T, Wang J Z, Hoffman E P, Arahata K (1998). Mutations in the integrin alpha7 gene cause congenital myopathy. Nat Genet. 19, 94-97.

He C, Qu X, Wan J, Rong R, Huang L, Cai C, Zhou K, Gu Y, Qian S Y, Kang J X (2012). Inhibiting delta-6 desaturase activity suppresses tumor growth in mice. PLoS. ONE. 7, e47567.

He J, Liu Y, Xie X, Zhu T, Soules M, Dimeco F, Vescovi A L, Fan X, Lubman D M (2010). Identification of cell surface glycoprotein markers for glioblastoma-derived stem-like cells using a lectin microarray and LC-MS/MS approach. J Proteome. Res 9, 2565-2572.

Hendrix M J, Seftor E A, Chu Y W, Seftor R E, Nagle R B, McDaniel K M, Leong S P, Yohem K H, Leibovitz A M, Meyskens F L, Jr., (1992). Coexpression of vimentin and keratins by human melanoma tumor cells: correlation with invasive and metastatic potential. J Natl. Cancer Inst. 84, 165-174.

Heni M, Hennenlotter J, Scharpf M, Lutz S Z, Schwentner C, Todenhofer T, Schilling D, Kuhs U, Gerber V, Machicao F, Staiger H, Haring H U, Stenzl A (2012). Insulin receptor isoforms A and B as well as insulin receptor substrates-1 and -2 are differentially expressed in prostate cancer. PLoS. ONE. 7, e50953.

Higgins J, Midgley C, Bergh A M, Bell S M, Askham J M, Roberts E, Binns R K, Sharif S M, Bennett C, Glover D M, Woods C G, Morrison E E, Bond J (2010). Human ASPM participates in spindle organisation, spindle orientation and cytokinesis. BMC. Cell Biol. 11, 85.

Hildebrandt F, Benzing T, Katsanis N (2011). Ciliopathies. N. Engl. J Med. 364, 1533-1543.

Hirama T, Miller C W, Koeffler H P (1999). Translocon-associated protein alpha transcripts are induced by granulocyte-macrophage colony-stimulating factor and exhibit complex alternative polyadenylation. FEBS Lett. 455, 223-227.

Hirao K, Hata Y, Ide N, Takeuchi M, Irie M, Yao I, Deguchi M, Toyoda A, Sudhof T C, Takai Y (1998). A novel multiple PDZ domain-containing molecule interacting with N-methyl-D-aspartate receptors and neuronal cell adhesion proteins. J Biol. Chem. 273, 21105-21110.

Hirayama T, Yagi T (2006). The role and expression of the protocadherin-alpha clusters in the CNS. Curr. Opin. Neurobiol. 16, 336-342.

Hirokawa N, Noda Y (2008). Intracellular transport and kinesin superfamily proteins, KIFs: structure, function, and dynamics. Physiol Rev. 88, 1089-1118.

Hjelmqvist L, Tuson M, Marfany G, Herrero E, Balcells S, Gonzalez-Duarte R (2002). ORMDL proteins are a conserved new family of endoplasmic reticulum membrane proteins. Genome Biol. 3, RESEARCH0027.

Hlavac V, Brynychova V, Vaclavikova R, Ehrlichova M, Vrana D, Pecha V, Kozevnikovova R, Trnkova M, Gatek J, Kopperova D, Gut I, Soucek P (2013). The expression profile of ATP-binding cassette transporter genes in breast carcinoma. Pharmacogenomics. 14, 515-529.

Hlavata I, Mohelnikova-Duchonova B, Vaclavikova R, Liska V, Pitule P, Novak P, Bruha J, Vycital O, Holubec L, Treska V, Vodicka P, Soucek P (2012). The role of ABC transporters in progression and clinical outcome of colorectal cancer. Mutagenesis 27, 187-196.

Holden S, Raymond F L (2003). The human gene CXorf17 encodes a member of a novel family of putative trans-membrane proteins: cDNA cloning and characterization of CXorf17 and its mouse ortholog orf34. Gene 318, 149-161.

Holtkamp N, Ziegenhagen N, Malzer E, Hartmann C, Giese A, von D A (2007). Characterization of the amplicon on chromosomal segment 4q12 in glioblastoma multiforme. Neuro Oncol 9, 291-297.

Hood F E, Royle S J (2011). Pulling it together: The mitotic function of TACC3. Bioarchitecture. 1, 105-109.

Hookham M B, O'Donovan H C, Church R H, Mercier-Zuber A, Luzi L, Curran S P, Carew R M, Droguett A, Mezzano S, Schubert M, White M F, Crean J K, Brazil D P (2013). Insulin receptor substrate-2 is expressed in kidney epithelium and up-regulated in diabetic nephropathy. FEBS J 280, 3232-3243.

Horvath S, Zhang B, Carlson M, Lu K V, Zhu S, Felciano R M, Laurance M F, Zhao W, Qi S, Chen Z, Lee Y, Scheck A C, Liau L M, Wu H, Geschwind D H, Febbo P G, Kornblum H I, Cloughesy T F, Nelson S F, Mischel P S (2006). Analysis of oncogenic signaling networks in glioblastoma identifies ASPM as a molecular target. Proc Natl. Acad. Sci. U.S.A 103, 17402-17407.

Hu C, Xiong J, Zhang L, Huang B, Zhang Q, Li Q, Yang M, Wu Y, Wu Q, Shen Q, Gao Q, Zhang K, Sun Z, Liu J, Jin Y, Tan J (2004). PEG10 activation by co-stimulation of CXCR5 and CCR7 essentially contributes to resistance to apoptosis in CD19+CD34+ B cells from patients with B cell lineage acute and chronic lymphocytic leukemia. Cell Mol. Immunol. 1, 280-294.

Huang C C, Tu S H, Lien H H, Jeng J Y, Huang C S, Huang C J, Lai L C, Chuang E Y (2013a). Concurrent gene signatures for han chinese breast cancers. PLoS. ONE. 8, e76421.

Huang F W, Hodis E, Xu M J, Kryukov G V, Chin L, Garraway L A (2013b). Highly recurrent TERT promoter mutations in human melanoma. Science 339, 957-959.

Huang X P, Rong T H, Wu Q L, Fu J H, Yang H, Zhao J M, Fang Y (2005). MCM4 expression in esophageal cancer from southern China and its clinical significance. J. Cancer Res. Clin. Oncol. 131, 677-682.

Huxley C, Fried M (1990). The mouse rpL7a gene is typical of other ribosomal protein genes in it's 5' region but differs in being located in a tight cluster of CpG-rich islands. Nucleic Acids Res. 18, 5353-5357.

Hwang M L, Lukens J R, Bullock T N (2007). Cognate memory CD4+ T cells generated with dendritic cell priming influence the expansion, trafficking, and differentiation of secondary CD8+ T cells and enhance tumor control. J Immunol. 179, 5829-5838.

Hwang Y S, Park K K, Cha I H, Kim J, Chung W Y (2012). Role of insulin-like growth factor-II mRNA-binding protein-3 in invadopodia formation and the growth of oral squamous cell carcinoma in athymic nude mice. Head Neck 34, 1329-1339.

Ideguchi H, Ueda A, Tanaka M, Yang J, Tsuji T, Ohno S, Hagiwara E, Aoki A, Ishigatsubo Y (2002). Structural and functional characterization of the USP11 deubiquitinating enzyme, which interacts with the RanGTP-associated protein RanBPM. Biochem. J 367, 87-95.

Ikenberg K et al (2010). Insulin-like growth factor II mRNA binding protein 3 (IMP3) is overexpressed in prostate cancer and correlates with higher Gleason scores. BMC. Cancer 10, 341.

Ikuerowo S O, Kuczyk M A, Mengel M, van der Heyde E, Shittu O B, Vaske B, Jonas U, Machtens S, Serth J (2006). Alteration of subcellular and cellular expression patterns of cyclin B1 in renal cell carcinoma is significantly related to clinical progression and survival of patients. Int. J Cancer 119, 867-874.

Ingley E, Hemmings B A (1994). Pleckstrin homology (PH) domains in signal transduction. J Cell Biochem. 56, 436-443.

Ishida N, Kawakita M (2004). Molecular physiology and pathology of the nucleotide sugar transporter family (SLC35). Pflugers Arch. 447, 768-775.

Ishii H, Baffa R, Numata S I, Murakumo Y, Rattan S, Inoue H, Mori M, Fidanza V, Alder H, Croce C M (1999). The FEZ1 gene at chromosome 8p22 encodes a leucine-zipper protein, and its expression is altered in multiple human tumors. Proc. Natl. Acad. Sci. U.S.A 96, 3928-3933.

Ishii H, Vecchione A, Murakumo Y, Baldassarre G, Numata S, Trapasso F, Alder H, Baffa R, Croce C M (2001). FEZ1/LZTS1 gene at 8p22 suppresses cancer cell growth and regulates mitosis. Proc. Natl. Acad. Sci. U.S.A 98, 10374-10379.

Ishiuchi S (2009). [New roles of glutamate receptors in glias and gliomas]. Brain Nerve 61, 753-764.

Ishiuchi S, Tsuzuki K, Yoshida Y, Yamada N, Hagimura N, Okado H, Miwa A, Kurihara H, Nakazato Y, Tamura M, Sasaki T, Ozawa S (2002). Blockage of Ca(2+)-permeable AMPA receptors suppresses migration and induces apoptosis in human glioblastoma cells. Nat. Med 8, 971-978.

Ishwad C S, Ferrell R E, Davare J, Meloni A M, Sandberg A A, Surti U (1995). Molecular and cytogenetic analysis of chromosome 7 in uterine leiomyomas. Genes Chromosomes. Cancer 14, 51-55.

Ito K, Takahashi A, Morita M, Suzuki T, Yamamoto T (2011). The role of the CNOT1 subunit of the CCR4-NOT complex in mRNA deadenylation and cell viability. Protein Cell 2, 755-763.

Jackson M, Song W, Liu M Y, Jin L, Dykes-Hoberg M, Lin C I, Bowers W J, Federoff H J, Sternweis P C, Rothstein J D (2001). Modulation of the neuronal glutamate transporter EAAT4 by two interacting proteins. Nature 410, 89-93.

Jacobson S G, Cideciyan A V, Aleman T S, Pianta M J, Sumaroka A, Schwartz S B, Smilko E E, Milam A H, Sheffield V C, Stone E M (2003). Crumbs homolog 1 (CRB1) mutations result in a thick human retina with abnormal lamination. Hum. Mol. Genet. 12, 1073-1078.

Jahr H, van D M, van Osch G J, Weinans H, van Leeuwen J P (2005). Identification of acid-sensing ion channels in bone. Biochem. Biophys. Res. Commun. 337, 349-354.

Jajoo S, Mukherjea D, Watabe K, Ramkumar V (2009). Adenosine A(3) receptor suppresses prostate cancer metastasis by inhibiting NADPH oxidase activity. Neoplasia. 11, 1132-1145.

Jamain S, Quach H, Betancur C, Rastam M, Colineaux C, Gillberg I C, Soderstrom H, Giros B, Leboyer M, Gillberg C, Bourgeron T (2003). Mutations of the X-linked genes encoding neuroligins NLGN3 and NLGN4 are associated with autism. Nat. Genet. 34, 27-29.

Jeng Y M, Wang T H, Lu S H, Yuan R H, Hsu H C (2009). Prognostic significance of insulin-like growth factor II mRNA-binding protein 3 expression in gastric adenocarcinoma. Br. J Surg 96, 66-73.

Jiang J C, Kirchman P A, Zagulski M, Hunt J, Jazwinski S M (1998). Homologs of the yeast longevity gene LAG1 in *Caenorhabditis elegans* and human. Genome Res. 8, 1259-1272.

Jiang S X, Kameya T, Asamura H, Umezawa A, Sato Y, Shinada J, Kawakubo Y, Igarashi T, Nagai K, Okayasu I (2004). hASH1 expression is closely correlated with endocrine phenotype and differentiation extent in pulmonary neuroendocrine tumors. Mod. Pathol. 17, 222-229.

Jiang W, Ren L, Jin N (2007). HIV-1 DNA vaccine efficacy is enhanced by coadministration with plasmid encoding IFN-alpha. J Virol. Methods 146, 266-273.

Jiang Z, Chu P G, Woda B A, Rock K L, Liu Q, Hsieh C C, Li C, Chen W, Duan H O, McDougal S, Wu C L (2006). Analysis of RNA-binding protein IMP3 to predict metastasis and prognosis of renal-cell carcinoma: a retrospective study. Lancet Oncol 7, 556-564.

Jin F, Zhao L, Zhao H Y, Guo S G, Feng J, Jiang X B, Zhang S L, Wei Y J, Fu R, Zhao J S (2008). Comparison between cells and cancer stem-like cells isolated from glioblastoma and astrocytoma on expression of anti-apoptotic and multidrug resistance-associated protein genes. Neuroscience 154, 541-550.

Jin J, Kim J M, Hur Y S, Cho W P, Lee K Y, Ahn S I, Hong K C, Park I S (2012). Clinical significance of clusterin expression in pancreatic adenocarcinoma. World J Surg. Oncol 10, 146.

Jin K M, Lu M, Liu F F, Gu J, Du X J, Xing B C (2013). N-WASP is highly expressed in hepatocellular carcinoma and associated with poor prognosis. Surgery 153, 518-525.

Jin L, Seys A R, Zhang S, Erickson-Johnson M R, Roth C W, Evers B R, Oliveira A M, Lloyd R V (2010). Diagnostic utility of IMP3 expression in thyroid neoplasms: a quantitative R T-PCR study. Diagn. Mol. Pathol. 19, 63-69.

Jogl G, Tong L (2003). Crystal structure of carnitine acetyltransferase and implications for the catalytic mechanism and fatty acid transport. Cell 112, 113-122.

Johnson M D, O'Connell M J, Silberstein H, Korones D (2013). Differential Expression of Somatostatin Receptors, P44/42 MAPK, and mTOR Activation in Medulloblastomas and Primitive Neuroectodermal Tumors. Appl. Immunohistochem. Mol. Morphol.

Jung C K, Jung J H, Park G S, Lee A, Kang C S, Lee K Y (2006). Expression of transforming acidic coiled-coil containing protein 3 is a novel independent prognostic marker in non-small cell lung cancer. Pathol. Int 56, 503-509.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Jung H M, Choi S J, Kim J K (2009). Expression profiles of SV40-immortalization-associated genes upregulated in various human cancers. J Cell Biochem. 106, 703-713.

Kabbarah O, Nogueira C, Feng B, Nazarian R M, Bosenberg M, Wu M, Scott K L, Kwong L N, Xiao Y, Cordon-Cardo C, Granter S R, Ramaswamy S, Golub T, Duncan L M, Wagner S N, Brennan C, Chin L (2010). Integrative genome comparison of primary and metastatic melanomas. PLoS. ONE. 5, e10770.

Kajiwara Y, Yamasaki F, Hama S, Yahara K, Yoshioka H, Sugiyama K, Arita K, Kurisu K (2003). Expression of survivin in astrocytic tumors: correlation with malignant grade and prognosis. Cancer 97, 1077-1083.

Kallenbach S, Khantane S, Carroll P, Gayet O, Alonso S, Henderson C E, Dudley K (2003). Changes in subcellular distribution of protocadherin gamma proteins accompany maturation of spinal neurons. J Neurosci. Res. 72, 549-556.

Kamalakaran S, Varadan V, Giercksky Russnes H E, Levy D, Kendall J, Janevski A, Riggs M, Banerjee N, Synnestvedt M, Schlichting E, Karesen R, Shama P K, Rotti H, Rao R, Rao L, Eric Tang M R, Satyamoorthy K, Lucito R, Wigler M, Dimitrova N, Naume B, Borresen-Dale A L, Hicks J B (2011). DNA methylation patterns in luminal breast cancers differ from non-luminal subtypes and can identify relapse risk independent of other clinical variables. Mol. Oncol 5, 77-92.

Kamnasaran D, Muir W J, Ferguson-Smith M A, Cox D W (2003). Disruption of the neuronal PAS3 gene in a family affected with schizophrenia. J Med. Genet. 40, 325-332.

Kang G H, Lee S, Cho N Y, Gandamihardja T, Long T I, Weisenberger D J, Campan M, Laird P W (2008). DNA methylation profiles of gastric carcinoma characterized by quantitative DNA methylation analysis. Lab Invest 88, 161-170.

Kang Y, Massague J (2004). Epithelial-mesenchymal transitions: twist in development and metastasis. Cell 118, 277-279.

Kastan M B, Schlaffer E, Russo J E, Colvin O M, Civin C I, Hilton J (1990). Direct demonstration of elevated aldehyde dehydrogenase in human hematopoietic progenitor cells. Blood 75, 1947-1950.

Katoh Y, Katoh M (2005). Hedgehog signaling pathway and gastric cancer. Cancer Biol. Ther. 4, 1050-1054.

Kaur J, Demokan S, Tripathi S C, Macha M A, Begum S, Califano J A, Ralhan R (2010). Promoter hypermethylation in Indian primary oral squamous cell carcinoma. Int. J Cancer 127, 2367-2373.

Kawahara Y, Ito K, Sun H, Ito M, Kanazawa I, Kwak S (2004). GluR4c, an alternative splicing isoform of GluR4, is abundantly expressed in the adult human brain. Brain Res. Mol. Brain Res. 127, 150-155.

Kee Y, Yoo J S, Hazuka C D, Peterson K E, Hsu S C, Scheller R H (1997). Subunit structure of the mammalian exocyst complex. Proc. Natl. Acad. Sci. U.S.A 94, 14438-14443.

Kennedy R C, Shearer M H, Watts A M, Bright R K (2003). CD4+T lymphocytes play a critical role in antibody production and tumor immunity against simian virus 40 large tumor antigen. Cancer Res. 63, 1040-1045.

Kenzelmann-Broz D, Tucker R P, Leachman N T, Chiquet-Ehrismann R (2010). The expression of teneurin-4 in the avian embryo: potential roles in patterning of the limb and nervous system. Int. J Dev. Biol. 54, 1509-1516.

Kettunen E, Anttila S, Seppanen J K, Karjalainen A, Edgren H, Lindstrom I, Salovaara R, Nissen A M, Salo J, Mattson K, Hollmen J, Knuutila S, Wikman H (2004). Differentially expressed genes in nonsmall cell lung cancer: expression profiling of cancer-related genes in squamous cell lung cancer. Cancer Genet. Cytogenet. 149, 98-106.

Khalil B D, El-Sibai M (2012). Rho GTPases in primary brain tumor malignancy and invasion. J Neurooncol. 108, 333-339.

Kikuno R, Nagase T, Ishikawa K, Hirosawa M, Miyajima N, Tanaka A, Kotani H, Nomura N, Ohara 0 (1999). Prediction of the coding sequences of unidentified human genes. XIV. The complete sequences of 100 new cDNA clones from brain which code for large proteins in vitro. DNA Res. 6, 197-205.

Kim C H, Bak K H, Kim Y S, Kim J M, Ko Y, Oh S J, Kim K M, Hong E K (2000). Expression of tenascin-C in astrocytic tumors: its relevance to proliferation and angiogenesis. Surg Neurol. 54, 235-240.

Kim D H, Mohapatra G, Bollen A, Waldman F M, Feuerstein B G (1995). Chromosomal abnormalities in glioblastoma multiforme tumors and glioma cell lines detected by comparative genomic hybridization. Int. J Cancer 60, 812-819.

Kim E J, Eom S J, Hong J E, Lee J Y, Choi M S, Park J H (2012a). Benzyl isothiocyanate inhibits basal and hepatocyte growth factor-stimulated migration of breast cancer cells. Mol. Cell Biochem. 359, 431-440.

Kim J, Reber H A, Hines O J, Kazanjian K K, Tran A, Ye X, Amersi F F, Martinez S R, Dry S M, Bilchik A J, Hoon D S (2006). The clinical significance of MAGEA3 expression in pancreatic cancer. Int. J Cancer 118, 2269-2275.

Kim K K, Park K S, Song S B, Kim K E (2010). Up regulation of GW112 Gene by N F kappaB promotes an antiapoptotic property in gastric cancer cells. Mol. Carcinog. 49, 259-270.

Kim N, Yoo J C, Han J Y, Hwang E M, Kim Y S, Jeong E Y, Sun C H, Yi G S, Roh G S, Kim H J, Kang S S, Cho G J, Park J Y, Choi W S (2012b). Human nuclear clusterin mediates apoptosis by interacting with Bcl-X L through C-terminal coiled coil domain. J Cell Physiol 227, 1157-1167.

Kim T Y, Bang Y J, Kim W S, Kang S H, Lee K U, Choe K J, Kim N K (1997). Mutation of ras oncogene in gastric adenocarcinoma: association with histological phenotype. Anticancer Res 17, 1335-1339.

Kimchi E T, Posner M C, Park J O, Darga T E, Kocherginsky M, Karrison T, Hart J, Smith K D, Mezhir J J, Weichselbaum R R, Khodarev N N (2005). Progression of Barrett's metaplasia to adenocarcinoma is associated with the suppression of the transcriptional programs of epidermal differentiation. Cancer Res. 65, 3146-3154.

Kimura J, Kudoh T, Miki Y, Yoshida K (2011). Identification of dihydropyrimidinase-related protein 4 as a novel target of the p53 tumor suppressor in the apoptotic response to DNA damage. Int. J Cancer 128, 1524-1531.

Kinsey M, Smith R, Lessnick S L (2006). NR0B1 is required for the oncogenic phenotype mediated by EWS/FLI in Ewing's sarcoma. Mol. Cancer Res. 4, 851-859.

Klejnot M, Kozielski F (2012). Structural insights into human Kif7, a kinesin involved in Hedgehog signalling. Acta Crystallogr. D. Biol. Crystallogr. 68, 154-159.

Klekner A, Varga I, Bognar L, Hutoczki G, Kenyeres A, Toth J, Hanzely Z, Scholtz B (2010). [Extracellular matrix of cerebral tumors with different invasiveness]. Ideggyogy. Sz 63, 38-43.

Knight H M, Pickard B S, Maclean A, Malloy M P, Soares D C, McRae A F, Condie A, White A, Hawkins W, McGhee K, van B M, MacIntyre D J, Starr J M, Deary I J, Visscher P M, Porteous D J, Cannon R E, St C D, Muir W J, Blackwood D H (2009). A cytogenetic abnormality and rare coding variants identify ABCA13 as a candidate gene in schizophrenia, bipolar disorder, and depression. Am J Hum. Genet. 85, 833-846.

Kobayashi A, Okuda H, Xing F, Pandey P R, Watabe M, Hirota S, Pai S K, Liu W, Fukuda K, Chambers C, Wilber A, Watabe K (2011). Bone morphogenetic protein 7 in dormancy and metastasis of prostate cancer stem-like cells in bone. J Exp. Med. 208, 2641-2655.

Kobayashi H, Omiya R, Ruiz M, Huarte E, Sarobe P, Lasarte J J, Herraiz M, Sangro B, Prieto J, Borras-Cuesta F, Celis E (2002). Identification of an antigenic epitope for helper T lymphocytes from carcinoembryonic antigen. Clin Cancer Res. 8, 3219-3225.

Kobayashi K, Nishioka M, Kohno T, Nakamoto M, Maeshima A, Aoyagi K, Sasaki H, Takenoshita S, Sugimura H, Yokota J (2004). Identification of genes whose expression is upregulated in lung adenocarcinoma cells in comparison with type II alveolar cells and bronchiolar epithelial cells in vivo. Oncogene 23, 3089-3096.

Kohannim O, Hibar D P, Stein J L, Jahanshad N, Hua X, Rajagopalan P, Toga A W, Jack C R, Jr., Weiner M W, de Zubicaray G I, McMahon K L, Hansell N K, Martin N G, Wright M J, Thompson P M (2012). Discovery and Replication of Gene Influences on Brain Structure Using LASSO Regression. Front Neurosci. 6, 115.

Koide T, Banno M, Aleksic B, Yamashita S, Kikuchi T, Kohmura K, Adachi Y, Kawano N, Kushima I, Nakamura Y, Okada T, Ikeda M, Ohi K, Yasuda Y, Hashimoto R, Inada T, Ujike H, Iidaka T, Suzuki M, Takeda M, Iwata N, Ozaki N (2012). Common variants in MAGI2 gene are associated with increased risk for cognitive impairment in schizophrenic patients. PLoS. ONE. 7, e36836.

Kolehmainen J, Black G C, Saarinen A, Chandler K, Clayton-Smith J, Traskelin A L, Perveen R, Kivitie-Kallio S, Norio R, Warburg M, Fryns J P, de la Chapelle A, Lehesjoki A E (2003). Cohen syndrome is caused by mutations in a novel gene, COH1, encoding a transmembrane protein with a presumed role in vesicle-mediated sorting and intracellular protein transport. Am. J Hum. Genet. 72, 1359-1369.

Koon N, Schneider-Stock R, Sarlomo-Rikala M, Lasota J, Smolkin M, Petroni G, Zaika A, Boltze C, Meyer F, Andersson L, Knuutila S, Miettinen M, El-Rifai W (2004). Molecular targets for tumour progression in gastrointestinal stromal tumours. Gut 53, 235-240.

Kordes U, Cheng Y C, Scotting P J (2005). Sox group E gene expression distinguishes different types and maturational stages of glial cells in developing chick and mouse. Brain Res. Dev. Brain Res. 157, 209-213.

Korn T, Magnus T, Jung S (2005). Autoantigen specific T cells inhibit glutamate uptake in astrocytes by decreasing expression of astrocytic glutamate transporter GLAST: a mechanism mediated by tumor necrosis factor-alpha. FASEB J 19, 1878-1880.

Kosari F, Parker A S, Kube D M, Lohse C M, Leibovich B C, Blute M L, Cheville J C, Vasmatzis G (2005). Clear cell renal cell carcinoma: gene expression analyses identify a potential signature for tumor aggressiveness. Clin Cancer Res. 11, 5128-5139.

Kostenko S, Dumitriu G, Moens U (2012). Tumour promoting and suppressing roles of the atypical MAP kinase signalling pathway ERK3/4-MKS. J Mol. Signal. 7, 9.

Kovacs E M, Verma S, Ali R G, Ratheesh A, Hamilton N A, Akhmanova A, Yap A S (2011). N-WASP regulates the epithelial junctional actin cytoskeleton through a non-canonical post-nucleation pathway. Nat Cell Biol. 13, 934-943.

Kraker J (2009). Treatment of anti-Ma2/Ta paraneoplastic syndrome. Curr. Treat. Options. Neurol. 11, 46-51.

Kramer R H, McDonald K A, Vu M P (1989). Human melanoma cells express a novel integrin receptor for laminin. J Biol. Chem. 264, 15642-15649.

Kramer R H, Vu M, Cheng Y F, Ramos D M (1991a). Integrin expression in malignant melanoma. Cancer Metastasis Rev. 10, 49-59.

Kramer R H, Vu M P, Cheng Y F, Ramos D M, Timpl R, Waleh N (1991b). Laminin-binding integrin alpha 7 beta 1: functional characterization and expression in normal and malignant melanocytes. Cell Regul. 2, 805-817.

Krepela E, Dankova P, Moravcikova E, Krepelova A, Prochazka J, Cermak J, Schutzner J, Zatloukal P, Benkova K (2009). Increased expression of inhibitor of apoptosis proteins, survivin and XIAP, in non-small cell lung carcinoma. Int. J Oncol 35, 1449-1462.

Krieg A M (2006). Therapeutic potential of Toll-like receptor 9 activation. Nat. Rev. Drug Discov. 5, 471-484.

Kroes R A, Jastrow A, McLone M G, Yamamoto H, Colley P, Kersey D S, Yong V W, Mkrdichian E, Cerullo L, Leestma J, Moskal J R (2000). The identification of novel therapeutic targets for the treatment of malignant brain tumors. Cancer Lett. 156, 191-198.

Kunisada M, Yogianti F, Sakumi K, Ono R, Nakabeppu Y, Nishigori C (2011). Increased Expression of Versican in the Inflammatory Response to UVB- and Reactive Oxygen Species-Induced Skin Tumorigenesis. Am J Pathol. 179, 3056-3065.

Kurimoto F, Gemma A, Hosoya Y, Seike M, Takenaka K, Uematsu K, Yoshimura A, Shibuya M, Kudoh S (2001). Unchanged frequency of loss of heterozygosity and size of the deleted region at 8p21-23 during metastasis of lung cancer. Int. J Mol. Med. 8, 89-93.

Kwak D H, Jin J W, Ryu J S, Ko K, Lee S D, Lee J W, Kim J S, Jung K Y, Ko K, Ma J Y, Hwang K A, Chang K T, Choo Y K (2011). Regulatory roles of ganglioside GQ1b in neuronal cell differentiation of mouse embryonic stem cells. BMB. Rep. 44, 799-804.

Kwak J M, Min B W, Lee J H, Choi J S, Lee S I, Park S S, Kim J, Um J W, Kim S H, Moon H Y (2007). The prognostic significance of E-cadherin and liver intestine-cadherin expression in colorectal cancer. Dis. Colon Rectum 50, 1873-1880.

Lamers F, van dP, I, Schild L, Ebus M E, Koster J, Hansen B R, Koch T, Versteeg R, Caron H N, Molenaar J J (2011). Knockdown of survivin (BIRC5) causes apoptosis in neuroblastoma via mitotic catastrophe. Endocr. Relat Cancer 18, 657-668.

Lane J, Mansel R E, Jiang W G (2003). Expression of human delta-6-desaturase is associated with aggressiveness of human breast cancer. Int. J Mol. Med. 12, 253-257.

Langley R R, Fan D, Guo L, Zhang C, Lin Q, Brantley E C, McCarty J H, Fidler I J (2009). Generation of an immortalized astrocyte cell line from H-2Kb-tsA58 mice to study the role of astrocytes in brain metastasis. Int. J Oncol 35, 665-672.

Laumonnier F, Bonnet-Brilhault F, Gomot M, Blanc R, David A, Moizard M P, Raynaud M, Ronce N, Lemonnier E, Calvas P, Laudier B, Chelly J, Fryns J P, Ropers H H, Hamel B C, Andres C, Barthelemy C, Moraine C, Briault S (2004). X-linked mental retardation and autism are associated with a mutation in the NLGN4 gene, a member of the neuroligin family. Am J Hum. Genet. 74, 552-557.

Lavedan C, Licamele L, Volpi S, Hamilton J, Heaton C, Mack K, Lannan R, Thompson A, Wolfgang C D, Polymeropoulos M H (2009). Association of the NPAS3 gene and five other loci with response to the antipsychotic iloperidone identified in a whole genome association study. Mol. Psychiatry 14, 804-819.

Lawson-Yuen A, Saldivar J S, Sommer S, Picker J (2008). Familial deletion within NLGN4 associated with autism and Tourette syndrome. Eur. J Hum. Genet. 16, 614-618.

Lazarini M, Traina F, Machado-Neto J A, Barcellos K S, Moreira Y B, Brandao M M, Verjovski-Almeida S, Ridley A J, Saad S T (2013). ARHGAP21 is a RhoGAP for RhoA and RhoC with a role in proliferation and migration of prostate adenocarcinoma cells. Biochim. Biophys. Acta 1832, 365-374.

Lee S Y, Kim J W, Jeong M H, An J H, Jang S M, Song K H, Choi K H (2008a). Microtubule-associated protein 1B light chain (MAP1B-LC1) negatively regulates the activity of tumor suppressor p53 in neuroblastoma cells. FEBS Lett. 582, 2826-2832.

Lee W R, Pan T L, Wang P W, Zhuo R Z, Huang C M, Fang J Y (2008b). Erbium:YAG laser enhances transdermal peptide delivery and skin vaccination. J Control Release 128, 200-208.

Lee Y, Ahn C, Han J, Choi H, Kim J, Yim J, Lee J, Provost P, Radmark O, Kim S, Kim V N (2003). The nuclear RNase III Drosha initiates microRNA processing. Nature 425, 415-419.

Leja J, Essaghir A, Essand M, Wester K, Oberg K, Totterman T H, Lloyd R, Vasmatzis G, Demoulin J B, Giandomenico V (2009). Novel markers for enterochromaffin cells and gastrointestinal neuroendocrine carcinomas. Mod. Pathol. 22, 261-272.

Leung E, Lim S P, Berg R, Yang Y, Ni J, Wang S X, Krissansen G W (1998). A novel extracellular domain variant of the human integrin alpha 7 subunit generated by alternative intron splicing. Biochem. Biophys. Res. Commun. 243, 317-325.

Lewis D A, Hashimoto T, Volk D W (2005). Cortical inhibitory neurons and schizophrenia. Nat Rev. Neurosci. 6, 312-324.

Li A, Walling J, Ahn S, Kotliarov Y, Su Q, Quezado M, Oberholtzer J C, Park J, Zenklusen J C, Fine H A (2009). Unsupervised analysis of transcriptomic profiles reveals six glioma subtypes. Cancer Res 69, 2091-2099.

Li C, Zota V, Woda B A, Rock K L, Fraire A E, Jiang Z, Lu D, Xu B, Dresser K, Lutman C V, Fischer A H (2007). Expression of a novel oncofetal mRNA-binding protein IMP3 in endometrial carcinomas: diagnostic significance and clinicopathologic correlations. Mod. Pathol. 20, 1263-1268.

Li H, Liu S, Zhu X, Yang S, Xiang J, Chen H (2010). Clusterin immunoexpression and its clinical significance in patients with non-small cell lung cancer. Lung 188, 423-431.

Li H G, Han J J, Huang Z Q, Wang L, Chen W L, Shen X M (2011a). IMP3 is a novel biomarker to predict metastasis and prognosis of tongue squamous cell carcinoma. J Craniofac. Surg. 22, 2022-2025.

Li J, Neumann I, Volkmer I, Staege M S (2011b). Down-regulation of achaete-scute complex homolog 1 (ASCL1) in neuroblastoma cells induces up-regulation of insulin-like growth factor 2 (IGF2). Mol. Biol. Rep. 38, 1515-1521.

Li J Q, Kubo A, Wu F, Usuki H, Fujita J, Bandoh S, Masaki T, Saoo K, Takeuchi H, Kobayashi S, Imaida K, Maeta H, Ishida T, Kuriyama S (2003). Cyclin B1, unlike cyclin G1, increases significantly during colorectal carcinogenesis and during later metastasis to lymph nodes. Int. J Oncol 22, 1101-1110.

Li M, Chen D, Shiloh A, Luo J, Nikolaev A Y, Qin J, Gu W (2002). Deubiquitination of p53 by HAUSP is an important pathway for p53 stabilization. Nature 416, 648-653.

Li W Q, Hu N, Hyland P L, Gao Y, Wang Z M, Yu K, Su H, Wang C Y, Wang L M, Chanock S J, Burdett L, Ding T, Qiao Y L, Fan J H, Wang Y, Xu Y, Shi J X, Gu F, Wheeler W, Xiong X Q, Giffen C, Tucker M A, Dawsey S M, Freedman N D, Abnet C C, Goldstein A M, Taylor P R (2013a). Genetic variants in DNA repair pathway genes and risk of esophageal squamous cell carcinoma and gastric adenocarcinoma in a Chinese population. Carcinogenesis.

Li X, LI Z, Li N, Qi J, Fan K, Yin P, Zhao C, Liu Y, Yao W, Cai X, Wang L, Zha X (2013b). MAGI2 enhances the sensitivity of BEL-7404 human hepatocellular carcinoma cells to staurosporine-induced apoptosis by increasing PTEN stability. Int. J Mol. Med.

Li Y, Fan S, Koo J, Yue P, Chen Z G, Owonikoko T K, Ramalingam S S, Khuri F R, Sun S Y (2012a). Elevated expression of eukaryotic translation initiation factor 4E is associated with proliferation, invasion and acquired resistance to erlotinib in lung cancer. Cancer Biol. Ther. 13, 272-280.

Li Z J, Nieuwenhuis E, Nien W, Zhang X, Zhang J, Puviindran V, Wainwright B J, Kim P C, Hui C C (2012b). Kif7 regulates Gli2 through Sufu-dependent and -independent functions during skin development and tumorigenesis. Development 139, 4152-4161.

Liang Y, Diehn M, Watson N, Bollen A W, Aldape K D, Nicholas M K, Lamborn K R, Berger M S, Botstein D, Brown P O, Israel M A (2005). Gene expression profiling reveals molecularly and clinically distinct subtypes of glioblastoma multiforme. Proc. Natl. Acad. Sci. U.S.A 102, 5814-5819.

Liao B, Hu Y, Brewer G (2011). RNA-binding protein insulin-like growth factor mRNA-binding protein 3 (IMP-3) promotes cell survival via insulin-like growth factor II signaling after ionizing radiation. J Biol. Chem. 286, 31145-31152.

Liao B, Hu Y, Herrick D J, Brewer G (2005). The RNA-binding protein IMP-3 is a translational activator of insulin-like growth factor II leader-3 mRNA during proliferation of human K562 leukemia cells. J Biol. Chem. 280, 18517-18524.

Lignitto L, Arcella A, Sepe M, Rinaldi L, Delle D R, Gallo A, Stefan E, Bachmann V A, Oliva M A, Tiziana S C, L'Abbate A, Brunetti A, Gargiulo S, Gramanzini M, Insabato L, Garbi C, Gottesman M E, Feliciello A (2013). Proteolysis of MOB1 by the ubiquitin ligase praja2 attenuates Hippo signalling and supports glioblastoma growth. Nat Commun. 4, 1822.

Ligon K L, Huillard E, Mehta S, Kesari S, Liu H, Alberta J A, Bachoo R M, Kane M, Louis D N, Depinho R A, Anderson D J, Stiles C D, Rowitch D H (2007). Olig2-regulated lineage-restricted pathway controls replication competence in neural stem cells and malignant glioma. Neuron 53, Lin C, Meng S, Zhu T, Wang X (2010a). PDCD10/CCM3 acts downstream of {gamma}-protocadherins to regulate neuronal survival. J Biol. Chem. 285, 41675-41685.

Lin L, Zhang J, Wang Y, Zheng L, Lin Z, Cai Y (2013). [Expression of insulin-like growth factor 2 mRNA-binding protein 3 expression and analysis of prognosis in the patients with lung squamous cell carcinoma]. Xi. Bao. Yu Fen. Zi. Mian. Yi. Xue. Za Zhi. 29, 694-697.

Lin S Y, Pan H W, Liu S H, Jeng Y M, Hu F C, Peng S Y, Lai P L, Hsu H C (2008). ASPM is a novel marker for vascular invasion, early recurrence, and poor prognosis of hepatocellular carcinoma. Clin Cancer Res 14, 4814-4820.

Lin Y, Mousa S S, Elshourbagy N, Mousa S A (2010b). Current status and future directions in lipid management: emphasizing low-density lipoproteins, high-density lipoproteins, and triglycerides as targets for therapy. Vasc. Health Risk Manag. 6, 73-85.

Liu J, Yue P, Artym V V, Mueller S C, Guo W (2009). The role of the exocyst in matrix metalloproteinase secretion and actin dynamics during tumor cell invadopodia formation. Mol. Biol. Cell 20, 3763-3771.

Liu R Z, Graham K, Glubrecht D D, Lai R, Mackey J R, Godbout R (2012a). A fatty acid-binding protein 7/RXR-beta pathway enhances survival and proliferation in triple-negative breast cancer. J Pathol. 228, 310-321.

Liu X, Chen N, Wang X, He Y, Chen X, Huang Y, Yin W, Zhou Q (2006). Apoptosis and proliferation markers in diffusely infiltrating astrocytomas: profiling of 17 molecules. J Neuropathol. Exp. Neurol. 65, 905-913.

Liu Y, Li Q, Zhu L (2012b). Expression of the hepatocyte growth factor and c-Met in colon cancer: correlation with clinicopathological features and overall survival. Tumori 98, 105-112.

Lo M L, Staibano S, Pannone G, Mignogna M D, Mariggio A, Salvatore G, Chieffi P, Tramontano D, De R G, Altieri D C (2001). Expression of the apoptosis inhibitor survivin in aggressive squamous cell carcinoma. Exp. Mol. Pathol. 70, 249-254.

Lobas M A, Helsper L, Vernon C G, Schreiner D, Zhang Y, Holtzman M J, Thedens D R, Weiner J A (2012). Molecular heterogeneity in the choroid plexus epithelium: the 22-member gamma-protocadherin family is differentially expressed, apically localized, and implicated in CSF regulation. J Neurochem. 120, 913-927.

Losada A, Hirano T (2005). Dynamic molecular linkers of the genome: the first decade of SMC proteins. Genes Dev. 19, 1269-1287.

Lossie A C, Nakamura H, Thomas S E, Justice M J (2005). Mutation of 17Rn3 shows that Odz4 is required for mouse gastrulation. Genetics 169, 285-299.

Loyo M, Brait M, Kim M S, Ostrow K L, Jie C C, Chuang A Y, Califano J A, Liegeois N J, Begum S, Westra W H, Hoque M O, Tao Q, Sidransky D (2011). A survey of methylated candidate tumor suppressor genes in nasopharyngeal carcinoma. Int. J Cancer 128, 1393-1403.

Lu D, Yang X, Jiang N Y, Woda B A, Liu Q, Dresser K, Mercurio A M, Rock K L, Jiang Z (2011). IMP3, a new biomarker to predict progression of cervical intraepithelial neoplasia into invasive cancer. Am. J Surg. Pathol. 35, 1638-1645.

Lu K V, Jong K A, Kim G Y, Singh J, Dia E Q, Yoshimoto K, Wang M Y, Cloughesy T F, Nelson S F, Mischel P S (2005). Differential induction of glioblastoma migration and growth by two forms of pleiotrophin. J Biol Chem. 280, 26953-26964.

Lu Q R, Park J K, Noll E, Chan J A, Alberta J, Yuk D, Alzamora M G, Louis D N, Stiles C D, Rowitch D H, Black P M (2001). Oligodendrocyte lineage genes (OLIG) as molecular markers for human glial brain tumors. Proc. Natl. Acad. Sci. U.S.A 98, 10851-10856.

Lu Q R, Yuk D, Alberta J A, Zhu Z, Pawlitzky I, Chan J, McMahon A P, Stiles C D, Rowitch D H (2000). Sonic hedgehog—regulated oligodendrocyte lineage genes encoding bHLH proteins in the mammalian central nervous system. Neuron 25, 317-329.

Lu Y, Lemon W, Liu P Y, Yi Y, Morrison C, Yang P, Sun Z, Szoke J, Gerald W L, Watson M, Govindan R, You M (2006). A gene expression signature predicts survival of patients with stage I non-small cell lung cancer. PLoS. Med. 3, e467.

Luksch H, Uckermann O, Stepulak A, Hendruschk S, Marzahn J, Bastian S, Staufner C, Temme A, Ikonomidou C (2011). Silencing of selected glutamate receptor subunits modulates cancer growth. Anticancer Res. 31, 3181-3192.

Mackie E J, Halfter W, Liverani D (1988). Induction of tenascin in healing wounds. J Cell Biol. 107, 2757-2767.

Mahlamaki E H, Barlund M, Tanner M, Gorunova L, Hoglund M, Karhu R, Kallioniemi A (2002). Frequent amplification of 8q24, 11q, 17q, and 20q-specific genes in pancreatic cancer. Genes Chromosomes. Cancer 35, 353-358.

Malagon M M, Cruz-Garcia D, Diaz-Ruiz A, Peinado J R, Pulido M R, Araujo J, Garcia-Navarro S, Gracia-Navarro F, Castano J P, Vazquez-Martinez R (2009). Identification of novel genes involved in the plasticity of pituitary melanotropes in amphibians. Ann N. Y. Acad. Sci. 1163, 233-240.

Mao X, Boyd L K, Yanez-Munoz R J, Chaplin T, Xue L, Lin D, Shan L, Berney D M, Young B D, Lu Y J (2011). Chromosome rearrangement associated inactivation of tumour suppressor genes in prostate cancer. Am. J Cancer Res. 1, 604-617.

Marchand M, Van B N, Weynants P, Brichard V, Dreno B, Tessier M R, Rankin E, Parmiani G, Arienti F, Humblet Y, Bourlond A, Vanwijck R, Lienard D, Beauduin M, Dietrich P Y, Russo V, Kerger J, Masucci G, Jager E, De G J, Atzpodien J, Brasseur F, Coulie P G, van der B P, Boon T (1999). Tumor regressions observed in patients with metastatic melanoma treated with an antigenic peptide encoded by gene MAGE-3 and presented by HLA-A1. Int. J. Cancer 80, 219-230.

Marchand M, Weynants P, Rankin E, Arienti F, *Belli* F, Parmiani G, Cascinelli N, Bourlond A, Vanwijck R, Humblet Y, (1995). Tumor regression responses in melanoma patients treated with a peptide encoded by gene MAGE-3. Int. J Cancer 63, 883-885.

Mardilovich K, Pankratz S L, Shaw L M (2009). Expression and function of the insulin receptor substrate proteins in cancer. Cell Commun. Signal. 7, 14.

Marei H E, Ahmed A E, Michetti F, Pescatori M, Pallini R, Casalbore P, Cenciarelli C, Elhadidy M (2012). Gene expression profile of adult human olfactory bulb and embryonic neural stem cell suggests distinct signaling pathways and epigenetic control. PLoS. ONE. 7, e33542.

Marie S K, Okamoto O K, Uno M, Hasegawa A P, Oba-Shinjo S M, Cohen T, Camargo A A, Kosoy A, Carlotti C G, Jr., Toledo S, Moreira-Filho C A, Zago M A, Simpson A J, Caballero O L (2008).

Maternal embryonic leucine zipper kinase transcript abundance correlates with malignancy grade in human astrocytomas. Int J Cancer 122, 807-815.

Marie Y, Sanson M, Mokhtari K, Leuraud P, Kujas M, Delattre J Y, Poirier J, Zalc B, Hoang-Xuan K (2001). OLIG2 as a specific marker of oligodendroglial tumour cells. Lancet 358, 298-300.

Marquardt A, Stohr H, White K, Weber B H (2000). cDNA cloning, genomic structure, and chromosomal localization of three members of the human fatty acid desaturase family. Genomics 66, 175-183.

Martineau Y, Azar R, Muller D, Lasfargues C, El K S, Anesia R, Pelletier J, Bousquet C, Pyronnet S (2013). Pancreatic tumours escape from translational control through 4E-BP1 loss. Oncogene.

Marzo A L, Kinnear B F, Lake R A, Frelinger J J, Collins E J, Robinson B W, Scott B (2000). Tumor-specific CD4+ T cells have a major "post-licensing" role in CTL mediated anti-tumor immunity. J Immunol. 165, 6047-6055.

Masuda H, Fukabori Y, Nakano K, Shimizu N, Yamanaka H (2004). Expression of bone morphogenetic protein-7 (BMP-7) in human prostate. Prostate 59, 101-106.

Mathew R M, Vandenberghe R, Garcia-Merino A, Yamamoto T, Landolfi J C, Rosenfeld M R, Rossi J E, Thiessen B, Dropcho E J, Dalmau J (2007). Orchiectomy for suspected microscopic tumor in patients with anti-Ma2-associated encephalitis. Neurology 68, 900-905.

Mattera L, Escaffit F, Pillaire M J, Selves J, Tyteca S, Hoffmann J S, Gourraud P A, Chevillard-Briet M, Cazaux C, Trouche D (2009). The p400/Tip60 ratio is critical for colorectal cancer cell proliferation through DNA damage response pathways. Oncogene 28, 1506-1517.

McCarthy P L, Mercer F C, Savicky M W, Carter B A, Paterno G D, Gillespie L L (2008). Changes in subcellular localisation of M I-ER1 alpha, a novel oestrogen receptor-alpha interacting protein, is associated with breast cancer progression. Br. J Cancer 99, 639-646.

McInroy L, Maatta A (2007). Down-regulation of vimentin expression inhibits carcinoma cell migration and adhesion. Biochem. Biophys. Res. Commun. 360, 109-114.

McManus K J, Barrett I J, Nouhi Y, Hieter P (2009). Specific synthetic lethal killing of RAD54B-deficient human colorectal cancer cells by FEN1 silencing. Proc. Natl. Acad. Sci. U.S.A 106, 3276-3281.

McMillan D R, Kayes-Wandover K M, Richardson J A, White P C (2002). Very large G protein-coupled receptor-1, the largest known cell surface protein, is highly expressed in the developing central nervous system. J Biol. Chem. 277, 785-792.

Megumi K, Ishigami S, Uchikado Y, Kita Y, Okumura H, Matsumoto M, Uenosono Y, Arigami T, Kijima Y, Kitazono M, Shinchi H, Ueno S, Natsugoe S (2012). Clinicopathological significance of BMP7 expression in esophageal squamous cell carcinoma. Ann Surg. Oncol 19, 2066-2071.

Mehrle A, Rosenfelder H, Schupp I, del V C, Arlt D, Hahne F, Bechtel S, Simpson J, Hofmann O, Hide W, Glatting K H, Huber W, Pepperkok R, Poustka A, Wiemann S (2006). The LIFEdb database in 2006. Nucleic Acids Res. 34, D415-D418.

Mellai M, Caldera V, Patrucco A, Annovazzi L, Schiffer D (2008). Survivin expression in glioblastomas correlates with proliferation, but not with apoptosis. Anticancer Res. 28, 109-118.

Melrose J, Numata Y, Ghosh P (1996). Biotinylated hyaluronan: a versatile and highly sensitive probe capable of detecting nanogram levels of hyaluronan binding proteins (hyaladherins) on electroblots by a novel affinity detection procedure. Electrophoresis 17, 205-212.

Mendez M G, Kojima S, Goldman R D (2010). Vimentin induces changes in cell shape, motility, and adhesion during the epithelial to mesenchymal transition. FASEB J 24, 1838-1851.

Mendiola M, Carrillo J, Garcia E, Lalli E, Hernandez T, de A E, Tirode F, Delattre O, Garcia-Miguel P, Lopez-Barea F, Pestana A, Alonso J (2006). The orphan nuclear receptor DAX1 is up-regulated by the EWS/FLI1 oncoprotein and is highly expressed in Ewing tumors. Int. J Cancer 118, 1381-1389.

Merighi S, Mirandola P, Varani K, Gessi S, Leung E, Baraldi P G, Tabrizi M A, Borea P A (2003). A glance at adenosine receptors: novel target for antitumor therapy. Pharmacol. Ther. 100, 31-48.

Merritt W M, et al. (2008). Dicer, Drosha, and outcomes in patients with ovarian cancer. N. Engl. J Med. 359, 2641-2650.

Meunier L, Puiffe M L, Le P C, Filali-Mouhim A, Chevrette M, Tonin P N, Provencher D M, Mes-Masson A M (2010). Effect of ovarian cancer ascites on cell migration and gene expression in an epithelial ovarian cancer in vitro model. Transl. Oncol 3, 230-238.

Meyer-Puttlitz B, Junker E, Margolis R U, Margolis R K (1996). Chondroitin sulfate proteoglycans in the developing central nervous system. II. Immunocytochemical localization of neurocan and phosphacan. J Comp Neurol. 366, 44-54.

Midorikawa Y, Tsutsumi S, Taniguchi H, Ishii M, Kobune Y, Kodama T, Makuuchi M, Aburatani H (2002). Identification of genes associated with dedifferentiation of hepatocellular carcinoma with expression profiling analysis. Jpn. J Cancer Res. 93, 636-643.

Miki M, Ball D W, Linnoila R I (2012). Insights into the achaete-scute homolog-1 gene (hASH1) in normal and neoplastic human lung. Lung Cancer 75, 58-65.

Miley P, Friedlander D R, Sakurai T, Karthikeyan L, Flad M, Margolis R K, Grumet M, Margolis R U (1994). Interactions of the chondroitin sulfate proteoglycan phosphacan, the extracellular domain of a receptor-type protein tyrosine phosphatase, with neurons, glia, and neural cell adhesion molecules. J Cell Biol. 127, 1703-1715.

Milkereit P, Strauss D, Bassler J, Gadal O, Kuhn H, Schutz S, Gas N, Lechner J, Hurt E, Tschochner H (2003). A Noc complex specifically involved in the formation and nuclear export of ribosomal 40 S subunits. J Biol. Chem. 278, 4072-4081.

Min J, Mesika A, Sivaguru M, Van Veldhoven P P, Alexander H, Futerman A H, Alexander S (2007). (Dihydro) ceramide synthase 1 regulated sensitivity to cisplatin is associated with the activation of p38 mitogen-activated protein kinase and is abrogated by sphingosine kinase 1. Mol. Cancer Res. 5, 801-812.

Minde D P, Anvarian Z, Rudiger S G, Maurice M M (2011). Messing up disorder: how do missense mutations in the tumor suppressor protein APC lead to cancer? Mol. Cancer 10, 101.

Mita R, Coles J E, Glubrecht D D, Sung R, Sun X, Godbout R (2007). B-FABP-expressing radial glial cells: the malignant glioma cell of origin? Neoplasia. 9, 734-744.

Miyamoto K, Fukutomi T, Akashi-Tanaka S, Hasegawa T, Asahara T, Sugimura T, Ushijima T (2005). Identification of 20 genes aberrantly methylated in human breast cancers. Int. J Cancer 116, 407-414.

Mobius W, Patzig J, Nave K A, Werner H B (2008). Phylogeny of proteolipid proteins: divergence, constraints, and the evolution of novel functions in myelination and neuroprotection. Neuron Glia Biol. 4, 111-127.

Mohamed A, Gonzalez R S, Lawson D, Wang J, Cohen C (2012). SOX10 Expression in Malignant Melanoma, Carcinoma, and Normal Tissues. Appl. Immunohistochem. Mol. Morphol.

Morales G, Hubert M, Brummendorf T, Treubert U, Tarnok A, Schwarz U, Rathjen F G (1993). Induction of axonal growth by heterophilic interactions between the cell surface recognition proteins F11 and Nr-CAM/Bravo. Neuron 11, 1113-1122.

Moreira F, Kiehl T R, So K, Ajeawung N F, Honculada C, Gould P, Pieper R O, Kamnasaran D (2011). NPAS3 demonstrates features of a tumor suppressive role in driving the progression of Astrocytomas. Am. J Pathol. 179, 462-476.

Morello S, Petrella A, Festa M, Popolo A, Monaco M, Vuttariello E, Chiappetta G, Parente L, Pinto A (2008). Cl-IB-MECA inhibits human thyroid cancer cell proliferation independently of A3 adenosine receptor activation. Cancer Biol. Ther. 7, 278-284.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A (2006). Cancer Regression in Patients After Transfer of Genetically Engineered Lymphocytes. Science.

Mori M, Beatty P G, Graves M, Boucher K M, Milford E L (1997). HLA gene and haplotype frequencies in the North American population: the National Marrow Donor Program Donor Registry. Transplantation 64, 1017-1027.

Morishita H, Yagi T (2007). Protocadherin family: diversity, structure, and function. Curr. Opin. Cell Biol. 19, 584-592.

Mortara L, Castellani P, Meazza R, Tosi G, De Lerma B A, Procopio F A, Comes A, Zardi L, Ferrini S, Accolla R S (2006). CIITA-induced MHC class II expression in mammary adenocarcinoma leads to a Th1 polarization of the tumor microenvironment, tumor rejection, and specific antitumor memory. Clin Cancer Res. 12, 3435-3443.

Mosavi L K, Cammett T J, Desrosiers D C, Peng Z Y (2004). The ankyrin repeat as molecular architecture for protein recognition. Protein Sci. 13, 1435-1448.

Motoyama K, Tanaka F, Kosaka Y, Mimori K, Uetake H, Inoue H, Sugihara K, Mori M (2008). Clinical significance of BMP7 in human colorectal cancer. Ann Surg. Oncol 15, 1530-1537.

Mu J, Roach P J (1998). Characterization of human glycogenin-2, a self-glucosylating initiator of liver glycogen metabolism. J Biol. Chem. 273, 34850-34856.

Mueller L N, Rinner O, Schmidt A, Letarte S, Bodenmiller B, Brusniak M Y, Vitek O, Aebersold R, Muller M (2007). SuperHirn—a novel tool for high resolution L C-M S-based peptide/protein profiling. Proteomics. 7, 3470-3480.

Muir K, Hazim A, He Y, Peyressatre M, Kim D Y, Song X, Beretta L (2013). Proteomic and Lipidomic Signatures of Lipid Metabolism in NASH-Associated Hepatocellular Carcinoma. Cancer Res. 73, 4722-4731.

Mulholland P J, Fiegler H, Mazzanti C, Gorman P, Sasieni P, Adams J, Jones T A, Babbage J W, Vatcheva R, Ichimura K, East P, Poullikas C, Collins V P, Carter N P, Tomlinson I P, Sheer D (2006). Genomic profiling identifies discrete deletions associated with translocations in glioblastoma multiforme. Cell Cycle 5, 783-791.

Muller S, Kunkel P, Lamszus K, Ulbricht U, Lorente G A, Nelson A M, von S D, Chin D J, Lohr S C, Westphal M, Melcher T (2003). A role for receptor tyrosine phosphatase zeta in glioma cell migration. Oncogene 22, 6661-6668.

Murray-Stewart T, Wang Y, Devereux W, Casero R A, Jr. (2002). Cloning and characterization of multiple human polyamine oxidase splice variants that code for isoenzymes with different biochemical characteristics. Biochem. J 368, 673-677.

Musacchio A, Gibson T, Rice P, Thompson J, Saraste M (1993). The PH domain: a common piece in the structural patchwork of signalling proteins. Trends Biochem. Sci. 18, 343-348.

Mykytyn K, Nishimura D Y, Searby C C, Beck G, Bugge K, Haines H L, Cornier A S, Cox G F, Fulton A B, Carmi R, Iannaccone A, Jacobson S G, Weleber R G, Wright A F, Riise R, Hennekam R C, Luleci G, Berker-Karauzum S, Biesecker L G, Stone E M, Sheffield V C (2003). Evaluation of complex inheritance involving the most common Bardet-Biedl syndrome locus (BBS1). Am. J Hum. Genet. 72, 429-437.

Myung P S, Takeo M, Ito M, Atit R P (2013). Epithelial Wnt ligand secretion is required for adult hair follicle growth and regeneration. J Invest Dermatol. 133, 31-41.

Na Y R, Seok S H, Kim D J, Han J H, Kim T H, Jung H, Lee B H, Park J H (2009). Bone morphogenetic protein 7 induces mesenchymal-to-epithelial transition in melanoma cells, leading to inhibition of metastasis. Cancer Sci. 100, 2218-2225.

Nagai M, Ichimiya S, Ozaki T, Seki N, Mihara M, Furuta S, Ohira M, Tomioka N, Nomura N, Sakiyama S, Kubo O, Takakura K, Hori T, Nakagawara A (2000). Identification of the full-length KIAA0591 gene encoding a novel kinesin-related protein which is mapped to the neuroblastoma suppressor gene locus at 1p36.2. Int. J Oncol 16, 907-916.

Nakada Y, Hunsaker T L, Henke R M, Johnson J E (2004). Distinct domains within Mash1 and Math1 are required for function in neuronal differentiation versus neuronal cell-type specification. Development 131, 1319-1330.

Nakamura Y, Suzuki T, Arai Y, Sasano H (2009). Nuclear receptor DAX1 in human prostate cancer: a novel independent biological modulator. Endocr. J 56, 39-44.

Nakayama J, Hamano K, Iwasaki N, Nakahara S, Horigome Y, Saitoh H, Aoki T, Maki T, Kikuchi M, Migita T, Ohto T, Yokouchi Y, Tanaka R, Hasegawa M, Matsui A, Hamaguchi H, Arinami T (2000). Significant evidence for linkage of febrile seizures to chromosome 5q14-q15. Hum. Mol. Genet. 9, 87-91.

Nakayama M, Miyake T, Gahara Y, Ohara O, Kitamura T (1995). A novel RING-H2 motif protein downregulated by axotomy: its characteristic localization at the postsynaptic density of axosomatic synapse. J Neurosci. 15, 5238-5248.

Nara Y, Kato Y, Torii Y, Tsuji Y, Nakagaki S, Goto S, Isobe H, Nakashima N, Takeuchi J (1997). Immunohistochemical localization of extracellular matrix components in human breast tumours with special reference to PG-M/versican. Histochem. J 29, 21-30.

Nasr Z, Robert F, Porco J A, Jr., Muller W J, Pelletier J (2013). eIF4F suppression in breast cancer affects maintenance and progression. Oncogene 32, 861-871.

Need A C, Keefe R S, Ge D, Grossman I, Dickson S, McEvoy J P, Goldstein D B (2009). Pharmacogenetics of antipsychotic response in the CATIE trial: a candidate gene analysis. Eur. J Hum. Genet. 17, 946-957.

Nestle F O, Alijagic S, Gilliet M, Sun Y, Grabbe S, Dummer R, Burg G, Schadendorf D (1998). Vaccination of melanoma patients with peptide- or tumor lysate-pulsed dendritic cells. Nat Med.

Niakan K K, McCabe E R (2005). DAX1 origin, function, and novel role. Mol. Genet. Metab 86, 70-83.

Nibbe R K, Markowitz S, Myeroff L, Ewing R, Chance M R (2009). Discovery and scoring of protein interaction subnetworks discriminative of late stage human colon cancer. Mol. Cell Proteomics. 8, 827-845.

Nichols A C, Chan-Seng-Yue M, Yoo J, Xu W, Dhaliwal S, Basmaji J, Szeto C C, Dowthwaite S, Todorovic B, Starmans M H, Lambin P, Palma D A, Fung K, Franklin J H, Wehrli B, Kwan K, Koropatnick J, Mymryk J S, Boutros P, Barrett J W (2012). A Pilot Study Comparing HPV-Positive and HPV-Negative Head and Neck Squamous Cell Carcinomas by Whole Exome Sequencing. ISRN. Oncol 2012, 809370.

Nigg E A, Raff J W (2009). Centrioles, centrosomes, and cilia in health and disease. Cell 139, 663-678.

Nikkila H, McMillan D R, Nunez B S, Pascoe L, Curnow K M, White P C (2000). Sequence similarities between a novel putative G protein-coupled receptor and Na+/Ca2+ exchangers define a cation binding domain. Mol. Endocrinol. 14, 1351-1364.

Nishioka M, Kohno T, Takahashi M, Niki T, Yamada T, Sone S, Yokota J (2000). Identification of a 428-kb homozygously deleted region disrupting the SEZ6L gene at 22q12.1 in a lung cancer cell line. Oncogene 19, 6251-6260.

Niu Z, Li X, Hu B, Li R, Wang L, Wu L, Wang X (2012). Small interfering RNA targeted to secretory clusterin blocks tumor growth, motility, and invasion in breast cancer. Acta Biochim. Biophys. Sin. (Shanghai) 44, 991-998. Novak P, Jensen T, Oshiro M M, Watts G S, Kim C J, Futscher B W (2008). Agglomerative epigenetic aberrations are a common event in human breast cancer. Cancer Res. 68, 8616-8625.

Nurmi E L, Dowd M, Tadevosyan-Leyfer O, Haines J L, Folstein S E, Sutcliffe J S (2003). Exploratory subsetting of autism families based on savant skills improves evidence of genetic linkage to 15q11-q13. J Am. Acad. Child Adolesc. Psychiatry 42, 856-863.

Nwankwo J O, Spector A A, Domann F E (2003). A nucleotide insertion in the transcriptional regulatory region of FADS2 gives rise to human fatty acid delta-6-desaturase deficiency. J Lipid Res. 44, 2311-2319.

Oda T, Tian T, Inoue M, Ikeda J, Qiu Y, Okumura M, Aozasa K, Morii E (2009). Tumorigenic role of orphan nuclear receptor NR0B1 in lung adenocarcinoma. Am. J Pathol. 175, 1235-1245.

Ohira M, et al. (2000). Identification and characterization of a 500-kb homozygously deleted region at 1p36.2-p36.3 in a neuroblastoma cell line. Oncogene 19, 4302-4307.

Ohmae S, Takemoto-Kimura S, Okamura M, Adachi-Morishima A, Nonaka M, Fuse T, Kida S, Tanji M, Furuyashiki T, Arakawa Y, Narumiya S, Okuno H, Bito H (2006). Molecular identification and characterization of a family of kinases with homology to Ca2+/calmodulin-dependent protein kinases I/IV. J Biol. Chem. 281, 20427-20439.

Ohtomo R, Mori T, Shibata S, Tsuta K, Maeshima A M, Akazawa C, Watabe Y, Honda K, Yamada T, Yoshimoto S, Asai M, Okano H, Kanai Y, Tsuda H (2013). SOX10 is a novel marker of acinus and intercalated duct differentiation in salivary gland tumors: a clue to the histogenesis for tumor diagnosis. Mod. Pathol. 26, 1041-1050.

Okada K, Fujiwara Y, Nakamura Y, Takiguchi S, Nakajima K, Miyata H, Yamasaki M, Kurokawa Y, Takahashi T, Mori M, Doki Y (2012). Oncofetal protein, IMP-3, a potential marker for prediction of postoperative peritoneal dissemination in gastric adenocarcinoma. J Surg. Oncol 105, 780-785.

Olsen M L, Sontheimer H (2008). Functional implications for Kir4.1 channels in glial biology: from K+ buffering to cell differentiation. J Neurochem. 107, 589-601.

Osada H, Tatematsu Y, Yatabe Y, Horio Y, Takahashi T (2005). ASH1 gene is a specific therapeutic target for lung cancers with neuroendocrine features. Cancer Res. 65, 10680-10685.

Ostrow K L, Park H L, Hoque M O, Kim M S, Liu J, Argani P, Westra W, Van C W, Sidransky D (2009). Pharmacologic unmasking of epigenetically silenced genes in breast cancer. Clin Cancer Res. 15, 1184-1191.

Otey C A, Pavalko F M, Burridge K (1990). An interaction between alpha-actinin and the beta 1 integrin subunit in vitro. J Cell Biol. 111, 721-729.

Ou X M, Chen K, Shih J C (2006). Monoamine oxidase A and repressor R1 are involved in apoptotic signaling pathway. Proc. Natl. Acad. Sci. U.S.A 103, 10923-10928.

Ozerdem U (2006). Targeting of pericytes diminishes neovascularization and lymphangiogenesis in prostate cancer. Prostate 66, 294-304.

Panico F, Casali C, Rossi G, Rizzi F, Morandi U, Bettuzzi S, Davalli P, Corbetta L, Storelli E S, *Corti* A, Fabbri L M, Astancolle S, Luppi F (2013). Prognostic role of clusterin in resected adenocarcinomas of the lung. Lung Cancer 79, 294-299.

Pannuti A, Lanfrancone L, Pascucci A, Pelicci P G, La M G, Lania L (1988). Isolation of cDNAs encoding finger proteins and measurement of the corresponding mRNA levels during myeloid terminal differentiation. Nucleic Acids Res. 16, 4227-4237.

Papachristou D J, Korpetinou A, Giannopoulou E, Antonacopoulou A G, Papadaki H, Grivas P, Scopa C D, Kalofonos H P (2011). Expression of the ribonucleases Drosha, Dicer, and Ago2 in colorectal carcinomas. Virchows Arch. 459, 431-440.

Parisi M, Glass I (1993). Joubert Syndrome and Related Disorders.

Park W J, Kothapalli K S, Lawrence P, Brenna J T (2011). FADS2 function loss at the cancer hotspot 11q13 locus diverts lipid signaling precursor synthesis to unusual eicosanoid fatty acids. PLoS. ONE. 6, e28186.

Paron I, Berchtold S, Voros J, Shamarla M, Erkan M, Hofler H, Esposito I (2011). Tenascin-C enhances pancreatic cancer cell growth and motility and affects cell adhesion through activation of the integrin pathway. PLoS. ONE. 6, e21684.

Pascolo S, Ginhoux F, Laham N, Walter S, Schoor O, Probst J, Rohrlich P, Obermayr F, Fisch P, Danos O, Ehrlich R, Lemonnier F A, Rammensee H G (2005). The non-classical HLA class I molecule HFE does not influence the NK-like activity contained in fresh human PBMCs and does not interact with NK cells. Int. Immunol. 17, 117-122.

Passon N, Gerometta A, Puppin C, Lavarone E, Puglisi F, Tell G, Di L C, Damante G (2012). Expression of Dicer and Drosha in triple-negative breast cancer. J Clin Pathol. 65, 320-326.

Paterno G D, Ding Z, Lew Y Y, Nash G W, Mercer F C, Gillespie L L (2002). Genomic organization of the human mi-er1 gene and characterization of alternatively spliced isoforms: regulated use of a facultative intron determines subcellular localization. Gene 295, 79-88.

Paterno G D, Li Y, Luchman H A, Ryan P J, Gillespie L L (1997). cDNA cloning of a novel, developmentally regulated immediate early gene activated by fibroblast growth factor and encoding a nuclear protein. J Biol. Chem. 272, 25591-25595.

Pattani K M, et al. (2010). Endothelin receptor type B gene promoter hypermethylation in salivary rinses is independently associated with risk of oral cavity cancer and premalignancy. Cancer Prev. Res. (Phila) 3, 1093-1103.

Pattyn A, Guillemot F, Brunet J F (2006). Delays in neuronal differentiation in Mash1/Ascl1 mutants. Dev. Biol. 295, 67-75.

Pegoraro E, Cepollaro F, Prandini P, Marin A, Fanin M, Trevisan C P, El-Messlemani A H, Tarone G, Engvall E, Hoffman E P, Angelini C (2002). Integrin alpha 7 beta 1 in muscular dystrophy/myopathy of unknown etiology. Am. J Pathol. 160, 2135-2143.

Pellikka M, Tanentzapf G, Pinto M, Smith C, McGlade C J, Ready D F, Tepass U (2002). Crumbs, the Drosophila homologue of human CRB1/RP12, is essential for photoreceptor morphogenesis. Nature 416, 143-149.

Pender-Cudlip M C, Krag K J, Martini D, Yu J, Guidi A, Skinner S S, Zhang Y, Qu X, He C, Xu Y, Qian S Y, Kang J X (2013). Delta-6-desaturase activity and arachidonic acid synthesis are increased in human breast cancer tissue. Cancer Sci. 104, 760-764.

Perrin F E, Rathjen F G, Stoeckli E T (2001). Distinct subpopulations of sensory afferents require F11 or axonin-1 for growth to their target layers within the spinal cord of the chick. Neuron 30, 707-723.

Piesche M, Hildebrandt Y, Zettl F, Chapuy B, Schmitz M, Wulf G, Trumper L, Schroers R (2007). Identification of a promiscuous HLA DR-restricted T-cell epitope derived from the inhibitor of apoptosis protein survivin. Hum. Immunol. 68, 572-576.

Pinheiro P S, Perrais D, Coussen F, Barhanin J, Bettler B, Mann J R, Malva J O, Heinemann S F, Mulle C (2007). GluR7 is an essential subunit of presynaptic kainate autoreceptors at hippocampal mossy fiber synapses. Proc. Natl. Acad. Sci. U.S.A 104, 12181-12186.

Poomsawat S, Buajeeb W, Khovidhunkit S O, Punyasingh J (2010). Alteration in the expression of cdk4 and cdk6 proteins in oral cancer and premalignant lesions. J Oral Pathol. Med. 39, 793-799.

Populo H, Lopes J M, Soares P (2012). The mTOR Signalling Pathway in Human Cancer. Int. J Mol. Sci. 13, 1886-1918.

Prades C, Arnould I, Annilo T, Shulenin S, Chen Z Q, Orosco L, Triunfol M, Devaud C, Maintoux-Larois C, Lafargue C, Lemoine C, Denefle P, Rosier M, Dean M (2002). The human ATP binding cassette gene ABCA13, located on chromosome 7p12.3, encodes a 5058 amino acid protein with an extracellular domain encoded in part by a 4.8-kb conserved exon. Cytogenet. Genome Res 98, 160-168.

Prajapati S C, Chauhan S S (2011). Dipeptidyl peptidase III: a multifaceted oligopeptide N-end cutter. FEBS J 278, 3256-3276.

Prakash S, Sarran L, Socci N, DeMatteo R P, Eisenstat J, Greco A M, Maki R G, Wexler L H, LaQuaglia M P, Besmer P, Antonescu C R (2005). Gastrointestinal stromal tumors in children and young adults: a clinicopathologic, molecular, and genomic study of 15 cases and review of the literature. J Pediatr. Hematol. Oncol 27, 179-187.

Prieto J L, McStay B (2007). Recruitment of factors linking transcription and processing of pre-rRNA to NOR chromatin is UBF-dependent and occurs independent of transcription in human cells. Genes Dev. 21, 2041-2054.

Pritchett J, Athwal V, Roberts N, Hanley N A, Hanley K P (2011). Understanding the role of SOX9 in acquired diseases: lessons from development. Trends Mol. Med. 17, 166-174.

Pryor J G, Bourne P A, Yang Q, Spaulding B O, Scott G A, Xu H (2008). IMP-3 is a novel progression marker in malignant melanoma. Mod. Pathol. 21, 431-437.

Puyol M, Martin A, Dubus P, Mulero F, Pizcueta P, Khan G, Guerra C, Santamaria D, Barbacid M (2010). A synthetic lethal interaction between K-Ras oncogenes and Cdk4 unveils a therapeutic strategy for non-small cell lung carcinoma. Cancer Cell 18, 63-73.

Qiao Y, Liu X, Harvard C, Hildebrand M J, Rajcan-Separovic E, Holden J J, Lewis M E (2008). Autism-associated familial microdeletion of Xp11.22. Clin Genet. 74, 134-144.

Qin Z, Blankenstein T (2000). CD4+ T cell-mediated tumor rejection involves inhibition of angiogenesis that is dependent on IFN gamma receptor expression by nonhematopoietic cells. Immunity. 12, 677-686.

Qin Z, Schwartzkopff J, Pradera F, Kammertoens T, Seliger B, Pircher H, Blankenstein T (2003). A critical requirement of interferon gamma-mediated angiostasis for tumor rejection by CD8+ T cells. Cancer Res. 63, 4095-4100.

Raji O Y, Agbaje O F, Duffy S W, Cassidy A, Field J K (2010). Incorporation of a genetic factor into an epidemiologic model for prediction of individual risk of lung cancer: the Liverpool Lung Project. Cancer Prev. Res. (Phila) 3, 664-669.

Rammensee H G, Bachmann J, Emmerich N P, Bachor O A, Stevanovic S (1999). SYFPEITHI: database for WIC ligands and peptide motifs. Immunogenetics 50, 213-219.

Rammensee H G, Bachmann J, Stevanovic S (1997). WIC Ligands and Peptide Motifs. (Heidelberg, Germany: Springer-Verlag).

Ramos S, Khademi F, Somesh B P, Rivero F (2002). Genomic organization and expression profile of the small GTPases of the RhoBTB family in human and mouse. Gene 298, 147-157.

Rao P, Fuller G N, Prieto V G (2010). Expression of Sox-9 in metastatic melanoma—a potential diagnostic pitfall. Am. J Dermatopathol. 32, 262-266.

Rapa I, Ceppi P, Bollito E, Rosas R, Cappia S, Bacillo E, Porpiglia F, Berruti A, Papotti M, Volante M (2008). Human ASH1 expression in prostate cancer with neuroendocrine differentiation. Mod. Pathol. 21, 700-707.

Rauch U (2004). Extracellular matrix components associated with remodeling processes in brain. Cell Mol. Life Sci. 61, 2031-2045.

Raverot G, Wierinckx A, Dantony E, Auger C, Chapas G, Villeneuve L, Brue T, Figarella-Branger D, Roy P, Jouanneau E, Jan M, Lachuer J, Trouillas J (2010). Prognostic factors in prolactin pituitary tumors: clinical, histological, and molecular data from a series of 94 patients with a long postoperative follow-up. J Clin Endocrinol. Metab 95, 1708-1716.

Reamy A A, Wolfgang M J (2011). Carnitine palmitoyltransferase-1c gain-of-function in the brain results in postnatal microencephaly. J Neurochem. 118, 388-398.

Reilly P T, Mak T W (2012). Molecular pathways: tumor cells Co-opt the brain-specific metabolism gene CPT1C to promote survival. Clin Cancer Res. 18, 5850-5855.

Reinert T, Modin C, Castano F M, Lamy P, Wojdacz T K, Hansen L L, Wiuf C, Bone M, Dyrskjot L, ORntoft T F (2011). Comprehensive genome methylation analysis in bladder cancer: identification and validation of novel methylated genes and application of these as urinary tumor markers. Clin Cancer Res. 17, 5582-5592.

Ren B, Yu Y P, Tseng G C, Wu C, Chen K, Rao U N, Nelson J, Michalopoulos G K, Luo J H (2007). Analysis of integrin alpha7 mutations in prostate cancer, liver cancer, glioblastoma multiforme, and leiomyosarcoma. J Natl. Cancer Inst. 99, 868-880.

Renkonen S, Heikkila P, Haglund C, Makitie A A, Hagstrom J (2012). Tenascin-C, GLUT-1, and syndecan-2 expression in juvenile nasopharyngeal angiofibroma: Correlations to vessel density and tumor stage. Head Neck.

Rheinbay E, Suva M L, Gillespie S M, Wakimoto H, Patel A P, Shahid M, Oksuz O, Rabkin S D, Martuza R L, Rivera M N, Louis D N, Kasif S, Chi A S, Bernstein B E (2013). An aberrant transcription factor network essential for Wnt signaling and stem cell maintenance in glioblastoma. Cell Rep. 3, 1567-1579.

Richiardi L, Fiano V, Grasso C, Zugna D, Delsedime L, Gillio-Tos A, Merletti F (2013). Methylation of APC and GSTP1 in Non-Neoplastic Tissue Adjacent to Prostate Tumour and Mortality from Prostate Cancer. PLoS. ONE. 8, e68162.

Richter P, Umbreit C, Franz M, Berndt A, Grimm S, Uecker A, Bohmer F D, Kosmehl H, Berndt A (2011). EGF/TGFbeta1 co-stimulation of oral squamous cell carcinoma cells causes an epithelial-mesenchymal transition cell phenotype expressing laminin 332. J Oral Pathol. Med. 40, 46-54.

Riener M O (2011). [Diagnosis of tumours of the liver and the biliary tract: new tissue and serum markers]. Pathologe 32 Suppl 2, 304-309.

Righi L, Rapa I, Votta A, Papotti M, Sapino A (2012). Human achaete-scute homolog-1 expression in neuroendocrine breast carcinoma. Virchows Arch. 460, 415-421.

Rimkus C, Friederichs J, Boulesteix A L, Theisen J, Mages J, Becker K, Nekarda H, Rosenberg R, Janssen K P, Siewert J R (2008). Microarray-based prediction of tumor response to neoadjuvant radiochemotherapy of patients with locally advanced rectal cancer. Clin Gastroenterol. Hepatol. 6, 53-61.

Rini B I, Weinberg V, Fong L, Conry S, Hershberg R M, Small E J (2006). Combination immunotherapy with prostatic acid phosphatase pulsed antigen-presenting cells (provenge) plus bevacizumab in patients with serologic progression of prostate cancer after definitive local therapy. Cancer 107, 67-74.

Rivero F, Dislich H, Glockner G, Noegel A A (2001). The Dictyostelium discoideum family of Rho-related proteins. Nucleic Acids Res. 29, 1068-1079.

Rodenko B, Toebes M, Hadrup S R, van Esch W J, Molenaar A M, Schumacher T N, Ovaa H (2006). Generation of peptide-MHC class I complexes through U V-mediated ligand exchange. Nat. Protoc. 1, 1120-1132.

Rodriguez-Martinez A, Alarmo E L, Saarinen L, Ketolainen J, Nousiainen K, Hautaniemi S, Kallioniemi A (2011). Analysis of BMP4 and BMP7 signaling in breast cancer cells unveils time-dependent transcription patterns and highlights a common synexpression group of genes. BMC. Med. Genomics 4, 80.

Rodriguez-Pineiro A M, Garcia-Lorenzo A, Blanco-Prieto S, Alvarez-Chaver P, Rodriguez-Berrocal F J, Cadena M P, Martinez-Zorzano V S (2012). Secreted clusterin in colon tumor cell models and its potential as diagnostic marker for colorectal cancer. Cancer Invest 30, 72-78.

Rose A, Meier I (2004). Scaffolds, levers, rods and springs: diverse cellular functions of long coiled-coil proteins. Cell Mol. Life Sci. 61, 1996-2009.

Rose A, Schraegle S J, Stahlberg E A, Meier I (2005). Coiled-coil protein composition of 22 proteomes—differences and common themes in subcellular infrastructure and traffic control. BMC. Evol. Biol. 5, 66.

Ross M T, et al (2005). The DNA sequence of the human X chromosome. Nature 434, 325-337.

Rostomily R C, Born D E, Beyer R P, Jin J, Alvord E C, Jr., Mikheev A M, Matthews R T, Pan C, Khorasani L, Sonnen J A, Montine T J, Shi M, Zhang J (2010). Quantitative proteomic analysis of oligodendrogliomas with and without 1p/19q deletion. J Proteome. Res. 9, 2610-2618.

Rothhammer T, Wild P J, Meyer S, Bataille F, Pauer A, Klinkhammer-Schalke M, Hein R, Hofstaedter F, Bosserhoff A K (2007). Bone morphogenetic protein 7 (BMP7) expression is a potential novel prognostic marker for recurrence in patients with primary melanoma. Cancer Biomark. 3, 111-117.

Rotunno M, Hu N, Su H, Wang C, Goldstein A M, Bergen A W, Consonni D, Pesatori A C, Bertazzi P A, Wacholder S, Shih J, Caporaso N E, Taylor P R, Landi M T (2011). A gene expression signature from peripheral whole blood for stage I lung adenocarcinoma. Cancer Prev. Res (Phila) 4, 1599-1608.

Rotunno M, Zhao Y, Bergen A W, Koshiol J, Burdette L, Rubagotti M, Linnoila R I, Marincola F M, Bertazzi P A, Pesatori A C, Caporaso N E, McShane L M, Wang E, Landi M T (2010). Inherited polymorphisms in the RNA-mediated interference machinery affect microRNA expression and lung cancer survival. Br. J Cancer 103, 1870-1874.

Rousseau A, Nutt C L, Betensky R A, Iafrate A J, Han M, Ligon K L, Rowitch D H, Louis D N (2006). Expression of oligodendroglial and astrocytic lineage markers in diffuse gliomas: use of YKL-40, ApoE, ASCL1, and NKX2-2. J Neuropathol. Exp. Neurol. 65, 1149-1156.

Rubinfeld B, Souza B, Albert I, Muller O, Chamberlain S H, Masiarz F R, Munemitsu S, Polakis P (1993). Association of the APC gene product with beta-catenin. Science 262, 1731-1734.

Saadoun S, Papadopoulos M C, Krishna S (2003). Water transport becomes uncoupled from K+ siphoning in brain contusion, bacterial meningitis, and brain tumours: immunohistochemical case review. J Clin Pathol. 56, 972-975.

Saarikangas J, Hakanen J, Mattila P K, Grumet M, Salminen M, Lappalainen P (2008). ABBA regulates plasma-membrane and actin dynamics to promote radial glia extension. J Cell Sci. 121, 1444-1454.

Saddoughi S A, Ogretmen B (2013). Diverse functions of ceramide in cancer cell death and proliferation. Adv. Cancer Res. 117, 37-58.

Sadeque A, Serao N V, Southey B R, Delfino K R, Rodriguez-Zas S L (2012). Identification and characterization of alternative exon usage linked glioblastoma multiforme survival. BMC. Med. Genomics 5, 59.

Sahashi K, Sakai K, Mano K, Hirose G (2003). Anti-Ma2 antibody related paraneoplastic limbic/brain stem encephalitis associated with breast cancer expressing Mal, Ma2, and Ma3 mRNAs. J Neurol. Neurosurg. Psychiatry 74, 1332-1335.

Saiki R K, Gelfand D H, Stoffel S, Scharf S J, Higuchi R, Horn G T, Mullis K B, Erlich H A (1988). Primer-directed enzymatic amplification of DNA with a thermostable DNA polymerase. Science 239, 487-491.

Saito S, Ito K, Suzuki T, Utsunomiya H, Akahira J, Sugihashi Y, Niikura H, Okamura K, Yaegashi N, Sasano H (2005). Orphan nuclear receptor DAX-1 in human endometrium and its disorders. Cancer Sci. 96, 645-652.

Saito T, Arifin M T, Hama S, Kajiwara Y, Sugiyama K, Yamasaki F, Hidaka T, Arita K, Kurisu K (2007). Survivin subcellular localization in high-grade astrocytomas: simultaneous expression in both nucleus and cytoplasm is negative prognostic marker. J Neurooncol. 82, 193-198.

Sakurai T, Friedlander D R, Grumet M (1996). Expression of polypeptide variants of receptor-type protein tyrosine phosphatase beta: the secreted form, phosphacan, increases dramatically during embryonic development and modulates glial cell behavior in vitro. J Neurosci. Res. 43, 694-706.

Sakurai T, Lustig M, Babiarz J, Furley A J, Tait S, Brophy P J, Brown S A, Brown L Y, Mason C A, Grumet M (2001). Overlapping functions of the cell adhesion molecules Nr-CAM and L1 in cerebellar granule cell development. J Cell Biol. 154, 1259-1273.

Sakurai T, Lustig M, Nativ M, Hemperly J J, Schlessinger J, Peles E, Grumet M (1997). Induction of neurite outgrowth through contactin and Nr-CAM by extracellular regions of glial receptor tyrosine phosphatase beta. J Cell Biol. 136, 907-918.

Salsano E, Paterra R, Figus M, Menghi F, Maderna E, Pollo B, Solero C L, Massimi L, Finocchiaro G (2012). Expression profile of frizzled receptors in human medulloblastomas. J Neurooncol. 106, 271-280.

Samanta S, Sharma V M, Khan A, Mercurio A M (2012). Regulation of IMP3 by EGFR signaling and repression by ERbeta: implications for triple-negative breast cancer. Oncogene 31, 4689-4697.

Samuelson A V, Narita M, Chan H M, Jin J, de S E, McCurrach M E, Narita M, Fuchs M, Livingston D M, Lowe S W (2005). p400 is required for E1A to promote apoptosis. J Biol. Chem. 280, 21915-21923.

Sarai N, Kagawa W, Fujikawa N, Saito K, Hikiba J, Tanaka K, Miyagawa K, Kurumizaka H, Yokoyama S (2008). Biochemical analysis of the N-terminal domain of human RAD54B. Nucleic Acids Res. 36, 5441-5450.

Sarria A J, Panini S R, Evans R M (1992). A functional role for vimentin intermediate filaments in the metabolism of lipoprotein-derived cholesterol in human SW-13 cells. J Biol. Chem. 267, Sasaki A, Masuda Y, Iwai K, Ikeda K, Watanabe K (2002a). A RING finger protein Praja1 regulates Dlx5-dependent transcription through its ubiquitin ligase activity for the Dlx/Msx-interacting MAGE/Necdin family protein, Dlxin-1. J Biol. Chem. 277, 22541-22546.

Sasaki T, Lopes M B, Hankins G R, Helm G A (2002b). Expression of survivin, an inhibitor of apoptosis protein, in tumors of the nervous system. Acta Neuropathol. 104, 105-109.

Satish L, O'Gorman D B, Johnson S, Raykha C, Gan B S, Wang J H, Kathju S (2013). Increased CCT-eta expression is a marker of latent and active disease and a modulator of fibroblast contractility in Dupuytren's contracture. Cell Stress. Chaperones. 18, 397-404.

Sato F, Abraham J M, Yin J, Kan T, Ito T, Mori Y, Hamilton J P, Jin Z, Cheng Y, Paun B, Berki A T, Wang S, Shimada Y, Meltzer S J (2006). Polo-like kinase and survivin are esophageal tumor-specific promoters. Biochem. Biophys. Res. Commun. 342, 465-471.

Schaefer C, Grouse L, Buetow K, Strausberg R L (2001). A new cancer genome anatomy project web resource for the community. Cancer J 7, 52-60.

Schaeffer D F, Owen D R, Lim H J, Buczkowski A K, Chung S W, Scudamore C H, Huntsman D G, Ng S S, Owen D A (2010). Insulin-like growth factor 2 mRNA binding protein 3 (IGF2BP3) overexpression in pancreatic ductal adenocarcinoma correlates with poor survival. BMC. Cancer 10, 59.

Schietke R, Brohl D, Wedig T, Mucke N, Herrmann H, Magin T M (2006). Mutations in vimentin disrupt the cytoskeleton in fibroblasts and delay execution of apoptosis. Eur. J Cell Biol. 85, 1-10.

Schoenfeld A R, Apgar S, Dolios G, Wang R, Aaronson S A (2004). BRCA2 is ubiquitinated in vivo and interacts with USP11, a deubiquitinating enzyme that exhibits prosurvival function in the cellular response to DNA damage. Mol. Cell Biol. 24, 7444-7455.

Scholey J M, Anderson K V (2006). Intraflagellar transport and cilium-based signaling. Cell 125, 439-442.

Schuller M, Jenne D, Voltz R (2005). The human PNMA family: novel neuronal proteins implicated in paraneoplastic neurological disease. J Neuroimmunol. 169, 172-176.

Seeger F H, Schirle M, Gatfield J, Arnold D, Keilholz W, Nickolaus P, Rammensee H G, Stevanovic S (1999). The HLA-A*6601 peptide motif: prediction by pocket structure and verification by peptide analysis. Immunogenetics 49, 571-576.

Sehgal A, Boynton A L, Young R F, Vermeulen S S, Yonemura K S, Kohler E P, Aldape H C, Simrell C R, Murphy G P (1998). Cell adhesion molecule Nr-CAM is over-expressed in human brain tumors. Int J Cancer 76, 451-458.

Sehgal A, Ricks S, Warrick J, Boynton A L, Murphy G P (1999). Antisense human neuroglia related cell adhesion molecule hNr-CAM, reduces the tumorigenic properties of human glioblastoma cells. Anticancer Res. 19, 4947-4953.

Seifert W, Kuhnisch J, Maritzen T, Horn D, Haucke V, Hennies H C (2011). Cohen syndrome-associated protein, COH1, is a novel, giant Golgi matrix protein required for Golgi integrity. J Biol. Chem. 286, 37665-37675.

Seki N, Ohira M, Nagase T, Ishikawa K, Miyajima N, Nakajima D, Nomura N, Ohara O (1997). Characterization of cDNA clones in size-fractionated cDNA libraries from human brain. DNA Res. 4, 345-349.

Senkal C E, Ponnusamy S, Rossi M J, Bialewski J, Sinha D, Jiang J C, Jazwinski S M, Hannun Y A, Ogretmen B (2007). Role of human longevity assurance gene 1 and C18-ceramide in chemotherapy-induced cell death in human head and neck squamous cell carcinomas. Mol. Cancer Ther. 6, 712-722.

Sentelle R D, Senkal C E, Jiang W, Ponnusamy S, Gencer S, Selvam S P, Ramshesh V K, Peterson Y K, Lemasters J J, Szulc Z M, Bielawski J, Ogretmen B (2012). Ceramide targets autophagosomes to mitochondria and induces lethal mitophagy. Nat Chem. Biol. 8, 831-838.

Seo M, Lee W H, Suk K (2010). Identification of novel cell migration-promoting genes by a functional genetic screen. FASEB J 24, 464-478.

Separovic D, Breen P, Joseph N, Bielawski J, Pierce J S, VAN B E, Gudz T I (2012). siRNA-mediated downregulation of ceramide synthase 1 leads to apoptotic resistance in human head and neck squamous carcinoma cells after photodynamic therapy. Anticancer Res. 32, 2479-2485.

Shaw L M (2011). The insulin receptor substrate (IRS) proteins: at the intersection of metabolism and cancer. Cell Cycle 10, 1750-1756.

Shedlock D J, Shen H (2003). Requirement for CD4 T cell help in generating functional CD8 T cell memory. Science 300, 337-339.

Shida T, Furuya M, Nikaido T, Kishimoto T, Koda K, Oda K, Nakatani Y, Miyazaki M, Ishikura H (2005). Aberrant expression of human achaete-scute homologue gene 1 in the gastrointestinal neuroendocrine carcinomas. Clin Cancer Res. 11, 450-458.

Shiota M, Zardan A, Takeuchi A, Kumano M, Beraldi E, Naito S, Zoubeidi A, Gleave M E (2012). Clusterin mediates TGF-beta-induced epithelial-mesenchymal transition and metastasis via Twist1 in prostate cancer cells. Cancer Res. 72, 5261-5272.

Shirahata A, Sakata M, Sakuraba K, Goto T, Mizukami H, Saito M, Ishibashi K, Kigawa G, Nemoto H, Sanada Y, Hibi K (2009). Vimentin methylation as a marker for advanced colorectal carcinoma. Anticancer Res. 29, 279-281.

Shiras A, Bhosale A, Shepal V, Shukla R, Baburao V S, Prabhakara K, Shastry P (2003). A unique model system for tumor progression in GBM comprising two developed human neuro-epithelial cell lines with differential transforming potential and coexpressing neuronal and glial markers. Neoplasia. 5, 520-532.

Shoji H, Tsuchida K, Kishi H, Yamakawa N, Matsuzaki T, Liu Z, Nakamura T, Sugino H (2000). Identification and characterization of a PDZ protein that interacts with activin type II receptors. J Biol. Chem. 275, 5485-5492.

Simaga S, Abramic M, Osmak M, Babic D, Ilic-Forko J (2008). Total tissue lactate dehydrogenase activity in endometrial carcinoma. Int. J Gynecol. Cancer 18, 1272-1278.

Simaga S, Babic D, Osmak M, Ilic-Forko J, Vitale L, Milicic D, Abramic M (1998). Dipeptidyl peptidase III in malignant and non-malignant gynaecological tissue. Eur. J Cancer 34, 399-405.

Simaga S, Babic D, Osmak M, Sprem M, Abramic M (2003). Tumor cytosol dipeptidyl peptidase III activity is increased with histological aggressiveness of ovarian primary carcinomas. Gynecol. Oncol 91, 194-200.

Singh S K, Hawkins C, Clarke I D, Squire J A, Bayani J, Hide T, Henkelman R M, Cusimano M D, Dirks P B (2004). Identification of human brain tumour initiating cells. Nature 432, 396-401.

Singh-Jasuja H, Emmerich N P, Rammensee H G (2004). The Tubingen approach: identification, selection, and validation of tumor-associated HLA peptides for cancer therapy. Cancer Immunol. Immunother. 53, 187-195.

Siow D L, Wattenberg B W (2012). Mammalian ORMDL proteins mediate the feedback response in ceramide biosynthesis. J Biol. Chem. 287, 40198-40204.

Siu A, Lee C, Pham E, Ramos D M (2012). Revisiting epithelial-to-mesenchymal transition through adenoid cystic carcinoma. Anticancer Res. 32, 3683-3688.

Sivasankaran B, Degen M, Ghaffari A, Hegi M E, Hamou M F, Ionescu M C, Zweifel C, Tolnay M, Wasner M, Mergenthaler S, Miserez A R, Kiss R, Lino M M, Merlo A, Chiquet-Ehrismann R, Boulay J L (2009). Tenascin-C is a novel RBPJkappa-induced target gene for Notch signaling in gliomas. Cancer Res 69, 458-465.

Skaletsky H, et al. (2003). The male-specific region of the human Y chromosome is a mosaic of discrete sequence classes. Nature 423, 825-837.

Slack F J, Weidhaas J B (2008). MicroRNA in cancer prognosis. N. Engl. J Med. 359, 2720-2722.

Small E J, Schellhammer P F, Higano C S, Redfern C H, Nemunaitis J J, Valone F H, Verjee S S, Jones L A, Hershberg R M (2006). Placebo-controlled phase III trial of immunologic therapy with sipuleucel-T (APC8015) in patients with metastatic, asymptomatic hormone refractory prostate cancer. J Clin Oncol. 24, 3089-3094.

Smith J A, White E A, Sowa M E, Powell M L, Ottinger M, Harper J W, Howley P M (2010). Genome-wide siRNA screen identifies SMCX, EP400, and Brd4 as E2-dependent regulators of human papillomavirus oncogene expression. Proc. Natl. Acad. Sci. U.S.A 107, 3752-3757.

Soderholm H, Ortoft E, Johansson I, Ljungberg J, Larsson C, Axelson H, Pahlman S (1999). Human achaete-scute homologue 1 (HASH-1) is downregulated in differentiating neuroblastoma cells. Biochem. Biophys. Res. Commun. 256, 557-563.

Somasundaram K, Reddy S P, Vinnakota K, Britto R, Subbarayan M, Nambiar S, Hebbar A, Samuel C, Shetty M, Sreepathi H K, Santosh V, Hegde A S, Hegde S, Kondaiah P, Rao M R (2005). Upregulation of ASCL1 and inhibition of Notch signaling pathway characterize progressive astrocytoma. Oncogene 24, 7073-7083.

Song Y, Zhao C, Dong L, Fu M, Xue L, Huang Z, Tong T, Zhou Z, Chen A, Yang Z, Lu N, Zhan Q (2008). Overexpression of cyclin B1 in human esophageal squamous cell carcinoma cells induces tumor cell invasive growth and metastasis. Carcinogenesis 29, 307-315.

Soon P S, Gill A J, Benn D E, Clarkson A, Robinson B G, McDonald K L, Sidhu S B (2009). Microarray gene expression and immunohistochemistry analyses of adrenocortical tumors identify IGF2 and Ki-67 as useful in differentiating carcinomas from adenomas. Endocr. Relat Cancer 16, 573-583.

Span P N, Sweep F C, Wiegerinck E T, Tjan-Heijnen V C, Manders P, Beex L V, de Kok J B (2004). Survivin is an independent prognostic marker for risk stratification of breast cancer patients. Clin Chem. 50, 1986-1993.

Splinter P L, Lazaridis K N, Dawson P A, LaRusso N F (2006). Cloning and expression of SLC10A4, a putative organic anion transport protein. World J Gastroenterol. 12, 6797-6805.

Srour M, Hamdan F F, Schwartzentruber J A, Patry L, Ospina L H, Shevell M I, Desilets V, Dobrzeniecka S, Mathonnet G, Lemyre E, Massicotte C, Labuda D, Amrom D, Andermann E, Sebire G, Maranda B, Rouleau G A, Majewski J, Michaud J L (2012). Mutations in TMEM231 cause Joubert syndrome in French Canadians. J Med. Genet. 49, 636-641.

Staehler M, Stenzl A, Dietrich P Y, Eisen T, Haferkamp A, Beck J, Mayer A, Walter S, Singh-Jasuja H, Stief C (2007). A phase I study to evaluate safety, immunogenicity and anti-tumor activity of the multi-peptide vaccine IMA901 in renal cell carcinoma patients (RCC). Journal of Clinical Oncology, 2007 ASCO Annual Meeting Proceedings Part I, Vol 25, No. 18S (June 20 Supplement), 2007: 5098 (Abstract).

Stepulak A, Luksch H, Gebhardt C, Uckermann O, Marzahn J, Sifringer M, Rzeski W, Staufner C, Brocke K S, Turski L, Ikonomidou C (2009). Expression of glutamate receptor subunits in human cancers. Histochem. Cell Biol. 132, 435-445.

Stoeckli E T, Landmesser L T (1995). Axonin-1, Nr-CAM, and Ng-CAM play different roles in the in vivo guidance of chick commissural neurons. Neuron 14, 1165-1179.

Stolt C C, Lommes P, Friedrich R P, Wegner M (2004). Transcription factors Sox8 and Sox10 perform non-equivalent roles during oligodendrocyte development despite functional redundancy. Development 131, 2349-2358.

Sugito N, Ishiguro H, Kuwabara Y, Kimura M, Mitsui A, Kurehara H, Ando T, Mori R, Takashima N, Ogawa R, Fujii Y (2006). RNASEN regulates cell proliferation and affects survival in esophageal cancer patients. Clin Cancer Res. 12, 7322-7328.

Sugiyama T, Sadzuka Y, Tanaka K, Sonobe T (2001). Inhibition of glutamate transporter by theanine enhances the therapeutic efficacy of doxorubicin. Toxicol. Lett. 121, 89-96.

Sulzbacher I, Birner P, Trieb K, Pichlbauer E, Lang S (2002). The expression of bone morphogenetic proteins in osteosarcoma and its relevance as a prognostic parameter. J Clin Pathol. 55, 381-385.

Sun C, Cheng M C, Qin R, Liao D L, Chen T T, Koong F J, Chen G, Chen C H (2011). Identification and functional characterization of rare mutations of the neuroligin-2 gene (NLGN2) associated with schizophrenia. Hum. Mol. Genet. 20, 3042-3051.

Sun J C, Bevan M J (2003). Defective CD8 T cell memory following acute infection without CD4 T cell help. Science 300, 339-342.

Sunavala-Dossabhoy G, Palaniyandi S, Clark C, Nathan C O, Abreo F W, Caldito G (2011). Analysis of eIF4E and 4EBP1 mRNAs in head and neck cancer. Laryngoscope 121, 2136-2141.

Suvasini R, Shruti B, Thota B, Shinde S V, Friedmann-Morvinski D, Nawaz Z, Prasanna K V, Thennarasu K, Hegde A S, Arivazhagan A, Chandramouli B A, Santosh V, Somasundaram K (2011). Insulin growth factor-2 binding protein 3 (IGF2BP3) is a glioblastoma-specific marker that activates phosphatidylinositol 3-kinase/mitogen-activated protein kinase (PI3K/MAPK) pathways by modulating IGF-2. J Biol. Chem. 286, 25882-25890.

Suzuki H, Gabrielson E, Chen W, Anbazhagan R, Van E M, Weijenberg M P, Herman J G, Baylin S B (2002). A genomic screen for genes upregulated by demethylation and histone deacetylase inhibition in human colorectal cancer. Nat Genet. 31, 141-149.

Suzuki N, Fukushi M, Kosaki K, Doyle A D, de V S, Yoshizaki K, Akazawa C, Arikawa-Hirasawa E, Yamada Y (2012). Teneurin-4 is a novel regulator of oligodendrocyte differentiation and myelination of small-diameter axons in the CNS. J Neurosci. 32, 11586-11599.

Suzuki T, Urano T, Miki Y, Moriya T, Akahira J, Ishida T, Horie K, Inoue S, Sasano H (2007). Nuclear cyclin B1 in human breast carcinoma as a potent prognostic factor. Cancer Sci. 98, 644-651.

Svendsen A, et al. (2011). Expression of the progenitor marker NG2/CSPG4 predicts poor survival and resistance to ionising radiation in glioblastoma. Acta Neuropathol. 122, 495-510.

Tagawa H, Miura I, Suzuki R, Suzuki H, Hosokawa Y, Seto M (2002). Molecular cytogenetic analysis of the breakpoint region at 6q21-22 in T-cell lymphoma/leukemia cell lines. Genes Chromosomes. Cancer 34, 175-185.

Takebayashi H, Yoshida S, Sugimori M, Kosako H, Kominami R, Nakafuku M, Nabeshima Y (2000). Dynamic expression of basic helix-loop-helix Olig family members: implication of Olig2 in neuron and oligodendrocyte differentiation and identification of a new member, Olig3. Mech. Dev. 99, 143-148.

Tan G, Sun S Q, Yuan D L (2008). Expression of Kir 4.1 in human astrocytic tumors: correlation with pathologic grade. Biochem. Biophys. Res. Commun. 367, 743-747.

Tan H Y, Liu J, Wu S M, Luo H S (2005). Expression of a novel apoptosis inhibitor-survivin in colorectal carcinoma. World J Gastroenterol. 11, 4689-4692.

Tatenhorst L, Senner V, Puttmann S, Paulus W (2004). Regulators of G-protein signaling 3 and 4 (RGS3, RGS4) are associated with glioma cell motility. J Neuropathol. Exp. Neurol. 63, 210-222.

Taylor T E, Furnari F B, Cavenee W K (2012). Targeting EGFR for treatment of glioblastoma: molecular basis to overcome resistance. Curr. Cancer Drug Targets. 12, 197-209.

Tchernitsa O, Kasajima A, Schafer R, Kuban R J, Ungethum U, Gyorffy B, Neumann U, Simon E, Weichert W, Ebert M P, Rocken C (2010). Systematic evaluation of the miRNA-ome and its downstream effects on mRNA expression identifies gastric cancer progression. J Pathol. 222, 310-319.

Teratani T, Domoto T, Kuriki K, Kageyama T, Takayama T, Ishikawa A, Ozono S, Nozawa R (2007). Detection of transcript for brain-type fatty Acid-binding protein in tumor and urine of patients with renal cell carcinoma. Urology 69, 236-240.

Thompson D M, Gill G N (1985). The EGF receptor: structure, regulation and potential role in malignancy. Cancer Surv. 4, 767-788.

Thomson S, Buck E, Petti F, Griffin G, Brown E, Ramnarine N, Iwata K K, Gibson N, Haley J D (2005). Epithelial to mesenchymal transition is a determinant of sensitivity of non-small-cell lung carcinoma cell lines and xenografts to epidermal growth factor receptor inhibition. Cancer Res. 65, 9455-9462.

Thurner B, et al. (1999). Vaccination with mage-3A1 peptide-pulsed mature, monocyte-derived dendritic cells expands specific cytotoxic T cells and induces regression of some metastases in advanced stage IV melanoma. J Exp. Med 190, 1669-1678.

Tina E, Lindqvist B M, Gabrielson M, Lubovac Z, Wegman P, Wingren S (2012). The mitochondrial transporter SLC25A43 is frequently deleted and may influence cell proliferation in HER2-positive breast tumors. BMC. Cancer 12, 350.

Tones A, Torres K, Paszkowski T, Jodlowska-Jedrych B, Radomanski T, Ksiazek A, Maciejewski R (2011). Major regulators of microRNAs biogenesis Dicer and Drosha are down-regulated in endometrial cancer. Tumour. Biol. 32, 769-776.

Toyooka S, Fukuyama Y, Wistuba I I, Tockman M S, Minna J D, Gazdar A F (2002). Differential expression of FEZ1/LZTS1 gene in lung cancers and their cell cultures. Clin Cancer Res. 8, 2292-2297.

Tsai J R, Chong I W, Chen Y H, Yang M J, Sheu C C, Chang H C, Hwang J J, Hung J Y, Lin S R (2007). Differential expression profile of MAGE family in non-small-cell lung cancer. Lung Cancer 56, 185-192.

Tsavachidou-Fenner D, Tannir N, Tamboli P, Liu W, Petillo D, Teh B, Mills G B, Jonasch E (2010). Gene and protein expression markers of response to combined antiangiogenic and epidermal growth factor targeted therapy in renal cell carcinoma. Ann Oncol 21, 1599-1606.

Tsourlakis M C, Walter E, Quaas A, Graefen M, Huland H, Simon R, Sauter G, Steurer S, Schlomm T, Minner S (2013). High Nr-CAM expression is associated with favorable phenotype and late PSA recurrence in prostate cancer treated by prostatectomy. Prostate Cancer Prostatic. Dis.

Tsuritani K, Irie T, Yamashita R, Sakakibara Y, Wakaguri H, Kanai A, Mizushima-Sugano J, Sugano S, Nakai K, Suzuki Y (2007). Distinct class of putative "non-conserved" promoters in humans: comparative studies of alternative promoters of human and mouse genes. Genome Res. 17, 1005-1014.

Tucker R P, Chiquet-Ehrismann R (2006). Teneurins: a conserved family of transmembrane proteins involved in intercellular signaling during development. Dev. Biol. 290, 237-245.

Turashvili G, Bouchal J, Baumforth K, Wei W, Dziechciarkova M, Ehrmann J, Klein J, Fridman E, Skarda J, Srovnal J, Haj duck M, Murray P, Kolar Z (2007). Novel markers for differentiation of lobular and ductal invasive breast carcinomas by laser microdissection and microarray analysis. BMC. Cancer 7, 55.

Tuy F P, Saillour Y, Kappeler C, Chelly J, Francis F (2008). Alternative transcripts of Dclk1 and Dclk2 and their expression in doublecortin knockout mice. Dev. Neurosci. 30, 171-186.

Uematsu M, Ohsawa I, Aokage T, Nishimaki K, Matsumoto K, Takahashi H, Asoh S, Teramoto A, Ohta S (2005). Prognostic significance of the immunohistochemical index of survivin in glioma: a comparative study with the MIB-1 index. J Neurooncol. 72, 231-238.

Ulbricht U, Brockmann M A, Aigner A, Eckerich C, Muller S, Fillbrandt R, Westphal M, Lamszus K (2003). Expression and function of the receptor protein tyrosine phosphatase zeta and its ligand pleiotrophin in human astrocytomas. J Neuropathol. Exp. Neurol. 62, 1265-1275.

Ulbricht U, Eckerich C, Fillbrandt R, Westphal M, Lamszus K (2006). RNA interference targeting protein tyrosine phosphatase zeta/receptor-type protein tyrosine phosphatase beta suppresses glioblastoma growth in vitro and in vivo. J Neurochem. 98, 1497-1506.

Unger T, Lakowa N, Bette S, Engele J (2012). Transcriptional regulation of the GLAST/EAAT-1 gene in rat and man. Cell Mol. Neurobiol. 32, 539-547.

Upton M P, Hirohashi S, Tome Y, Miyazawa N, Suemasu K, Shimosato Y (1986). Expression of vimentin in surgically resected adenocarcinomas and large cell carcinomas of lung. Am. J Surg. Pathol. 10, 560-567.

Urban P, Bilecova-Rabajdova M, Stefekova Z, Ostro A, Marekova M (2011). [Overview of potential oncomarkers for detection of early stages of ovarian cancer]. Klin. Onkol. 24, 106-111.

Usadel H, Brabender J, Danenberg K D, Jeronimo C, Harden S, Engles J, Danenberg P V, Yang S, Sidransky D (2002). Quantitative adenomatous polyposis coli promoter methylation analysis in tumor tissue, serum, and plasma DNA of patients with lung cancer. Cancer Res. 62, 371-375.

Utreras E, Jimenez-Mateos E M, Contreras-Vallejos E, Tortosa E, Perez M, Rojas S, Saragoni L, Maccioni R B, Avila J, Gonzalez-Billault C (2008). Microtubule-associated protein 1B interaction with tubulin tyrosine ligase contributes to the control of microtubule tyrosination. Dev. Neurosci.

Vaarala M H, Porvari K S, Kyllonen A P, Mustonen M V, Lukkarinen O, Vihko P T (1998). Several genes encoding ribosomal proteins are over-expressed in prostate-cancer cell lines: confirmation of L7a and L37 over-expression in prostate-cancer tissue samples. Int. J Cancer 78, 27-32.

Valiente M, Andres-Pons A, Gomar B, Torres J, Gil A, Tapparel C, Antonarakis S E, Pulido R (2005). Binding of PTEN to specific PDZ domains contributes to PTEN protein stability and phosphorylation by microtubule-associated serine/threonine kinases. J Biol. Chem. 280, 28936-28943.

van de Pavert S A, Sanz A S, Aartsen W M, Vos R M, Versteeg I, Beck S C, Klooster J, Seeliger M W, Wijnholds J (2007). Crb 1 is a determinant of retinal apical Muller glia cell features. Glia 55, 1486-1497.

van A M, Schepens M, de B D, Janssen B, Merkx G, Geurts van K A (2000). Construction of a 350-kb sequence-ready 11q13 cosmid contig encompassing the markers D11S4933 and D11S546: mapping of 11 genes and 3 tumor-associated translocation breakpoints. Genomics 66, 35-42.

Van C E, Rivera F, Berry S, Kretzschmar A, Michael M, DiBartolomeo M, Mazier M A, Canon J L, Georgoulias V, Peeters M, Bridgewater J, Cunningham D (2009). Safety and efficacy of first-line bevacizumab with FOLFOX, XELOX, FOLFIRI and fluoropyrimidines in metastatic colorectal cancer: the BEAT study. Ann Oncol 20, 1842-1847.

Van dA, I, et al. (2008). Aberrant methylation of the Adenomatous Polyposis Coli (APC) gene promoter is associated with the inflammatory breast cancer phenotype. Br. J Cancer 99, 1735-1742.

Varga I, Hutoczki G, Petras M, Scholtz B, Miko E, Kenyeres A, Toth J, Zahuczky G, Bognar L, Hanzely Z, Klekner A (2010). Expression of invasion-related extracellular matrix molecules in human glioblastoma versus intracerebral lung adenocarcinoma metastasis. Cent. Eur. Neurosurg. 71, 173-180.

Varga I, Hutoczki G, Szemcsak C D, Zahuczky G, Toth J, Adamecz Z, Kenyeres A, Bognar L, Hanzely Z, Klekner A (2012). Brevican, neurocan, tenascin-C and versican are mainly responsible for the invasiveness of low-grade astrocytoma. Pathol. Oncol Res. 18, 413-420.

Vasquez K, Kuizon S, Junaid M, Idrissi A E (2013). The effect of folic acid on GABA(A)-B 1 receptor subunit. Adv. Exp. Med. Biol. 775, 101-109.

Vecchione A, Ishii H, Baldassarre G, Bassi P, Trapasso F, Alder H, Pagano F, Gomella L G, Croce C M, Baffa R (2002). FEZ1/LZTS1 is down-regulated in high-grade bladder cancer, and its restoration suppresses tumorigenicity in transitional cell carcinoma cells. Am. J Pathol. 160, 1345-1352.

Vecchione A, Ishii H, Shiao Y H, Trapasso F, Rugge M, Tamburrino J F, Murakumo Y, Alder H, Croce C M, Baffa R (2001). Fez1/lzts1 alterations in gastric carcinoma. Clin Cancer Res. 7, 1546-1552.

Vignier N, Moghadaszadeh B, Gary F, Beckmann J, Mayer U, Guicheney P (1999). Structure, genetic localization, and identification of the cardiac and skeletal muscle transcripts of the human integrin alpha7 gene (ITGA7). Biochem. Biophys. Res. Commun. 260, 357-364.

Visnyei K, Onodera H, Damoiseaux R, Saigusa K, Petrosyan S, De V D, Ferrari D, Saxe J, Panosyan E H, Masterman-Smith M, Mottahedeh J, Bradley K A, Huang J, Sabatti C, Nakano I, Kornblum H I (2011). A molecular screening approach to identify and characterize inhibitors of glioblastoma stem cells. Mol. Cancer Ther. 10, 1818-1828.

Vissers J H, Nicassio F, van L M, Di Fiore P P, Citterio E (2008). The many faces of ubiquitinated histone H2A: insights from the DUBs. Cell Div. 3, 8.

Volkmer H, Leuschner R, Zacharias U, Rathjen F G (1996). Neurofascin induces neurites by heterophilic interactions with axonal NrCAM while NrCAM requires F11 on the axonal surface to extend neurites. J Cell Biol. 135, 1059-1069.

Voltz R, Gultekin S H, Rosenfeld M R, Gerstner E, Eichen J, Posner J B, Dalmau J (1999). A serologic marker of paraneoplastic limbic and brain-stem encephalitis in patients with testicular cancer. N. Engl. J Med. 340, 1788-1795.

Vranic S, Gurjeva O, Frkovic-Grazio S, Palazzo J, Tawfik O, Gatalica Z (2011). IMP3, a proposed novel basal phenotype marker, is commonly overexpressed in adenoid cystic carcinomas but not in apocrine carcinomas of the breast. Appl. Immunohistochem. Mol. Morphol. 19, 413-416.

Vulcani-Freitas T M, Saba-Silva N, Cappellano A, Cavalheiro S, Marie S K, Oba-Shinjo S M, Malheiros S M, de Toledo S R (2011). ASPM gene expression in medulloblastoma. Childs Nerv. Syst. 27, 71-74.

Wachter D L, Kristiansen G, Soll C, Hellerbrand C, Breuhahn K, Fritzsche F, Agaimy A, Hartmann A, Riener M O (2012). Insulin-like growth factor II mRNA-binding protein 3 (IMP3) expression in hepatocellular carcinoma. A clinicopathological analysis with emphasis on diagnostic value. Histopathology 60, 278-286.

Wachter D L, Schlabrakowski A, Hoegel J, Kristiansen G, Hartmann A, Riener M O (2011). Diagnostic value of immunohistochemical IMP3 expression in core needle biopsies of pancreatic ductal adenocarcinoma. Am. J Surg. Pathol. 35, 873-877.

Walia S, Fishman G A, Jacobson S G, Aleman T S, Koenekoop R K, Traboulsi E I, Weleber R G, Pennesi M E, Heon E, Drack A, Lam B L, Allikmets R, Stone E M (2010). Visual acuity in patients with Leber's congenital amaurosis and early childhood-onset retinitis pigmentosa. Ophthalmology 117, 1190-1198.

Wang J, Svendsen A, Kmiecik J, Immervoll H, Skaftnesmo K O, Planaguma J, Reed R K, Bjerkvig R, Miletic H, Enger P O, Rygh C B, Chekenya M (2011a). Targeting the NG2/CSPG4 proteoglycan retards tumour growth and angiogenesis in preclinical models of GBM and melanoma. PLoS. ONE. 6, e23062.

Wang J C, Livingstone A M (2003). Cutting edge: CD4+ T cell help can be essential for primary CD8+ T cell responses in vivo. J Immunol. 171, 6339-6343.

Wang K S, Liu X, Aragam N, Jian X, Mullersman J E, Liu Y, Pan Y (2011b). Family-based association analysis of alcohol dependence in the COGA sample and replication in the Australian twin-family study. J Neural Transm. 118, 1293-1299.

Wang L, He S, Yuan J, Mao X, Cao Y, Zong J, Tu Y, Zhang Y (2012a). Oncogenic role of SOX9 expression in human malignant glioma. Med. Oncol 29, 3484-3490.

Wang L, Li H G, Xia Z S, Lu J, Peng T S (2010). IMP3 is a novel biomarker to predict metastasis and prognosis of gastric adenocarcinoma: a retrospective study. Chin Med. J (Engl.) 123, 3554-3558.

Wang R, Ferrell L D, Faouzi S, Maher J J, Bishop J M (2001). Activation of the Met receptor by cell attachment induces and sustains hepatocellular carcinomas in transgenic mice. J. Cell Biol. 153, 1023-1034.

Wang S, Pang T, Gao M, Kang H, Ding W, Sun X, Zhao Y, Zhu W, Tang X, Yao Y, Hu X (2013). HPV E6 induces eIF4E transcription to promote the proliferation and migration of cervical cancer. FEBS Lett. 587, 690-697.

Wang X, Su H, Bradley A (2002). Molecular mechanisms governing Pcdh-gamma gene expression: evidence for a multiple promoter and cis-alternative splicing model. Genes Dev. 16, 1890-1905.

Wang X L, Cai H P, Ge J H, Su X F (2012b). Detection of eukaryotic translation initiation factor 4E and its clinical significance in hepatocellular carcinoma. World J Gastroenterol. 18, 2540-2544.

Wang X Z, Kuroda M, Sok J, Batchvarova N, Kimmel R, Chung P, Zinszner H, Ron D (1998). Identification of novel stress-induced genes downstream of chop. EMBO J 17, 3619-3630.

Wang Y, Cheong D, Chan S, Hooi S C (2000). Ribosomal protein L7a gene is up-regulated but not fused to the tyrosine kinase receptor as chimeric trk oncogene in human colorectal carcinoma. Int. J Oncol 16, 757-762.

Warth A, Mittelbronn M, Wolburg H (2005). Redistribution of the water channel protein aquaporin-4 and the K+ channel protein Kir4.1 differs in low- and high-grade human brain tumors. Acta Neuropathol. (Berl) 109, 418-426.

Watabe-Uchida M, John K A, Janas J A, Newey S E, Van A L (2006). The Rac activator DOCK7 regulates neuronal polarity through local phosphorylation of stathmin/Op18. Neuron 51, 727-739.

Weake V M, Workman J L (2008). Histone ubiquitination: triggering gene activity. Mol. Cell 29, 653-663.

Wegner A M, Nebhan C A, Hu L, Majumdar D, Meier K M, Weaver A M, Webb D J (2008). N-wasp and the arp2/3 complex are critical regulators of actin in the development of dendritic spines and synapses. J Biol. Chem. 283, 15912-15920.

Weiskirchen R, Erdel M, Utermann G, Bister K (1997). Cloning, structural analysis, and chromosomal localization of the human CSRP2 gene encoding the LIM domain protein CRP2. Genomics 44, 83-93.

Wellstein A (2012). ALK receptor activation, ligands and therapeutic targeting in glioblastoma and in other cancers. Front Oncol 2, 192.

Werner H, Dimou L, Klugmann M, Pfeiffer S, Nave K A (2001). Multiple splice isoforms of proteolipid M6B in neurons and oligodendrocytes. Mol. Cell Neurosci. 18, 593-605.

Wheater M J, Johnson P W, Blaydes J P (2010). The role of MNK proteins and eIF4E phosphorylation in breast cancer cell proliferation and survival. Cancer Biol. Ther. 10, 728-735.

White M F (2002). IRS proteins and the common path to diabetes. Am. J Physiol Endocrinol. Metab 283, E413-E422.

Wiame E, Tyteca D, Pierrot N, Collard F, Amyere M, Noel G, Desmedt J, Nassogne M C, Vikkula M, Octave J N, Vincent M F, Courtoy P J, Boltshauser E, van S E (2010).

Molecular identification of aspartate N-acetyltransferase and its mutation in hypoacetylaspartia. Biochem. J 425, 127-136.

Wiemann S, Arlt D, Huber W, Wellenreuther R, Schleeger S, Mehrle A, Bechtel S, Sauermann M, Korf U, Pepperkok R, Sultmann H, Poustka A (2004). From ORFeome to biology: a functional genomics pipeline. Genome Res. 14, 2136-2144.

Wikman H, Kettunen E, Seppanen J K, Karjalainen A, Hollmen J, Anttila S, Knuutila S (2002). Identification of differentially expressed genes in pulmonary adenocarcinoma by using cDNA array. Oncogene 21, 5804-5813.

Williams A A, Higgins J P, Zhao H, Ljunberg B, Brooks J D (2009). CD 9 and vimentin distinguish clear cell from chromophobe renal cell carcinoma. BMC. Clin Pathol. 9, 9.

Williamson S M, Silva D A, Richey E, Qin H (2012). Probing the role of IFT particle complex A and B in flagellar entry and exit of IFT-dynein in *Chlamydomonas*. Protoplasma 249, 851-856.

Willoughby V, Sonawala A, Werlang-Perurena A, Donner L R (2008). A comparative immunohistochemical analysis of small round cell tumors of childhood: utility of peripherin and alpha-internexin as markers for neuroblastomas. Appl. Immunohistochem. Mol. Morphol. 16, 344-348.

Wiltshire T D, Lovejoy C A, Wang T, Xia F, O'Connor M J, Cortez D (2010). Sensitivity to poly(ADP-ribose) polymerase (PARP) inhibition identifies ubiquitin-specific peptidase 11 (USP11) as a regulator of DNA double-strand break repair. J Biol. Chem. 285, 14565-14571.

Winkler G S, Mulder K W, Bardwell V J, Kalkhoven E, Timmers H T (2006). Human Ccr4-Not complex is a ligand-dependent repressor of nuclear receptor-mediated transcription. EMBO J 25, 3089-3099.

Wolfgang M J, Kurama T, Dai Y, Suwa A, Asaumi M, Matsumoto S, Cha S H, Shimokawa T, Lane M D (2006). The brain-specific carnitine palmitoyltransferase-1c regulates energy homeostasis. Proc. Natl. Acad. Sci. U.S.A 103, 7282-7287.

Wood J D, Yuan J, Margolis R L, Colomer V, Duan K, Kushi J, Kaminsky Z, Kleiderlein J J, Sharp A H, Ross C A (1998). Atrophin-1, the DRPLA gene product, interacts with two families of W W domain-containing proteins. Mol. Cell Neurosci. 11, 149-160.

Wool I G (1996). Extraribosomal functions of ribosomal proteins. Trends Biochem. Sci. 21, 164-165.

Wu A, Wu B, Guo J, Luo W, Wu D, Yang H, Zhen Y, Yu X, Wang H, Zhou Y, Liu Z, Fang W, Yang Z (2011). Elevated expression of CDK4 in lung cancer. J Transl. Med. 9, 38.

Wu H, Xu H, Miraglia L J, Crooke S T (2000). Human RNase III is a 160-kDa protein involved in preribosomal RNA processing. J Biol. Chem. 275, 36957-36965.

Wu M, Liu Y, Di X, Kang H, Zeng H, Zhao Y, Cai K, Pang T, Wang S, Yao Y, Hu X (2013). EIF4E over-expresses and enhances cell proliferation and cell cycle progression in nasopharyngeal carcinoma. Med. Oncol 30, 400.

Xiao L, Rao J N, Zou T, Liu L, Marasa B S, Chen J, Turner D J, Passaniti A, Wang J Y (2007). Induced JunD in intestinal epithelial cells represses CDK4 transcription through its proximal promoter region following polyamine depletion. Biochem. J 403, 573-581.

Xie D, Zeng Y X, Wang H J, Wen J M, Tao Y, Sham J S, Guan X Y (2006). Expression of cytoplasmic and nuclear Survivin in primary and secondary human glioblastoma. Br. J Cancer 94, 108-114.

Xin W J, Weng H R, Dougherty P M (2009). Plasticity in expression of the glutamate transporters GLT-1 and GLAST in spinal dorsal horn glial cells following partial sciatic nerve ligation. Mol. Pain 5, 15.

Xu C, Mullersman J E, Wang L, Bin S B, Mao C, Posada Y, Camarillo C, Mao Y, Escamilla M A, Wang K S (2013). Polymorphisms in seizure 6-like gene are associated with bipolar disorder I: evidence of gene x gender interaction. J Affect. Disord. 145, 95-99.

Yamada A, Irie K, Deguchi-Tawarada M, Ohtsuka T, Takai Y (2003). Nectin-dependent localization of synaptic scaffolding molecule (S-SCAM) at the puncta adherentia junctions formed between the mossy fibre terminals and the dendrites of pyramidal cells in the CA3 area of the mouse hippocampus. Genes Cells 8, 985-994.

Yamamoto K, Murata H, Putranto E W, Kataoka K, Motoyama A, Hibino T, Inoue Y, Sakaguchi M, Huh N H (2013). DOCK7 is a critical regulator of the RAGE-Cdc42 signaling axis that induces formation of dendritic pseudopodia in human cancer cells. Oncol Rep. 29, 1073-1079.

Yamamoto Y, Izumi K, Otsuka H (1992). An immunohistochemical study of epithelial membrane antigen, cytokeratin, and vimentin in papillary thyroid carcinoma. Recognition of lethal and favorable prognostic types. Cancer 70, 2326-2333.

Yamashita S, Masuda Y, Kurizaki T, Haga Y, Murayama T, Ikei S, Kamei M, Takeno S, Kawahara K (2007). Survivin expression predicts early recurrence in early-stage breast cancer. Anticancer Res. 27, 2803-2808.

Yamauchi J, Miyamoto Y, Chan J R, Tanoue A (2008). ErbB2 directly activates the exchange factor Dock7 to promote Schwann cell migration. J Cell Biol. 181, 351-365.

Yan J, Feng J, Schroer R, Li W, Skinner C, Schwartz C E, Cook E H, Jr., Sommer S S (2008). Analysis of the neuroligin 4Y gene in patients with autism. Psychiatr. Genet. 18, 204-207.

Yan Y, Lagenaur C, Narayanan V (1993). Molecular cloning of M6: identification of a PLP/DM20 gene family. Neuron 11, 423-431.

Yang G F, Li X M, Xie D (2009). Overexpression of clusterin in ovarian cancer is correlated with impaired survival. Int. J Gynecol. Cancer 19, 1342-1346.

Yang H, Li L W, Shi M, Wang J H, Xiao F, Zhou B, Diao L Q, Long X L, Liu X L, Xu L (2012a). In vivo study of breast carcinoma radiosensitization by targeting eIF4E. Biochem. Biophys. Res. Commun. 423, 878-883.

Yang H Y, Lieska N, Shao D, Kriho V, Pappas G D (1994). Proteins of the intermediate filament cytoskeleton as markers for astrocytes and human astrocytomas. Mol. Chem. Neuropathol. 21, 155-176.

Yang H Y, Xue L Y, Xing L X, Wang J, Wang J L, Yan X, Zhang X H (2013). Putative role of the mTOR/4E-BP1 signaling pathway in the carcinogenesis and progression of gastric cardiac adenocarcinoma. Mol. Med. Rep. 7, 537-542.

Yang Y, Wang F, Shi C, Zou Y, Qin H, Ma Y (2012b). Cyclin D1 G870A Polymorphism Contributes to Colorectal Cancer Susceptibility: Evidence from a Systematic Review of 22 Case-Control Studies. PLoS. ONE. 7, e36813.

Yantiss R K, Cosar E, Fischer A H (2008). Use of IMP3 in identification of carcinoma in fine needle aspiration biopsies of pancreas. Acta Cytol. 52, 133-138.

Yasukawa M, Ishida K, Yuge Y, Hanaoka M, Minami Y, Ogawa M, Sasaki T, Saito M, Tsuji T (2013). Dpys14 is involved in tooth germ morphogenesis through growth regulation, polarization and differentiation of dental epithelial cells. Int. J Biol. Sci. 9, 382-390.

Yau C, Esserman L, Moore D H, Waldman F, Sninsky J, Benz C C (2010). A multigene predictor of metastatic outcome in early stage hormone receptor-negative and triple-negative breast cancer. Breast Cancer Res 12, R85.

Yeh I T, Lenci R E, Qin Y, Buddavarapu K, Ligon A H, Leteurtre E, Do C C, Cardot-Bauters C, Pigny P, Dahia P L (2008). A germline mutation of the KIF1B beta gene on 1p36 in a family with neural and nonneural tumors. Hum. Genet. 124, 279-285.

Yi H J, Zhang B Q, Guo W, Zhao L D, Yang S M (2012). The role of molecular margins as prognostic factors in laryngeal carcinoma in Chinese patients. Acta Otolaryngol. 132, 874-878.

Ylisaukko-oja T, Rehnstrom K, Auranen M, Vanhala R, Alen R, Kempas E, Ellonen P, Turunen J A, Makkonen I, Riikonen R, Nieminen-von W T, von W L, Peltonen L, Jarvela I (2005). Analysis of four neuroligin genes as candidates for autism. Eur. J Hum. Genet. 13, 1285-1292.

Yokoi K, Thaker P H, Yazici S, Rebhun R R, Nam D H, He J, Kim S J, Abbruzzese J L, Hamilton S R, Fidler I J (2005). Dual inhibition of epidermal growth factor receptor and vascular endothelial growth factor receptor phosphorylation by AEE788 reduces growth and metastasis of human colon carcinoma in an orthotopic nude mouse model. Cancer Res. 65, 3716-3725.

Yokota S, Yanagi H, Yura T, Kubota H (2001). Cytosolic chaperonin-containing t-complex polypeptide 1 changes the content of a particular subunit species concomitant with substrate binding and folding activities during the cell cycle. Eur. J Biochem. 268, 4664-4673.

Yoon H, Liyanarachchi S, Wright F A, Davuluri R, Lockman J C, de la C A, Pellegata N S (2002). Gene expression profiling of isogenic cells with different TP53 gene dosage reveals numerous genes that are affected by TP53 dosage and identifies CSPG2 as a direct target of p53. Proc Natl. Acad. Sci. U.S.A 99, 15632-15637.

Yue Y, Stout K, Grossmann B, Zechner U, Brinckmann A, White C, Pilz D T, Haaf T (2006). Disruption of TCBA1 associated with a de novo t(1; 6)(q32.2; q22.3) presenting in a child with developmental delay and recurrent infections. J Med. Genet. 43, 143-147.

yuso-Sacido A, Graham C, Greenfield J P, Boockvar J A (2006). The duality of epidermal growth factor receptor (EGFR) signaling and neural stem cell phenotype: cell enhancer or cell transformer? Curr. Stem Cell Res. Ther. 1, 387-394.

Zacharias U, Norenberg U, Rathj en F G (1999). Functional interactions of the immunoglobulin superfamily member F11 are differentially regulated by the extracellular matrix proteins tenascin-R and tenascin-C. J Biol. Chem. 274, 24357-24365.

Zadravec D, Tvrdik P, Guillou H, Haslam R, Kobayashi T, Napier J A, Capecchi M R, Jacobsson A (2011). ELOVL2 controls the level of n-6 28:5 and 30:5 fatty acids in testis, a prerequisite for male fertility and sperm maturation in mice. J Lipid Res. 52, 245-255.

Zangen I, Kneitz S, Monoranu C M, Rutkowski S, Hinkes B, Vince G H, Huang B, Roggendorf W (2007). Ependymoma gene expression profiles associated with histological subtype, proliferation, and patient survival. Acta Neuropathol. 113, 325-337.

Zaremba S, Barzaga E, Zhu M, Soares N, Tsang K Y, Schlom J (1997). Identification of an enhancer agonist cytotoxic T lymphocyte peptide from human carcinoembryonic antigen. Cancer Res. 57, 4570-4577.

Zekri A R, Hassan Z K, Bahnassy A A, Sherif G M, ELdahshan D, Abouelhoda M, Ali A, Hafez M M (2012). Molecular prognostic profile of Egyptian HCC cases infected with hepatitis C virus. Asian Pac. J Cancer Prev. 13, 5433-5438.

Zelano J, Mikulovic S, Patra K, Kuhnemund M, Larhammar M, Emilsson L, Leao R, Kullander K (2013). The synaptic protein encoded by the gene Slc10A4 suppresses epileptiform activity and regulates sensitivity to cholinergic chemoconvulsants. Exp. Neurol. 239, 73-81.

Zhai L, Mu J, Zong H, DePaoli-Roach A A, Roach P J (2000). Structure and chromosomal localization of the human glycogenin-2 gene GYG2. Gene 242, 229-235.

Zhang H, Baader S L, Sixt M, Kappler J, Rauch U (2004). Neurocan-GFP fusion protein: a new approach to detect hyaluronan on tissue sections and living cells. J Histochem. Cytochem. 52, 915-922.

Zhang Q W, Liu L, Gong C Y, Shi H S, Zeng Y H, Wang X Z, Zhao Y W, Wei Y Q (2012). Prognostic significance of tumor-associated macrophages in solid tumor: a meta-analysis of the literature. PLoS. ONE. 7, e50946.

Zhao C, Ma H, Bu X, Wang W, Zhang N (2012a). SFRP5 inhibits gastric epithelial cell migration induced by macrophage-derived Wnt5a. Carcinogenesis.

Zhao J, He H, Zhou K, Ren Y, Shi Z, Wu Z, Wang Y, Lu Y, Jiao J (2012b). Neuronal transcription factors induce conversion of human glioma cells to neurons and inhibit tumorigenesis. PLoS. ONE. 7, e41506.

Zhao M, Kim Y T, Yoon B S, Kim S W, Kang M R, Kim S H, Kim J H, Kim J W, Park Y W (2006). Expression profiling of cyclin B1 and D1 in cervical carcinoma. Exp. Oncol 28, 44-48.

Zhao W, Yue L, Zhou F, Xu C, Liang W, Sui A, Ding A, Qiu W (2013). Clinical significance of vimentin expression and Her-2 status in patients with gastric carcinoma. Clin Transl. Sci. 6, 184-190.

Zhen H N, Zhang X, Hu P Z, Yang T T, Fei Z, Zhang J N, Fu L A, He X S, Ma F C, Wang X L (2005). Survivin expression and its relation with proliferation, apoptosis, and angiogenesis in brain gliomas. Cancer 104, 2775-2783.

Zheng D, Gu S, Li Y, Ji C, Xie Y, Mao Y (2011). A global genomic view on LNX siRNA-mediated cell cycle arrest. Mol. Biol. Rep. 38, 2771-2783.

Zheng D, Niu S, Yu D, Zhan X H, Zeng X, Cui B, Chen Y, Yoon J, Martin S S, Lu X, Zhan X (2010). Abba promotes PDGF-mediated membrane ruffling through activation of the small GTPase Rac1. Biochem. Biophys. Res. Commun. 401, 527-532.

Zheng P S, Wen J, Ang L C, Sheng W, Viloria-Petit A, Wang Y, Wu Y, Kerbel R S, Yang B B (2004). Versican/PG-M G3 domain promotes tumor growth and angiogenesis. FASEB J 18, 754-756.

Zheng S E, Yao Y, Dong Y, Lin F, Zhao H, Shen Z, Sun Y J, Tang L N (2009). Down-regulation of ribosomal protein L7A in human osteosarcoma. J Cancer Res. Clin Oncol 135, 1025-1031.

Zhou D, Yang L, Zheng L, Ge W, Li D, Zhang Y, Hu X, Gao Z, Xu J, Huang Y, Hu H, Zhang H, Zhang H, Liu M, Yang H, Zheng L, Zheng S (2013). Exome capture sequencing of adenoma reveals genetic alterations in multiple cellular pathways at the early stage of colorectal tumorigenesis. PLoS. ONE. 8, e53310.

Zhou L, Picard D, Ra Y S, Li M, Northcott P A, Hu Y, Stearns D, Hawkins C, Taylor M D, Rutka J, Der S D, Huang A (2010). Silencing of thrombospondin-1 is critical for myc-induced metastatic phenotypes in medulloblastoma. Cancer Res. 70, 8199-8210.

Zhou S, Schuetz J D, Bunting K D, Colapietro A M, Sampath J, Morris J J, Lagutina I, Grosveld G C, Osawa M, Nakauchi H, Sorrentino B P (2001). The ABC transporter Bcrp1/ABCG2 is expressed in a wide variety of stem cells and is a molecular determinant of the side-population phenotype. Nat. Med 7, 1028-1034.

Zhu Z H, Yu Y P, Shi Y K, Nelson J B, Luo J H (2009). CSR1 induces cell death through inactivation of CPSF3. Oncogene 28, 41-51.

Zimmermann D R, Dours-Zimmermann M T, Schubert M, Bruckner-Tuderman L, Heitz P U (1994). [Expression of the extracellular matrix proteoglycan, versican, in human skin]. Verh. Dtsch. Ges. Pathol. 78, 481-484.

Zimmermann G, Moghaddam A, Wagner C, Vock B, Wentzensen A (2006). [Clinical experience with bone morphogenetic protein 7 (BMP 7) in nonunions of long bones]. Unfallchirurg 109, 528-537.

Zindy P, Berge Y, Allal B, Filleron T, Pierredon S, Cammas A, Beck S, Mhamdi L, Fan L, Favre G, Delord J P, Roche H, Dalenc F, Lacroix-Triki M, Vagner S (2011). Formation of the eIF4F translation-initiation complex determines sensitivity to anticancer drugs targeting the EGFR and HER2 receptors. Cancer Res. 71, 4068-4073.

Zody M C, et al. (2006). DNA sequence of human chromosome 17 and analysis of rearrangement in the human lineage. Nature 440, 1045-1049.

Zou J X, Revenko A S, Li L B, Gemo A T, Chen H W (2007). ANCCA, an estrogen-regulated AAA+ ATPase coactivator for ERalpha, is required for coregulator occupancy and chromatin modification. Proc Natl. Acad. Sci. U.S.A 104, 18067-18072.

Zuo L, Wang K, Zhang X Y, Krystal J H, Li C S, Zhang F, Zhang H, Luo X (2013). NKAIN1-SERINC2 is a functional, replicable and genome-wide significant risk gene region specific for alcohol dependence in subjects of European descent. Drug Alcohol Depend. 129, 254-264.

Zuo X, Zhang J, Zhang Y, Hsu S C, Zhou D, Guo W (2006). Exo70 interacts with the Arp2/3 complex and regulates cell migration. Nat Cell Biol. 8, 1383-1388.

Seibold P, Hein R, Schmezer P, Hall P, Liu J, Dahmen N, Flesch-Janys D, Popanda O, Chang-Claude J (2011). Polymorphisms in oxidative stress-related genes and postmenopausal breast cancer risk. Int. J Cancer 129, 1467-1476.

Song J S, Cho H H, Lee B J, Bae Y C, Jung J S (2011). Role of thioredoxin 1 and thioredoxin 2 on proliferation of human adipose tissue-derived mesenchymal stem cells. Stem Cells Dev. 20, Tanaka T, Hosoi F, Yamaguchi-Iwai Y, Nakamura H, Masutani H, Ueda S, Nishiyama A, Takeda S, Wada H, Spyrou G, Yodoi J (2002). Thioredoxin-2 (TRX-2) is an essential gene regulating mitochondria-dependent apoptosis. EMBO J 21, 1695-1703.

The invention claimed is:

1. A method of treating a patient who has brain cancer, comprising administering to said patient a population of activated T cells that kill cancer cells that present a peptide consisting of the amino acid sequence of FLVDGSWSI (SEQ ID NO: 28).

2. The method of claim 1, further comprising administering to said patient an adjuvant selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

3. The method of claim 1, wherein the activated T cells are cytotoxic T cells produced by contacting T cells with an antigen presenting cell that expresses the peptide in a complex with an MHC class I molecule on the surface of the antigen presenting cell, for a period of time sufficient to activate said T cell.

4. The method of claim 2, wherein the adjuvant is IL-1.
5. The method of claim 2, wherein the adjuvant is IL-2.
6. The method of claim 2, wherein the adjuvant is IL-7.
7. The method of claim 2, wherein the adjuvant is IL-12.
8. The method of claim 2, wherein the adjuvant is IL-13.
9. The method of claim 2, wherein the adjuvant is IL-15.
10. The method of claim 2, wherein the adjuvant is IL-21.

11. A method of eliciting an immune response in a patient who has brain cancer, comprising administering to said patient a population of activated T cells that kill cancer cells that present a peptide consisting of the amino acid sequence of FLVDGSWSI (SEQ ID NO: 28).

12. The method of claim 11, further comprising administering to said patient an adjuvant selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

13. The method of claim 11, wherein the activated T cells are cytotoxic T cells produced by contacting T cells with an antigen presenting cell that expresses the peptide in a complex with an MHC class I molecule on the surface of the antigen presenting cell, for a period of time sufficient to activate said T cell.

14. The method of claim 12, wherein the adjuvant is IL-1.
15. The method of claim 12, wherein the adjuvant is IL-2.
16. The method of claim 12, wherein the adjuvant is IL-7.
17. The method of claim 12, wherein the adjuvant is IL-12.
18. The method of claim 12, wherein the adjuvant is IL-13.
19. The method of claim 12, wherein the adjuvant is IL-15.
20. The method of claim 12, wherein the adjuvant is IL-21.

\* \* \* \* \*

SEQUENCE LISTING

```
<160> NUMBER OF SEQ ID NOS: 133

<210> SEQ ID NO 1
<211> LENGTH: 9
<212> TYPE: PRT
<213> ORGANISM: Homo sapiens

<400> SEQUENCE: 1

Arg Leu Gly Ile Lys Pro Glu Ser Val
1               5

<210> SEQ ID NO 2
<211> LENGTH: 9
<212> TYPE: PRT
<213> ORGANISM: Homo sapiens

<400> SEQUENCE: 2

Ala Leu Ala Phe Lys Leu Asp Glu Val
1               5

<210> SEQ ID NO 3
<211> LENGTH: 9
<212> TYPE: PRT
<213> ORGANISM: Homo sapiens

<400> SEQUENCE: 3

Tyr Leu Pro Thr Phe Phe Leu Thr Val
1               5

<210> SEQ ID NO 4
<211> LENGTH: 10
<212> TYPE: PRT
<213> ORGANISM: Homo sapiens

<400> SEQUENCE: 4

Gly Leu Pro Ser Gly Ala Pro Pro Gly Val
1               5                   10
```

```
<210> SEQ ID NO 5
<211> LENGTH: 9
<212> TYPE: PRT
<213> ORGANISM: Homo sapiens

<400> SEQUENCE: 5

Met Ile Trp Glu His Asn Val Glu Val
1               5

<210> SEQ ID NO 6
<211> LENGTH: 9
<212> TYPE: PRT
<213> ORGANISM: Homo sapiens

<400> SEQUENCE: 6

Leu Leu Trp Gly Asn Ala Ile Phe Leu
1               5

<210> SEQ ID NO 7
<211> LENGTH: 11
<212> TYPE: PRT
<213> ORGANISM: Homo sapiens

<400> SEQUENCE: 7

Gly Leu Asp Pro Ser Ser Gly Ala Ile His Val
1               5                   10

<210> SEQ ID NO 8
<211> LENGTH: 9
<212> TYPE: PRT
<213> ORGANISM: Homo sapiens

<400> SEQUENCE: 8

Leu Leu Tyr Asp Ala Val His Ile Val
1               5

<210> SEQ ID NO 9
<211> LENGTH: 9
<212> TYPE: PRT
<213> ORGANISM: Homo sapiens

<400> SEQUENCE: 9

Leu Leu Leu Gly Ser Pro Ala Ala Ala
1               5

<210> SEQ ID NO 10
<211> LENGTH: 8
<212> TYPE: PRT
<213> ORGANISM: Homo sapiens

<400> SEQUENCE: 10

Ala Leu Gly Asp Ile Arg Glu Val
1               5

<210> SEQ ID NO 11
<211> LENGTH: 9
<212> TYPE: PRT
<213> ORGANISM: Homo sapiens

<400> SEQUENCE: 11

Ser Leu Asp Thr Leu Met Thr Tyr Val
1               5
```

```
<210> SEQ ID NO 12
<211> LENGTH: 9
<212> TYPE: PRT
<213> ORGANISM: Homo sapiens

<400> SEQUENCE: 12

Ala Leu Ser Val Arg Ile Ser Asn Val
1               5

<210> SEQ ID NO 13
<211> LENGTH: 9
<212> TYPE: PRT
<213> ORGANISM: Homo sapiens

<400> SEQUENCE: 13

Phe Leu Trp Ser Asp Gly Val Pro Leu
1               5

<210> SEQ ID NO 14
<211> LENGTH: 9
<212> TYPE: PRT
<213> ORGANISM: Homo sapiens

<400> SEQUENCE: 14

Ala Val Ala Pro Gly Pro Trp Lys Val
1               5

<210> SEQ ID NO 15
<211> LENGTH: 12
<212> TYPE: PRT
<213> ORGANISM: Homo sapiens

<400> SEQUENCE: 15

Phe Leu Leu Pro Asp Thr Asp Gly Leu Thr Ala Leu
1               5                   10

<210> SEQ ID NO 16
<211> LENGTH: 9
<212> TYPE: PRT
<213> ORGANISM: Homo sapiens

<400> SEQUENCE: 16

Ser Leu Gly Leu Phe Leu Ala Gln Val
1               5

<210> SEQ ID NO 17
<211> LENGTH: 9
<212> TYPE: PRT
<213> ORGANISM: Homo sapiens

<400> SEQUENCE: 17

Val Leu Ile Gln Asp Val Pro Thr Leu
1               5

<210> SEQ ID NO 18
<211> LENGTH: 12
<212> TYPE: PRT
<213> ORGANISM: Homo sapiens

<400> SEQUENCE: 18

Lys Leu Phe Asp Ser Asp Pro Ile Thr Val Thr Val
1               5                   10

<210> SEQ ID NO 19
<211> LENGTH: 10
```

```
<212> TYPE: PRT
<213> ORGANISM: Homo sapiens

<400> SEQUENCE: 19

Phe Leu His Asp Ile Ser Asp Val Gln Leu
1               5                   10

<210> SEQ ID NO 20
<211> LENGTH: 9
<212> TYPE: PRT
<213> ORGANISM: Homo sapiens

<400> SEQUENCE: 20

Arg Val Ala Asp Tyr Ile Val Lys Val
1               5

<210> SEQ ID NO 21
<211> LENGTH: 11
<212> TYPE: PRT
<213> ORGANISM: Homo sapiens

<400> SEQUENCE: 21

Ala Leu Phe Asn Lys Gly Gly Ser Val Phe Leu
1               5                   10

<210> SEQ ID NO 22
<211> LENGTH: 9
<212> TYPE: PRT
<213> ORGANISM: Homo sapiens

<400> SEQUENCE: 22

Lys Val Phe Asp Glu Val Ile Glu Val
1               5

<210> SEQ ID NO 23
<211> LENGTH: 9
<212> TYPE: PRT
<213> ORGANISM: Homo sapiens

<400> SEQUENCE: 23

Gly Leu Met Glu Lys Ile Lys Glu Leu
1               5

<210> SEQ ID NO 24
<211> LENGTH: 9
<212> TYPE: PRT
<213> ORGANISM: Homo sapiens

<400> SEQUENCE: 24

Gly Met Met Thr Ala Ile Leu Gly Val
1               5

<210> SEQ ID NO 25
<211> LENGTH: 9
<212> TYPE: PRT
<213> ORGANISM: Homo sapiens

<400> SEQUENCE: 25

Phe Leu Tyr Lys Val Ile Leu Ser Leu
1               5

<210> SEQ ID NO 26
<211> LENGTH: 9
<212> TYPE: PRT
<213> ORGANISM: Homo sapiens
```

```
<400> SEQUENCE: 26

Ala Leu Thr Thr Leu Met His Gln Leu
1               5

<210> SEQ ID NO 27
<211> LENGTH: 9
<212> TYPE: PRT
<213> ORGANISM: Homo sapiens

<400> SEQUENCE: 27

Glu Ile Leu Asp Tyr Ile Tyr Glu Val
1               5

<210> SEQ ID NO 28
<211> LENGTH: 9
<212> TYPE: PRT
<213> ORGANISM: Homo sapiens

<400> SEQUENCE: 28

Phe Leu Val Asp Gly Ser Trp Ser Ile
1               5

<210> SEQ ID NO 29
<211> LENGTH: 9
<212> TYPE: PRT
<213> ORGANISM: Homo sapiens

<400> SEQUENCE: 29

Tyr Gln Asp Pro His Ser Thr Ala Val
1               5

<210> SEQ ID NO 30
<211> LENGTH: 9
<212> TYPE: PRT
<213> ORGANISM: Homo sapiens

<400> SEQUENCE: 30

Lys Leu Thr Asp Ile Gln Ile Glu Leu
1               5

<210> SEQ ID NO 31
<211> LENGTH: 9
<212> TYPE: PRT
<213> ORGANISM: Homo sapiens

<400> SEQUENCE: 31

Thr Met Met Ser Arg Pro Pro Val Leu
1               5

<210> SEQ ID NO 32
<211> LENGTH: 9
<212> TYPE: PRT
<213> ORGANISM: Homo sapiens

<400> SEQUENCE: 32

Arg Val Ala Ser Pro Thr Ser Gly Val
1               5

<210> SEQ ID NO 33
<211> LENGTH: 10
<212> TYPE: PRT
<213> ORGANISM: Homo sapiens

<400> SEQUENCE: 33
```

```
Ser Leu Ala Glu Arg Leu Phe Phe Gln Val
1               5                   10

<210> SEQ ID NO 34
<211> LENGTH: 9
<212> TYPE: PRT
<213> ORGANISM: Homo sapiens

<400> SEQUENCE: 34

Ala Met Thr Gln Leu Leu Ala Gly Val
1               5

<210> SEQ ID NO 35
<211> LENGTH: 9
<212> TYPE: PRT
<213> ORGANISM: Homo sapiens

<400> SEQUENCE: 35

Gly Leu Ser Glu Phe Thr Glu Tyr Leu
1               5

<210> SEQ ID NO 36
<211> LENGTH: 9
<212> TYPE: PRT
<213> ORGANISM: Homo sapiens

<400> SEQUENCE: 36

Val Leu Cys Gly Pro Pro Pro Ala Val
1               5

<210> SEQ ID NO 37
<211> LENGTH: 9
<212> TYPE: PRT
<213> ORGANISM: Homo sapiens

<400> SEQUENCE: 37

Ala Leu Ala Asp Ile Ala Val Gly Val
1               5

<210> SEQ ID NO 38
<211> LENGTH: 10
<212> TYPE: PRT
<213> ORGANISM: Homo sapiens

<400> SEQUENCE: 38

Leu Leu Tyr Thr Gly Asp Leu Glu Ala Leu
1               5                   10

<210> SEQ ID NO 39
<211> LENGTH: 9
<212> TYPE: PRT
<213> ORGANISM: Homo sapiens

<400> SEQUENCE: 39

Gly Leu Leu Asp Gln Ile Gln Ala Leu
1               5

<210> SEQ ID NO 40
<211> LENGTH: 9
<212> TYPE: PRT
<213> ORGANISM: Homo sapiens

<400> SEQUENCE: 40

Asn Ile Leu Glu Gln Ile Val Ser Val
```

```
<210> SEQ ID NO 41
<211> LENGTH: 10
<212> TYPE: PRT
<213> ORGANISM: Homo sapiens

<400> SEQUENCE: 41

Phe Leu Tyr Asn Glu Ala Leu Tyr Ser Leu
1               5                   10

<210> SEQ ID NO 42
<211> LENGTH: 11
<212> TYPE: PRT
<213> ORGANISM: Homo sapiens

<400> SEQUENCE: 42

Met Leu Phe Gly His Pro Leu Leu Val Ser Val
1               5                   10

<210> SEQ ID NO 43
<211> LENGTH: 9
<212> TYPE: PRT
<213> ORGANISM: Homo sapiens

<400> SEQUENCE: 43

Arg Leu Ile Ser Lys Phe Asp Thr Val
1               5

<210> SEQ ID NO 44
<211> LENGTH: 9
<212> TYPE: PRT
<213> ORGANISM: Homo sapiens

<400> SEQUENCE: 44

Leu Leu Gln Asp Arg Leu Val Ser Val
1               5

<210> SEQ ID NO 45
<211> LENGTH: 11
<212> TYPE: PRT
<213> ORGANISM: Homo sapiens

<400> SEQUENCE: 45

Thr Leu Leu Ala Ala Glu Phe Leu Lys Gln Val
1               5                   10

<210> SEQ ID NO 46
<211> LENGTH: 11
<212> TYPE: PRT
<213> ORGANISM: Homo sapiens

<400> SEQUENCE: 46

Leu Thr Ala Pro Pro Glu Ala Leu Leu Met Val
1               5                   10

<210> SEQ ID NO 47
<211> LENGTH: 9
<212> TYPE: PRT
<213> ORGANISM: Homo sapiens

<400> SEQUENCE: 47

Phe Leu Asp Ser Lys Phe Tyr Leu Leu
1               5
```

```
<210> SEQ ID NO 48
<211> LENGTH: 9
<212> TYPE: PRT
<213> ORGANISM: Homo sapiens

<400> SEQUENCE: 48

Lys Leu Cys Glu Gly Phe Asn Glu Val
1               5

<210> SEQ ID NO 49
<211> LENGTH: 9
<212> TYPE: PRT
<213> ORGANISM: Homo sapiens

<400> SEQUENCE: 49

Lys Leu Ala Asp Gln Tyr Pro His Leu
1               5

<210> SEQ ID NO 50
<211> LENGTH: 9
<212> TYPE: PRT
<213> ORGANISM: Homo sapiens

<400> SEQUENCE: 50

Lys Val Phe Ala Gly Ile Pro Thr Val
1               5

<210> SEQ ID NO 51
<211> LENGTH: 9
<212> TYPE: PRT
<213> ORGANISM: Homo sapiens

<400> SEQUENCE: 51

Ala Leu Trp Ala Trp Pro Ser Glu Leu
1               5

<210> SEQ ID NO 52
<211> LENGTH: 9
<212> TYPE: PRT
<213> ORGANISM: Homo sapiens

<400> SEQUENCE: 52

Thr Leu Trp Tyr Arg Ala Pro Glu Val
1               5

<210> SEQ ID NO 53
<211> LENGTH: 10
<212> TYPE: PRT
<213> ORGANISM: Homo sapiens

<400> SEQUENCE: 53

Ile Leu Phe Pro Asp Ile Ile Ala Arg Ala
1               5                   10

<210> SEQ ID NO 54
<211> LENGTH: 9
<212> TYPE: PRT
<213> ORGANISM: Homo sapiens

<400> SEQUENCE: 54

Ala Ile Ile Asp Gly Val Glu Ser Val
1               5

<210> SEQ ID NO 55
```

```
<211> LENGTH: 9
<212> TYPE: PRT
<213> ORGANISM: Homo sapiens

<400> SEQUENCE: 55

Asn Leu Asp Thr Leu Met Thr Tyr Val
1               5

<210> SEQ ID NO 56
<211> LENGTH: 9
<212> TYPE: PRT
<213> ORGANISM: Homo sapiens

<400> SEQUENCE: 56

Ser Leu Trp Gly Gly Asp Val Val Leu
1               5

<210> SEQ ID NO 57
<211> LENGTH: 9
<212> TYPE: PRT
<213> ORGANISM: Homo sapiens

<400> SEQUENCE: 57

Gly Leu Trp His His Gln Thr Glu Val
1               5

<210> SEQ ID NO 58
<211> LENGTH: 9
<212> TYPE: PRT
<213> ORGANISM: Homo sapiens

<400> SEQUENCE: 58

Ser Leu Tyr Lys Gly Leu Leu Ser Val
1               5

<210> SEQ ID NO 59
<211> LENGTH: 9
<212> TYPE: PRT
<213> ORGANISM: Homo sapiens

<400> SEQUENCE: 59

Leu Thr Phe Gly Asp Val Val Ala Val
1               5

<210> SEQ ID NO 60
<211> LENGTH: 9
<212> TYPE: PRT
<213> ORGANISM: Homo sapiens

<400> SEQUENCE: 60

Thr Met Leu Ala Arg Leu Ala Ser Ala
1               5

<210> SEQ ID NO 61
<211> LENGTH: 9
<212> TYPE: PRT
<213> ORGANISM: Homo sapiens

<400> SEQUENCE: 61

Thr Leu Thr Asn Ile Ile His Asn Leu
1               5

<210> SEQ ID NO 62
<211> LENGTH: 10
<212> TYPE: PRT
```

<213> ORGANISM: Homo sapiens

<400> SEQUENCE: 62

Lys Leu Val Glu Phe Asp Phe Leu Gly Ala
1               5                   10

<210> SEQ ID NO 63
<211> LENGTH: 11
<212> TYPE: PRT
<213> ORGANISM: Homo sapiens

<400> SEQUENCE: 63

Lys Leu Gly Asp Phe Gly Leu Ala Thr Val Val
1               5                   10

<210> SEQ ID NO 64
<211> LENGTH: 9
<212> TYPE: PRT
<213> ORGANISM: Homo sapiens

<400> SEQUENCE: 64

Gly Val Leu Glu Asn Ile Phe Gly Val
1               5

<210> SEQ ID NO 65
<211> LENGTH: 9
<212> TYPE: PRT
<213> ORGANISM: Homo sapiens

<400> SEQUENCE: 65

Asn Leu Leu Ala Glu Ile His Gly Val
1               5

<210> SEQ ID NO 66
<211> LENGTH: 9
<212> TYPE: PRT
<213> ORGANISM: Homo sapiens

<400> SEQUENCE: 66

Lys Ile Gln Glu Ile Leu Thr Gln Val
1               5

<210> SEQ ID NO 67
<211> LENGTH: 9
<212> TYPE: PRT
<213> ORGANISM: Homo sapiens

<400> SEQUENCE: 67

Ala Val Val Glu Phe Leu Thr Ser Val
1               5

<210> SEQ ID NO 68
<211> LENGTH: 9
<212> TYPE: PRT
<213> ORGANISM: Homo sapiens

<400> SEQUENCE: 68

Ile Leu Phe Glu Ile Asn Pro Lys Leu
1               5

<210> SEQ ID NO 69
<211> LENGTH: 9
<212> TYPE: PRT

```
<400> SEQUENCE: 69

Ile Leu Ile Asp Trp Leu Val Gln Val
1               5

<210> SEQ ID NO 70
<211> LENGTH: 9
<212> TYPE: PRT
<213> ORGANISM: Homo sapiens

<400> SEQUENCE: 70

Ser Leu Ala Asp Phe Met Gln Glu Val
1               5

<210> SEQ ID NO 71
<211> LENGTH: 18
<212> TYPE: PRT
<213> ORGANISM: Homo sapiens

<400> SEQUENCE: 71

Val Lys Val Asn Glu Ala Tyr Arg Phe Arg Val Ala Leu Pro Ala Tyr
1               5                   10                  15

Pro Ala

<210> SEQ ID NO 72
<211> LENGTH: 15
<212> TYPE: PRT
<213> ORGANISM: Homo sapiens

<400> SEQUENCE: 72

Thr Leu Gly Glu Phe Leu Lys Leu Asp Arg Glu Arg Ala Lys Asn
1               5                   10                  15

<210> SEQ ID NO 73
<211> LENGTH: 14
<212> TYPE: PRT
<213> ORGANISM: Homo sapiens

<400> SEQUENCE: 73

Glu Ile Gly Trp Ser Tyr Thr Gly Ala Leu Asn Gln Lys Asn
1               5                   10

<210> SEQ ID NO 74
<211> LENGTH: 9
<212> TYPE: PRT
<213> ORGANISM: Homo sapiens

<400> SEQUENCE: 74

Tyr Tyr Pro Gly Val Ile Leu Gly Phe
1               5

<210> SEQ ID NO 75
<211> LENGTH: 9
<212> TYPE: PRT
<213> ORGANISM: Homo sapiens

<400> SEQUENCE: 75

Val Tyr Tyr Phe His Pro Gln Tyr Leu
1               5

<210> SEQ ID NO 76
<211> LENGTH: 9
<212> TYPE: PRT
<213> ORGANISM: Homo sapiens
```

```
<400> SEQUENCE: 76

Met Tyr Pro Tyr Ile Tyr His Val Leu
1               5

<210> SEQ ID NO 77
<211> LENGTH: 9
<212> TYPE: PRT
<213> ORGANISM: Homo sapiens

<400> SEQUENCE: 77

Tyr Tyr His Phe Ile Phe Thr Thr Leu
1               5

<210> SEQ ID NO 78
<211> LENGTH: 9
<212> TYPE: PRT
<213> ORGANISM: Homo sapiens

<400> SEQUENCE: 78

Tyr Tyr Thr Val Arg Asn Phe Thr Leu
1               5

<210> SEQ ID NO 79
<211> LENGTH: 9
<212> TYPE: PRT
<213> ORGANISM: Homo sapiens

<400> SEQUENCE: 79

Asn Tyr Thr Ser Leu Leu Val Thr Trp
1               5

<210> SEQ ID NO 80
<211> LENGTH: 10
<212> TYPE: PRT
<213> ORGANISM: Homo sapiens

<400> SEQUENCE: 80

Glu Tyr Met Lys Ala Leu Gly Val Gly Phe
1               5                   10

<210> SEQ ID NO 81
<211> LENGTH: 9
<212> TYPE: PRT
<213> ORGANISM: Homo sapiens

<400> SEQUENCE: 81

Lys Tyr Asn Asp Phe Gly Asn Ser Phe
1               5

<210> SEQ ID NO 82
<211> LENGTH: 10
<212> TYPE: PRT
<213> ORGANISM: Homo sapiens

<400> SEQUENCE: 82

Leu Tyr Ile Tyr Pro Gln Ser Leu Asn Phe
1               5                   10

<210> SEQ ID NO 83
<211> LENGTH: 9
<212> TYPE: PRT
<213> ORGANISM: Homo sapiens

<400> SEQUENCE: 83
```

```
Ile Phe Thr Tyr Ile His Leu Gln Leu
1               5

<210> SEQ ID NO 84
<211> LENGTH: 11
<212> TYPE: PRT
<213> ORGANISM: Homo sapiens

<400> SEQUENCE: 84

Arg Tyr Gln Glu Ser Leu Gly Asn Thr Val Phe
1               5                   10

<210> SEQ ID NO 85
<211> LENGTH: 9
<212> TYPE: PRT
<213> ORGANISM: Homo sapiens

<400> SEQUENCE: 85

Lys Tyr Asn Glu Phe Ser Val Ser Leu
1               5

<210> SEQ ID NO 86
<211> LENGTH: 9
<212> TYPE: PRT
<213> ORGANISM: Homo sapiens

<400> SEQUENCE: 86

Thr Tyr Asn Tyr Ala Val Leu Lys Phe
1               5

<210> SEQ ID NO 87
<211> LENGTH: 9
<212> TYPE: PRT
<213> ORGANISM: Homo sapiens

<400> SEQUENCE: 87

Ser Tyr Phe Glu Asn Val His Gly Phe
1               5

<210> SEQ ID NO 88
<211> LENGTH: 9
<212> TYPE: PRT
<213> ORGANISM: Homo sapiens

<400> SEQUENCE: 88

Val Tyr Asp Thr Met Ile Glu Lys Phe
1               5

<210> SEQ ID NO 89
<211> LENGTH: 9
<212> TYPE: PRT
<213> ORGANISM: Homo sapiens

<400> SEQUENCE: 89

Gln Tyr Val Phe Ile His Asp Thr Leu
1               5

<210> SEQ ID NO 90
<211> LENGTH: 9
<212> TYPE: PRT
<213> ORGANISM: Homo sapiens

<400> SEQUENCE: 90

Asn Tyr Thr Ser Leu Leu Val Thr Trp
1               5
```

<210> SEQ ID NO 91
<211> LENGTH: 9
<212> TYPE: PRT
<213> ORGANISM: Homo sapiens

<400> SEQUENCE: 91

Ile Tyr Gly Gly His His Ala Gly Phe
1               5

<210> SEQ ID NO 92
<211> LENGTH: 9
<212> TYPE: PRT
<213> ORGANISM: Homo sapiens

<400> SEQUENCE: 92

Thr Tyr Val Asp Ser Ser His Thr Ile
1               5

<210> SEQ ID NO 93
<211> LENGTH: 9
<212> TYPE: PRT
<213> ORGANISM: Homo sapiens

<400> SEQUENCE: 93

Val Tyr Asn Leu Thr Gln Glu Phe Phe
1               5

<210> SEQ ID NO 94
<211> LENGTH: 9
<212> TYPE: PRT
<213> ORGANISM: Homo sapiens

<400> SEQUENCE: 94

Tyr Tyr Gln Ile Arg Ser Ser Gln Leu
1               5

<210> SEQ ID NO 95
<211> LENGTH: 9
<212> TYPE: PRT
<213> ORGANISM: Homo sapiens

<400> SEQUENCE: 95

Arg Tyr Ser Asp Gly Leu Leu Arg Phe
1               5

<210> SEQ ID NO 96
<211> LENGTH: 9
<212> TYPE: PRT
<213> ORGANISM: Homo sapiens

<400> SEQUENCE: 96

Gln Tyr Gln Ile Ile Met Thr Met Ile
1               5

<210> SEQ ID NO 97
<211> LENGTH: 10
<212> TYPE: PRT
<213> ORGANISM: Homo sapiens

<400> SEQUENCE: 97

Thr Tyr Ile Pro Pro Leu Leu Val Ala Phe
1               5                   10

```
<210> SEQ ID NO 98
<211> LENGTH: 9
<212> TYPE: PRT
<213> ORGANISM: Homo sapiens

<400> SEQUENCE: 98

Glu Tyr Ile Arg Ala Leu Gln Gln Leu
1               5

<210> SEQ ID NO 99
<211> LENGTH: 9
<212> TYPE: PRT
<213> ORGANISM: Homo sapiens

<400> SEQUENCE: 99

Thr Tyr Ile Ile Lys Ser Val Gly Phe
1               5

<210> SEQ ID NO 100
<211> LENGTH: 9
<212> TYPE: PRT
<213> ORGANISM: Homo sapiens

<400> SEQUENCE: 100

Gln Trp Ala Pro Ile Leu Ala Asn Phe
1               5

<210> SEQ ID NO 101
<211> LENGTH: 8
<212> TYPE: PRT
<213> ORGANISM: Homo sapiens

<400> SEQUENCE: 101

Arg Tyr Gly Pro Gln Phe Thr Leu
1               5

<210> SEQ ID NO 102
<211> LENGTH: 9
<212> TYPE: PRT
<213> ORGANISM: Homo sapiens

<400> SEQUENCE: 102

Arg Tyr Ile Pro Leu Ile Val Asp Ile
1               5

<210> SEQ ID NO 103
<211> LENGTH: 9
<212> TYPE: PRT
<213> ORGANISM: Homo sapiens

<400> SEQUENCE: 103

Ala Tyr Val Leu Arg Leu Glu Thr Leu
1               5

<210> SEQ ID NO 104
<211> LENGTH: 9
<212> TYPE: PRT
<213> ORGANISM: Homo sapiens

<400> SEQUENCE: 104

Pro Tyr Asn His Gln His Glu Tyr Phe
1               5

<210> SEQ ID NO 105
<211> LENGTH: 11
```

<212> TYPE: PRT
<213> ORGANISM: Homo sapiens

<400> SEQUENCE: 105

Val Leu Pro Asp Ala Asp Thr Leu Leu His Phe
1               5                   10

<210> SEQ ID NO 106
<211> LENGTH: 9
<212> TYPE: PRT
<213> ORGANISM: Homo sapiens

<400> SEQUENCE: 106

Phe Tyr Gly Pro Gln Val Asn Asn Ile
1               5

<210> SEQ ID NO 107
<211> LENGTH: 9
<212> TYPE: PRT
<213> ORGANISM: Homo sapiens

<400> SEQUENCE: 107

Lys Tyr Phe Ser Phe Pro Gly Glu Leu
1               5

<210> SEQ ID NO 108
<211> LENGTH: 9
<212> TYPE: PRT
<213> ORGANISM: Homo sapiens

<400> SEQUENCE: 108

Ala Tyr Ser Asp Gly His Phe Leu Phe
1               5

<210> SEQ ID NO 109
<211> LENGTH: 9
<212> TYPE: PRT
<213> ORGANISM: Homo sapiens

<400> SEQUENCE: 109

Arg Tyr Leu Pro Ser Ser Val Phe Leu
1               5

<210> SEQ ID NO 110
<211> LENGTH: 10
<212> TYPE: PRT
<213> ORGANISM: Homo sapiens

<400> SEQUENCE: 110

Val Tyr Leu Thr Ile Lys Pro Leu Asn Leu
1               5                   10

<210> SEQ ID NO 111
<211> LENGTH: 9
<212> TYPE: PRT
<213> ORGANISM: Homo sapiens

<400> SEQUENCE: 111

Pro Tyr Leu Asp Lys Phe Phe Ala Leu
1               5

<210> SEQ ID NO 112
<211> LENGTH: 9
<212> TYPE: PRT
<213> ORGANISM: Homo sapiens

<400> SEQUENCE: 112

Val Tyr Gln Val Leu Gln Glu His Leu
1               5

<210> SEQ ID NO 113
<211> LENGTH: 11
<212> TYPE: PRT
<213> ORGANISM: Homo sapiens

<400> SEQUENCE: 113

Ala Phe Ser Pro Asp Ser His Tyr Leu Leu Phe
1               5                   10

<210> SEQ ID NO 114
<211> LENGTH: 9
<212> TYPE: PRT
<213> ORGANISM: Homo sapiens

<400> SEQUENCE: 114

Asn Tyr Asn Asp Arg Tyr Asp Glu Ile
1               5

<210> SEQ ID NO 115
<211> LENGTH: 9
<212> TYPE: PRT
<213> ORGANISM: Homo sapiens

<400> SEQUENCE: 115

Lys Tyr Asn Leu Ile Asn Glu Tyr Phe
1               5

<210> SEQ ID NO 116
<211> LENGTH: 9
<212> TYPE: PRT
<213> ORGANISM: Homo sapiens

<400> SEQUENCE: 116

Asn Tyr Gln Asp Thr Ile Gly Arg Leu
1               5

<210> SEQ ID NO 117
<211> LENGTH: 9
<212> TYPE: PRT
<213> ORGANISM: Homo sapiens

<400> SEQUENCE: 117

Ala Tyr Leu Ile Asp Ile Lys Thr Ile
1               5

<210> SEQ ID NO 118
<211> LENGTH: 9
<212> TYPE: PRT
<213> ORGANISM: Homo sapiens

<400> SEQUENCE: 118

Ala Tyr Pro Arg Leu Ser Leu Ser Phe
1               5

<210> SEQ ID NO 119
<211> LENGTH: 9
<212> TYPE: PRT
<213> ORGANISM: Homo sapiens

<400> SEQUENCE: 119

Lys Phe Ala Glu Glu Phe Tyr Ser Phe
1               5

<210> SEQ ID NO 120
<211> LENGTH: 9
<212> TYPE: PRT
<213> ORGANISM: Homo sapiens

<400> SEQUENCE: 120

Tyr Tyr Leu Asp Lys Ser Val Ser Ile
1               5

<210> SEQ ID NO 121
<211> LENGTH: 10
<212> TYPE: PRT
<213> ORGANISM: Homo sapiens

<400> SEQUENCE: 121

Asn Tyr Lys Asp Leu Asn Gly Asn Val Phe
1               5                   10

<210> SEQ ID NO 122
<211> LENGTH: 9
<212> TYPE: PRT
<213> ORGANISM: Homo sapiens

<400> SEQUENCE: 122

Ala Tyr Leu Lys Gly Thr Val Leu Phe
1               5

<210> SEQ ID NO 123
<211> LENGTH: 11
<212> TYPE: PRT
<213> ORGANISM: Homo sapiens

<400> SEQUENCE: 123

Asn Tyr Ile Asp Asn Val Gly Asn Leu His Phe
1               5                   10

<210> SEQ ID NO 124
<211> LENGTH: 9
<212> TYPE: PRT
<213> ORGANISM: Homo sapiens

<400> SEQUENCE: 124

Pro Phe Ala Lys Pro Leu Pro Thr Phe
1               5

<210> SEQ ID NO 125
<211> LENGTH: 9
<212> TYPE: PRT
<213> ORGANISM: Homo sapiens

<400> SEQUENCE: 125

Val Tyr Leu Lys Glu Ala Asn Ala Ile
1               5

<210> SEQ ID NO 126
<211> LENGTH: 10
<212> TYPE: PRT
<213> ORGANISM: Homo sapiens

<400> SEQUENCE: 126

Lys Tyr Phe Gly Gly Val Leu Glu Tyr Phe

```
<210> SEQ ID NO 127
<211> LENGTH: 9
<212> TYPE: PRT
<213> ORGANISM: Homo sapiens

<400> SEQUENCE: 127

Lys Tyr Phe Asp Lys Val Val Thr Leu
1               5

<210> SEQ ID NO 128
<211> LENGTH: 11
<212> TYPE: PRT
<213> ORGANISM: Homo sapiens

<400> SEQUENCE: 128

Val Tyr Asn Asp Ile Gly Lys Glu Met Leu Leu
1               5                   10

<210> SEQ ID NO 129
<211> LENGTH: 9
<212> TYPE: PRT
<213> ORGANISM: Homo sapiens

<400> SEQUENCE: 129

Thr Tyr Thr Ser Tyr Leu Asp Lys Phe
1               5

<210> SEQ ID NO 130
<211> LENGTH: 9
<212> TYPE: PRT
<213> ORGANISM: Homo sapiens

<400> SEQUENCE: 130

Ser Tyr Asn Pro Leu Trp Leu Arg Ile
1               5

<210> SEQ ID NO 131
<211> LENGTH: 9
<212> TYPE: PRT
<213> ORGANISM: Homo sapiens

<400> SEQUENCE: 131

His Tyr Lys Pro Thr Pro Leu Tyr Phe
1               5

<210> SEQ ID NO 132
<211> LENGTH: 1304
<212> TYPE: DNA
<213> ORGANISM: Homo sapiens

<400> SEQUENCE: 132
ttcccagatg cacaggagga gaagcaggag ctgtcgggaa gatcagaagc cagtcatgga      60
tgaccagcgc gaccttatct ccaacaatga gcaactgccc atgctgggcc ggcgccctgg     120
ggccccggag agcaagtgca gccgcggagc cctgtacaca ggcttttcca tcctggtgac     180
tctgctcctc gctggccagg ccaccaccgc ctacttcctg taccagcagc agggccggct     240
ggacaaactg acagtcacct cccagaacct gcagctggag aacctgcgca tgaagcttcc     300
caagcctccc aagcctgtga gcaagatgcg catggccacc ccgctgctga tgcaggcgct     360
gcccatggga gccctgcccc aggggcccat gcagaatgcc accaagtatg gcaacatgac     420
```

```
agaggaccat gtgatgcacc tgctccagaa tgctgacccc ctgaaggtgt acccgccact    480 gaagggagc ttcccggaga acctgagaca ccttaagaac accatggaga ccatagactg     540
gaaggtcttt gagagctgga tgcaccattg gctcctgttt gaaatgagca ggcactcctt    600
ggagcaaaag cccactgacg ctccaccgaa agagtcactg gaactggagg acccgtcttc    660
tgggctgggt gtgaccaagc aggatctggg cccagtcccc atgtgagagc agcagaggcg    720
gtcttcaaca tcctgccagc cccacacagc tacagctttc ttgctcccct cagccccag    780 cccctccccc atgtcccacc ctgtacctca tcccatgaga cctggtgcct ggctctttcg    840
tcacccttgt acaagacaaa ccaagtcgga acagcagata caatgcagc aaggccctgc     900 tgcccaatct ccatctgtca acaggggcgt gaggtcccag gaagtggcca aaagctagac    960
agatccccgt tcctgacatc acagcagcct ccaacacaag gctccaagac ctaggctcat   1020
ggacgagatg ggaaggcaca gggagaaggg ataaccctac acccagaccc caggctggac   1080
atgctgactg tcctctcccc tccagccttt ggccttggct tttctagcct atttacctgc   1140
aggctgagcc actctcttcc ctttccccag catcactccc caaggaagag ccaatgttt    1200 ggacccataa tcctttctgc cgaccccctag ttccctctgc tcagccaagc ttgttatcag   1260
ctttcagggc catggttcac attagaataa aaggtagtaa ttag                    1304
```

<210> SEQ ID NO 133
<211> LENGTH: 232
<212> TYPE: PRT
<213> ORGANISM: Homo sapiens

<400> SEQUENCE: 133

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205
```

```
Glu Ser Leu Glu Leu Glu Asp Pro Ser Ser Gly Leu Gly Val Thr Lys
    210                 215                 220

Gln Asp Leu Gly Pro Val Pro Met
225                 230
```